(12) United States Patent
Rodgers et al.

(10) Patent No.: US 9,359,358 B2
(45) Date of Patent: Jun. 7, 2016

(54) CYCLOHEXYL AZETIDINE DERIVATIVES AS JAK INHIBITORS

(75) Inventors: James D. Rodgers, Landenberg, PA (US); Argyrios G. Arvanitis, Kennett Square, PA (US)

(73) Assignees: Incyte Holdings Corporation, Wilmington, DE (US); Incyte Corporation, Wilimington, DE (US)

( * ) Notice: Subject to any disclaimer, the term of this patent is extended or adjusted under 35 U.S.C. 154(b) by 421 days.

(21) Appl. No.: 13/588,776

(22) Filed: Aug. 17, 2012

(65) Prior Publication Data
US 2013/0045963 A1 Feb. 21, 2013

Related U.S. Application Data

(60) Provisional application No. 61/674,694, filed on Jul. 23, 2012, provisional application No. 61/525,081, filed on Aug. 18, 2011.

(51) Int. Cl.
| | | |
|---|---|---|
| C07D 487/04 | (2006.01) | |
| A61K 31/519 | (2006.01) | |
| A61P 35/00 | (2006.01) | |
| A61P 35/02 | (2006.01) | |
| C07D 473/04 | (2006.01) | |

(52) U.S. Cl.
CPC ............ *C07D 473/04* (2013.01); *C07D 487/04* (2013.01)

(58) Field of Classification Search
CPC .................................................... C07D 487/04
See application file for complete search history.

(56) References Cited

U.S. PATENT DOCUMENTS

| | | | |
|---|---|---|---|
| 2,985,589 A | 5/1961 | Broughton et al. | |
| 3,832,460 A | 8/1974 | Kosti | |
| 4,402,832 A | 9/1983 | Gerhold | |
| 4,498,991 A | 2/1985 | Oroskar | |
| 4,512,984 A | 4/1985 | Seufert et al. | |
| 4,548,990 A | 10/1985 | Mueller et al. | |
| 4,814,477 A | 3/1989 | Wijnberg et al. | |
| 5,378,700 A | 1/1995 | Sakuma et al. | |
| 5,510,101 A | 4/1996 | Stroppolo | |
| 5,521,184 A | 5/1996 | Zimmermann | |
| 5,630,943 A | 5/1997 | Grill | |
| 5,795,909 A | 8/1998 | Shashoua et al. | |
| 5,856,326 A | 1/1999 | Anthony | |
| 5,919,779 A | 7/1999 | Proudfoot et al. | |
| 6,060,038 A | 5/2000 | Burns | |
| 6,075,056 A | 6/2000 | Quigley, Jr. et al. | |
| 6,136,198 A | 10/2000 | Adam et al. | |
| 6,217,895 B1 | 4/2001 | Guo | |
| 6,335,342 B1 | 1/2002 | Longo et al. | |
| 6,375,839 B1 | 4/2002 | Adam et al. | |
| 6,413,419 B1 | 7/2002 | Adam et al. | |
| 6,486,322 B1 | 11/2002 | Longo et al. | |
| 6,548,078 B2 | 4/2003 | Guo | |
| 6,569,443 B1 | 5/2003 | Dawson | |
| 6,579,882 B2 | 6/2003 | Stewart et al. | |
| 6,624,138 B1 | 9/2003 | Sung et al. | |
| 6,635,762 B1 | 10/2003 | Blumenkopf et al. | |
| 6,712,973 B2 | 3/2004 | Adam et al. | |
| 6,713,089 B1 | 3/2004 | Bertelsen et al. | |
| 6,852,727 B2 | 2/2005 | Goulet et al. | |
| 6,953,776 B2 | 10/2005 | Di Napoli | |

(Continued)

FOREIGN PATENT DOCUMENTS

| | | |
|---|---|---|
| DE | 30 36 390 | 5/1982 |
| EP | 0223420 | 5/1987 |

(Continued)

OTHER PUBLICATIONS

26th Annual JPMorgan Healthcare Conference presentation dated Jan. 8, 2008 (28 pages).

(Continued)

*Primary Examiner* — Susanna Moore

(74) *Attorney, Agent, or Firm* — Fish & Richardson P.C.

(57) ABSTRACT

The present invention provides cyclohexyl azetidine derivatives of Formula I:

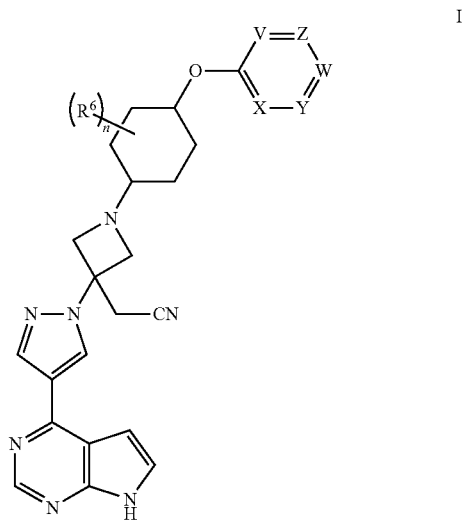

or pharmaceutically acceptable salts thereof, as well as their compositions and methods of use, that modulate the activity of Janus kinase (JAK) and are useful in the treatment of diseases related to the activity of JAK including, for example, inflammatory disorders, autoimmune disorders, cancer, and other diseases.

30 Claims, No Drawings

(56) References Cited

U.S. PATENT DOCUMENTS

| | | |
|---|---|---|
| 7,005,436 B2 | 2/2006 | Lloyd et al. |
| 7,167,750 B2 | 1/2007 | Knudson et al. |
| 7,265,108 B2 | 9/2007 | Ozaki |
| 7,335,667 B2 | 2/2008 | Rodgers et al. |
| 7,358,255 B2 | 4/2008 | Nakamura |
| 7,517,870 B2 | 4/2009 | Auricchio |
| 7,598,257 B2 | 10/2009 | Rodgers et al. |
| 7,745,437 B2 | 6/2010 | Ren et al. |
| 7,750,007 B2 | 7/2010 | Bearss et al. |
| 7,834,022 B2 | 11/2010 | Rodgers et al. |
| 8,053,433 B2 | 11/2011 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,415,362 B2 | 4/2013 | Rodgers et al. |
| 8,420,629 B2 | 4/2013 | Rodgers et al. |
| 8,445,488 B2 | 5/2013 | Rodger et al. |
| 8,486,902 B2 | 7/2013 | Rodgers et al. |
| 8,513,270 B2 | 8/2013 | Arvanitis et al. |
| 8,530,485 B2 | 9/2013 | Rodgers et al. |
| 8,541,425 B2 | 9/2013 | Rodgers et al. |
| 8,563,541 B2 | 10/2013 | Arvanitis et al. |
| 8,604,043 B2 | 12/2013 | Li et al. |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,741,895 B2 | 6/2014 | Rodgers et al. |
| 8,748,401 B2 | 6/2014 | Rodgers et al. |
| 8,765,734 B2 | 7/2014 | Huang et al. |
| 8,822,481 B1 | 9/2014 | Rodgers et al. |
| 8,829,013 B1 | 9/2014 | Rodgers et al. |
| 8,835,423 B2 | 9/2014 | Arvanitis et al. |
| 8,841,318 B2 | 9/2014 | Arvanitis et al. |
| 8,883,806 B2 | 11/2014 | Zhou et al. |
| 8,889,697 B2 | 11/2014 | Rodgers et al. |
| 8,933,085 B2 | 1/2015 | Rodgers et al. |
| 8,933,086 B2 | 1/2015 | Rodgers et al. |
| 8,946,245 B2 | 2/2015 | Rodgers et al. |
| 2002/0111353 A1 | 8/2002 | Ledeboer et al. |
| 2003/0064969 A1 | 4/2003 | Bhagwat et al. |
| 2003/0100756 A1 | 5/2003 | Adams et al. |
| 2003/0144309 A1 | 7/2003 | Choon-Moon |
| 2003/0165576 A1 | 9/2003 | Fujii et al. |
| 2004/0009222 A1 | 1/2004 | Chou et al. |
| 2004/0009983 A1 | 1/2004 | Cox et al. |
| 2004/0029857 A1 | 2/2004 | Hale et al. |
| 2004/0077654 A1 | 4/2004 | Bouillot |
| 2004/0198737 A1 | 10/2004 | Cox et al. |
| 2004/0204404 A1 | 10/2004 | Zelle |
| 2004/0214928 A1 | 10/2004 | Aronov |
| 2004/0235862 A1 | 11/2004 | Burns |
| 2005/0014966 A1 | 1/2005 | Tabe |
| 2005/0054568 A1 | 3/2005 | Ling |
| 2005/0153989 A1 | 7/2005 | Grotzfeld et al. |
| 2006/0004010 A1 | 1/2006 | Habashita et al. |
| 2006/0020011 A1 | 1/2006 | Wu et al. |
| 2006/0079511 A1 | 4/2006 | Liu et al. |
| 2006/0106020 A1 | 5/2006 | Rodgers et al. |
| 2006/0106027 A1 | 5/2006 | Furet et al. |
| 2006/0128803 A1 | 6/2006 | Klimko |
| 2006/0135537 A1 | 6/2006 | Knegtel et al. |
| 2006/0178393 A1 | 8/2006 | Pitts |
| 2006/0183761 A1 | 8/2006 | Ledeboer et al. |
| 2006/0183906 A1 | 8/2006 | Rodgers et al. |
| 2006/0223864 A1 | 10/2006 | Biju |
| 2006/0293311 A1 | 12/2006 | Li et al. |
| 2007/0135461 A1 | 6/2007 | Rodgers et al. |
| 2007/0135466 A1 | 6/2007 | Ledeboer et al. |
| 2007/0149506 A1 | 6/2007 | Arvanitis et al. |
| 2007/0149561 A1 | 6/2007 | Dhanak et al. |
| 2007/0191364 A1 | 8/2007 | Braun et al. |
| 2007/0191405 A1 | 8/2007 | Noronha |
| 2007/0208053 A1 | 9/2007 | Wang et al. |
| 2007/0259904 A1 | 11/2007 | Noronha |
| 2008/0021026 A1 | 1/2008 | Borchardt et al. |
| 2008/0085898 A1 | 4/2008 | Lu |
| 2008/0096852 A1 | 4/2008 | Yanni |
| 2008/0119496 A1 | 5/2008 | Ohlmeyer |
| 2008/0161346 A1 | 7/2008 | Cheng |
| 2008/0188500 A1 | 8/2008 | Arvanitis et al. |
| 2008/0194468 A1 | 8/2008 | Bodor |
| 2008/0207570 A1 | 8/2008 | Segura-Orsoni |
| 2008/0207584 A1 | 8/2008 | Habashita et al. |
| 2008/0280876 A1 | 11/2008 | Hobson et al. |
| 2008/0312258 A1 | 12/2008 | Rodgers et al. |
| 2008/0312259 A1 | 12/2008 | Rodgers et al. |
| 2009/0018156 A1 | 1/2009 | Tang et al. |
| 2009/0076070 A1 | 3/2009 | Harada et al. |
| 2009/0088445 A1 | 4/2009 | Ledeboer et al. |
| 2009/0131403 A1 | 5/2009 | Kusuda |
| 2009/0181959 A1 | 7/2009 | Rodgers et al. |
| 2009/0197869 A1 | 8/2009 | Arvanitis et al. |
| 2009/0203637 A1 | 8/2009 | Hocek et al. |
| 2009/0215766 A1 | 8/2009 | Rodgers et al. |
| 2009/0221608 A1 | 9/2009 | Cui et al. |
| 2009/0233903 A1 | 9/2009 | Rodgers et al. |
| 2009/0318405 A1 | 12/2009 | Li et al. |
| 2010/0022522 A1 | 1/2010 | Rodgers et al. |
| 2010/0069381 A1 | 3/2010 | Itoh et al. |
| 2010/0113416 A1 | 5/2010 | Friedman et al. |
| 2010/0190981 A1 | 7/2010 | Zhou et al. |
| 2010/0210627 A1 | 8/2010 | Mao et al. |
| 2010/0298334 A1 | 11/2010 | Rodgers et al. |
| 2010/0298355 A1 | 11/2010 | Li et al. |
| 2011/0059951 A1 | 3/2011 | Rodgers et al. |
| 2011/0082159 A1 | 4/2011 | Rodgers et al. |
| 2011/0086810 A1 | 4/2011 | Rodgers et al. |
| 2011/0086835 A1 | 4/2011 | Rodgers et al. |
| 2011/0201593 A1 | 8/2011 | Babu et al. |
| 2011/0207754 A1 | 8/2011 | Li et al. |
| 2011/0223210 A1 | 9/2011 | Rodgers et al. |
| 2011/0224157 A1 | 9/2011 | Rodgers et al. |
| 2011/0224190 A1 | 9/2011 | Huang et al. |
| 2011/0288107 A1 | 11/2011 | Parikh et al. |
| 2012/0014989 A1 | 1/2012 | Rodgers |
| 2012/0077798 A1 | 3/2012 | Rodgers et al. |
| 2012/0149681 A1 | 6/2012 | Rodgers |
| 2012/0149682 A1 | 6/2012 | Rodgers et al. |
| 2012/0214825 A1 | 8/2012 | Vannucchi et al. |
| 2012/0301464 A1 | 11/2012 | Friedman et al. |
| 2012/0329782 A1 | 12/2012 | Arvanitis et al. |
| 2013/0018034 A1 | 1/2013 | Yao et al. |
| 2013/0040973 A1 | 2/2013 | Vannucchi et al. |
| 2013/0060026 A1 | 3/2013 | Zhou et al. |
| 2013/0137681 A1 | 5/2013 | Rodgers et al. |
| 2013/0225556 A1 | 8/2013 | Rodgers et al. |
| 2013/0253190 A1 | 9/2013 | Zhou et al. |
| 2013/0253191 A1 | 9/2013 | Zhou et al. |
| 2013/0253193 A1 | 9/2013 | Zhou et al. |
| 2013/0274257 A1 | 10/2013 | Arvanitis et al. |
| 2013/0296299 A1 | 11/2013 | Rodgers et al. |
| 2014/0005166 A1 | 1/2014 | Rodgers et al. |
| 2014/0005210 A1 | 1/2014 | Rodgers et al. |
| 2014/0018374 A1 | 1/2014 | Rodgers et al. |
| 2014/0031344 A1 | 1/2014 | Arvanitis et al. |
| 2014/0073657 A1 | 3/2014 | Li et al. |
| 2014/0094477 A1 | 4/2014 | Rodgers et al. |
| 2014/0121198 A1 | 5/2014 | Li et al. |
| 2014/0171409 A1 | 6/2014 | Yao et al. |
| 2014/0221379 A1 | 8/2014 | Rodgers et al. |
| 2014/0228346 A1 | 8/2014 | Rodgers et al. |
| 2014/0243360 A1 | 8/2014 | Rodgers et al. |
| 2014/0256941 A1 | 9/2014 | Liu et al. |
| 2014/0275031 A1 | 9/2014 | Huang et al. |
| 2014/0303196 A1 | 10/2014 | Rodgers et al. |
| 2014/0343030 A1 | 11/2014 | Li et al. |
| 2015/0087632 A1 | 3/2015 | Rodgers et al. |

FOREIGN PATENT DOCUMENTS

| | | |
|---|---|---|
| EP | 0587473 | 3/1994 |
| EP | 0727217 | 8/1996 |
| EP | 0795556 | 9/1997 |
| EP | 1104764 | 6/2001 |

(56) References Cited

FOREIGN PATENT DOCUMENTS

| | | |
|---|---|---|
| JP | 07-010876 | 1/1995 |
| JP | 2003/155285 | 5/2003 |
| WO | WO 96/30343 | 10/1996 |
| WO | WO 97/02262 | 1/1997 |
| WO | WO 97/02266 | 1/1997 |
| WO | WO 97/36587 | 10/1997 |
| WO | WO 97/38664 | 10/1997 |
| WO | WO 97/45412 | 12/1997 |
| WO | WO 98/44797 | 10/1998 |
| WO | WO 98/51391 | 11/1998 |
| WO | WO 99/00654 | 1/1999 |
| WO | WO 99/62908 | 12/1999 |
| WO | WO 99/65908 | 12/1999 |
| WO | WO 99/65909 | 12/1999 |
| WO | WO 00/09495 | 2/2000 |
| WO | WO 00/51614 | 9/2000 |
| WO | WO 00/53595 | 9/2000 |
| WO | WO 00/63168 | 10/2000 |
| WO | WO 01/14402 | 3/2001 |
| WO | WO 01/27104 | 4/2001 |
| WO | WO 01/42246 | 6/2001 |
| WO | WO 01/64655 | 9/2001 |
| WO | WO 01/81345 | 11/2001 |
| WO | WO 01/98344 | 12/2001 |
| WO | WO 02/00196 | 1/2002 |
| WO | WO 02/00661 | 1/2002 |
| WO | WO 02/16370 | 2/2002 |
| WO | WO 02/046184 | 6/2002 |
| WO | WO 02/055084 | 7/2002 |
| WO | WO 02/055496 | 7/2002 |
| WO | WO 02/060492 | 8/2002 |
| WO | WO 02/080926 | 10/2002 |
| WO | WO 02/092573 | 11/2002 |
| WO | WO 02/096909 | 12/2002 |
| WO | WO 03/000695 | 1/2003 |
| WO | WO 03/011285 | 2/2003 |
| WO | WO 03/024967 | 3/2003 |
| WO | WO 03/037347 | 5/2003 |
| WO | WO 03/048162 | 6/2003 |
| WO | WO 03/092595 | 11/2003 |
| WO | WO 03/099771 | 12/2003 |
| WO | WO 03/099796 | 12/2003 |
| WO | WO 2004/003026 | 1/2004 |
| WO | WO 2004/005281 | 1/2004 |
| WO | WO 2004/005282 | 1/2004 |
| WO | WO 2004/026406 | 4/2004 |
| WO | WO 2004/041814 | 5/2004 |
| WO | WO 2004/046120 | 6/2004 |
| WO | WO 2004/047843 | 6/2004 |
| WO | WO 2004/056786 | 7/2004 |
| WO | WO 2004/072063 | 8/2004 |
| WO | WO 2004/080980 | 9/2004 |
| WO | WO 2004/092154 | 10/2004 |
| WO | WO 2004/099204 | 11/2004 |
| WO | WO 2004/099205 | 11/2004 |
| WO | WO 2005/005988 | 1/2005 |
| WO | WO 2005/013986 | 2/2005 |
| WO | WO 2005/020921 | 3/2005 |
| WO | WO 2005/026129 | 3/2005 |
| WO | WO 2005/028444 | 3/2005 |
| WO | WO 2005/049033 | 6/2005 |
| WO | WO 2005/051393 | 6/2005 |
| WO | WO 2005/060972 | 7/2005 |
| WO | WO 2005/061463 | 7/2005 |
| WO | WO 2005/062795 | 7/2005 |
| WO | WO 2005/089502 | 9/2005 |
| WO | WO 2005/095400 | 10/2005 |
| WO | WO 2005/105146 | 11/2005 |
| WO | WO 2005/105814 | 11/2005 |
| WO | WO 2005/105988 | 11/2005 |
| WO | WO 2005/110410 | 11/2005 |
| WO | WO 2005/117909 | 12/2005 |
| WO | WO 2005/121130 | 12/2005 |
| WO | WO 2005/123719 | 12/2005 |
| WO | WO 2006/004984 | 1/2006 |
| WO | WO 2006/013114 | 2/2006 |
| WO | WO 2006/022459 | 3/2006 |
| WO | WO 2006/039718 | 4/2006 |
| WO | WO 2006/046023 | 5/2006 |
| WO | WO 2006/046024 | 5/2006 |
| WO | WO 2006/052913 | 5/2006 |
| WO | WO 2006/056399 | 6/2006 |
| WO | WO 2006/067445 | 6/2006 |
| WO | WO 2006/069080 | 6/2006 |
| WO | WO 2006/077499 | 7/2006 |
| WO | WO 2006/096270 | 9/2006 |
| WO | WO 2006/101783 | 9/2006 |
| WO | WO 2006/108103 | 10/2006 |
| WO | WO 2006/122806 | 11/2006 |
| WO | WO 2006/127587 | 11/2006 |
| WO | WO 2006/129199 | 12/2006 |
| WO | WO 2006/136823 | 12/2006 |
| WO | WO 2007/002433 | 1/2007 |
| WO | WO 2007/025090 | 3/2007 |
| WO | WO 2007/041130 | 4/2007 |
| WO | WO 2007/043677 | 4/2007 |
| WO | WO 2007/044894 | 4/2007 |
| WO | WO 2007/049041 | 5/2007 |
| WO | WO 2007/062459 | 6/2007 |
| WO | WO 2007/070514 | 6/2007 |
| WO | WO 2007/076423 | 7/2007 |
| WO | WO 2007/077949 | 7/2007 |
| WO | WO 2007/084557 | 7/2007 |
| WO | WO 2007/090141 | 8/2007 |
| WO | WO 2007/090748 | 8/2007 |
| WO | WO 2007/116313 | 10/2007 |
| WO | WO 2007/117494 | 10/2007 |
| WO | WO 2007/129195 | 11/2007 |
| WO | WO 2007/135461 | 11/2007 |
| WO | WO 2007/140222 | 12/2007 |
| WO | WO 2008/013925 | 1/2008 |
| WO | WO 2008/028937 | 3/2008 |
| WO | WO 2008/035376 | 3/2008 |
| WO | WO 2008/043031 | 4/2008 |
| WO | WO 2008/058126 | 5/2008 |
| WO | WO 2008/064157 | 5/2008 |
| WO | WO 2008/067119 | 6/2008 |
| WO | WO 2008/077712 | 7/2008 |
| WO | WO 2008/079291 | 7/2008 |
| WO | WO 2008/079292 | 7/2008 |
| WO | WO 2008/082198 | 7/2008 |
| WO | WO 2008/082839 | 7/2008 |
| WO | WO 2008/082840 | 7/2008 |
| WO | WO 2008/106692 | 9/2008 |
| WO | WO 2008/124323 | 10/2008 |
| WO | WO 2008/139161 | 11/2008 |
| WO | WO 2008/145681 | 12/2008 |
| WO | WO 2008/145688 | 12/2008 |
| WO | WO 2008/157207 | 12/2008 |
| WO | WO 2008/157208 | 12/2008 |
| WO | WO 2009/016460 | 2/2009 |
| WO | WO 2009/049028 | 4/2009 |
| WO | WO 2009/064486 | 5/2009 |
| WO | WO 2009/064835 | 5/2009 |
| WO | WO 2009/071577 | 6/2009 |
| WO | WO 2009/100130 | 8/2009 |
| WO | WO 2009/109576 | 9/2009 |
| WO | WO 2009/114512 | 9/2009 |
| WO | WO 2009/115572 | 9/2009 |
| WO | WO 2009/155156 | 12/2009 |
| WO | WO 2009/158687 | 12/2009 |
| WO | WO 2010/000978 | 1/2010 |
| WO | WO 2010/001169 | 1/2010 |
| WO | WO 2010/020905 | 2/2010 |
| WO | WO 2010/022076 | 2/2010 |
| WO | WO 2010/022081 | 2/2010 |
| WO | WO 2010/026121 | 3/2010 |
| WO | WO 2010/026122 | 3/2010 |
| WO | WO 2010/026124 | 3/2010 |
| WO | WO 2010/039939 | 4/2010 |
| WO | WO 2010/081692 | 7/2010 |
| WO | WO 2010/083283 | 7/2010 |
| WO | WO 2010/135621 | 11/2010 |
| WO | WO 2010/135650 | 11/2010 |

(56) References Cited

FOREIGN PATENT DOCUMENTS

| | | |
|---|---|---|
| WO | WO 2011/003418 | 1/2011 |
| WO | WO 2011/025685 | 3/2011 |
| WO | WO 2011/028685 | 3/2011 |
| WO | WO 2011/029802 | 3/2011 |
| WO | WO 2011/031554 | 3/2011 |
| WO | WO 2011/035900 | 3/2011 |
| WO | WO 2011/044481 | 4/2011 |
| WO | WO 2011/057784 | 5/2011 |
| WO | WO 2011/069141 | 6/2011 |
| WO | WO 2011/112662 | 9/2011 |
| WO | WO 2011/130146 | 10/2011 |
| WO | WO 2011/144338 | 11/2011 |
| WO | WO 2011/146808 | 11/2011 |
| WO | WO 2012/003457 | 1/2012 |
| WO | WO 2012/068440 | 5/2012 |
| WO | WO 2012/068450 | 5/2012 |
| WO | WO 2012/177606 | 12/2012 |
| WO | WO 2013/007765 | 1/2013 |
| WO | WO 2013/007768 | 1/2013 |
| WO | WO 2013/023119 | 2/2013 |
| WO | WO 2013/036611 | 3/2013 |
| WO | WO 2013/173720 | 11/2013 |
| WO | WO 2014/071031 | 5/2014 |
| WO | WO 2014/138168 | 9/2014 |

OTHER PUBLICATIONS

Abe, et al., Heterocycles, "Effective Methods for Introducing Some Aryl and Heteroaryl Substituent onto 1-Azaazulene Nuclei", 66, 229-240 (2005).

Abelson et al., "Alternate reference values for tear film break-up time in normal and dry eye populations, Lacrimal Gland, Tear Film, and Dry Eye Syndromes 3 Part B", Adv Exp Med Biol, 2002; 506:1121-1125.

Abelson et al., "Dry eye syndrome: diagnosis, clinical trials, and pharmaceutical treatment-'improving clinical trials'. Lacrimal Gland, Tear Film, and Dry Eye Syndromes 3 Part B", Adv Exp Med Biol, 2002; 506:1079-86.

Abstract of Chilean patent application No. 3496-06 published in Official Gazette of the Republic of Chile (Jun. 1, 2007) and publication (2 pages).

Aho, T. et al., Expression of human pim family genes is selectively up-regulated by cytokines promoting T helper type 1, but not T helper type 2, cell differentiation, Immunology 116: 82-88, 2005.

Albach et al., "Diagnosis of keratoconjunctivitis sicca in rheumatoid arthritis. The value of various tests", Ophthalmologe, Apr. 1994; 91(2):229-34—in German (with English abstract/summary contained therein).

Anderson et al., "Biochemical characterization of GSK1070916, a potent and selective inhibitor of Aurora B and Aurora C kinases with an extremely long residence time", Biochem. J., 420(2), 259-265 (2009).

Bachmann, et al., "The serine/threonine kinease Pim-1," The International Journal of Biochechemistry and Cell Biology 37: 726-730 (2005).

Banker, et al., "Modern Pharmaceuticals" p. 596 (1996).

Barabino et al., "Tear film and ocular surface tests in animal models of dry eye; uses and limitations", Experimental Eye Research, 2004, 79, 613-621.

Barr et al., "Corneal scarring in the Collaborative Longitudinal Evaluation of Keratoconus (CLEK) Study: baseline prevalence and repeatability of detection", Cornea, 1999; 18(1):34-46.

Baudouin et al., "Flow cytometry in impression cytology specimens. A new method for evaluation of conjunctival Inflammation", Invest Ophthalmol Vis Sci, 1997; 38:1458-1464.

Baytel et al., "The human Pim-2 proto-oncogene and its testicular expression" Biochimica et Biophysica Acta 1442: 274-285, (1998).

Begley, et al., "Use of the dry eye questionnaire to measure symptoms of ocular irritation in patients with aqueous tear deficient dry eye", Cornea, 2002:21:664-70.

Bell, Malcolm, and Zalay, Andrew, "Synthesis of Substituted 3-Amino[6, 5-b] triazinoindoles." Journal of Heterocyclic Chemistry, 12(5):1001-1004, Oct. 1975.

Berge, et al., "Pharmaceutical salts", J. Pharma. Science (1977) vol. 66(1) pp. 1-19.

Beyer, "Uber die Synthese von 2-Methylmercapto-1.3.4-thiodiazinen und deren Umlagerung in Pyrazolderivate (The synthesis of 2-methylthio-1,3,4-thiadiazines and their rearrangement to pyrazole derivatives)", Chem. Berichte Jahrg., 92:2593-2599 (1959) (abstract provided).

Bhovi, et al., "1,3-Dipolar Cycloaddition Reaction: Synthesis and Antimicrobial, Activity of Some New 3-Ethoxycarbonyl-s-Methoxy-6-Bromo-2-Triazolylmethylindoles", Indian Journal of Heterocyclic Chemistry, vol. 14, (Jul.-Sep. 2004), pp. 15-18.

Bioreversible Carriers in Drug Design, ed. Edward B. Roche, American Pharmaceutical Association and Pergamon Press, 1987*too voluminous to provide.

Blume-Jensen, et al, "Oncogenic kinase signaling", Nature 2001, 411(6835):355-365.

Bock, C., et al. "Managing drug resistance in cancer: lessons from HIV therapy." Nature. (Jul. 2012), vol. 12, pp. 494-501.

Bolen, "Nonreceptor tyrosine protein kinases", Oncogene, 1993, 8(8):2025-31.

Bollrath et al., "gp130-Mediated Stat3 Activation in Enterocytes Regulates Cell Survival and Cell-Cycle Progression during Colitis-Associated Tumorigenesis," Cancer Cell, 15:91-102 (2009).

Borie, et al., "Combined Use of the Jak3 Inhibitor CP-690, 550 with Mycophenolate Mofetil to Prevent Kidney Allograft Rejection in Nonhuman Primates", Transplantation, Dec. 27, 2005;80(12):1756-64.

Bosworth, JAK1/JAK2 Inhibitor Ruxolitinib Is a Rising Start, Clinical Oncology, vol. 06:04 (Apr. 2011) 3 pages.

Boudny, et al., "JAK/STAT signaling pathways and cancer", Neoplasm, 49:349-355, 2002.

Bourcier et al., "Expression of CD40 and CD40 ligand in the human conjunctival epithelium", Invest Ophthalmol Vis Sci, 2000;41:120-126.

Bowman, et al. "STATs in oncogenesis", Oncogene, 19:2474-2488, 2000.

Brignole et al., "Expression of Fas-Fas Ligand Antigens and Apoptotic Marker APO2-7 by the Human Conjunctival Epithelium. Positive correlation with class II HLA DR expression in inflammatory Ocular Surface Disorders", Exp Eye Res, 1998;67:687-697.

Brignole et al., "Flow cytometric analysis of inflammatory markers in conjunctival epithelial cells of patients with dry eyes", Invest Ophthalmol Vis Sci, 2000; 41:1356-1363.

Brignole et al., "Flow cytometric analysis of inflammatory markers in KCS: 6-month treatment with topical cyclosporin A", Invest Ophthalmol Vis Sci, 2001; 42:90-95.

Brignole et al., "Flow cytometry in conjunctival impression cytology: a new tool for exploring ocular surface pathologies", Exp Eye Res, 2004;78:473-481.

Bromberg et al., "Inflammation and Cancer: IL-6 and STAT3 Complete the Link," Cancer Cell, 15:79-80 (2009).

Bron, et al., "Grading of corneal and conjunctival staining in the context of other dry eye tests", Cornea, 2003;22(7):640-50.

Bron, et al., "Methodologies to Diagnose and Monitor Dry Eye Disease: Report of the Diagnostic Methodology Subcommittee of the International Dry Eye Workshop (2007)", The Ocular Surface, 5(2), 108-152 (Apr. 2007).

Burger et al., "Janus kinase inhibitor INCB20 has antiproliferative and apoptotic effects on human myeloma cells in vitro and in vivo", Mol. Cancer Ther. 2009:8(1), Jan. 2009 pp. 26-35.

Burger, et al., "Gp130 and ras mediated signaling in human plasma cell line IN/a-6: a cytokine-regulated tumor model for plasmacytoma", Hematol J., 2:42-53, 2001.

Campas-Moya, C., "Ruxolitinib. Tyrosine-protein kinase JAK1/2 inhibitor, treatment of myelofibrosis, treatment of myeloproliferative neoplasms, treatment of psoriasis", Drugs of the Future, (Jun. 2010) vol. 35, No. 6, pp. 457-465.

Candotti, et al. (2002). "Molecular aspects of primary immunodeficiencies: lessons from cytokine and other signaling pathways.", J Clin Invest, 109(10): 1261-9.

(56) References Cited

OTHER PUBLICATIONS

Candotti, F., et al. (1997). "Structural and functional basis for JAK3-deficient severe combined immunodeficiency.", Blood, 90(10): 3996-4003.
Carey and Sundberg, Advanced Organic Chemistry, Part B: Reactions and Synthesis, 4th ed., Kluwer Academic/Plenum Publishers:New York, pp. 111-119 (2001).
Carey and Sundberg, Advanced Organic Chemistry, Part B: Reactions and Synthesis, Oxidations, 4th ed., Kluwer Academic/Plenum Publishers:New York, pp. 747-757 (2001).
Cermak, et al, "Is complete androgen insensitivity syndrome associated with alterations in the meibomium gland and ocular surface", Cornea, 2003;22:516-521.
Cetkovic-Cvrlje, et al. (2003). "Targeting JAK3 with JANEX-1 for prevention of autoimmune type 1 diabetes in NOD mice.", Clin Immunol, 106(3): 213-25.
Chalandon, "Targeting mutated protein tyrosine kinases and their signaling pathways in hematologic malignancies", Haematologica, 90 (7):949-68 (2005).
Changelian, et al., "Prevention of Organ Allograft Rejection by a Specific Janus Kinase 3 Inhibitor", Science, 2003, 302, 875-878.
Chauhan, et al, "Autoimmunity in Dry Eye due to resistance of Th17 to Treg Suppression", J. Immunology, 182(3):1247-52 (2009).
Chen, et al., "Stat3 Activation in Human Endometrial and Cervical Cancer", British Journal of Cancer, 96, 591-599, 2007.
Chew, et al., "An instrument for quantifying meibomian lipid on the lid margin: the Meibometer", Curr Eye Res, 1993a;12:247-254.
Chew, et al., "The casual level of meibomian lipids in humans", Current Eye Research, 1993b;12:255-259.
Cho, et al, "Review of the tear break-up time and a closer look at the tear break-up time of Hong Kong Chinese", Optom Vis Sci, 1993;70(1):30-8.
Choi Ha-Soon, et al, "Design and synthesis of 7H-pyrrolo[2,3-d]pyrimidines as focal adhesion kinase inhibitors. Part 1", Bioorg. & Med. Chem. Lett., 16(8):2173-2176 (2006).
Chu-Moyer, et al., "Preparation of the Four Regioisomeric 2-(Methylthio)oxazolopyridines: Useful Synthons for Elaboration to 2-(Amino substituted)oxazolopyridines", J. Org. Chem. 60(17): 5721-5725 (1995).
Cilloni et al., "Emerging drugs for chronic myeloid leukemia", Expert Opinion on Emerging Drugs, (Jun. 2010) vol. 15, No. 2, pp. 175-184.
Coligan, J.E. et al, Wiley Press; Methods in Molecular Biology: vol. 225, Inflammation Protocols., Winyard, P.G. and Willoughby, D.A., Humana Press (2003)* too voluminous to provide.
Communication dated Jan. 22, 2009 for European Appln. No. 06839328.9 (5 pgs.).
Conklyn, M. et al., "The JAK3 inhibitor CP0690550 selectively reduces NK and CD8+ cell numbers in cynomolgus monkey blood following chronic oral dosing", Journal of Leukocyte Biology, 2004, 76, 1248-1255.
Costa Rican Office Action in CR Application No. 10065, dated Jul. 16, 2013, 8 pages.
Craig et al. "Tear lipid layer structure and stability following expression of the meibomian glands.", Ophthalmic Physiol Opt, 1995, 15(6):569-74.
Current Protocols in Immunology, vol. 3., Coligan, J.E. et al, Wiley Press (1988)* too voluminous to provide.
Daniels et al., "Imatinib mesylate inhibits the profibrogenic activity of TGF-? and prevents bleomycinmediated lung fibrosis." J. Clin. Invest., 114(9):1308-1316, Nov. 2004.
Danjo et al., "Observation of precorneal tear film in patients with Sjogren's syndrome", Acta Ophthalmol Scand, 73:501-505 (1995).
De Paiva, et al, "IL-17 disrupts corneal barrier following desiccating stress", Mucosal Immunol. 2(3):243-53 (2009).
De Vos, J., et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haematol, 109(4): 823-8.

Deng Jun, et al, "Rh-catalyzed asymmetric hydrogenation of gamma-phthalimido-substituted esters: an efficient enantioselective synthesis of beta-aryl-gamma-amino acids", Org. Lett. 9(23):4825-4827 (2007).
Deuse, T. et al., "Novel Immunosuppression: R348, a JAK3- and Syk-Inhibitor Attenuates Acute Cardiac Allograft Rejection", Transplantation, 2008, 85(6) 885-892.
Doane, "An instrument for in vivo tear film interferometry", Optom Vis Sci, 1989; 66: 383-8.
Doleschall G., et al., "Thermal and Acid Catalysed Degradations of 3-alkylthio-6,7-dihydro[1.2.4]triazino[1,6-c]quinazolin-5-ium-1-olates", Tetrahedron, 30:3997-4012, 1974.
Dudley, A.C., et al. "AVEGF/JAK2/STAT5 axis may partially mediate endothelial cell tolerance to hypoxia", Biochem. J. 2005, 390(Pt 2):427-36.
Eghtedar, "Phase II Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), Abstract/poster 509.
Einmahl, et al., "Therapeutic applications of viscous and injectable poly(ortho esters)", Adv. Drug. Deliv. Rev. 53:45-73 (2001).
Eliason, et al., "Staining of the conjunctiva and conjunctival tear film", Br J Ophthalmol, 1990;74:519-22.
Expert Scientific Group on Phase One Clinical Trials Final Report, Nov. 30, 2006, pp. C1, C35-C38.
Fabrizio Saettone, "Ocular inserts for topical delivery", Advanced Drug Delivery Reviews 16:95-106 (1998).
Farrell et al., "A classification for dry eyes following comparison of tear thinning time with Schirmer tear test", Acta Ophthalmol (Copenh), 1992; 70(3):357-60.
Farrell et al., "A clinical procedure to predict the value of temporary occlusion therapy in keratoconjunctivitis sicca" Ophthal Physiol Opt, 2003;23:1-8.
Farris, "Tear osmolarity—a new gold standard?" Adv Exp Med Biol, 350:495-503, 1994.
Fiskus, W. et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications; vol. 116, No. 21 Nov. 1, 2010 p. 349, XP002667216, ISSN: 0002-7863 (1 page).
Flex E., et al., "Somatically acquired JAK1 mutations in adult acute lymphoblastic leukemia", J. Exp Med. 205:751-8, (2008).
Fonseca, J.E. et al., "Interleukin-6 as a key player in systemic inflammation and joint destruction", Autoimmunity Reviews, 8:538-42, (2009).
Fridman, et al., "Preclinical evaluation of local JAK1 and JAK2 inhibition in cutaneous inflammation", Journal of Investigative Dermatology, (Sep. 2011) vol. 131, No. 9, pp. 1838-1844.
Fridman, J. et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).
Fridman, Jordan et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).
Fridman, Jordan et al. "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285 (1 page).
Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (1 page).
Fridman, Jordan, et al. "Discovery and Preclinical Development of Selective JAK Inhibitors for the Treatment of Myeloproliferative

(56) References Cited

OTHER PUBLICATIONS

Disorders" poster presented at the 4th International Congress on Myeloproliferative Diseases and Myelodysplastic Syndromes, New York, NY. Nov 8-10, 2007. Poster 0009 (1 page).
Fujihara et al., "Evaluation of human conjunctival epithelium by a combination of brush cytology and flow cytometry: an approach to the quantitative technique", Diagn Cytopathol, 1997;17:456-60.
Fujii, C. et al., "Aberrant expression of serine.thereonine kinase Pim-3 in hepatocellular carcinoma development and its role in the proliferation of human hepatoma cell lines" International Journal of Cancer 114: 209-218, (2005).
Fukagawa et al., "Histological evaluation of brush cytology of rabbit conjunctiva", Nippon Ganka Gakkai Zasshi, 1993;97:1173-8 (contains English abstract within the article).
Gaertner, "Cyclization of 1-Alkylamino-3-halo-2-alkanolst o 1-Alkyl-3-azetidinols," J. Org. Chem., 1967, 32, 2972-76.
Ghelardi, et al., "A Mucoadhesive Polymer Extracted from Tamarind Seed Improves the Intraocular Penetration and Efficacy of Rufloxacin in Topical Treatment of Experimental Bacterial Keratitis", Antimicrob. Agents Chemother. 48:3396-3401 (2004).
Glasson et al., "Differences in clinical parameters and tear film of tolerant and intolerant contact lens wearers", Invest Ophthalmol Vis Sci, 2003;44:5116-5124.
Glattfeld, "Improvements in the Preparation of DL-Threonic and DL-Erythronic Acids", J. Am. Chem. Soc. 62:974-977 (1940).
Gobbels et al., Tear secretion in dry eyes as assessed by objective fluorophotometry. Ger J Ophthalmol, 1992; 1:350-353.
Golding et al., "X-ray and scanning electron microscopic analysis of the structural composition of tear ferns", Cornea Jan. 1994;13(1):58-66.
Gomtsyan, et al, "Design, synthesis, and structure-activity relationship of 6-alkynylpyrimidines as potent adenosine kinase inhibitors", J. Med. Chem. 45(17):3639-3648 (2002).
Gooseman, et al., "The intramolecular b-fluorine . . . ammonium interaction in 4- and 8-membered rings", Chem. Commun, vol. 30, pp. 3190-3192 (2006).
Gorre, M.E. et al., "Clinical Resistance to STI-571 Cancer Therapy Caused by BCR-ABL Gene Mutation or Amplification." Science, 293:876, 2001.
Gotlieb, Alice, Presentation at the 2008 American Academy of Dermatology, 66th Annual Meeting, San Antonio, TX. Feb. 1, 2008, symposium-303 (12 pp.).
Goto et al., Color mapping of tear lipid layer thickness distribution from the image analysis in DR-1 tear lipid layer interference images (ARVO abstract). ARVO 2004.
Goto et al., "Computer-synthesis of an interference color chart of human tear lipid layer by a colorimetric approach",Invest Ophthalmol Vis Sci, 2003;44:4693-7.
Goto et al., "Differentiation of lipid tear deficiency dry eye by kinetic analysis of tear interference images", Arch Ophthalmol, 2003;121:173-80.
Goto et al., "Evaluation of the tear film stability after laser in situ keratomileusis using the tear film stability analysis system", Am J Ophthalmol, Jan. 2004b;137(1):116-20.
Goto et al., "Tear Film Stability Analysis System: Introducing a new application for videokeratography", Cornea, Nov. 2004a; 23(8):S65-S70.
Goto, et al., Kinetic analysis of tear interference images in aqueous tear deficiency dry eye before and after punctal occlusion. Invest Ophthalmol Vis Sci, 2003;44:1897-905.
Gottlieb, A.B., et al, "Psoriasis: Emerging Therapeutic Strategies", Nat Rev Drug Disc., 4:19-34 (2005).
Grabbe, et al., "Immunoregulatory mechanisms involved in elicitation of allergic-contact hypersensitivity", Immunol Today, Jan; 19(1):37-44 (1998) (only 1 page provide and marked "best available copy").
Green, T.W. and Wuts, P.G.M.. Protective Groups in Organic Synthesis, 3rd. Ed., Wiley & Sons, Inc., New York (1999)* too voluminous to provide.
Gregory, et al., "Clinical and laboratory features of myelofibrosis and limitations of current therapies", Clinical Advances in Hematology and Oncology, (Sep. 2011) vol. 9, No. 9, pp. 1-3.
Grivennikov, et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, 2003, 58, 1101-1113.
Guillon, Jean-Pierre, "Tear film photography and contact lens wear", J Br Contact Lens Assoc, 1982;5:84-7.
Gura, Science, vol. 278, No. 5340, pp. 1041-1042 (1997).
Guschin, et al, "A major role for the protein tyrosine kinase JAK1 in the JAKISTAT signal transduction pathway in response to interleukin-6", Embo J 14:1421-1429 (1995).
Hamze' et al., "Synthesis of Various 3-Substituted 1,2,4-Oxadiazole-Containing Chiral β3- and r-Amino Acids from Fmoc-Protected Aspartic Acid," J. Org. Chem., 2003, 68(19), pp. 7316-7321.
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Helal et al., "Stereoselective Synthesis of cis-1,3-Disubstituted Cyclobutyl Kinase Inhibitors," Organic Letters, (2004), 6(11), pp. 1853-1856.
Higuchi, et al., "Pro-drugs as Novel Delivery Systems," vol. 14 of the A.C.S. Symposium Series (1975)* too voluminous to provide.
Holly et al., "Lacrimation kinetics in Humans as determined by a novel technique", in Holly FJ (ed). The preocular tear film. Lubbock TX, Lubbock Dry Eye Institute, 1986, pp. 76-88).
Hong, et al., "Total Synthesis of Onnamide A", J. Am. Chem. Soc., 113:9693-94 (1991).
Huang, "Inhibition of STAT3 activity with AG490 decreases the invasion of human pancreatic cancer cells in vitro", Cancer Sci. 97(12):1417-23 (2006).
Huttel, et al., "Lithium pyrazole compounds", Liebigs Ann. Chem. Bd., 625:55-65 (1959) (abstract provided).
International Preliminary Report on Patentability (with Written Opinion) dated Jun. 18, 2008 for International Appln. No. PCT/US2006/047369 (10 pgs.).
International Preliminary Report on Patentability (with Written Opinion) dated Mar. 6, 2012 for International Appln. No. PCT/US2010/047252 (7 pgs.).
International Preliminary Report on Patentability (with Written Opinion) dated Nov. 22, 2011 for International Appln. No. PCT/US2010/035728 (8 pgs.).
International Preliminary Report on Patentability (with Written Opinion) dated Nov. 22, 2011 for International Appln. No. PCT/US2010/035783 (5 pgs.).
International Preliminary Report on Patentability for International Appln. No. PCT/US2008/066662 dated Dec. 17, 2009 (7 pgs.).
International Preliminary Report on Patentability for PCT/US2008/66658 mailed Dec. 17, 2009 (7 pages).
International Preliminary Report on Patentability for PCT/US2009/036635 mailed Sep. 14, 2010 (6 pages).
International Preliminary Report on Patentability for PCT/US2009/059203 mailed Apr. 5, 2011 (6 pages).
International Preliminary Report on Patentability for PCT/US2010/021003 mailed Jul. 19, 2011(11 pages).
International Preliminary Report on Patentability for PCT/US2010/052011 mailed Apr. 11, 2012 (4 pages).
International Preliminary Report on Patentability for PCT/US2011/025433 mailed Aug. 21, 2012 (7 pages).
International Preliminary Report on Patentability for PCT/US2011/027665 mailed Sep. 11, 2012 (7 pages).
International Preliminary Report on Patentability for PCT/US2011/061351 mailed May 30, 2013 (7 pages).
International Preliminary Report on Patentability for PCT/US2011/061374 mailed May 30, 2013 (5 pages).
International Preliminary Report on Patentability for PCT/US2011/037291 mailed Nov. 27, 2012 (7 pages).
International Search Report and the Written Opinion, PCT/US2012/051439, mailed Nov. 30, 2012 (15 pages).

(56) References Cited

OTHER PUBLICATIONS

International Search Report and the Written Opinion, PCT/US2012/053921, mailed Nov. 7, 2012 (19 pages).
International Search Report and Written Opinion dated Feb. 9, 2010 for International Appln. No. PCT/US2009/059203 (10 pages).
International Search Report and Written Opinion for International Appln. No. PCT/US2005/046207 dated May 15, 2007 (6 pages).
International Search Report and Written Opinion for International Appln. No. PCT/US2008/066662 dated Dec. 23, 2008 (11 pgs.).
International Search Report and Written Opinion for International Appln. No. PCT/US2009/036635 dated Jun. 3, 2009 14 pages.
International Search Report and Written Opinion for PCT/US2006/047369, 16 pages (Apr. 24, 2007).
International Search Report and Written Opinion for PCT/US2008/083319, 29 pages mailed Mar. 13, 2009.
International Search Report and Written Opinion for PCT/US2011/025433, 12 pages (mailed Jul. 20, 2011).
International Search Report and Written Opinion for PCT/US2011/027665 mailed Jun. 27, 2011 (14 pages).
International Search Report and Written Opinion for PCT/US2011/037291, 11 pages (Apr. 19, 2012).
International Search Report and Written Opinion for PCT/US2011/061351 mailed Feb. 17, 2012 (12 pages).
International Search Report and Written Opinion for PCT/US2011/061374 mailed Mar. 27, 2012 (10 pages).
International Search Report and Written Opinion for PCT/US2012/025581, 16 pages (mailed Apr. 26, 2011).
International Search Report and Written Opinion for PCT/US2012/043099, 11 pages (Sep. 13, 2012).
International Search Report and Written Opinion for PCT/US2012/050252 mailed Jan. 2, 2013, 17 pages.
International Search Report for PCT/US2008/66658 mailed Dec. 23, 2008 (4 pages).
International Search Report for PCT/US2010/021003 mailed Aug. 16, 2010 (8 pages).
International Search Report for PCT/US2010/035728 mailed Jul. 8, 2010 (3 pages).
International Search Report for PCT/US2010/035783 mailed Aug. 23, 2010 (4 pages).
International Search Report for PCT/US2010/047252 mailed Nov. 17, 2010 (4 pages).
International Search Report for PCT/US2010/052011 mailed Nov. 30, 2010 (3 pages).
Iranpoor, N.; Firouzabadi, H.; Aghapour, "A Rapid and Facile Conversion of Primary Amides and Aldoximes to Nitriles and Ketoximes to Amides with Triphenylphosphine and N-Chlorosuccinimide", G Syn. Commun 32:2535-41 (2002).
Ishizaki, et al., "Pharmacological Properties of Y-27632, a Specific Inhibitor of Rho-Associated Kinases", Molecular Pharmacology, 2000, 57, 976-983.
Itagaki, et al,"Expedient Synthesis of Potent Cannabinoid Receptor Agonist (−)-CP55,940", Organic Letters, 2005; 7(19); 4181-4183.
James, et al., "A unique clonal JAK2 mutation leading to constitutive signalling causes polycythaemia vera", Nature, 434 (7037):1144-8 (2005).
Janes, M. et al., "Effective and selective targeting of leukemia cells using a TORC1/2 kinase inhibitor.", Nature Medicine (2010) LNKD-PUBMED:20072130, vol. 16, No. 2, pp. 205-213 XP002673719.
Jee, et al., "Overview: animal models of osteopenia and osteoporosis", J Musculoskel. Neuron, Interact., 1(3):193-207 (2001).
Jester, et al., "In vivo biomcroscopy and photography of meibomian glands in a rabbit model of meibomian gland dysfunction", Invest Ophthalmol Vis Sci, 1982;22:660-7.
Johnson, et al., "The effect of instilled fluorescein solution volume on the values and repeatability of TBUT measurements", Cornea, 2005;24:811-7.
Kaercher, T., "Ocular symptoms and signs in patients with ectodermal dysplasia symdromes", Grafes Arch Clin Exp Ophthalmol, 2004;495-500.

Kamb, Nature Reviews Drug Discovery 4, pp. 161-165 (2005).
Kaushansky, K., "Lineage-Specific Hematopoietic Growth Factors", NEJM 354:2034-45 (2006).
Kawamura, et al. (1994). "Molecular cloning of L-JAK, a Janus family protein-tyrosine kinase expressed in natural killer cells and activated leukocytes.", Proc Natl Acad Sci U S A, 91(14): 6374-8.
Kharas, et al., "ABL Oncogenes and Phosphoinositide 3-Kinase: Mechanism of Activation and Downstream Effectors.", Cancer Res., 65(6):2047-2053, Mar. 15, 2005.
Kim, et al., "Zinc-Modified Cyanoborohydride as a Selective Reducing Agent", J. Org. Chem. 50: 1927-1932 (1985).
King-Smith et al., "Three interferometric methods for measuring the thickness of layers of the tear film", Optom Vis Sci, 1999; 76:19-32.
Kiss, Robert, "Recent developments on JAK2 inhibitors: A patent review", Expert Opinion on Therapeutic Patents, (Apr. 2010) vol. 20, No. 4, pp. 471-495.
Kojima et al., "A new noninvasive tear stability analysis system for the assessment of dry eyes", Invest Ophthalmol Vis Sci, May 2004; 45(5):1369-74.
Kola, Nature Reviews Drug Discovery 3, pp. 711-715 (2004).
Komuro et al., "Assessment of meibomian gland function by a newly developed laser meibometer", Adv Exp Med Biol, 2002; 506:517-520.
Korb et al., "The effect of two novel lubricant eye drops on tear film lipid layer thickness in subjects with dry eye symptoms", Optom Vis Sci, 2005; 82: 594-601.
Korb, et al., "Increase in tear film lipid layer thickness following treatment of meibomian gland dysfunction", Adv Exp Med Biol, 1994;350:293-8.
Korolev, et al., "Pd-EDTA as an efficient catalyst for Suzuki-Miyaura reactions in water", Tet. Lett. 46: 5751-5754 (2005).
Kortylewski, et al., "Regulation of the IL-23 and IL-12 balance by Stat3 signaling in the tumor microenvironment", Cancer Cell, 15:114-123 (2009).
Kruh et al., "The complete coding sequence of arg defines the Abelson subfamily of cytoplasmic tyrosine kinases.", Proc. Natl. Acad. Sci., 87:5802-5806, Aug. 1990.
Kubinyi, H. "QSAR: Hansch Analysis and Related Approaches," Methods and Principles in Medicinal Chemistry, Manhold, R. ed. Weinhein, NY, 1993.
Kudelacz, et al. "The JAK-3 inhibitor CP-690550 is a potent anti-inflammatory agent in a murine model of pulmonary eosinophilia", European Journal of Pharmacology 582 (2008) 154-161.
Kumar, C., "Kinase drug discovery approaches in chronic myeloproliferative disorders", Oncogene, (Jun. 18, 2009) vol. 28, No. 24, pp. 2305-2323.
Kuo, et al., "Pd-EDTA as an efficient catalyst for Suzuki-Miyaura reactions in water", Chem Commun 301-3 (2007).
Kuppens et al., "Basal tear turnover and topical timolol in glaucoma patients and healthy controls by Fluorophotometry", Invest Ophthalmol Vis Sci, 1992; 33:3442-3448.
Lai, et al., "Mechanistic Study on the Inactivation of General Acyl-CoA Dehydrogenase by a Metabolite of Hypoglycin A", J. Am. Chem. Soc. 113: 7388-7397 (1991).
Lam, et al, "Tear Cytokine Profiles in Dysfunctional Tear Syndrome", Am J Ophthalmol., 147(2):198-205 (2009).
Larock, R., "Comprehensive Organic Transformations", Wiley-VCH, 2nd Ed. (1999) pp. 1949-1950, 1958-1959, 1976, and 1983-1985.
Leaf, Clifton, Health Administrator vol. XVII, No. 1:172-183 (2005).
Lemp "Report of National Eye Institute/Industry Workshop on clinical trials in dry eyes", CLAO J, 1995;21:221-232.
Lemp et al., "Corneal desiccation despite normal tear volume", Ann Ophthalmol, 1970 (2) pp. 258-261 & 284.
Lemp et al., "The Definition and Classification of Dry Eye Disease: Report of the Definition and Classification Subcommittee of the International Dry Eye WorkShop", The Ocular Surface, 5(2), 75-92 Apr. 2007.
Letter translation of Office Action, Chilean Application No. 3496-2006 as received from the foreign associate (Jul. 5, 2010) (4 pages).
Levine, et al., "Activating mutation in the tyrosine kinase JAK2 in polycythemia vera, essential thrombocythemia, and myeloid metaplasia with myelofibrosis", Cancer Cell, vol. 7, 2005: 387-397.

(56) References Cited

OTHER PUBLICATIONS

Levitzki, "Tyrosine kinases as targets for cancer therapy", Eur. J. Cancer 38(suppl. 5):S11-S18 (2002).
Levy, et al. "INCB018424 A Selective Janus Kinase 1/2 Inhibitor" Presentation at the 50th American Society of Hematology Annual Meeting (ASH), Dec. 8, 2008.
Levy, et al., INCB18424 Discussion presentation at the American Society of Hematology, 49th Annual Meeting and Exposition, Atlanta, GA. Abstract #558, Dec. 10, 2007 (25 pages).
Li, et al., "Pim-3, a proto-oncogene with serine/threonine kinase activity, is aberrantly expressed in human pancreatic cancer and phosphorylates Bad-mediated apoptosis in human pancreatic cell lines" Cancer Research 66(13): 6741-7 (2006).
Lin, "Constitutive Activation of JAK3/STAT3 in Colon Carcinoma Tumors and Cell Lines", Am J Pathol. 167(4):969-80 (2005).
Lin, et al., "Enantioselective synthesis of Janus kinase inhibitor INCB018424 via an organocatalytic aza-Michael reaction," Organic Letters, (2009), 11(9), 1999-2002.
Liu, et al., "Combined Inhibition of Janus Kinase 1/2 for the Treatment of JAK2V617F-Driven Neoplasms: Selective Effects on Mutant Cells and Improvements in Measures of Disease Severity", Clin Cancer Res 2009;15(22) pp. 6891-6900; Nov. 15, 2009; Published Online First on Nov. 3, 2009 as 10.1158/1078-0432.CCR-09-1298.
Macchi, et al., "Mutations of Jak-3 gene in patients with autosomal severe combined immune deficiency (SCID)", Nature 377:65-8 (1995).
Madden et al. Comparative study of two non-invasive tear film stability techniques. Curr Eye Res, 1994; 13(4):263-9.
Madhusudan et al., "Tyrosine kinase inhibitors in cancer therapy", Clin Biochem., 2004, 37(7):618-35.
Maffioli, et al., "Mild and Reversible Dehydration of Primary Amides with PdCl2 in Aqueous Acetonitrile", Organic Letters vol. 7 No. 23, 5237-39 (2005).
Main et al, "High throughput synthesis of diverse 2,5-disubstituted indoles using titanium carbenoids bearing boronate functionality", Tetrahedron, 64(5):901-914 (2007).
Mainstone et al., "Tear meniscus measurement in the diagnosis of dry eye", Curr Eye Res, 1996; 15:653-661.
Mancini, M. et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720 vol. 109, No. 2 (2010) pp. 320-328.
Manjula, et al., "Rapid Method of Converting Primary Amides to Nitriles and Nitriles to Primary Amides by ZnCl2 using Microwaves under Different Reaction Conditions", Syn. Commun 37:1545-50 (2007).
Manning, et al., "The Protein Kinase Complement of the Human Genome", Science. 2002, 298(5600):1912-16 and 1933-34.
March, Jerry, Advanced Organic Chemistry: Reactions, Mechanisms, and Structure, 3rd ed., John Wiley & Sons:New York, pp. 845-855 (1985).
Marquardt et al., "Modification of tear film break-up time test for increased reliability" in Holly ed. The Preocular Tear Film inHealth, Disease and Contact Lens Wear. Lubbock, Texas: Dry Eye Institute, 1986:57-63.
Maruyama et al., "Effect of environmental conditions on tear dynamics in soft contact lens wearers", Invest Ophthalmol Vis Sci, 2004;45(8):2563-8.
Mathers et al., "Assessment of the tear film with tandem scanning confocal microscopy", Cornea, 1997;16:162-8.
Mathers et al., "Tear film changes associated with normal aging", Cornea, 1996; 15:229-334.
Mathers et al., "Tear flow and evaporation in patients with and without dry eye", Ophthalmology, 1996; 103:664-669.
Mathers et al., "Video imaging of the meibomian gland", Arch Ophthalmol, 1994;112:448-9.
Mathers, "Evaporation from the ocular surface", Exp Eye Res, 2004; 78:389-394.

Mayo Clinic. Available at: < http://www.mayoclinic.com/health/pancreatic-cancer/DS00357 >. 2 pages, retrieved from the Internet Apr. 3, 2013.
Mayo Clinic. Available at: < http://www.mayoclinic.com/health/prostate-cancer-prevention/MC00027 >. 3 pages, retrieved from the Internet Apr. 3, 2013.
Mayo Clinic. Available at: <http://www.mayoclinic.com/health/crohns-disease/DS00104/DSECTION=treatments-and-drugs>  6 pages, retrieved from the Internet May 27, 2013.
Mayo Clinic. Available at: <http://www.mayoclinic.com/health/multiple-sclerosis/DS00188/DSECTION=treatments-and-drugs>. 3 pages, retrieved from the Internet May 27, 2013.
Mayo Clinic. Available at: <http://www.mayoclinic.com/health/myasthenia-gravis/DS00375> 2 pages, retrieved from the Internet May 27, 2013.
Mayo Clinic. Available at: <http://www.mayoclinic.com/health/rheumatoid-arthritis/DS00020/DSECTION=treatments-and-drugs> 3 pages, retrieved from the Internet Jun. 26, 2013.
McNamara et al., "Fluorometry in contact lens research: The next step", Optom Vis Sci, 1998; 75:316-322.
Mengher et al., "Non-invasive tear film break-up time: sensitivity and specificity", Acta Ophthalmol (Copenh), 1986; 64(4):441-4.
Mesa, et al. "INCB018424, a Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).
Mesa, et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, (Nov. 1, 2011) vol. 117, No. 21, pp. 4869-4877.
Mesa, R. et al., "Emerging drugs for the therapy of primary and post essential thrombocythemia, post polycythemia vera myelofibrosis", Expert Opinion on Emerging Drugs England, vol. 14, No. 3 (2009) pp. 471-479.
Methods in Molecular Biology: vol. 225, Inflammation Protocols., Winyard, P.G. and Willoughby, D.A., Humana Press, 2003* too voluminous to provide.
Meydan et al., "Inhibition of acute lymphoblastic leukaemia by a Jak-2 inhibitor", Nature. Feb. 15, 1996;379(6566):645-8.
Miethchen, "Micelle-activated reactions. I. Micelle-activated iodination and partial dehalogenation of pyrazoles and 1,2,4-triazoles", Journal F. prakt. Chemie, Band 331, Heft 5, S. 799-805 (1989) (1 page abstract also provided).
Milici, A.J., et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).
Minegishi, et al., "Human Tyrosine Kinase 2 Deficiency Reveals Its Requisite Roles in Multiple Cytokine Signals Involved in Innate and Acquired Immunity", Immunity 25:745-55 (2006).
Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol. Sep. 2010;85(3):192-9. Epub Jun. 2, 2010.
Mishima, et al., "Determination of tear volume and tear flow", Invest Ophthalmol, 1966; 5:264-276.
Mishima, S., "Some physiological aspects of the precorneal tear film", Arch Ophthalmol, 1965;73:233-241.
Mitsunobu, O., "The Use of Diethyl Axodicarboxylate and Triphenylphosphine in Synthesis and Transformation of Natural Products." Synthesis (1): 1-28 (1981).
Miyata, et al., "Stereospecific nucleophilic addition reactions to olefins.", J. Org. Chem. 56:6556-6564 (1991).
Miyaura et al., "Palladium-Catalyzed Cross-Coupling Reactions of Organoboron Compounds," Chem. Rev., 1995, 95, 2457-2483.
Miyoshi et al., "Interleukin-8 concentrations in conjunctival epithelium brush cytology samples correlate with neutrophil, eosinophil infiltration, and corneal damage", Cornea, 2001;20:743-7.
Moreland, et al. "A Randomized Placebo-Controlled Study of INCB018424, a Selective Janus Kinase 1&2 (JAK 1&2) Inhibitor in

(56) References Cited

OTHER PUBLICATIONS

Rheumatoid Arthritis (RA)" Presentation at the American College of Rheumatology meeting, Oct. 26, 2008. (20 pages).

Moriarty, et al., "The synthesis and SAR of 2-amino-pyrrolo[2,3-d]pyrimidines: A new class of Aurora-A kinase inhibitors", Bioorganic and Medicinal Chemistry Letters, 16(22), 5778-5783 (2006).

Mosby's Dictionary of Medicine, Nursing, & Health Professions, sicca complex, 2009, Elsevier, printed from http://www.credoreference.com/entry/ehsmosbymed/sicca_complex, 2 pages.

Mullighan, et al, "JAK mutations in high-risk childhood acute lymphoblastic leukemia", Proc Natl Acad Sci USA. 106:9414-8 (2009).

Naka T., "The paradigm of IL-6: from basic science to medicine", Arthritis Res. 2002;4 Suppl 3:S233-42. Epub May 9, 2002.

Nakagawara, Akira, "Trk receptor tyrosine kinases: A bridge between cancer and neural development." Cancer Letters, 169:107-114, 2001.

Nally et al., "Ocular discomfort and tear film break-up time in dry eye patients: A correlation", Invest Ophthalmol Vis Sci, 2000;41:4:1436 (Poster Presentation).

Naqvi, et al., "A potential role of ruxolitinib in leukemia", Expert Opinion on Investigational Drugs, (Aug. 2011) vol. 20, No. 8, pp. 1159-1166.

National Cancer Institute, "FDA Approval for Ruxolitinib Phosphate", http://www.cancer.gov/cancertopics/druginfo/fda-ruxolitinibphosphate posted Nov. 18, 2011 (3 pages).

Naus, et al., "6-(Het)aryl-7-Deazapurine Ribonucleosides as Novel Potent Cytostatic Agents", J. Med. Chem., 53(1):460-470 (2010).

Neidle, Stephen, Cancer Drug Design and Discovery, (Elsevier/Academic Press, 2008) pp. 427-431.

Nelson et al., "Tear film osmolality determination: an evaluation of potential errors in measurement" Curr Eye Res, Sep;5(9):677-81, 1986.

Neubauer, H., et al., "Jak2 Deficiency Defines an Essential Developmental Checkpoint in Definitive Hematopoiesis", Cell, 93(3): 397-409 (1998).

Nicholoff et al., "Recent Insights into the immunopathogenesis of psoriasis provide new therapeutic opportunities", J. Clin. Invest., 113; 1664-1675 (2004).

Nichols et al., "The lack of association between signs and symptoms in patients with dry eye disease", Cornea, vol. 23(8):762-770 (2004).

Nichols et al., "The repeatability of clinical measurements of dry eye", Cornea, vol. 23(3):272-85 (2004).

Nishio, et al., "Tyrosine kinase-dependent modulation by interferon-α of the ATP-sensitive K+ current in rabbit ventricular myocytes", FEBS Letters, (1999), 445, 87-91.

Nitta, et al., "Peptide-Titanium Complex as Catalyst for Asymmetric Addition of Hydrogen Cyanide to Aldehyde", J. Am. Chem. Soc., 1992, 114, 7969-75 (1992).

Norman, "Selective JAK1 inhibitor and selective Tyk2 inhibitor patents," *Expert Opinion*, Informa Healthcare. 2012, available at: <http://informahealthcare.com/dol/pdfplus/10.1517/13543776.2012.723693>.

Norn, M., "Quantitative tear ferning. Clinical investigations", Acta Ophthalmol (Copenh), Jun. 1994;72(3):369-72.

Notice of Allowance and Fee(s) Due dated Sep. 21, 2007 in connection with U.S. Appl. No. 11/313,394 (6 pages).

Notice of Hearing and Preliminary Report for EP Patent 1966202, dated Mar. 18, 2013 (7 pages).

Office Action (Non-final) dated Aug. 22, 2007 in connection with U.S. Appl. No. 11/115,702 (9 pages).

Office Action (Non-final) dated Dec. 3, 2007 in connection with U.S. Appl. No. 11/524,641 (13 pages).

Office Action (Non-final) dated Feb. 25, 2009 for U.S. Appl. No. 12/137,892 (13 pgs.).

Office Action (Final) dated Feb. 7, 2008 for U.S. Appl. No. 11/115,702 (5 pages).

Office Action (Final) dated Nov. 30, 2009 for U.S. Appl. No. 12/137,892 (9 pgs.).

Office Action (Non-final) dated Apr. 20, 2007 in connection with U.S. Appl. No. 11/313,394 (16 pages).

Office Action received for European Application No. 06 839 328.9 (Jan. 22, 2009) (5 pages).

Office Action received for Japanese Application No. 2008-545733 dated Oct. 11, 2011 (5 pages).

Office Action received for New Zealand Application No. 569015 dated Feb. 24, 2010 (2 pages).

Office Action received for Singapore Application No. 2008-04386-1 (Aug. 24, 2010).

Office Action received for Vietnamese Patent Application No. 1-2011-03188 dated Mar. 8, 2012 as translated by foreign associate (10 pages).

Office Action, Canadian Patent Office, Application No. 2,632,466, dated May 8, 2012 (3 pages).

Office Action, China, Patent Application No. 201080033308.6 dated Aug. 2, 2013, 10 pages.

Office Action, Eurasian Patent Office, prepared Feb. 5, 2010.

Office Action, European Patent Office, Application No. 06 839 328.9 mailed Oct. 21, 2010.

Office Action, European Patent Office, mailed Nov. 6, 2009.

Office Action, Mexico, Patent Appl. No. MX/a/2008/007635 as received from foreign associate dated Jun. 15, 2010 (1 page).

Office Action, Mexico, Patent Appl. No. MX/a/2008/007635 as received from foreign associate dated Nov. 13, 2009 (4 pages).

Office Action/Examination Report received for Pakistan Application No. 211/2009 dated Jan. 18, 2010 (1 page).

Oguz, et al., "The height and radius of the tear meniscus and methods for examining these parameters", Cornea, 2000;19:497-500.

Opposition for EP Patent 1966202, filed on Jun. 21, 2012 (30 pages).

Opposition for India Patent Application No. 2365/KOLNP/2008 dated Nov. 12, 2012 (received by Applicants from Indian associate on Apr. 17, 2013) 37 pages.

Opposition, Costa Rica, translation from Foreign Associate Dated Jun. 13, 2012, 6 pages.

Opposition, Ecuador Patent Office, mailed Nov. 18, 2008 1 page letter from Foreign Associate enclosing the translation (5 pages) of the Opposition.

Ortmann, et al., "Janus kinases and signal transducers and activators of transcription: their roles in cytokine signaling, development and immunoregulation." Arthritis Res, 2(1): 16-32 (2000).

Ostojic et al., "Ruxolitinib for the treatment of myelofibrosis", Drugs of Today, (Nov. 2011) vol. 47, No. 11, pp. 817-827.

Ousler, et al., "Factors that influence the inter-blink interval (IBI) as measured by the ocular protection index (OPI)", Invest Ophthalmol Vis Sci 2001; 43: E-abstract 56 (Poster presentation) ARVO (2002) 2 pages, downloaded from http://abstracts.iov.s.org/cgi/content/abstract/43/12/56?maxtoshow on Aug. 14, 2009.

Palmer, et al., "Multiple roles of ephrins in morphogenesis, neuronal networking, and brain function." Genes & Dev., 17:1429-1450, 2003.

Pardanani A., "JAK2 inhibitor therapy in myeloproliferative disorders: rationale, preclinical studies and ongoing clinical trials JAK2 inhibitor therapy in MPD", Leukemia 22, 23-30 (Jan. 2008).

Parganas, E., D. Wang, et al., "Jak2 is Essential for Signaling through a Variety of Cytokine Receptors", (1998). Cell, 93(3): 385-95.

Park et al., "Homogeneous Proximity Tyrosine Kinase Assays: Scintillation Proximity Assay versus Homogeneous Time-Resolved Fluorescense", Analytical Biochemistry, 1999, 269, 94-104.

Patani, et al., "Bioisosterism: A Rational Approach in Drug Design", Chem. Rev., 1996, 96, 3147-3176.

Patrick, Graham L., "An Introduction to medicinal chemistry" *Oxford University Press Inc.*, New York, 1995 (31 pages) (cited in Opposition from India dated Nov. 12, 2012).

Pearce et al., "Spatial location studies on the chemical composition of human tear ferns", Ophthalmic Physiol Opt, (2000) vol. 20(4):306-13.

Pearce, et al., "An improved fluorophotometric method for tear turnover assessment", Optom Vis Sci, (2001) 78(1):30-36).

Pensyl et al., "The repeatability of tear mucus ferning grading", Optom Vis Sci, Aug. 1998;75(8):600-4.

Pernis, et al., "JAK-STAT signaling in asthma." J Clin Invest, 109(10): 1279-83 (2002).

(56) References Cited

OTHER PUBLICATIONS

Peters, K. G. et al., "Functional Significance of Tie2 Signaling in the Adult Vasculature", 2004, © The Endocrine Society.
Pflugfelder, et al., "Evaluation of subjective assessments and objective diagnostic tests for diagnosing tear-film disorders known to cause ocular irritation", Cornea, 1998;17(1):38-56.
Pillonel, Christian, "Evaluation of phenylaminopyrimidines as antifungal protein kinase inhibitors", Pest Management Science, Wiley & Sons, vol. 61, Jun. 13, 2005 pp. 1069-1076.
Pirard, B. et al., "Classification of Kinase Inhibitors Using BCUT Descriptors", J. Chem. Inf. Comput. Sci., 2000, 40, 1431-1440.
Pisella et al., Flow cytometric analysis of conjunctival epithelium in ocular rosacea and keratoconjunctivitis sicca. Ophthalmology, 2000;107:1841-1849.
Pisella, et al., Conjunctival proinflammatory and proapoptotic effects of latanoprost, preserved timolol and unpreserved timolol: an ex vivo and in vitro study. Invest Ophthalmol Vis Sci, 2004;45:1360-1368).
Portnaya, et. al., "Azomethine dyes. IV. Indoaniline dyes derived from heterocyclic N-substituted 1-hydroxy-2-naphthamid", Ts Vses Nauchn Issled Kinofotoinst, Issue 40, (1960) pp. 106-108 (with English abstract 20 pages total).
Press Release dated Sep. 18, 2008: "Incyte's Topical JAK Inhibitor Demonstrates Positive Proof-of-Concept Results in Patients with Mild to Moderate Psoriasis" (4 pages).
Prezent, et al., "Boron chelates as intermediates in the synthesis of new functionalized pyridines and pyrimidines from a, a-dioxoketene aminals", Proceedings of the International Conference on the Chemistry of Boron, vol. 11 (2003) (abstract only—1 page).
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Quesada et al, "One-pot conversion of activated alcohols into 1,1-dibromoalkenes and terminal alkynes using tandem oxidation processes with manganese dioxide", Tetrahedron, 62 (2006) 6673-6680.
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957.
Ravin, L., "Preformulation", Remington's Pharmaceutical Sciences, 17th ed., Mack Publishing Company, Easton, Pa., 1985, Chapter 76, pp. 1409-1423.
Ren et al., "Compounds and Compositions as Protein Kinase Inhibitors," U.S. Appl. No. 60/578,491, filed Jun. 10, 2004 (56 pages).
Response and Amendment dated Aug. 25, 2009 to non-final Office Action for U.S. Appl. No. 12/137,892 (34 pgs.).
Response and Amendment in Reply to Action of Apr. 20, 2007 filed Jul. 17, 2007 for U.S. Appl. No. 11/313,394 (39 pages).
Response to Action of Aug. 22, 2007 dated Nov. 19, 2007, U.S. Appl. No. 11/115,702 (7 pages).
Response to Restriction Requirement dated May 29, 2007, U.S. Appl. No. 11/115,702 (8 pages).
Restriction Requirement dated Mar. 6, 2007 in connection with U.S. Appl. No. 11/115,702 (8 pages).
Roberts, Jr., et al., JAMA 292(17):2130-2140 (2004).
Robin et al., In vivo transillumination biomicroscopy and photography of meibomian gland dysfunction. Ophthalmology, 1985;92:1423-6.
Rodig, et al., "Disruption of the Jak1 gene demonstrates obligatory and nonredundant roles of the Jaks in cytokine-induced biologic responses." Cell, 93(3): 373-83 (1998).
Rolando et al., "Tear mucus crystallization in children with cystic fibrosis", Ophthalmologica, 1988;197(4):202-6).
Rolando et al., "Tear mucus ferning test in keratoconjunctivitis sicca", Holly FJ, Lamberts DW, MacKeen DL (eds.): The preocular tear film in health, disease, and contact lens wear,. 1st Intern Tear Film Symposium. Lubbok (Texas, USA), Dry Eye Institute, 1986, 203-210.

Rolando et al., "The effect of hyperosmolarity on tear mucus ferning", Fortschr Ophthalmol, 1986;83:644-646.
Rolando et al., The Ocular Surface and Tear Film and Their Dysfuntion in Dry Eye Disease, Survey of Ophthalmology, Mar. 2001, vol. 45, Supplement 2, S203-S210.
Rolando, M. "Tear mucus ferning test in normal and keratoconjunctivitis sicca eyes." Chibret Int J Ophthalmol, 1984;2(4):32-41.
Roudebush et al., "Pharmacologic manipulation of a four day marine delayed type hyper sensitivity model", Agents Actions, 1993, 38(1-2):116-21.
Rousvoal, G. et al. "Janus kinase 3 inhibition with CP-690,550 prevents allograft vasculopathy", Transpl Int., 2006 19(12):1014-21.
Saemann, et al., "Prevention of CD40-triggered dendritic cell maturation and induction of T-cell hyporeactivity by targeting of Janus kinase 3." Am J Transplant, 3(11): 1341-9 (2003).
Saettone et al. "Ocular inserts for topical delivery," Advanced Drug Delivery Reviews, 16: 95-106, 1995.
Samanta et al., "Janus kinase 2: a critical target in chronic myelogenous leukemia", Cancer Res. Jul. 1, 2006;66(13):6468-72.
Sawada et al, "Increased Lipophilicity and Subsequent Cell Partitioning Decrease Passive Transcellular Diffusion of Novel, Highly Lipophilic Antioxidents", The Journal of Pharmacology and Experimental Therapeutics, 1999, No. 288, vol. 3, pp. 1317-1326, p. 1321, compound 26.
Schindler et al., "Hormones and Signaling: Cytokines and STAT Signaling", Adv Pharmacol. 2000; 47:113-74.
Schrader et al., "Animal Models of Dry Eye," Developmental Opthalmology, Karger 2008, 41, 298-312.
Scott, et al., "Jaks, STATs, Cytokines, and Sepsis." Clin Diagn Lab Immunol, 9(6): 1153-9 (2002).
Seefeld, et al, "Discovery of 5-pyrrolopyridinyl-2-thiophenecarboxamides as potent AKT kinase", Bioorganic & Medicinal Chemistry Letters, 19(8):2244-2248 (2009).
Seela, et al., "Synthesis of Pyrrolo[2,3-d]pyrimidine 2', 3'-Dideoxyribenucleosides Related to 2',3'-Dideoxyadenosine and 2',3'-Dideoxgtuanosine and Inhibitory Activity of 5'-Triphosphates on HIV-1 Reverse Transcriptase", Helvetica Chimica, Acta, 1991, 74(3), 554-64.
Seki, "STAT3 and MAPK in human lung cancer tissues and suppression of oncogenic growth by JAB and dominant negative STAT3", Int J Oncol. 24(4):931-4 (2004).
Seto, et al. (2003). "Enhanced Th2 cell-mediated allergic inflammation in Tyk2-deficient mice." J Immunol, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.
Shi, et al., "The pharmacokinetics, pharmacodynamics, and safety of orally dosed INCB018424 phosphate in healthy volunteers", Journal of Clinical Pharmacology, (Dec. 2011) vol. 51, No. 12, pp. 1644-1654.
Shimazaki et al., "Meibomian gland dysfunction in patients with Sjogren syndrome", Ophthalmology, 1998;105(8):1485-8.
Smith et al, "Basic pathogenic mechanisms operating in experimental model acute anterior uveitis," Immunology and Cell Biology, 1998, 76, 497-512.
Smolen, et al, "Effect of interleukin-6 receptor inhibition with tocilizumab in patients with rheumatoid arthritis (Option study): a double-blind, placebo-controlled, randomized trial", Lancet 371:987, 2008.
Sriram, K. et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodengeneration", J. Biol. Chem., 2004, 279(19):19936-47. Epub Mar. 2, 2004.
Staerk, J., et. al., "JAK1 and Tyk2 activation by the homologous polycythemia vera JAK2 V617F mutation: cross-talk with IGF1 receptor", J Biol Chem., 280:41893-41899 (2005).
State Intellectual Property Office, PR China, Office Action, dated Sep. 3, 2010 Pat. Appl. No. 200680052750.7 (8 pages).

(56) References Cited

OTHER PUBLICATIONS

Stirewalt et al., "Predictors of relapse and overall survival in Philadelphia chromosome-positive acute lymphoblastic leukemia after transplantation", Biol Blood Marrow Transplant. Mar. 2003;9(3):206-12.
STN Search conducted Aug. 30, 2010 (17 pages).
STN Search conducted Jun. 24, 2011 (24 pages).
STN Search conducted Nov. 5, 2010 (5 pages).
STN Search conducted Nov. 9, 2010 (43 pages).
STN Search, Nov. 12, 2009 (180 pages).
STN Search, Oct. 20, 2009 (601 pages).
STN Search, Sep. 20, 2009 (864 pages).
Sullivan et al., "4th International Conference on the Lacrimal Gland, Tear Film & Ocular Surface and Dry Eye Syndromes, Nov. 20, 2004" (2 pages).
Takahashi, et al., "Solvent-Free Reaction Using Pmospwonium Salts: Chlorination of Hydroxyheteroaromatics and dehydration of Primary Amides", Heterocycles 68: 1973-1979 (2006).
Takano et al., "Inflammatory cells in brush cytology samples correlate with the severity of corneal lesions in atopic keratoconjunctivitis", Br J Ophthalmol, 2004;88:1504-5.
Takemoto, et al. (1997). "Proliferation of adult T cell leukemia/lymphoma cells is associated with the constitutive activation of JAK/STAT protein." Proc Natl Acad Sci U S A, 94(25): 13897-902.
Tan, et al, "Racemization processes at a quaternary carbon center in the context of the asymmetric Michael reaction", Tetrahedron Lett., 42(30):5021-5023 (2001).
Tang et al., "Knowledge-based design of 7-azaindoles as selective B-Raf inhibitors", Bioorganic & Medicinal Chemistry Letters (2008), 18(16):4610-4614.
Tasian et al., "Understanding the biology of CRLF2-overexpressing acute lymphoblastic leukemia", Critical Reviews in Oncogenesis, (2011) vol. 16, No. 1-2, pp. 13-24.
Tefferi, A. et al. "The Clinical Phenotype of Myelofibrosis Encompasses a Chronic Inflammatory State that is Favorably Altered by INCB018424, a Selective Inhibitor of JAK1/2" Poster #2804 at the American Society of Hematology Annual Meeting (ASH), Dec. 7, 2008, (18 pages).
Tefferi, Ayalew, "Primary myelofibrosis: 2012 update on diagnosis, risk stratification, and management", American Journal of Hematology, (Dec. 2011) vol. 86, No. 12, pp. 1017-1026.
Tefferi, et al., "Serious adverse events during ruxolitinib treatment discontinuation in patients with myelofibrosis", Mayo Clinic Proceedings, (Dec. 2011) vol. 86, No. 12, pp. 1188-1191.
Thompson, J., et al., "Photochemical Preparation of a Pyridone Containing Tetracycle: A Jak Protein Kinase Inhibitor", Bioorganic & Medicinal Chemistry Letters, 12 (2002) 1219-1223.
Tiffany et al., Meniscometry using the Tearscope-plus (ARVO abstract). Invest Ophthalmol Vis Sci, (2001);42, s37 (1 page).
Tiffany, J., "Refractive index of meibomian and other lipids", Curr Eye Res, (1986);5:887-9.
Ting, et al., "The Synthesis of substituted bipiperidine amide compounds as CCR3 antagonists", Bioorg. Med. Chem. Lett., vol. 15, No. 5, 1 (2005) pp. 1375-1378.
Toyonaga, "Blockade of constitutively activated Janus kinase/signal transducer and activator of transcription-3 pathway inhibits growth of human pancreatic cancer", Cancer Lett. 201(1):107-16 (2003).
Tsubota et al., "Brush cytology for the evaluation of dry-eye", Nippon Ganka Gakkai Zasshi, 1990a;94:224-30; in Japanese with English abstract.
Tsubota et al., "Conjunctival brush cytology", Acta Cytol, (1990) vol. 34(2):233-5.
Tsubota et al., "Detection by brush cytology of mast cells and eosinophils in allergic and vernal conjunctivitis"; Cornea, (1991) vol. 10(6):525-31.
Ueda et al., "1,2-Benzisoxazol-3-yl Diphenyl Phosphate: A New, Reactive Activating Agent for the Synthesis of Amides, Esters, and Peptides via Condensation", J. Org. Chem. 50:760-763 (1985).
van Best et al., "Measurement of basal tear turnover using a standardized protocol", Graefe's Arch Clin Exp Ophthalmol, 1995; 233:1-7.
van Bijsterveld, O., "Diagnostic tests in the sicca syndrome", Arch Ophthalmol, 1969;82:10-14.
Vannucchi A. et al., "The mTOR Inhibitor, RAD001, Inhibits the Growth of Cells From Patients with Myeloproliferative Neoplasms", Blood: ASH Annual Meeting Absracts, $51^{st}$ Annual Meeting of the American Society of Hematology, vol. 114, No. 22 (2009) 2 pages.
Vannucchi, A. et al., "Inhibitors of PI3K/Akt and/or mTOR Inhibit the Growth of Cells of Myeloproliferative Neoplasms and Synergize with JAK2 Inhibitor and Interferon", Blood, vol. 118, No. 21, pp. 1638-1639, XP008150742ASH Annual Meeting Abstract 3835 American Society of Hematology (2011).
Vannucchi, A. et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, vol. 114, No. 22 (2009) 2 pages.
Vasilevsky, et al., "Ethyl Vinyl Ether—an Agent for Protection of the Pyrazole NH-Fragment. A Convenient Method for the Preparation of N-Unsubstituted 6Alkynylpyrazoles", Heterocycles, 60(4):879-886 (2003).
Verma, et al., "Jak family of kinases in cancer", Cancer and Metastasis Reviews, vol. 22, No. 4, 423-434, DOI: 10.1023/A:1023805715476 (2003).
Verstovsek, "Therapeutic Potential of JAK2 Inhibitors", Hematology Am Soc Hematol Educ Program, 2009:636-42.
Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).
Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).
Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).
Verstovsek, Srdan et al., "Characterization of JAKS V617F Allele Burden in Advanced Myelofibrosis (MF) Patients: No Change in V617F:WT JAK2 Ratio in Patients with High Allele Burdens despite Profound Clinical Improvement Following Treatment with the JAKL Inhibitor, INCB018424," 50th ASH Annual Meeting and Exposition, Abstract No. 2802 (2008).
Vitali et al. "The European Community Study Group on diagnostic criteria for Sjogren's syndrome. Sensitivity and specificity of tests for ocular and oral involvement in Sjogren's syndrome." 1994; Ann Rheum Dis, 53(10): 637-47.
Wagh, et al., "Polymers used in ocular dosage form and drug delivery systems", Asian J. Pharm., pp. 12-17 (Jan. 2008).
WebMD. "Diabetes Health Center." Available at: < http://diabetes.webmd.com/guide/diabetestreatment_care >. 3 pages, retrieved from the Internet May 28, 2013.
Webster's New World Medical Dictionary, Sjogren's syndrome, 2003, Wiley Publishing, printed fro http://www.credoreference.com/entry/webstermed/sjogren_s_syndrome, 2 pages.
Weiss, et al., "Evaluation of a Series of Naphthamides as Potent, Orally Active Vascular Endothelial Growth Factor Receptor-2 Tyrosine Kinase Inhibitors", J. Med Chem., 51:1668-1680 (2008).
Welch et al., "An approach to a more standardized method of evaluating tear film break-up time", Invest Ophthalmol Vis Sci, 2003; 2485/B324 (abstract only—2 pages).
White et al., "Human basic tear fluid osmolality. I. Importance of sample collection strategy", Acta Ophthalmol (Copenh), Aug;71(4):524-9, 1993.
Williams et al., "Carbohydrate Chemistry: Recent Advances", Chem. Rev. 81:589-636 (1981).

(56) References Cited

OTHER PUBLICATIONS

Williams, et al. "Initial Efficacy of INCB018424, a selective Janus Kinase1& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.
Wolf, et al., "Burger's Medicinal Chemistry and Drug Discovery", 5th Ed. Part I, pp. 975-977 (1995).
Wu et al., One-Pot Two-Step Microwave-Assisted Reaction in Construction 4,5-Disubstituted Pyrazolopyrimidines Organic Letters, 2003, 5(20), 3587-3590.
Xiaoyang et al., "Knockdown of STAT3 Expression by RNA Interference Inhibits the Induction of Breast Tumors in Immunocompetent Mice", Cancer Res Apr. 1, 2005 65; 2532.
Yamaoka et al., "Janus kinase (JAK) inhibitors in rheumatoid arthritis", Current Rheumatology Reviews, (Nov. 2011) vol. 7, No. 4, pp. 306-312.
Yang et al., "Constitutive NF-kB activation confers interleukin 6 (IL6) independence and resistance to dexamethasone and Janus kinase inhibitor INCB018424 in murine plasmacytoma cells", Journal of Biological Chemistry, (Aug. 12, 2011) vol. 286, No. 32, pp. 27988-27997.
Yao, et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 58(11):3485-3497 (2008).
Yao, et al., "Glucocorticoid Excess in Mice Results in Early Activation of Osteoclastogenesis and Adipogenesis and Prolonged Suppression of Osteogenesis", Arthritis and Rheumatism, 58(6), 1674-1686 (2008).
Ye et al., "The synthesis and the antitumor activity of 5,7-disubstituted pyrazolo [1,5-a] pyrimidines," Chinese J Med Chem., Feb. 28, 2007, 17(1):18-22.
Yokoi et al., "A newly developed video-meibography system featuring a newly designed probe", Jpn J Ophthalmol, 2007; 51: 53-6).
Yokoi et al., "Assessment of meibomian gland function in dry eye using meibometry", Arch Ophthalmol, 1999;117:723-9).
Yokoi et al., "Correlation of tear lipid layer interference patterns with the diagnosis and severity of dry eye", Am J Ophthalmol, 1996;122:818-24.
Yokoi et al., "Non-invasive methods of assessing the tear film", Exp Eye Res, 2004;78:399-407).
Yongjun et al., "Advances in research of tyrosine kinases inhibitor of vascular endothelial growth factor receptor," Chinese J New Drugs, Dec. 31, 2008, 17(7):544-550.
Yu, et al., "Constitutive activation of the Janus kinase-STAT pathway in T lymphoma overexpressing the Lck protein tyrosine kinase", J Immunol. 159(11):5206-10 (1997).
Zheng, et al., "Discovery of INCB108201PF-4178903, a potent, selective, and orally bioavailable dual CCR2 and CCR5 antagonist", Bioorganic & Medicinal Chemistry Letters 21 (2011) 1442-45.
Zoppellaro, et al., "A Multifunctional High-Spin Biradical Pyrazolylbipyridine-bisnitronylnitroxide", Org. Lett. 6(26):4929-4932 (2004).
Zou, et al., "Signaling Pathways Activated by Oncogenic Forms of Abl Tyrosine Kinase." Journal of Biological Chemistry, 274(26):18141-18144, 1999.
Bhattacharya et al., "Brittain, ed. Polymorphism in Pharmaceutical Solids," 2009, p. 327-345.
Chemical encyclopedia, vol. 1, pp. 242-243, publication "Soviet Encyclopedia," Moscow, 1988.
Clark et al., "Discovery and Development of Janus Kinase (JAK) inhibitors for Inflammatory Diseases," J Med Chem., 2014, pp. A-P.
Hickenbottom "Reactions of organic compounds," State Scientific-Technical Publishing Association, Chemical Literature Section, Moscow, 1939, pp. 360-362.
International Preliminary Report on Patentability for PCT/US2012/043099 mailed Dec. 23, 2013, 6 pages.
International Preliminary Report on Patentability for PCT/US2012/050210 mailed Feb. 11, 2014, 8 pages.
International Preliminary Report on Patentability for PCT/US2012/051439 mailed Feb. 27, 2014, 7 pages.
International Preliminary Report on Patentability for PCT/US2012/053921 mailed Mar. 20, 2014, 8 pages.
International Search Report and Written Opinion in International Application No. PCT/US2014/020554, dated Jul. 16, 2014, 17 pages.
Lucet et al., "The structural basis of Janus kinas 2 inhibition by a potent and specific pan-Janus kinase inhibitor," Blood, 2006, 107(1):176-183.
Mandal, "Cancer Classification," 2014. Available from: <http://www.news-medical.net/health/Cancer-Classification.aspx, 6 pages.
Mayo Clinic. Available at: <http://www.mayoclinic.org/diseases-conditions/type-1-diabetes/basics/prevention> 2014, 19 pages.
MD Anderson Cancer Center. "Leukemia Prevention and Screening," 2014, 2 pages.
MD Anderson Cancer Center. "Myeloproliferative Disease Prevention and Screening," 2014, 2 pages.
Office Action (Final) dated Jan. 29, 2014 in U.S. Appl. No. 13/043,986, 10 pages.
Office Action in U.S. Appl. No. 14/186,338, mailed May 5, 2014, 18 pages.
Opposition, Costa Rica, translation from Foreign Associate Dated Nov. 20, 2013, 9 pages.
Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Offer_New_Approach_to_Treating_Rheumatoi.html>, 12 pages.
Brett et al., "Structural chemistry of polycyclic heteroaromatic compound. Part 4. Electronic structures of angular dithienopyridines," J Chem Soc, Perkin Trans 2, Jan. 1, 1994, 9:2045.
Claridge; Bioorganic and Medicinal Chemistry Letters, 2008, 18,2793-2798.
Cottet and Schlosser, "Three Chloro(trifluoromethyl)pyridines as Model Substrates for Regioexhaustive Functionalization," Eur J Org Chem, 2004, 18:3793-3798.
Dorwald; "Side Reactions in Organic Synthesis: A Guide to Successful Synthesis Design" 2005 Wiley-VCH Verlag GmbH & Co. KGaA, Wienheim, chapter 1, 32 pages.
Gaestel et al., "Targeting innate immunity protein kinase signalling in inflammation," Nat Rev Drug Discov., Jun. 2009, 8(6):480-99.
Gilchrist et al., "5H-2-Pyrindines from 2-Bromocyclopentene-1-carboxaldehyde," Tetrahedron, Jan. 1, 1995, pp. 9119-9126.
International Preliminary Report on Patentability for PCT/US2013/041601, issued Nov. 18, 2014, 7 pages.
International Search Report in International Application No. PCT/US2013/041601, mailed Sep. 3, 2013, 3 pages.
International Search Report and Written Opinion in International Application No. PCT/US2013/067794, mailed Dec. 17, 2013, 14 pages.
Lima and Barreiro, "Bioisosterism: a useful strategy for molecular modification and drug design," Curr Med Chem. 2005;12(1):23-49.
Search Report in TW Application No. 100117866, dated Dec. 2014, 1 page.
Vaillant et al., "Turbidity of pulpy fruit juice: A key factor for predicting cross-flow microfiltration performance," J Membrane Sci., 2008, 325:404-412.

CYCLOHEXYL AZETIDINE DERIVATIVES AS JAK INHIBITORS

This application claims the benefit of priority of U.S. Provisional Application No. 61/525,081, filed Aug. 18, 2011, and U.S. Provisional Application No. 61/674,694, filed Jul. 23, 2012, each of which is incorporated herein by reference in its entirety.

TECHNICAL FIELD

The present invention provides cyclohexyl azetidine derivatives, as well as their compositions and methods of use, that modulate the activity of Janus kinase (JAK) and are useful in the treatment of diseases related to the activity of JAK including, for example, inflammatory disorders, autoimmune disorders, cancer, and other diseases.

BACKGROUND

Protein kinases (PKs) regulate diverse biological processes including cell growth, survival, differentiation, organ formation, morphogenesis, neovascularization, tissue repair, and regeneration, among others. Protein kinases also play specialized roles in a host of human diseases including cancer. Cytokines, low-molecular weight polypeptides or glycoproteins, regulate many pathways involved in the host inflammatory response to sepsis. Cytokines influence cell differentiation, proliferation and activation, and can modulate both pro-inflammatory and anti-inflammatory responses to allow the host to react appropriately to pathogens. Signaling of a wide range of cytokines involves the Janus kinase family (JAKs) of protein tyrosine kinases and Signal Transducers and Activators of Transcription (STATs). There are four known mammalian JAKs: JAK1 (Janus kinase-1), JAK2, JAK3 (also known as Janus kinase, leukocyte; JAKL; and L-JAK), and TYK2 (protein-tyrosine kinase 2).

Cytokine-stimulated immune and inflammatory responses contribute to pathogenesis of diseases: pathologies such as severe combined immunodeficiency (SCID) arise from suppression of the immune system, while a hyperactive or inappropriate immune/inflammatory response contributes to the pathology of autoimmune diseases (e.g., asthma, systemic lupus erythematosus, thyroiditis, myocarditis), and illnesses such as scleroderma and osteoarthritis (Ortmann, R. A., T. Cheng, et al. (2000) *Arthritis Res* 2(1): 16-32).

Deficiencies in expression of JAKs are associated with many disease states. For example, Jak1–/– mice are runted at birth, fail to nurse, and die perinatally (Rodig, S. J., M. A. Meraz, et al. (1998) Cell 93(3): 373-83). Jak2–/– mouse embryos are anemic and die around day 12.5 postcoitum due to the absence of definitive erythropoiesis.

The JAK/STAT pathway, and in particular all four JAKs, are believed to play a role in the pathogenesis of asthmatic response, chronic obstructive pulmonary disease, bronchitis, and other related inflammatory diseases of the lower respiratory tract. Multiple cytokines that signal through JAKs have been linked to inflammatory diseases/conditions of the upper respiratory tract, such as those affecting the nose and sinuses (e.g., rhinitis and sinusitis) whether classically allergic reactions or not. The JAK/STAT pathway has also been implicated in inflammatory diseases/conditions of the eye and chronic allergic responses.

Activation of JAK/STAT in cancers may occur by cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm.* 49:349-355, 2002). Activation of STAT signaling, as well as other pathways downstream of JAKs (e.g., Akt), has been correlated with poor prognosis in many cancer types (Bowman, T., et al. *Oncogene* 19:2474-2488, 2000). Elevated levels of circulating cytokines that signal through JAK/STAT play a causal role in cachexia and/or chronic fatigue. As such, JAK inhibition may be beneficial to cancer patients for reasons that extend beyond potential anti-tumor activity.

JAK2 tyrosine kinase can be beneficial for patients with myeloproliferative disorders, e.g., polycythemia vera (PV), essential thrombocythemia (ET), myeloid metaplasia with myelofibrosis (MMM) (Levin, et al., *Cancer Cell, vol.* 7, 2005: 387-397). Inhibition of the JAK2V617F kinase decreases proliferation of hematopoietic cells, suggesting JAK2 as a potential target for pharmacologic inhibition in patients with PV, ET, and MMM.

Inhibition of the JAKs may benefit patients suffering from skin immune disorders such as psoriasis, and skin sensitization. The maintenance of psoriasis is believed to depend on a number of inflammatory cytokines in addition to various chemokines and growth factors (JCI, 113:1664-1675), many of which signal through JAKs (*Adv Pharmacol.* 2000; 47:113-74).

Thus, new or improved agents which inhibit kinases such as JAKs are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases, diseases involving a hyperactive inflammatory response (e.g., eczema), allergies, cancer (e.g., prostate, leukemia, multiple myeloma), and some immune reactions (e.g., skin rash or contact dermatitis or diarrhea) caused by other therapeutics. The compounds of the invention, as well as its compositions and methods described herein are directed toward these needs and other ends.

SUMMARY

The present invention provides, inter alia, compounds of Formula I:

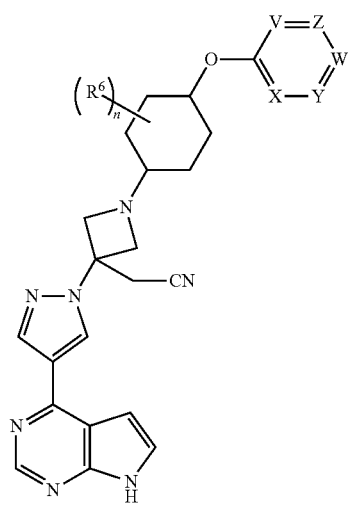

and pharmaceutically acceptable salts thereof; wherein X, Y, W, Z, V, $R^6$, and n are defined infra.

The present invention further provides compositions comprising a compound of Formula I, or a pharmaceutically acceptable salt thereof, and a pharmaceutically acceptable carrier.

The present invention further provides methods of modulating an activity of JAK1 comprising contacting JAK1 with a compound of Formula I, or a pharmaceutically acceptable salt thereof.

The present invention further provides methods of treating a disease or a disorder associated with abnormal kinase expression or activity in a patient by administering to a patient a therapeutically effective amount of a compound of Formula I, or a pharmaceutically acceptable salt thereof.

The present invention further provides methods of treating an autoimmune disease, a cancer, a myeloproliferative disorder, an inflammatory disease, a bone resorption disease, or organ transplant rejection in a patient in need thereof, comprising administering to said patient a therapeutically effective amount of a compound of Formula I, or a pharmaceutically acceptable salt thereof.

The present invention also provides compounds of Formula I, or pharmaceutically acceptable salts thereof, as described herein for use in treatment of autoimmune diseases, cancer, myeloproliferative disorders, inflammatory diseases, a bone resorption disease, or organ transplant rejection.

The present invention further provides compounds of Formula I as described herein, or pharmaceutically acceptable salts thereof, for use in modulating JAK1.

The present invention also provides uses of compounds of Formula I as described herein, or pharmaceutically acceptable salts thereof, for the preparation of medicaments for use in methods of modulating JAK1.

DETAILED DESCRIPTION

The present invention provides, inter alia, a compound of Formula I:

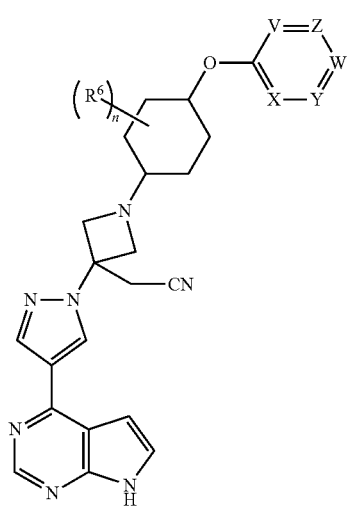

or a pharmaceutically acceptable salt thereof, wherein:
X is $CR^1$ or N;
Y is $CR^2$ or N;
W is $CR^3$ or N;
Z is $CR^4$ or N;
V is $CR^5$ or N;

wherein the 6-membered aromatic ring formed by carbon atom, X, Y, W, Z, and V has 0, 1, or 2 nitrogen ring members;

$R^1$, $R^2$, $R^3$, $R^4$, and $R^5$ are each independently selected from H, halo, CN, $NO_2$, $C_{1-6}$ alkyl, $C_{2-6}$ alkenyl, $C_{2-6}$ alkynyl, $C_{1-6}$ haloalkyl, Cy, —$C_{1-3}$ alkylene-Cy, $OR^a$, $NR^eR^f$, $SR^b$, $S(=O)_2R^b$, $S(=O)_2NR^eR^f$, $C(=O)R^b$, $C(=O)NR^eR^f$, $OC(=O)R^b$, $OC(=O)NR^eR^f$, $NR^cC(=O)R^d$, $NR^cC(=O)OR^d$, $NR^cC(=O)N(R^d)_2$, $NR^cS(=O)_2R^d$, $NR^cS(=O)_2NR^eR^f$, and $CR^oR^pOR^{a1}$, and $CR^oR^pNR^{e1}R^{f1}$; wherein said $C_{1-6}$ alkyl is optionally substituted by 1, 2, or 3 independently selected $R^x$ groups;

$R^6$ is F, methyl, —OH, or —$OCH_3$;

each Cy is independently selected from 3-6-membered monocyclic cycloalkyl, 4-6 membered monocyclic heterocycloalkyl, phenyl, and 5-6 membered monocyclic heteroaryl, which are each optionally substituted by 1, 2, or 3 independently selected $R^g$ groups;

each $R^a$, $R^c$, $R^d$, $R^e$, and $R^f$ is independently selected from H, $C_{1-6}$ alkyl, $C_{1-6}$ haloalkyl, $Cy^1$, and —$C_{1-3}$ alkylene-$Cy^1$; wherein said $C_{1-6}$ alkyl is optionally substituted with 1, 2, or 3 independently selected $R^h$ groups; or each $R^e$ and $R^f$, together with the nitrogen atom to which they are attached, form a 4-6 membered monocyclic heterocycloalkyl ring; which is optionally substituted with 1, 2, or 3 independently selected $R^g$ groups;

each $R^b$ is independently selected from $C_{1-6}$ alkyl, $C_{1-6}$ haloalkyl, $Cy^1$, and —$C_{1-3}$ alkylene-$Cy^1$; wherein said $C_{1-6}$ alkyl is optionally substituted with 1, 2, or 3 independently selected $R^h$ groups;

$R^o$ and $R^p$, taken together with the carbon atom to which they are attached, form a 3-4 membered monocyclic cycloalkyl ring;

each $Cy^1$ is independently selected from 3-6-membered monocyclic cycloalkyl, 4-6 membered monocyclic heterocycloalkyl, phenyl, and 5-6 membered monocyclic heteroaryl, which are each optionally substituted by 1, 2, or 3 independently selected $R^g$ groups;

each $R^g$ is independently selected from halo, CN, hydroxy, $C_{1-4}$ alkyl, $C_{1-4}$ haloalkyl, $C_{1-4}$ alkoxy, $C_{1-4}$ haloalkoxy, hydroxyl-$C_{1-4}$ alkyl, $C_{1-4}$ alkoxy-$C_{1-4}$ alkyl, cyano-$C_{1-4}$ alkyl, amino, $C_{1-4}$ alkylamino, di-$C_{1-4}$-alkylamino, carbamyl, $C_{1-4}$ alkylcarbamyl, di($C_{1-4}$ alkyl)carbamyl, $C_{1-4}$ alkylcarbonyl, $C_{1-4}$ alkoxycarbonyl, $C_{1-4}$ alkylcarbonyloxy, $C_{1-4}$ alkylsulfonyl, $C_{1-4}$ alkylcarbonylamino, $C_{1-4}$ alkylsulfonylamino, aminosulfonyl, $C_{1-4}$ alkylaminosulfonyl, di-$C_{1-4}$ alkylaminosulfonyl, aminosulfonylamino, $C_{1-4}$ alkylaminosulfonylamino, and di-$C_{1-4}$ alkylaminosulfonylamino;

each $R^h$ is independently selected from halo, CN, hydroxy, $C_{1-4}$ alkoxy, $C_{1-4}$ haloalkoxy, hydroxyl-$C_{1-4}$ alkyl, $C_{1-4}$ alkoxy-$C_{1-4}$ alkyl, cyano-$C_{1-4}$ alkyl, amino, $C_{1-4}$ alkylamino, di-$C_{1-4}$-alkylamino, carbamyl, $C_{1-4}$ alkylcarbamyl, di($C_{1-4}$ alkyl)carbamyl, $C_{1-4}$ alkylcarbonyl, $C_{1-4}$ alkoxycarbonyl, $C_{1-4}$ alkylcarbonyloxy, $C_{1-4}$ alkylcarbonylamino, $C_{1-4}$ alkylsulfonylamino, aminosulfonyl, $C_{1-4}$ alkylaminosulfonyl, di-$C_{1-4}$ alkylaminosulfonyl, aminosulfonylamino, $C_{1-4}$ alkylaminosulfonylamino, and di-$C_{1-4}$ alkylaminosulfonylamino;

each $R^x$ group is independently selected from halo, CN, $NO_2$, $OR^{a1}$, $NR^{e1}R^{f1}$, $SR^{b1}$, $S(=O)_2R^{b1}$, $S(=O)_2NR^{e1}R^{f1}$, $C(=O)R^{b1}$, $C(=O)OR^{a1}$, $C(=O)NR^{e1}R^{f1}$, $OC(=O)R^{b1}$, $OC(=O)NR^{e1}R^{f1}$, $NR^{c1}C(=O)R^{d1}$, $NR^{c1}C(=O)OR^{d1}$, $NR^{c1}C(=O)N(R^{d1})_2$, $NR^{c1}S(=O)_2R^{d1}$, and $NR^{c1}S(=O)_2NR^{e1}R^{f1}$;

each $R^{a1}$, $R^{c1}$, $R^{d1}$, $R^{e1}$, and $R^{f1}$ is independently selected from H, $C_{1-6}$ alkyl, $C_{1-6}$ haloalkyl, $Cy^2$, and —$C_{1-3}$ alkylene-$Cy^2$; wherein said $C_{1-6}$ alkyl is optionally substituted by 1, 2, or 3 independently selected $R^k$ groups; or each $R^{e1}$ and $R^{f1}$, together with the nitrogen atom to which they are attached, forms a 4-6 membered monocyclic heterocycloalkyl ring; which is optionally substituted with 1, 2, or 3 independently selected $R^m$ groups;

each $R^{b1}$ is independently selected from $C_{1-6}$ alkyl, $C_{1-6}$ haloalkyl, $Cy^2$, and —$C_{1-3}$ alkylene-$Cy^2$; wherein said $C_{1-6}$ alkyl is optionally substituted by 1, 2, or 3 independently selected $R^k$ groups;

each $Cy^2$ is independently selected from 3-6-membered monocyclic cycloalkyl, 4-6 membered monocyclic heterocycloalkyl, phenyl, and 5-6 membered monocyclic heteroaryl, which are each optionally substituted by 1, 2, or 3 independently selected $R^m$ groups;

each $R^k$ is independently selected from halo, CN, hydroxy, $C_{1-4}$ alkoxy, $C_{1-4}$ haloalkoxy, hydroxyl-$C_{1-4}$ alkyl, $C_{1-4}$ alkoxy-$C_{1-4}$ alkyl, cyano-$C_{1-4}$ alkyl, amino, $C_{1-4}$ alkylamino, di-$C_{1-4}$-alkylamino, carbamyl, $C_{1-4}$ alkylcarbamyl, di($C_{1-4}$ alkyl)carbamyl, $C_{1-4}$ alkylcarbonyl, $C_{1-4}$ alkoxycarbonyl, $C_{1-4}$ alkylcarbonyloxy, $C_{1-4}$ alkylcarbonylamino, $C_{1-4}$ alkylsulfonyl, $C_{1-4}$ alkylsulfonylamino, aminosulfonyl, $C_{1-4}$ alkylaminosulfonyl, di-$C_{1-4}$ alkylaminosulfonyl, aminosulfonylamino, $C_{1-4}$ alkylaminosulfonylamino, and di-$C_{1-4}$ alkylaminosulfonylamino;

each $R^m$ is independently selected from halo, CN, hydroxy, $C_{1-4}$ alkyl, $C_{1-4}$ haloalkyl, $C_{1-4}$ alkoxy, $C_{1-4}$ haloalkoxy, hydroxyl-$C_{1-4}$ alkyl, $C_{1-4}$ alkoxy-$C_{1-4}$ alkyl, cyano-$C_{1-4}$ alkyl, amino, $C_{1-4}$ alkylamino, di-$C_{1-4}$-alkylamino, carbamyl, $C_{1-4}$ alkylcarbamyl, di($C_{1-4}$ alkyl)carbamyl, $C_{1-4}$ alkylcarbonyl, $C_{1-4}$ alkoxycarbonyl, $C_{1-4}$ alkylcarbonyloxy, $C_{1-4}$ alkylsulfonyl, $C_{1-4}$ alkylcarbonylamino, $C_{1-4}$ alkylsulfonylamino, aminosulfonyl, $C_{1-4}$ alkylaminosulfonyl, di-$C_{1-4}$ alkylaminosulfonyl, aminosulfonylamino, $C_{1-4}$ alkylaminosulfonylamino, and di-$C_{1-4}$ alkylaminosulfonylamino; and n is 0, 1, or 2.

In some embodiments:

X is $CR^1$ or N;
Y is $CR^2$ or N;
W is $CR^3$ or N;
Z is $CR^4$ or N;
V is $CR^5$ or N;

wherein the 6-membered aromatic ring formed by carbon atom, X, Y, W, Z, and V has 0, 1, or 2 nitrogen ring members;

$R^1$, $R^2$, $R^3$, $R^4$, and $R^5$ are each independently selected from H, halo, CN, $NO_2$, $C_{1-6}$ alkyl, $C_{2-6}$ alkenyl, $C_{2-6}$ alkynyl, $C_{1-6}$ haloalkyl, Cy, —$C_{1-3}$ alkylene-Cy, $OR^a$, $NR^eR^f$, $S(=O)_2R^b$, $S(=O)_2NR^eR^f$, $C(=O)R^b$, $C(=O)OR^a$, $C(=O)NR^eR^f$, $OC(=O)R^b$, $OC(=O)NR^eR^f$, $NR^cC(=O)R^d$, $NR^cC(=O)OR^d$, $NR^cS(=O)_2R^d$, $NR^cS(=O)_2NR^eR^f$, and $CR^oR^pOR^{a1}$, and $CR^oR^pNR^{e1}R^{f1}$; wherein said $C_{1-6}$ alkyl is optionally substituted by 1, 2, or 3 independently selected $R^x$ groups;

$R^6$ is F, methyl, —OH, or —$OCH_3$;

each Cy is independently selected from 3-6-membered monocyclic cycloalkyl, 4-6 membered monocyclic heterocycloalkyl, phenyl, and 5-6 membered monocyclic heteroaryl, which are each optionally substituted by 1, 2, or 3 independently selected $R^g$ groups;

each $R^a$, $R^c$, $R^d$, $R^e$, and $R^f$ is independently selected from H, $C_{1-6}$ alkyl, $C_{1-6}$ haloalkyl, $Cy^1$, and —$C_{1-3}$ alkylene-$Cy^1$; wherein said $C_{1-6}$ alkyl is optionally substituted with 1, 2, or 3 independently selected $R^h$ groups; or each $R^e$ and $R^f$, together with the nitrogen atom to which they are attached, form a 4-6 membered monocyclic heterocycloalkyl ring; which is optionally substituted with 1, 2, or 3 independently selected $R^g$ groups;

each $R^b$ is independently selected from $C_{1-6}$ alkyl, $C_{1-6}$ haloalkyl, $Cy^1$, and —$C_{1-3}$ alkylene-$Cy^1$; wherein said $C_{1-6}$ alkyl is optionally substituted with 1, 2, or 3 independently selected $R^h$ groups;

$R^o$ and $R^p$, taken together with the carbon atom to which they are attached, form a 3-4 membered monocyclic cycloalkyl ring;

each $Cy^1$ is independently selected from 3-6-membered monocyclic cycloalkyl, 4-6 membered monocyclic heterocycloalkyl, phenyl, and 5-6 membered monocyclic heteroaryl, which are each optionally substituted by 1, 2, or 3 independently selected $R^g$ groups;

each $R^g$ is independently selected from halo, CN, hydroxy, $C_{1-4}$ alkyl, $C_{1-4}$ haloalkyl, $C_{1-4}$ alkoxy, $C_{1-4}$ haloalkoxy, hydroxyl-$C_{1-4}$ alkyl, $C_{1-4}$ alkoxy-$C_{1-4}$ alkyl, cyano-$C_{1-4}$ alkyl, amino, $C_{1-4}$ alkylamino, di-$C_{1-4}$-alkylamino, carbamyl, $C_{1-4}$ alkylcarbamyl, di($C_{1-4}$ alkyl)carbamyl, $C_{1-4}$ alkylcarbonyl, $C_{1-4}$ alkoxycarbonyl, $C_{1-4}$ alkylcarbonyloxy, $C_{1-4}$ alkylsulfonyl, $C_{1-4}$ alkylcarbonylamino, $C_{1-4}$ alkylsulfonylamino, aminosulfonyl, $C_{1-4}$ alkylaminosulfonyl, di-$C_{1-4}$ alkylaminosulfonyl, aminosulfonylamino, $C_{1-4}$ alkylaminosulfonylamino, and di-$C_{1-4}$ alkylaminosulfonylamino;

each $R^h$ is independently selected from halo, CN, hydroxy, $C_{1-4}$ alkoxy, $C_{1-4}$ haloalkoxy, hydroxyl-$C_{1-4}$ alkyl, $C_{1-4}$ alkoxy-$C_{1-4}$ alkyl, cyano-$C_{1-4}$ alkyl, amino, $C_{1-4}$ alkylamino, di-$C_{1-4}$-alkylamino, carbamyl, $C_{1-4}$ alkylcarbamyl, di($C_{1-4}$ alkyl)carbamyl, $C_{1-4}$ alkylcarbonyl, $C_{1-4}$ alkoxycarbonyl, $C_{1-4}$ alkylcarbonyloxy, $C_{1-4}$ alkylcarbonylamino, $C_{1-4}$ alkylsulfonylamino, aminosulfonyl, $C_{1-4}$ alkylaminosulfonyl, di-$C_{1-4}$ alkylaminosulfonyl, aminosulfonylamino, $C_{1-4}$ alkylaminosulfonylamino, and di-$C_{1-4}$ alkylaminosulfonylamino;

each $R^x$ group is independently selected from halo, CN, $NO_2$, $OR^{a1}$, $NR^{e1}R^{f1}$, $SR^{b1}$, $S(=O)_2R^{b1}$, $S(=O)_2NR^{e1}R^{f1}$, $C(=O)R^{b1}$, $C(=O)OR^{a1}$, $C(=O)NR^{e1}R^{f1}$, $OC(=O)R^{b1}$, $OC(=O)NR^{e1}R^{f1}$, $NR^{c1}C(=O)R^{d1}$, $NR^{c1}C(=O)OR^{d1}$, and $NR^{c1}S(=O)_2R^{d1}$, and $NR^{c1}S(=O)_2NR^{e1}R^{f1}$;

each $R^{a1}$, $R^{c1}$, $R^{d1}$, $R^{e1}$, and $R^{f1}$ is independently selected from H, $C_{1-6}$ alkyl, $C_{1-6}$ haloalkyl, $Cy^2$, and —$C_{1-3}$ alkylene-$Cy^2$; wherein said $C_{1-6}$ alkyl is optionally substituted by 1, 2, or 3 independently selected $R^k$ groups; or each $R^{e1}$ and $R^{f1}$, together with the nitrogen atom to which they are attached, forms a 4-6 membered monocyclic heterocycloalkyl ring; which is optionally substituted with 1, 2, or 3 independently selected $R^m$ groups;

each $R^{b1}$ is independently selected from $C_{1-6}$ alkyl, $C_{1-6}$ haloalkyl, $Cy^2$, and —$C_{1-3}$ alkylene-$Cy^2$; wherein said $C_{1-6}$ alkyl is optionally substituted by 1, 2, or 3 independently selected $R^k$ groups;

each $Cy^2$ is independently selected from 3-6-membered monocyclic cycloalkyl, 4-6 membered monocyclic heterocycloalkyl, phenyl, and 5-6 membered monocyclic heteroaryl, which are each optionally substituted by 1, 2, or 3 independently selected $R^m$ groups;

each $R^k$ is independently selected from halo, CN, hydroxy, $C_{1-4}$ alkoxy, $C_{1-4}$ haloalkoxy, hydroxyl-$C_{1-4}$ alkyl, $C_{1-4}$ alkoxy-$C_{1-4}$ alkyl, cyano-$C_{1-4}$ alkyl, amino, $C_{1-4}$ alkylamino, di-$C_{1-4}$-alkylamino, carbamyl, $C_{1-4}$ alkylcarbamyl, di($C_{1-4}$ alkyl)carbamyl, $C_{1-4}$ alkylcarbonyl, $C_{1-4}$ alkoxycarbonyl, $C_{1-4}$ alkylcarbonyloxy, $C_{1-4}$ alkylcarbonylamino, $C_{1-4}$ alkylsulfonyl, $C_{1-4}$ alkylsulfonylamino, amino sulfonyl, $C_{1-4}$ alkylaminosulfonyl, di-$C_{1-4}$ alkylaminosulfonyl, aminosulfonylamino, $C_{1-4}$ alkylaminosulfonylamino, and di-$C_{1-4}$ alkylaminosulfonylamino;

each $R^m$ is independently selected from halo, CN, hydroxy, $C_{1-4}$ alkyl, $C_{1-4}$ haloalkyl, $C_{1-4}$ alkoxy, $C_{1-4}$ haloalkoxy, hydroxyl-$C_{1-4}$ alkyl, $C_{1-4}$ alkoxy-$C_{1-4}$ alkyl, cyano-$C_{1-4}$ alkyl, amino, $C_{1-4}$ alkylamino, di-$C_{1-4}$-alkylamino, carbamyl, $C_{1-4}$ alkylcarbamyl, di($C_{1-4}$ alkyl)carbamyl, $C_{1-4}$ alkylcarbonyl, $C_{1-4}$ alkoxycarbonyl, $C_{1-4}$ alkylcarbonyloxy, $C_{1-4}$ alkylsulfonyl, $C_{1-4}$ alkylcarbonylamino, $C_{1-4}$ alkylsulfonylamino, aminosulfonyl, $C_{1-4}$ alkylaminosulfonyl, di-$C_{1-4}$ alkylaminosulfonyl, aminosulfonylamino, $C_{1-4}$ alkylaminosulfonylamino, and di-$C_{1-4}$ alkylaminosulfonylamino; and n is 0, 1, or 2.

In some embodiments, $R^1$, $R^2$, $R^3$, $R^4$, and $R^5$ are each independently selected from H, halo, CN, $C_{1-6}$ alkyl, $C_{1-6}$ haloalkyl, $OR^a$, and $NR^eR^f$; wherein said $C_{1-6}$ alkyl is optionally substituted by 1, 2, or 3 independently selected $R^x$ groups.

In some embodiments, $R^1$, $R^2$, $R^3$, $R^4$, and $R^5$ are each independently selected from H, halo, CN, $C_{1-6}$ alkyl, $C_{1-6}$ haloalkyl, Cy, $OR^a$, $NR^eR^f$, $C(=O)OR^a$, and $C(=O)NR^eR^f$; wherein said $C_{1-6}$ alkyl is optionally substituted by 1, 2, or 3 independently selected $R^x$ groups.

In some embodiments, $R^1$, $R^2$, $R^3$, $R^4$, and $R^5$ are each independently selected from H, $C_{1-6}$ alkyl, and $C_{1-6}$ haloalkyl; wherein said $C_{1-6}$ alkyl is optionally substituted by 1 $R^x$ group.

In some embodiments, $R^1$, $R^2$, $R^3$, $R^4$, and $R^5$ are each independently selected from H, —$CF_3$, —$CH_2R^x$, and —$C(CH_3)_2R^x$.

In some embodiments, each $R^x$ group is independently selected from $OR^{a1}$ and $NR^{e1}R^{f1}$.

In some embodiments, each $R^{a1}$, $R^{c1}$, $R^{d1}$, $R^{e1}$, and $R^{f1}$ is independently selected from H, methyl, ethyl, n-propyl, isopropyl, n-butyl, isobutyl, tert-butyl, $Cy^2$, and —$C_{1-3}$ alkylene-$Cy^2$; wherein said $C_{1-6}$ alkyl is optionally substituted by 1, 2, or 3 independently selected $R^k$ groups; or each $R^{e1}$ and $R^{f1}$, together with the nitrogen atom to which they are attached, forms a 4-6 membered monocyclic heterocycloalkyl ring; which is optionally substituted with 1, 2, or 3 independently selected $R^m$ groups.

In some embodiments, each $Cy^2$ is independently selected from cyclopropyl, cyclobutyl, cyclopentyl, cyclohexyl, tetrahydrofuran-2-yl, and 1H-imidazol-4-yl, which are each optionally substituted by 1, 2, or 3 independently selected $R^m$ groups.

In some embodiments, each $R^m$ is independently selected from halo, hydroxy, $C_{1-4}$ alkoxy, hydroxyl-$C_{1-4}$ alkyl, and $C_{1-4}$ alkoxy-$C_{1-4}$ alkyl.

In some embodiments, each $R^k$ is independently selected from hydroxy, $C_{1-4}$ alkoxy, hydroxyl-$C_{1-4}$ alkyl, and $C_{1-4}$ alkoxy-$C_{1-4}$ alkyl.

In some embodiments, X is N.
In some embodiments, X is $CR^1$.
In some embodiments, Y is N.
In some embodiments, Y is $CR^2$.
In some embodiments, $R^2$ is $C_{1-6}$ haloalkyl.
In some embodiments, $R^2$ is $CF_3$.
In some embodiments, W is N.
In some embodiments, W is $CR^3$.
In some embodiments, $R^3$ is H.
In some embodiments, Z is N.
In some embodiments, Z is $CR^4$.
In some embodiments, V is N.
In some embodiments, V is $CR^5$.
In some embodiments, $R^5$ is H.

In some embodiments, the 6-membered aromatic ring formed by carbon atom, X, Y, W, Z, and V is a pyridine ring or a pyrimidine ring.

In some embodiments, the 6-membered aromatic ring formed by carbon atom, X, Y, W, Z, and V is a pyrimidine ring.

In some embodiments, the 6-membered aromatic ring formed by carbon atom, X, Y, W, Z, and V is a pyridine ring.

In some embodiments, the 6-membered aromatic ring formed by carbon atom, X, Y, W, Z, and V is selected from:

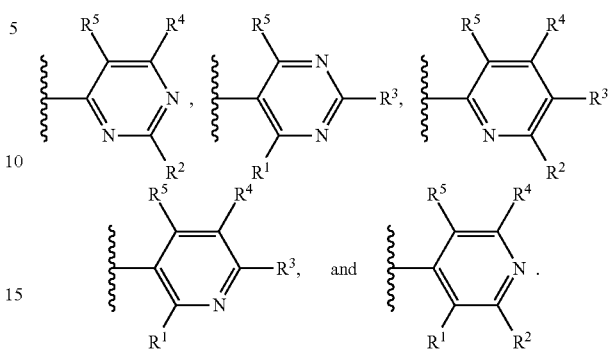

In some embodiments, the 6-membered aromatic ring formed by carbon atom, X, Y, W, Z, and V is selected from:

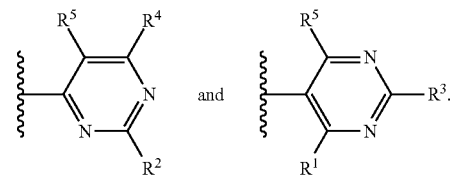

In some embodiments, the 6-membered aromatic ring formed by carbon atom, X, Y, W, Z, and V is selected from:

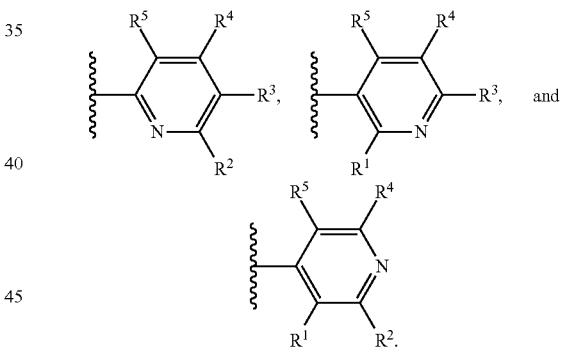

In some embodiments, n is 0.
In some embodiments:
X is N;
Y is $CR^2$;
W is N;
Z is $CR^4$;
V is $CR^5$;
$R^2$, $R^4$, K and $R^5$ are each independently selected from H, halo, CN, $C_{1-6}$ alkyl, and $C_{1-6}$ haloalkyl; wherein said $C_{1-6}$ alkyl is optionally substituted by 1, 2, or 3 independently selected $R^x$ groups;

each $R^x$ group is independently selected from $OR^{a1}$ and $NR^{e1}R^{f1}$;

each $R^{a1}$, $R^{e1}$, and $R^{f1}$ is independently selected from H, $C_{1-6}$ alkyl, $C_{1-6}$ haloalkyl, $Cy^2$, and —$C_{1-3}$ alkylene-$Cy^2$; wherein said $C_{1-6}$ alkyl is optionally substituted by 1, 2, or 3 independently selected $R^k$ groups; or each $R^{e1}$ and $R^{f1}$, together with the nitrogen atom to which they are attached, forms a 4-6 membered monocyclic heterocycloalkyl ring; which is optionally substituted with 1, 2, or 3 independently selected $R^m$ groups;

each $Cy^2$ is independently selected from 3-6-membered monocyclic cycloalkyl, 4-6 membered monocyclic heterocycloalkyl, and 5-6 membered monocyclic heteroaryl, which are each optionally substituted by 1, 2, or 3 independently selected $R^m$ groups;

each $R^k$ is independently selected from hydroxy, $C_{1-4}$ alkoxy, hydroxyl-$C_{1-4}$ alkyl, and $C_{1-4}$ alkoxy-$C_{1-4}$ alkyl; and each $R^m$ is independently selected from halo, hydroxy, $C_{1-4}$ alkoxy, hydroxyl-$C_{1-4}$ alkyl, and $C_{1-4}$ alkoxy-$C_{1-4}$ alkyl.

In some embodiments:
X is N;
Y is $CR^2$;
W is N;
Z is $CR^4$;
V is $CR^5$;
$R^2$, $R^4$, and $R^5$ are each independently selected from H, —$CF_3$, —$CH_2R^x$, and —$C(CH_3)_2R^x$;

each $R^x$ group is independently selected from $OR^{a1}$ and $NR^{e1}R^{f1}$;

each $R^{a1}$, $R^{e1}$, and $R^{f1}$ is independently selected from H, $C_{1-6}$ alkyl, $C_{1-6}$ haloalkyl, $Cy^2$, and —$C_{1-3}$ alkylene-$Cy^2$; wherein said $C_{1-6}$ alkyl is optionally substituted by 1, 2, or 3 independently selected $R^k$ groups; or each $R^{e1}$ and $R^{f1}$, together with the nitrogen atom to which they are attached, forms a 4-6 membered monocyclic heterocycloalkyl ring; which is optionally substituted with 1, 2, or 3 independently selected $R^m$ groups each $Cy^2$ is independently selected from 3-6-membered monocyclic cycloalkyl, 4-6 membered monocyclic heterocycloalkyl, and 5-6 membered monocyclic heteroaryl, which are each optionally substituted by 1, 2, or 3 independently selected $R^m$ groups;

each $R^k$ is independently selected from hydroxy, $C_{1-4}$ alkoxy, hydroxyl-$C_{1-4}$alkyl, and $C_{1-4}$ alkoxy-$C_{1-4}$ alkyl; and each $R^m$ is independently selected from halo, hydroxy, $C_{1-4}$ alkoxy, hydroxyl-$C_{1-4}$ alkyl, and $C_{1-4}$ alkoxy-$C_{1-4}$ alkyl.

In some embodiments:
X is N;
Y is $CR^2$;
W is N;
Z is $CR^4$;
V is $CR^5$;
$R^2$, $R^4$, and $R^5$ are each independently selected from H, halo, CN, $C_{1-6}$ alkyl, $C_{1-6}$ haloalkyl, Cy, $OR^a$, $C(=O)OR^a$, and $C(=O)NR^eR^f$; wherein said $C_{1-6}$ alkyl is optionally substituted by 1, 2, or 3 independently selected $R^x$ groups;

each Cy is independently selected from 3-6-membered monocyclic cycloalkyl optionally substituted by 1, 2, or 3 independently selected $R^g$ groups;

each $R^a$, $R^e$, and $R^f$ is, independently, H or $C_{1-6}$ alkyl; wherein said $C_{1-6}$ alkyl is optionally substituted with 1, 2, or 3 independently selected $R^h$ groups; or each $R^e$ and $R^f$, together with the nitrogen atom to which they are attached, form a 4-6 membered monocyclic heterocycloalkyl ring;

each $R^g$ is independently selected from hydroxy and hydroxyl-$C_{1-4}$ alkyl;

each $R^h$ is independently selected from halo, hydroxy, and $C_{1-4}$ alkoxy;

each $R^x$ group is independently selected from $OR^{a1}$ and $NR^{e1}R^{f1}$;

each $R^{a1}$, $R^{e1}$, and $R^{f1}$ is independently selected from H, $C_{1-6}$ alkyl, $C_{1-6}$ haloalkyl, $Cy^2$, and —$C_{1-3}$ alkylene-$Cy^2$; wherein said $C_{1-6}$ alkyl is optionally substituted by 1, 2, or 3 independently selected $R^k$ groups; or each $R^{e1}$ and $R^{f1}$, together with the nitrogen atom to which they are attached, forms a 4-6 membered monocyclic heterocycloalkyl ring; which is optionally substituted with 1, 2, or 3 independently selected $R^m$ groups;

each $Cy^2$ is independently selected from 3-6-membered monocyclic cycloalkyl, 4-6 membered monocyclic heterocycloalkyl, and 5-6 membered monocyclic heteroaryl, which are each optionally substituted by 1, 2, or 3 independently selected $R^m$ groups;

each $R^k$ is independently selected from hydroxy, $C_{1-4}$ alkoxy, hydroxyl-$C_{1-4}$ alkyl, and $C_{1-4}$ alkoxy-$C_{1-4}$ alkyl; and each $R^m$ is independently selected from halo, hydroxy, $C_{1-4}$ alkoxy, hydroxyl-$C_{1-4}$ alkyl, and $C_{1-4}$ alkoxy-$C_{1-4}$ alkyl.

In some embodiments:
X is N;
Y is $CR^2$;
W is N;
Z is $CR^4$;
V is $CR^5$;
$R^2$, $R^4$, and $R^5$ are each independently selected from H, CN, Cy, $OR^a$, $C(=O)OR^a$, —$CF_3$, —$CH_2R^x$, —$C(CH_3)_2R^x$ and $C(=O)NR^eR^f$;

each Cy is independently 3-6-membered monocyclic cycloalkyl, which is optionally substituted by 1, 2, or 3 independently selected $R^g$ groups;

each $R^a$, $R^e$, and $R^f$ is independently H or $C_{1-6}$ alkyl; wherein said $C_{1-6}$ alkyl is optionally substituted with 1 or 2 independently selected $R^h$ groups; or each $R^e$ and $R^f$, together with the nitrogen atom to which they are attached, form a 4-6 membered monocyclic heterocycloalkyl ring;

each $R^g$ is independently selected from hydroxy and hydroxyl-$C_{1-4}$ alkyl;

each $R^h$ is independently hydroxy or $C_{1-4}$ alkoxy;

each $R^x$ group is independently selected from $OR^{a1}$ and $NR^{e1}R^{f1}$;

each $R^{a1}$, $R^{e1}$, and $R^{f1}$ is independently selected from H, $C_{1-6}$ alkyl, $C_{1-6}$ haloalkyl, $Cy^2$, and —$C_{1-3}$ alkylene-$Cy^2$; wherein said $C_{1-6}$ alkyl is optionally substituted by 1, 2, or 3 independently selected $R^k$ groups; or each $R^{e1}$ and $R^{f1}$, together with the nitrogen atom to which they are attached, forms a 4-6 membered monocyclic heterocycloalkyl ring; which is optionally substituted with 1, 2, or 3 independently selected $R^m$ groups each $Cy^2$ is independently selected from 3-6-membered monocyclic cycloalkyl, 4-6 membered monocyclic heterocycloalkyl, and 5-6 membered monocyclic heteroaryl, which are each optionally substituted by 1, 2, or 3 independently selected $R^m$ groups;

each $R^k$ is independently selected from hydroxy, $C_{1-4}$ alkoxy, hydroxyl-$C_{1-4}$ alkyl, and $C_{1-4}$ alkoxy-$C_{1-4}$ alkyl; and each $R^m$ is independently selected from halo, hydroxy, $C_{1-4}$ alkoxy, hydroxyl-$C_{1-4}$ alkyl, and $C_{1-4}$ alkoxy-$C_{1-4}$ alkyl.

In some embodiments:
X is N;
Y is $CR^2$;
W is $CR^3$ or N;
Z is $CR^4$;
V is $CR^5$;
$R^2$, $R^4$, and $R^5$ are each independently selected from H, halo, CN, $C_{1-6}$ alkyl, $C_{1-6}$ haloalkyl, Cy, $OR^a$, $C(=O)OR^a$, and $C(=O)NR^eR^f$; wherein said $C_{1-6}$ alkyl is optionally substituted by 1, 2, or 3 independently selected $R^x$ groups;

each Cy is independently selected from 3-6-membered monocyclic cycloalkyl optionally substituted by 1, 2, or 3 independently selected $R^g$ groups;

each $R^a$, $R^e$, and $R^f$ is, independently, H or $C_{1-6}$ alkyl; wherein said $C_{1-6}$ alkyl is optionally substituted with 1, 2, or 3 independently selected $R^h$ groups; or each $R^e$ and $R^f$, together with the nitrogen atom to which they are attached, form a 4-6 membered monocyclic heterocycloalkyl ring;

each $R^g$ is independently selected from hydroxy and hydroxyl-$C_{1-4}$ alkyl;

each $R^h$ is independently selected from halo, hydroxy, and $C_{1-4}$ alkoxy;

each $R^x$ group is independently selected from $OR^{a1}$ and $NR^{e1}R^{f1}$;

each $R^{a1}$, $R^{e1}$, and $R^{f1}$ is independently selected from H, $C_{1-6}$ alkyl, $C_{1-6}$ haloalkyl, $Cy^2$, and —$C_{1-3}$ alkylene-$Cy^2$; wherein said $C_{1-6}$ alkyl is optionally substituted by 1, 2, or 3 independently selected $R^k$ groups; or each $R^{e1}$ and $R^{f1}$, together with the nitrogen atom to which they are attached, forms a 4-6 membered monocyclic heterocycloalkyl ring; which is optionally substituted with 1, 2, or 3 independently selected $R^m$ groups;

each $Cy^2$ is independently selected from 3-6-membered monocyclic cycloalkyl, 4-6 membered monocyclic heterocycloalkyl, and 5-6 membered monocyclic heteroaryl, which are each optionally substituted by 1, 2, or 3 independently selected $R^m$ groups;

each $R^k$ is independently selected from hydroxy, $C_{1-4}$ alkoxy, hydroxyl-$C_{1-4}$ alkyl, and $C_{1-4}$ alkoxy-$C_{1-4}$ alkyl; and each $R^m$ is independently selected from halo, hydroxy, $C_{1-4}$ alkoxy, hydroxyl-$C_{1-4}$ alkyl, and $C_{1-4}$ alkoxy-$C_{1-4}$ alkyl.

In some embodiments:

X is N;
Y is $CR^2$;
W is $CR^3$ or N;
Z is $CR^4$;
V is $CR^5$;

$R^2$, $R^4$, and $R^5$ are each independently selected from H, CN, Cy, $OR^a$, $C(=O)OR^a$, —$CF_3$, —$CH_2R^x$, —$C(CH_3)_2R^x$ and $C(=O)NR^eR^f$;

each Cy is independently 3-6-membered monocyclic cycloalkyl, which is optionally substituted by 1, 2, or 3 independently selected $R^g$ groups;

each $R^a$, $R^e$, and $R^f$ is independently H or $C_{1-6}$ alkyl; wherein said $C_{1-6}$ alkyl is optionally substituted with 1 or 2 independently selected $R^h$ groups; or each $R^e$ and $R^f$, together with the nitrogen atom to which they are attached, form a 4-6 membered monocyclic heterocycloalkyl ring;

each $R^g$ is independently selected from hydroxy and hydroxyl-$C_{1-4}$ alkyl;

each $R^h$ is independently hydroxy or $C_{1-4}$ alkoxy;

each $R^x$ group is independently selected from $OR^{a1}$ and $NR^{e1}R^{f1}$;

each $R^{a1}$, $R^{e1}$, and $R^{f1}$ is independently selected from H, $C_{1-6}$ alkyl, $C_{1-6}$ haloalkyl, $Cy^2$, and —$C_{1-3}$ alkylene-$Cy^2$; wherein said $C_{1-6}$ alkyl is optionally substituted by 1, 2, or 3 independently selected $R^k$ groups; or each $R^{e1}$ and $R^{f1}$, together with the nitrogen atom to which they are attached, forms a 4-6 membered monocyclic heterocycloalkyl ring; which is optionally substituted with 1, 2, or 3 independently selected $R^m$ groups each $Cy^2$ is independently selected from 3-6-membered monocyclic cycloalkyl, 4-6 membered monocyclic heterocycloalkyl, and 5-6 membered monocyclic heteroaryl, which are each optionally substituted by 1, 2, or 3 independently selected $R^m$ groups;

each $R^k$ is independently selected from hydroxy, $C_{1-4}$ alkoxy, hydroxyl-$C_{1-4}$ alkyl, and $C_{1-4}$ alkoxy-$C_{1-4}$ alkyl; and each $R^m$ is independently selected from halo, hydroxy, $C_{1-4}$ alkoxy, hydroxyl-$C_{1-4}$ alkyl, and $C_{1-4}$ alkoxy-$C_{1-4}$ alkyl.

In some embodiments, each Cy is independently selected from 3-6-membered monocyclic cycloalkyl, 4-6 membered monocyclic heterocycloalkyl, and 5-6 membered monocyclic heteroaryl, which are each optionally substituted by 1, 2, or 3 independently selected $R^g$ groups.

In some embodiments, each $Cy^1$ is independently selected from 3-6-membered monocyclic cycloalkyl, 4-6 membered monocyclic heterocycloalkyl, and 5-6 membered monocyclic heteroaryl, which are each optionally substituted by 1, 2, or 3 independently selected $R^g$ groups.

In some embodiments, each $Cy^2$ is independently selected from 3-6-membered monocyclic cycloalkyl, 4-6 membered monocyclic heterocycloalkyl, and 5-6 membered monocyclic heteroaryl, which are each optionally substituted by 1, 2, or 3 independently selected $R^m$ groups.

In some embodiments, the compound is a compound of Formula II:

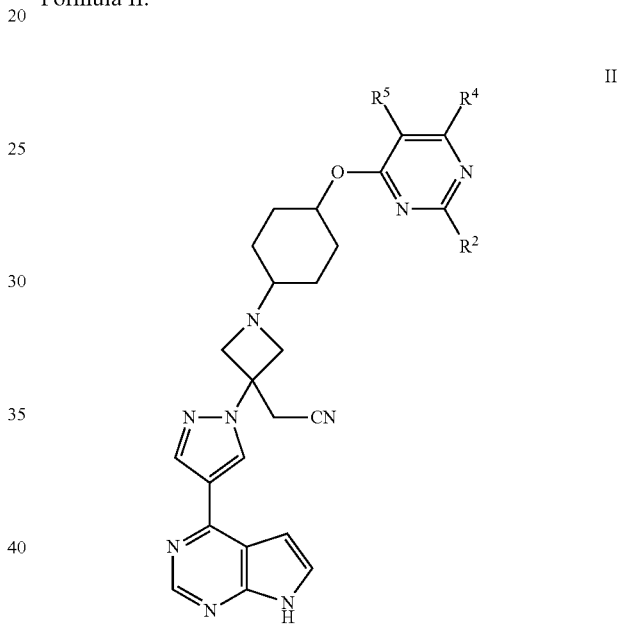

or a pharmaceutically acceptable salt thereof.

In some embodiments, the compound is a compound of Formula II, wherein:

$R^2$ is $C_{1-3}$ haloalkyl;
$R^4$ is selected from —$CH_2OH$, —$C(CH_3)_2OH$, and —$CH_2NR^{e1}R^{f1}$;
$R^{e1}$ is H or $C_{1-4}$ alkyl;
$R^{f1}$ is H, $C_{1-6}$ alkyl, $C_{1-6}$ haloalkyl, $Cy^2$, or —$C_{1-2}$ alkylene-$Cy^2$; wherein said $C_{1-6}$ alkyl is optionally substituted with 1 or 2 groups selected from —OH and —$OCH_3$;
or $R^{e1}$ and $R^{f1}$ together with the nitrogen atom to which they are attached form a 4-6-membered monocyclic heterocycloalkyl ring, which is optionally substituted by one —F, —OH, or —$CH_2OH$ group; and
$Cy^2$ is cyclopropyl, cyclobutyl, 5-membered monocyclic heterocycloalkyl, or 5-membered monocyclic heteroaryl; each of which is optionally substituted by a —$CH_2OH$ group.

In some embodiments, the compound is a compound of Formula II, wherein:

$R^2$ is $C_{1-3}$ haloalkyl;
$R^4$ is selected from CN, Cy, $OR^a$, $C(=O)OR^a$, —$CH_2OH$, —$CH_2CH_2OH$, —$C(CH_3)_2OH$, —$CH_2NR^{e1}R^{f1}$, and $C(=O)NR^eR^f$;

Cy is cyclopropyl substituted by a —CH$_2$OH group;

each R$^a$, R$^e$, and R$^f$ is independently H, methyl, ethyl, —CH$_2$CH$_2$OH or —CH$_2$CH$_2$OCH$_3$; or R$^e$ and R$^f$, together with the nitrogen atom to which they are attached, form a pyrrolidine ring; and, R$^{e1}$ is H, methyl or ethyl;

R$^{f1}$ is H, methyl, ethyl, isopropyl, n-propyl, n-butyl, isobutyl, sec-butyl, tert-butyl, 2-fluoroethyl, 2,2,2-trifluoroethyl, cyclopropyl, cyclobutyl, 2-hydroxyethyl, 3-hydroxypropyl, 2-methoxyethyl, 3-methoxypropyl, 2-hydroxy-1-methylethyl, 2-methoxy-1-methylethyl, 2-hydroxy-2-methylethyl, 2-hydroxy-2,2-dimethylethyl, 2,3-dihydroxypropyl, cyclopropylmethyl, (1-(hydroxymethyl)cyclopropyl)methyl, 2-(hydroxymethyl)tetrahydrofuran-2-yl, or 1H-imidazol-4-ylethyl, 2-hydroxy-1,1-dimethylethyl, or 1-methylcyclopropyl; or R$^{e1}$ and R$^{f1}$, together with the nitrogen atom to which they are attached, form a group selected from azetidinyl, 3-hydroxy-azetidinyl, 3-fluoro-azetidinyl, pyrrolidinyl, 3-hydroxypyrrolidinyl, 3-fluoropyrrolidinyl, 2-(hydroxymethyl)pyrrolidinyl, and piperidinyl.

In some embodiments, the compound is a compound of Formula II, wherein:

R$^2$ is C$_{1-3}$ haloalkyl;

R$^4$ is selected from CN, Cy, OR$^a$, C(═O)OR$^a$, —CH$_2$OH, —CH$_2$CH$_2$OH, —C(CH$_3$)$_2$OH, —CH$_2$NR$^{e1}$R$^{f1}$, —C(Me)(OH)CH$_2$OH, —CH(Me)OH, —CH(Me)CH$_2$OH, —CH$_2$CH$_2$F, —C(CH$_3$)$_2$F, and C(═O)NR$^e$R$^f$;

Cy is 3-6-membered monocyclic cycloalkyl, which is optionally substituted by an R$^g$ group;

each R$^a$, R$^e$, and R$^f$ is independently H or C$_{1-6}$ alkyl; wherein said C$_{1-6}$ alkyl is optionally substituted with 1 or 2 independently selected R$^h$ groups; or each R$^e$ and R$^f$, together with the nitrogen atom to which they are attached, form a 4-6 membered monocyclic heterocycloalkyl ring;

R$^g$ is hydroxyl-C$_{1-4}$ alkyl;

each R$^h$ is independently hydroxy or C$_{1-4}$ alkoxy;

R$^{e1}$ is H or C$_{1-4}$ alkyl;

R$^{f1}$ is H, C$_{1-6}$ alkyl, C$_{1-6}$ haloalkyl, Cy$^2$, or —C$_{1-2}$ alkylene-Cy$^2$; wherein said C$_{1-6}$ alkyl is optionally substituted with 1 or 2 groups selected from —OH and —OCH$_3$;

or R$^{e1}$ and R$^{f1}$ together with the nitrogen atom to which they are attached form a 4-6-membered monocyclic heterocycloalkyl ring, which is optionally substituted by one —F, —OH, or —CH$_2$OH group; and Cy$^2$ is cyclopropyl, cyclobutyl, 5-membered monocyclic heterocycloalkyl, or 5-membered monocyclic heteroaryl; each of which is optionally substituted by a —CH$_2$OH group.

In some embodiments, the compound is a compound of Formula II, wherein:

R$^2$ is C$_{1-3}$ haloalkyl;

R$^4$ is selected from CN, Cy, OR$^a$, C(═O)OR$^a$, —CH$_2$OH, —CH$_2$CH$_2$OH, —C(CH$_3$)$_2$OH, —CH$_2$NR$^{e1}$R$^{f1}$, and C(═O)NR$^e$R$^f$;

Cy is cyclopropyl substituted by a —CH$_2$OH group;

each R$^a$, R$^e$, and R$^f$ is independently H, methyl, ethyl, —CH$_2$CH$_2$OH or —CH$_2$CH$_2$OCH$_3$; or R$^e$ and R$^f$, together with the nitrogen atom to which they are attached, form a pyrrolidine ring; and, R$^{e1}$ is H, methyl or ethyl;

R$^{f1}$ is H, methyl, ethyl, isopropyl, n-propyl, n-butyl, isobutyl, sec-butyl, tert-butyl, 2-fluoroethyl, 2,2,2-trifluoroethyl, cyclopropyl, cyclobutyl, 2-hydroxyethyl, 3-hydroxypropyl, 2-methoxyethyl, 3-methoxypropyl, 2-hydroxy-1-methylethyl, 2-methoxy-1-methylethyl, 2-hydroxy-2-methylethyl, 2-hydroxy-2,2-dimethylethyl, 2,3-dihydroxypropyl, cyclopropylmethyl, (1-(hydroxymethyl)cyclopropyl)methyl, 2-(hydroxymethyl)tetrahydrofuran-2-yl, or 1H-imidazol-4-ylethyl, 2-hydroxy-1,1-dimethylethyl, or 1-methylcyclopropyl; or R$^{e1}$ and R$^{f1}$, together with the nitrogen atom to which they are attached, form a group selected from azetidinyl, 3-hydroxy-azetidinyl, 3-fluoro-azetidinyl, pyrrolidinyl, 3-hydroxypyrrolidinyl, 3-fluoropyrrolidinyl, 2-(hydroxymethyl)pyrrolidinyl, and piperidinyl.

In some embodiments, the compound is a compound of Formula III:

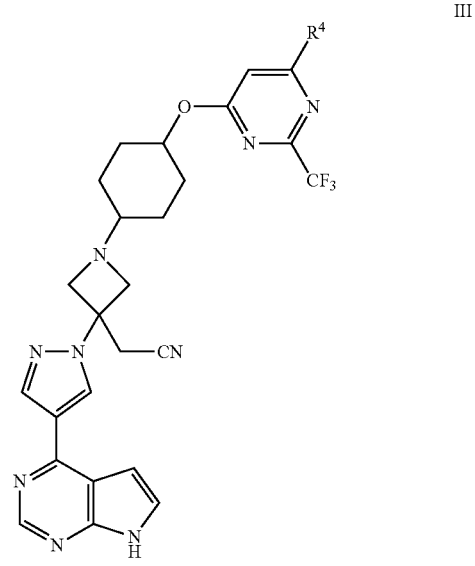

III or a pharmaceutically acceptable salt thereof.

In some embodiments, the compound is a compound of Formula III-A:

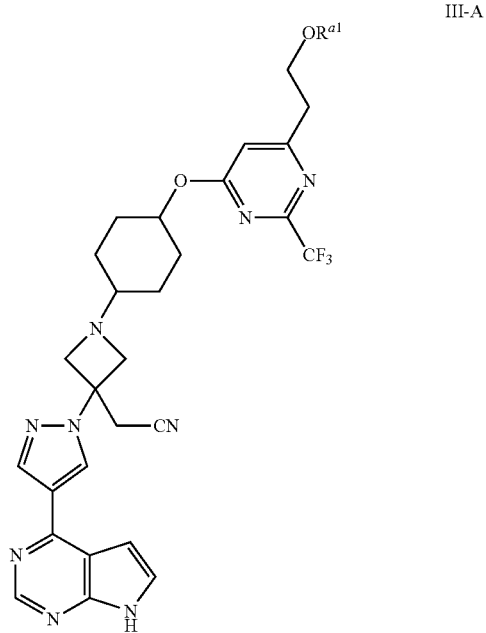

III-A or a pharmaceutically acceptable salt thereof.

In some embodiments, the compound is a compound of Formula III-A, wherein $R^{a1}$ is H, methyl or ethyl.

In some embodiments, the compound is a compound of Formula III-A, wherein $R^{a1}$ is H.

In some embodiments, the compound is a compound of Formula III-B:

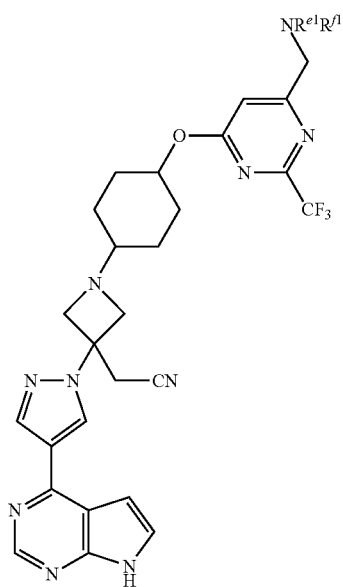

III-B or a pharmaceutically acceptable salt thereof.

In some embodiments, the compound is a compound of Formula I, wherein:
X is N;
Y is $CR^2$;
W is $CR^3$;
Z is $CR^4$;
V is $CR^5$;
$R^2$, $R^3$, $R^4$, and $R^5$ are each independently selected from H, halo, CN, $C_{1-6}$ alkyl, $C_{1-6}$ haloalkyl, Cy, $OR^a$, $C(=O)OR^a$, and $C(=O)NR^eR^f$; wherein said $C_{1-6}$ alkyl is optionally substituted by 1, 2, or 3 independently selected $R^x$ groups;

each Cy is independently selected from 3-6-membered monocyclic cycloalkyl, which is optionally substituted by 1, 2, or 3 independently selected $R^g$ groups;

each $R^a$, $R^e$, and $R^f$ is independently H, $C_{1-6}$ alkyl, or 3-6-membered monocyclic cycloalkyl; wherein said $C_{1-6}$ alkyl is optionally substituted with 1, 2, or 3 independently selected $R^h$ groups; or each $R^e$ and $R^f$, together with the nitrogen atom to which they are attached, form a 4-6 membered monocyclic heterocycloalkyl ring optionally substituted with 1, 2, or 3 independently selected $R^g$ groups;

each $R^g$ is independently selected from CN, hydroxy and hydroxyl-$C_{1-4}$ alkyl;

each $R^h$ is independently selected from halo, hydroxy, and $C_{1-4}$alkoxy;

each $R^x$ group is independently selected from $OR^{a1}$ and $NR^{e1}R^{f1}$;

each $R^{a1}$, $R^{e1}$, and $R^{f1}$ is independently selected from H, $C_{1-6}$ alkyl, $C_{1-6}$ haloalkyl, $Cy^2$, and $-C_{1-3}$ alkylene-$Cy^2$; wherein said $C_{1-6}$ alkyl is optionally substituted by 1, 2, or 3 independently selected $R^k$ groups; or each $R^{e1}$ and $R^{f1}$, together with the nitrogen atom to which they are attached, forms a 4-6 membered monocyclic heterocycloalkyl ring; which is optionally substituted with 1, 2, or 3 independently selected $R^m$ groups;

each $Cy^2$ is independently selected from 3-6-membered monocyclic cycloalkyl, 4-6 membered monocyclic heterocycloalkyl, and 5-6 membered monocyclic heteroaryl, which are each optionally substituted by 1, 2, or 3 independently selected $R^m$ groups;

each $R^k$ is independently selected from hydroxy, $C_{1-4}$ alkoxy, hydroxyl-$C_{1-4}$ alkyl, and $C_{1-4}$ alkoxy-$C_{1-4}$ alkyl; and each $R^m$ is independently selected from halo, hydroxy, $C_{1-4}$ alkoxy, hydroxyl-$C_{1-4}$ alkyl, and $C_{1-4}$ alkoxy-$C_{1-4}$ alkyl.

In some embodiments, the compound is a compound of Formula I, wherein:
X is N;
Y is $CR^2$;
W is $CR^3$;
Z is $CR^4$;
V is $CR^5$;
$R^2$, $R^3$, $R^4$, and $R^5$ are each independently selected from H, $-CF_3$, $-CH_2R^x$, $-C(CH_3)_2R^x$, and $C(=O)NR^eR^f$;

each $R^e$ and $R^f$ is independently H, $C_{1-6}$ alkyl, or 3-6-membered monocyclic cycloalkyl; wherein said $C_{1-6}$ alkyl is optionally substituted with an hydroxy group; or each $R^e$ and $R^f$, together with the nitrogen atom to which they are attached, form a 4-6 membered monocyclic heterocycloalkyl ring, wherein said 3-6-membered monocyclic cycloalkyl is optionally substituted with 1, 2, or 3 independently selected $R^g$ groups;

each $R^x$ group is independently selected from OH and $NR^{e1}R^{f1}$;

each $R^{e1}$, and $R^{f1}$ is independently selected from H, $C_{1-6}$ alkyl, $Cy^2$, and $-C_{1-3}$ alkylene-$Cy^2$; wherein said $C_{1-6}$ alkyl is optionally substituted with an hydroxy group; or each $R^{e1}$ and $R^{f1}$, together with the nitrogen atom to which they are attached, forms a 4-6 membered monocyclic heterocycloalkyl ring; which is optionally substituted with an hydroxy group; and, each $Cy^2$ is independently 3-6-membered monocyclic cycloalkyl.

In some embodiments, the compound is a compound of Formula IV:

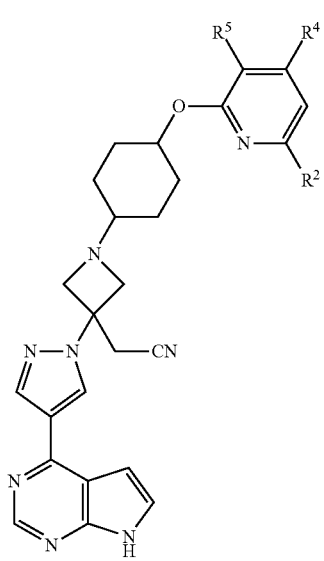

IV or a pharmaceutically acceptable salt thereof.

In some embodiments, the compound is a compound of Formula V:

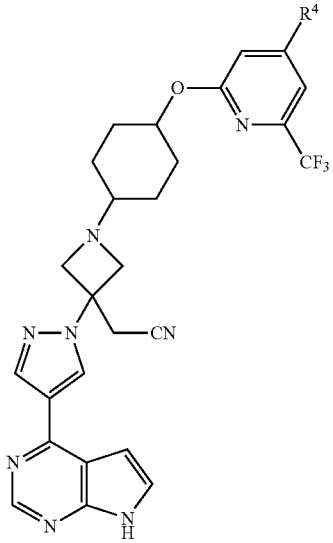

or a pharmaceutically acceptable salt thereof.

In some embodiments, the compound is a compound of Formula V, wherein:

$R^4$ is selected from —$CH_2OH$, —$C(CH_3)_2OH$, —$CH_2NR^{e1}R^{f1}$ and $C(=O)NR^eR^f$;

$R^{e1}$ is H, methyl or ethyl;

$R^{f1}$ is H, methyl, ethyl, isopropyl, n-propyl, n-butyl, isobutyl, tert-butyl, cyclopropyl, cyclobutyl, 2-hydroxyethyl, 3-hydroxypropyl, 2-hydroxy-1-methylethyl, or cyclopropylmethyl; or $R^{e1}$ and $R^{f1}$, together with the nitrogen atom to which they are attached, form a group selected from azetidinyl, 3-hydroxy-azetidinyl, 3-fluoro-azetidinyl, 3-cyano-azetidinyl, pyrrolidinyl, 3-hydroxypyrrolidinyl, 3-fluoropyrrolidinyl, 2-(hydroxymethyl)pyrrolidinyl, piperidinyl, 4-hydroxypiperidinyl, 3-methyloxetan-3-yl, pyrazolyl, and imidazolyl;

$R^e$ is H or methyl; and $R^f$ is H, methyl, ethyl, isopropyl, n-propyl, n-butyl, isobutyl, tert-butyl, cyclopropyl, or cyclobutyl; or $R^e$ and $R^f$, together with the nitrogen atom to which they are attached, form a group selected from azetidinyl, 3-hydroxy-azetidinyl, 3-fluoro-azetidinyl, 3-cyano-azetidinyl, pyrrolidinyl, 3-hydroxypyrrolidinyl, 3-fluoropyrrolidinyl, 2-(hydroxymethyl)pyrrolidinyl, and piperidinyl.

In some embodiments, the compound is a compound of Formula V-A:

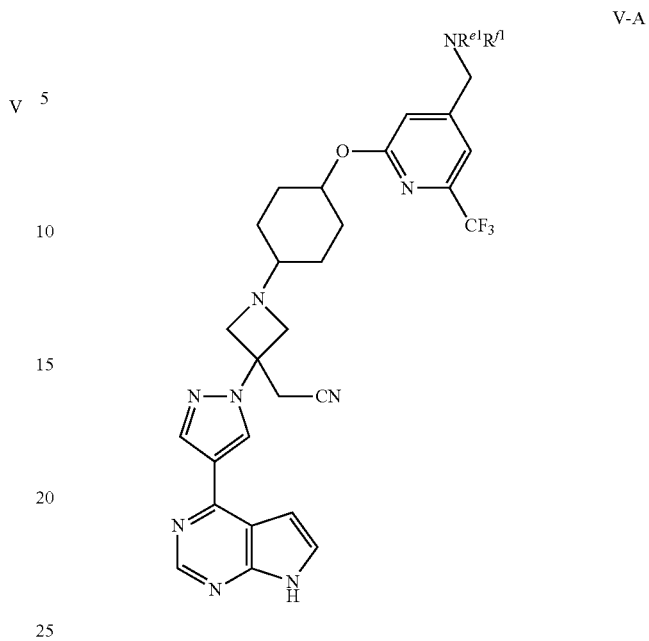

or a pharmaceutically acceptable salt thereof.

In some embodiments, the cyclohexyl ring in the formula has a cis-conformation.

In some embodiments, the compound is selected from:

{1-(cis-4-{[6-[(dimethylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-(hydroxymethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-(aminomethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-[(methylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-[(ethylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-[(isopropylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-[(cyclopropylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[ethyl(methyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[(cyclopropylmethyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-[(cyclobutylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[(2-hydroxyethyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[(2-hydroxyethyl)(methyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[ethyl(2-hydroxyethyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

[3-[4-(7H-pyrrolo[2,3-d]pyrimidin-4-yl)-1H-pyrazol-1-yl]-1-(cis-4-{[6-{[(2,2,2-trifluoroethyl)amino]methyl}-2-(trifluoromethyl)pyrimidin-4-yl]oxy}cyclohexyl)azetidin-3-yl]acetonitrile;

{1-(cis-4-{[6-{[(2-fluoroethyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-({[(1S)-2-hydroxy-1-methylethyl]amino}methyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-({[(1R)-2-hydroxy-1-methylethyl]amino}methyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-({[(2S)-2-hydroxypropyl]amino}methyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-({[(2R)-2-hydroxypropyl]amino}methyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[(2-hydroxy-2-methylpropyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[(3-hydroxypropyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[(2-methoxyethyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-(azetidin-1-ylmethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-[(3-hydroxyazetidin-1-yl)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-(pyrrolidin-1-ylmethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-[(3S)-3-hydroxypyrrolidin-1-yl]methyl-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

[3-[4-(7H-pyrrolo[2,3-d]pyrimidin-4-yl)-1H-pyrazol-1-yl]-1-(cis-4-{[6-({[(2S)-tetrahydrofuran-2-ylmethyl]amino}methyl)-2-(trifluoromethyl)pyrimidin-4-yl]oxy}cyclohexyl)azetidin-3-yl]acetonitrile;

{1-(cis-4-{[6-{[(2R)-2-(hydroxymethyl)pyrrolidin-1-yl]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[(2S)-2-(hydroxymethyl)pyrrolidin-1-yl]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-(piperidin-1-ylmethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[(3S)-3-fluoropyrrolidin-1-yl]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-[(propylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[(2,3-dihydroxypropyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-[(butylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-[(isobutylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[butyl(methyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-[(3-fluoroazetidin-1-yl)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-[({[1-(hydroxymethyl)cyclopropyl]methyl}amino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

2-(1-(cis-4-((6-(((2-(1H-imidazol-4-yl)ethyl)amino)methyl)-2-(trifluoromethyl)pyrimidin-4-yl)oxy)cyclohexyl)-3-(4-(7H-pyrrolo[2,3-d]pyrimidin-4-yl)-1H-pyrazol-1-yl)azetidin-3-yl)acetonitrile;

{1-(cis-4-{[6-{[(3-methoxypropyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[(2-methoxy-1-methylethyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[(2-methoxyethyl)(methyl)amino]methyl}-2-(trifluoromethyl)pyrimidin-4-yl]oxy}cyclohexyl)-3-[4-(7H-pyrrolo[2,3-d]pyrimidin-4-yl)-1,1-pyrazol-1-yl]azetidin-3-yl}acetonitrile;

{1-(cis-4-{[6-(1-hydroxy-1-methylethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile; and {1-(cis-4-{[6-[(tert-butylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

or a pharmaceutically acceptable salt thereof.

In some embodiments, the compound is selected from:

6-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-ethyl-2-(trifluoromethyl)pyrimidine-4-carboxamide;

{1-(cis-4-{[6-(pyrrolidin-1-ylcarbonyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[(2-hydroxy-1,1-dimethylethyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[(1-methylcyclopropyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

6-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-2-(trifluoromethyl)pyrimidine-4-carbonitrile;

{1-(cis-4-{[6-(2-hydroxyethoxy)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-(1,2-dihydroxy-1-methylethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-(1-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-(2-hydroxy-1-methylethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-(1-fluoro-1-methylethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-(2-hydroxy-1,1-dimethylethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-[1-(hydroxymethyl)cyclopropyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

6-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N,N-dimethyl-2-(trifluoromethyl)pyrimidine-4-carboxamide;

6-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-ethyl-N-methyl-2-(trifluoromethyl)pyrimidine-4-carboxamide;

6-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-(2-methoxyethyl)-2-(trifluoromethyl)pyrimidine-4-carboxamide;

{1-(cis-4-{[6-(2-fluoroethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-(hydroxymethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-(aminomethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-[(methylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-[(dimethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-{[(3-hydroxypropyl)amino]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-{[(2-hydroxy-1,1-dimethylethyl)amino]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-[(cyclopropylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-({[(1S)-2-hydroxy-1-methylethyl]amino}methyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-{[(2-hydroxyethyl)amino]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-({[(1R)-2-hydroxy-1-methylethyl]amino}methyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-{[(cyclopropylmethyl)amino]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-[(cyclobutylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-(azetidin-1-ylmethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-[(3-hydroxyazetidin-1-yl)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-methyl-6-(trifluoromethyl)isonicotinamide;

2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N,N-dimethyl-6-(trifluoromethyl)isonicotinamide;

2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-(2-hydroxyethyl)-N-methyl-6-(trifluoromethyl)isonicotinamide;

2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-isopropyl-6-(trifluoromethyl)isonicotinamide;

2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-[(1S)-2-hydroxy-1-methylethyl]-6-(trifluoromethyl)isonicotinamide;

2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-[(1R)-2-hydroxy-1-methylethyl]-6-(trifluoromethyl)isonicotinamide;

2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-cyclopropyl-6-(trifluoromethyl)isonicotinamide;

2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-cyclopropyl-N-methyl-6-(trifluoromethyl)isonicotinamide;

N-(sec-butyl)-2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-6-(trifluoromethyl)isonicotinamide;

{1-(cis-4-{[4-[(3-hydroxyazetidin-1-yl)carbonyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-cyclobutyl-6-(trifluoromethyl)isonicotinamide;

1-[2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-6-(trifluoromethyl)isonicotinoyl]azetidine-3-carbonitrile;

{1-(cis-4-{[4-(morpholin-4-ylmethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-{[(2R)-2-(hydroxymethyl)pyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-{[(2S)-2-(hydroxymethyl)pyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-[(4-hydroxypiperidin-1-yl)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-{[(3-methyloxetan-3-yl)amino]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-(1H-imidazol-1-ylmethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-(1H-pyrazol-1-ylmethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

or a pharmaceutically acceptable salt thereof.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. It is specifically intended that each linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups. For example, if the structure requires a linking group and the Markush group definition for that variable lists "alkyl" or "aryl" then it is to be understood that the "alkyl" or "aryl" represents a linking alkylene group or arylene group, respectively.

At various places in the present specification, rings are described (e.g., "a piperidine ring"). Unless otherwise specified, these rings can be attached to the rest of the molecule at any ring member as permitted by valency. For example, the term "a pyridine ring" may refer to a pyridin-2-yl, pyridin-3-yl, or pyridin-4-yl ring.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

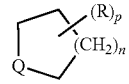

then it is to be understood that substituent R can occur p number of times on the ring, and R can be a different moiety at each occurrence. It is to be understood that each R group may replace any hydrogen atom attached to a ring atom, including one or both of the $(CH_2)_n$ hydrogen atoms. Further, in the above example, should the variable Q be defined to include hydrogens, such as when Q is said to be $CH_2$, NH, etc., any floating substituent such as R in the above example, can replace a hydrogen of the Q variable as well as a hydrogen in any other non-variable component of the ring.

As used herein, the phrase "optionally substituted" means unsubstituted or substituted. As used herein, the term "substituted" means that a hydrogen atom is removed and replaced by a substituent. It is to be understood that substitution at a given atom is limited by valency.

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 6, 1 to 4 or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like.

As used herein, the term "alkylene", employed alone or in combination with other terms, refers to a divalent alkyl linking group. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, "$C_{n-m}$ alkenyl" refers to an alkyl group having one or more double carbon-carbon bonds and having n to m carbons. In some embodiments, the alkenyl moiety contains 2 to 6 or to 2 to 4 carbon atoms. Example alkenyl groups include, but are not limited to, ethenyl, n-propenyl, isopropenyl, n-butenyl, sec-butenyl, and the like.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, the term "amino" refers to a group of formula —$NH_2$.

As used herein, the term "$C_{n-m}$ alkylamino" refers to a group of formula —NH(alkyl), wherein the alkyl group has n to m carbon atoms. In some embodiments, the alkyl group has 1 to 6 or 1 to 4 carbon atoms.

As used herein, the term "di-$C_{n-m}$-alkylamino" refers to a group of formula —N(alkyl)$_2$, wherein the two alkyl groups each has, independently, n to m carbon atoms. In some embodiments, each alkyl group independently has 1 to 6 or 1 to 4 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6 or 1 to 4 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6 or 1 to 4 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6 or 1 to 4 carbon atoms.

As used herein, the term "$C_{n-m}$ alkylcarbonyloxy" refers to a group of formula —OC(O)-alkyl, wherein the alkyl group has n to m carbon atoms. In some embodiments, the alkyl group has 1 to 6 or 1 to 4 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6 or 1 to 4 carbon atoms.

As used herein, the term "carbamyl" refers to a group of formula —C(O)—$NH_2$.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6 or 1 to 4 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6 or 1 to 4 carbon atoms.

As used herein, the term "$C_{1-4}$ alkylsulfonylamino" refers to a group of formula —NHS(O)$_2$-alkyl, wherein said alkyl has 1 to 4 carbon atoms.

As used herein, the term "aminosulfonyl" refers to a group of formula —S(O)$_2NH_2$.

As used herein, the term "$C_{1-4}$ alkylaminosulfonyl" refers to a group of formula —S(O)$_2$NH(alkyl), wherein said alkyl has 1 to 4 carbon atoms.

As used herein, the term "di-$C_{1-4}$ alkylaminosulfonyl" refers to a group of formula —S(O)$_2$N(alkyl)$_2$, wherein each alkyl independently has 1 to 4 carbon atoms.

As used herein, the term "aminosulfonylamino" refers to a group of formula —NHS(O)$_2NH_2$, wherein said alkyl has 1 to 4 carbon atoms.

As used herein, the term "$C_{1-4}$ alkylaminosulfonylamino," refers to a group of formula —NHS(O)$_2$NH(alkyl), wherein said alkyl has 1 to 4 carbon atoms.

As used herein, the term "di-$C_{1-4}$ alkylaminosulfonylamino" refers to a group of formula —NHS(O)$_2$N(alkyl)$_2$, wherein each alkyl independently has 1 to 4 carbon atoms.

As used herein, the term "hydroxyl-$C_{n-m}$-alkyl" refers to a group of formula -alkylene-OH, wherein said alkylene group has n to m carbon atoms. In some embodiments, the alkylene group has 1 to 6 or 1 to 4 carbon atoms.

As used herein, the term "$C_{o-p}$ alkoxy-$C_{n-m}$-alkyl" refers to a group of formula -alkylene-O-alkyl, wherein said alkylene group has n to m carbon atoms and said alkyl group has o to p carbon atoms. In some embodiments, the alkyl and alkylene groups each independently have 1 to 6 or 1 to 4 carbon atoms.

As used herein, the term "carbonyl", employed alone or in combination with other terms, refers to a —C(O)— group.

As used herein, "halo" or "halogen", employed alone or in combination with other terms, includes fluoro, chloro, bromo, and iodo.

As used herein, the term "$C_{n-m}$ haloalkyl", employed alone or in combination with other terms, refers to an $C_{n-m}$ alkyl group having up to {2(n to m)+1} halogen atoms which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like. In some embodiments, the haloalkyl group is a fluoroalkyl group.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6 or 1 to 4 carbon atoms.

As used herein, the term "$C_{n-m}$ fluoroalkyl" refers to a $C_{n-m}$ haloalkyl wherein the halogen atoms are selected from fluorine. In some embodiments, fluorinated $C_{n-m}$ haloalkyl is fluoromethyl, difluoromethyl, or trifluoromethyl. In some embodiments, the alkyl group has 1 to 6 or 1 to 4 carbon atoms.

As used herein, the term "cyano-$C_{n-m}$ alkyl" refers to a $C_{n-m}$ alkyl substituted by a cyano group. In some embodiments, the alkyl group has 1 to 6 or 1 to 4 carbon atoms.

As used herein, the appearance of the term "monocyclic" before the name of a moiety indicates that the moiety has a single ring.

As used herein, the term "monocyclic cycloalkyl", employed alone or in combination with other terms, refers to a non-aromatic monocyclic hydrocarbon which may include cyclized alkyl and/or alkenyl groups. One or more ring-forming carbon atoms of a cycloalkyl group can be optionally substituted by oxo. In some embodiments, the cycloalkyl group has 3, 4, 5, or 6 ring members, 3 to 5 ring members, or 3 to 4 ring members. Example cycloalkyl groups include cyclopropyl, cyclobutyl, cyclopentyl, cyclohexyl, cyclopentenyl, cyclohexenyl, cyclohexadienyl, and the like.

As used herein, the term "monocyclic heterocycloalkyl", employed alone or in combination with other terms, refers to non-aromatic monocyclic, which may optionally contain one or more alkenylene groups as part of the ring structure and which has at least one heteroatom ring member independently selected from nitrogen, sulfur, and oxygen. One or more carbon atoms or heteroatoms in the ring(s) of the heterocycloalkyl group can be oxidized to form a carbonyl, an N-oxide, or a sulfonyl group (or other oxidized linkage), or a nitrogen atom can be quaternized. In some embodiments, the heterocycloalkyl group is a monocyclic group having 1, 2, or 3 heteroatoms independently selected from nitrogen, sulfur and oxygen. In some embodiments, the heterocycloalkyl group has 4, 5, or 6 ring members or 5-6 ring members. In some embodiments, the heterocycloalkyl group is a 6-membered ring, a 5-membered ring, or a 4-membered ring. Examples of heterocycloalkyl groups include azetidine, pyrrolidine, piperidine, piperazine, morpholine, thiomorpholine, tetrahydrofuran, and pyran.

As used herein, the term "monocyclic heteroaryl", employed alone or in combination with other terms, refers to a monocyclic aromatic hydrocarbon moiety having at least one heteroatom ring member. In some embodiments, the heteroaryl group has 1, 2, or 3 hetereoatoms independently selected from nitrogen, sulfur and oxygen. In some embodiments, the heteroaryl ring has 5 or 6 ring members. In some embodiments, the heteroaryl is a 5-membered heteroaryl ring. In some embodiments, the heteroaryl is a 6-membered heteroaryl ring. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, thiazole, imidazole, furan, thiophene, or the like.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. In some embodiments, 1, 2, or 3 $CH_2$ groups in the azetidine ring of Formula I are replaced by a CHD or $CD_2$ group. In some embodiments, 1, 2, or 3 $CH_2$ or CH groups in the piperidine ring of Formula I are replaced by a CHD, $CD_2$ or CD group, respectively. In some embodiments, 1, 2, 3, 4, or 5 $CH_2$ or CH groups in the piperidine ring of Formula I are replaced by a CHD, $CD_2$ or CD group, respectively.

The term, "compound," as used herein is meant to include all stereoisomers, geometric isomers, tautomers, and isotopes of the structures depicted.

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. In some embodiments, the compounds described herein include the N-oxide forms.

Synthesis

Compounds of the invention, including salts and N-oxides thereof, can be prepared using known organic synthesis techniques and can be synthesized according to any of numerous possible synthetic routes, such as those in the Schemes below. The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2007), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Compounds of Formula I can be synthesized by procedures analogous to those in Scheme I. For example, the appropriate ketone 1 may be reacted with an azetidine 2, or hydrochloride salt thereof (prepared by the procedures summarized in US 2009/0233903, which is incorporated by reference herein in its entirety) in the presence of a reducing agent such as NaB(OAc)$_3$ to give a mixture of diastereomeric alcohols 3. The diastereomers can be separated by liquid chromatography (LC) (e.g., at pH 10) and then deprotected (e.g., by treatment with trifluoroacetic acid in dichloromethane, followed by solvent and trifluoroacetic acid (TFA) removal and treatment with concentrated ammonium hydroxide in methanol) to afford the corresponding compound of Formula I.

Scheme I

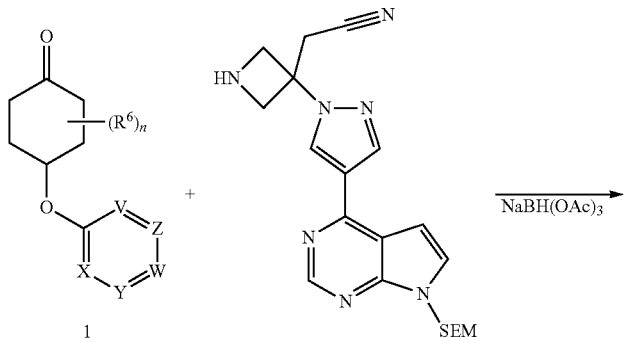

-continued

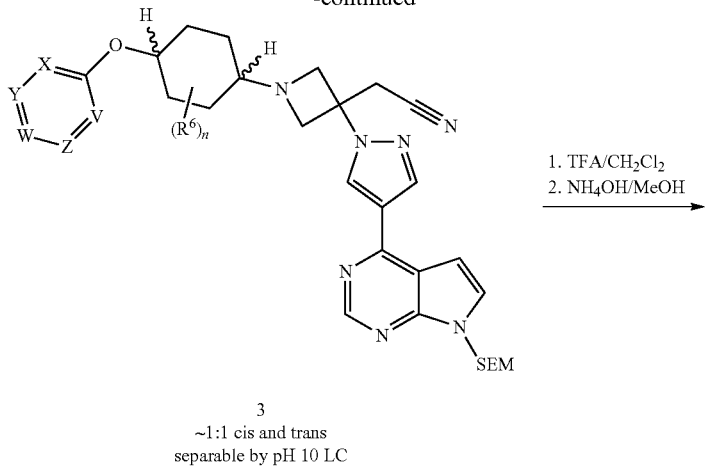

3
~1:1 cis and trans
separable by pH 10 LC

1. TFA/CH$_2$Cl$_2$
2. NH$_4$OH/MeOH

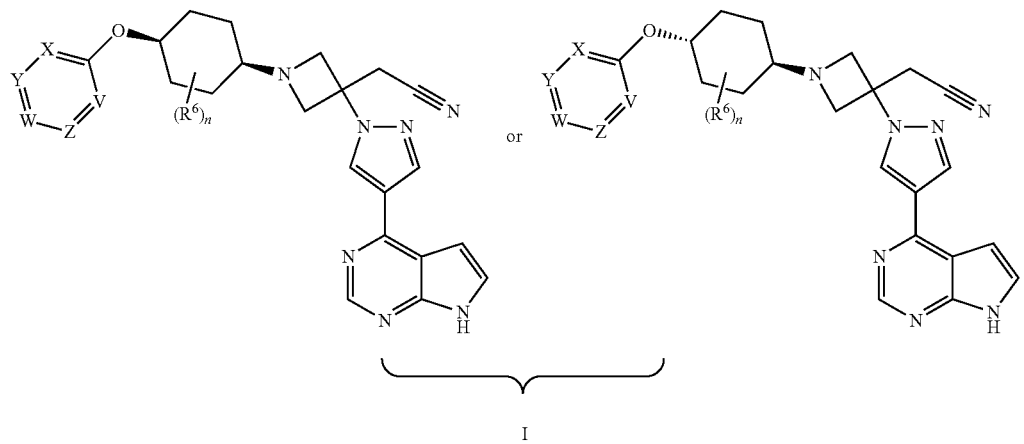

I

Compounds of formula 1 can be formed by procedures analogous to those in Scheme II. For example, 1,4-dioxaspiro[4.5]decan-8-ol 4 can be reacted with an appropriate halide 5 in the presence of a strong base such as sodium hydride in an aprotic solvent to give the ether 6. Ether 6 may then be converted to the ketone 1 by acid hydrolysis.

Scheme II

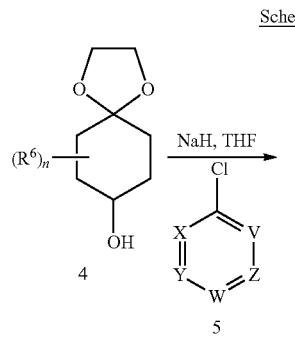

-continued

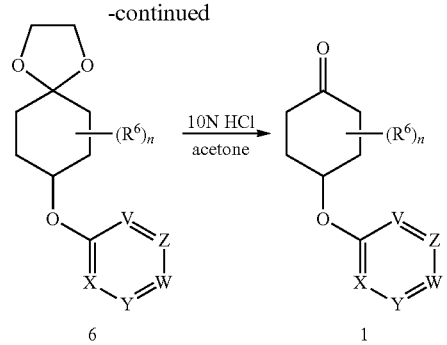

Specific compounds of Formula I, wherein X and W are N, Y is C(CF$_3$), V is CH, Z is C(CH$_2$OH), and n is 0, can be formed as shown in Scheme III. For example, 1,4-dioxaspiro[4.5]decan-8-ol 7 may be reacted with 4,6-dichloro-2-(trifluoromethyl)-pyrimidine 8 in the presence of a strong base such as sodium hydride in an aprotic solvent to give the chloropyrimidine ether 9. This can be reacted with an organometalic reagent such as 10 in the presence of a palladium catalyst to give vinyl ether 11. Alkene 11 can be cleaved to the aldehyde 12 with NaIO$_4$ and catalytic amount of OsO$_4$. Aldehyde 12 can be reduced to the corresponding alcohol 13 via a hydride reagent such as NaBH$_4$ and 13 may then be converted to the ketone 14 by acid hydrolysis.

Scheme III

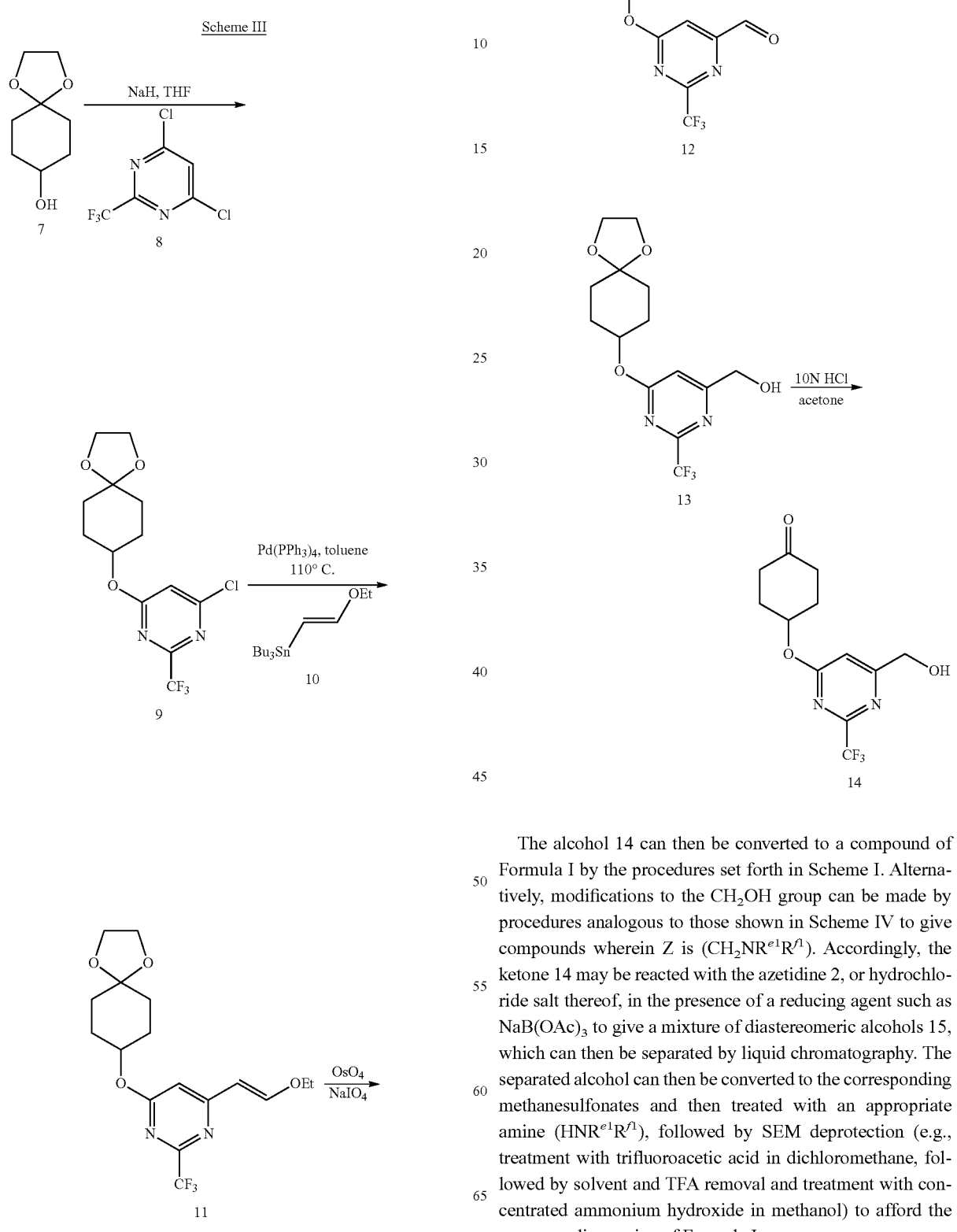

The alcohol 14 can then be converted to a compound of Formula I by the procedures set forth in Scheme I. Alternatively, modifications to the CH$_2$OH group can be made by procedures analogous to those shown in Scheme IV to give compounds wherein Z is (CH$_2$NR$^{e1}$R$^{f1}$). Accordingly, the ketone 14 may be reacted with the azetidine 2, or hydrochloride salt thereof, in the presence of a reducing agent such as NaB(OAc)$_3$ to give a mixture of diastereomeric alcohols 15, which can then be separated by liquid chromatography. The separated alcohol can then be converted to the corresponding methanesulfonates and then treated with an appropriate amine (HNR$^{e1}$R$^{f1}$), followed by SEM deprotection (e.g., treatment with trifluoroacetic acid in dichloromethane, followed by solvent and TFA removal and treatment with concentrated ammonium hydroxide in methanol) to afford the corresponding amine of Formula I.

Scheme IV

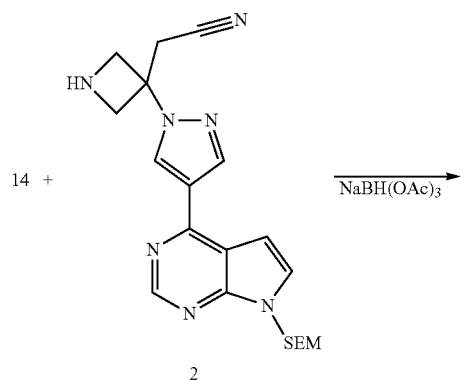

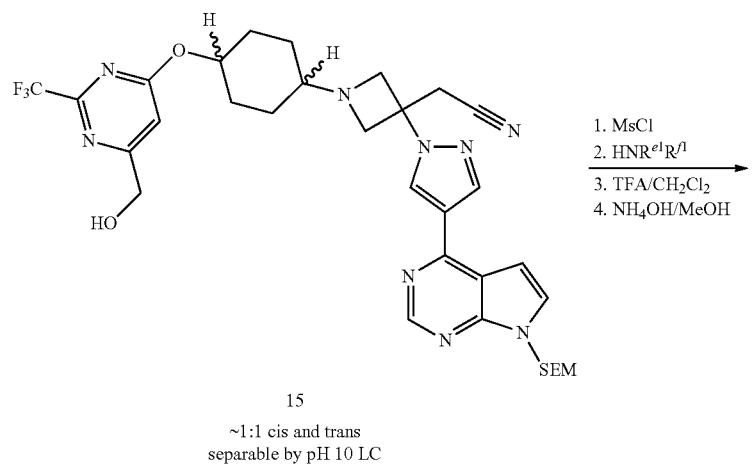

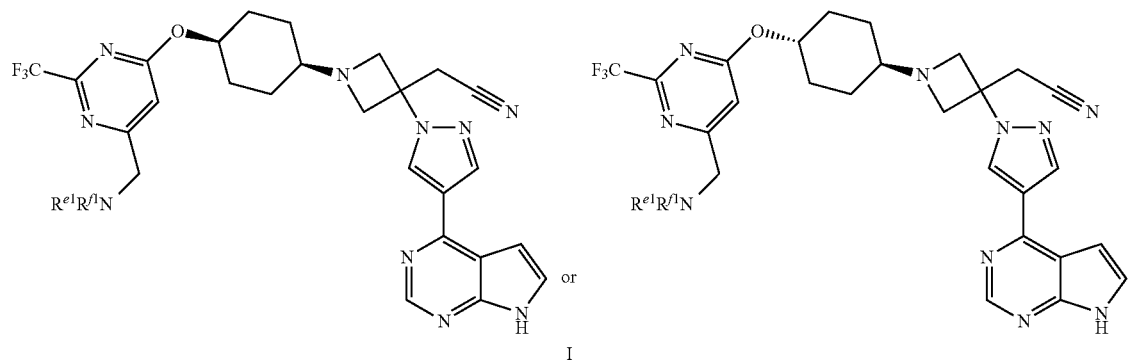

Specific compounds of Formula I, wherein X and W are N, Y is C(CF$_3$), V is CH, Z is C(CH$_2$CH$_2$OH), and n is 0, can be formed as shown in Scheme V. Reaction of ether 9, described in Scheme III with ethyl malonate in the presence of a base in an aprotic solvent such as tetrahydrofuran can afford the corresponding adduct 16A which can be decarboxylated to the ester 16B. Ester 16B can be reduced to the corresponding alcohol 17 using a reducing agent such as sodium borohydride. The ketal group on alcohol 17 can be hydrolyzed to the corresponding ketone 18 which can be coupled with azetidine 2 under reductive conditions to give alcohol 19 after purification. Alcohol 19 can be deprotected to a desired compound 20 under standard conditions.

Scheme V

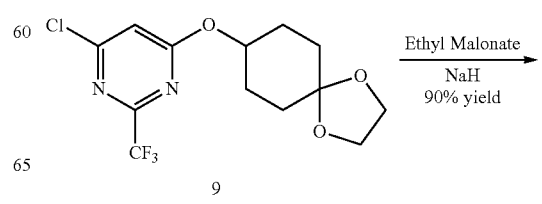

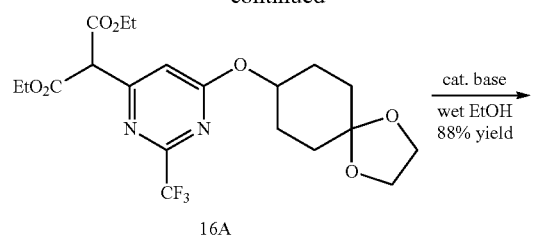

16A

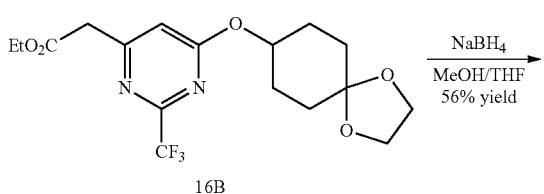

16B

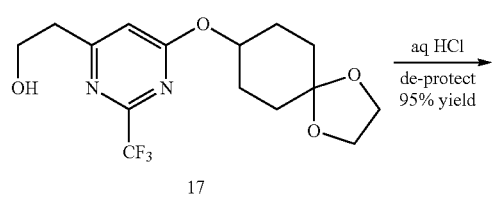

17

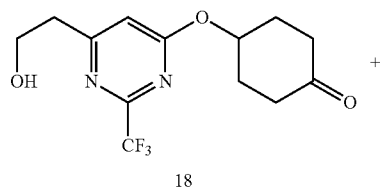

18

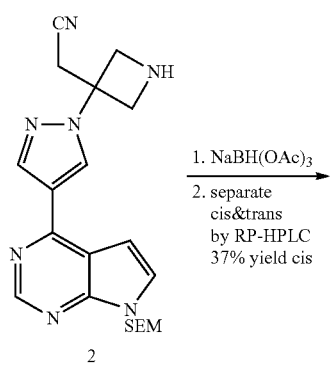

2

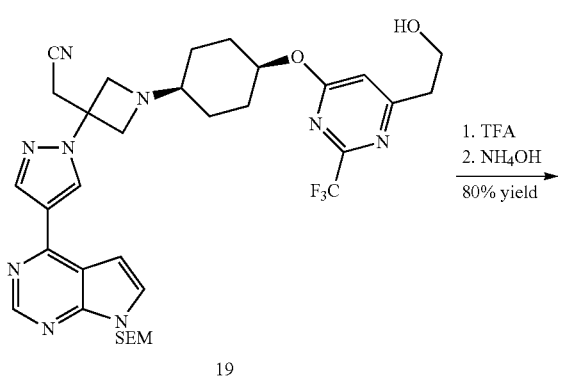

19

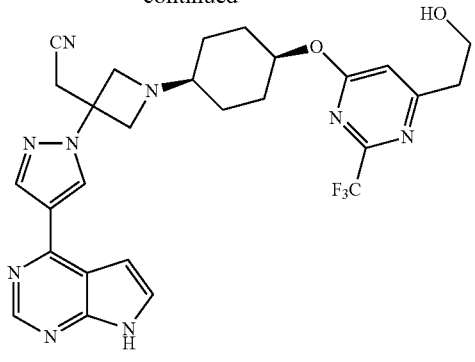

20

Compounds with a higher oxidation state at Z on the hetero aromatic ring of Formula I can be obtained via a route in Scheme VI. Compound 11 can be oxidized with an oxidizing agent such as KMnO₄ to give the corresponding carboxylic acid 21 which can be transformed to the ketone 22 by acid hydrolysis of the ketal group. Modifications to the CO₂H group can be made by procedures analogous to those shown in Scheme VII to give compounds wherein Z is $C(CONR^{e1}R^{f1})$.

Scheme VI

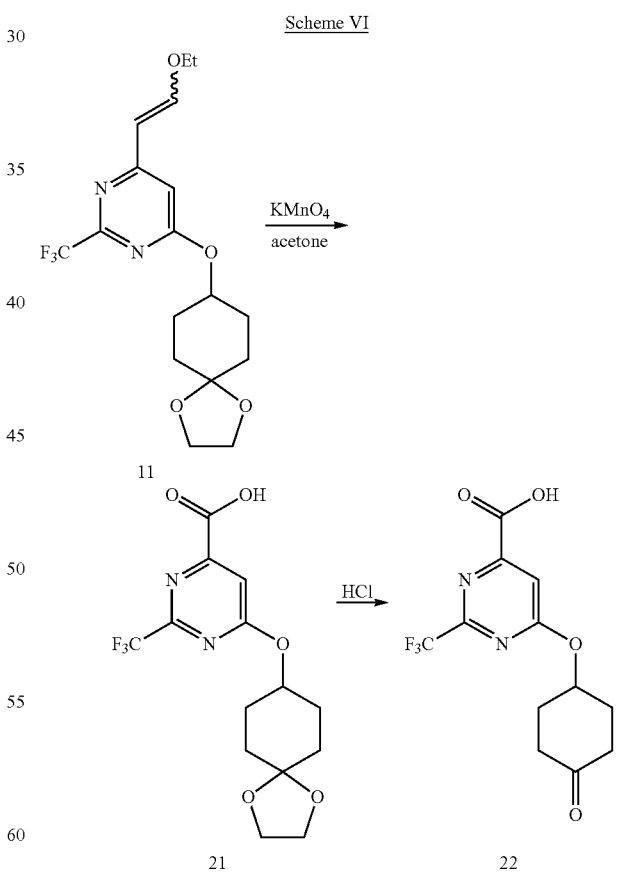

Accordingly, the ketone 22 may be reacted with the azetidine 2, or hydrochloride salt thereof, in the presence of a reducing agent such as NaB(OAc)₃ to give a mixture of diastereomeric alcohols 23, which can then be separated by liquid chromatography. The separated carboxylic acids can then be converted to the corresponding amides upon treatment with an appropriate amine (HNR$^{e1}$R$^{f1}$), in the presence of a coupling agent such as HATU followed by SEM deprotection (e.g., treatment with trifluoroacetic acid in dichloromethane, followed by solvent and TFA removal and treatment with concentrated ammonium hydroxide in methanol) to afford the corresponding amides of Formula I. (Scheme VII).

Scheme VII

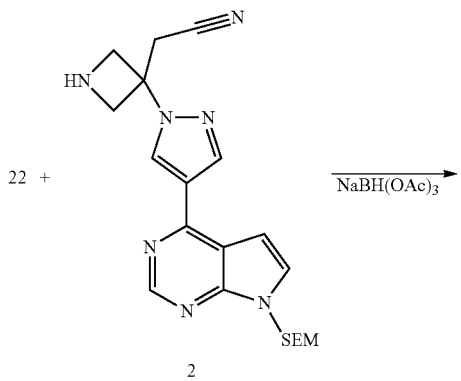

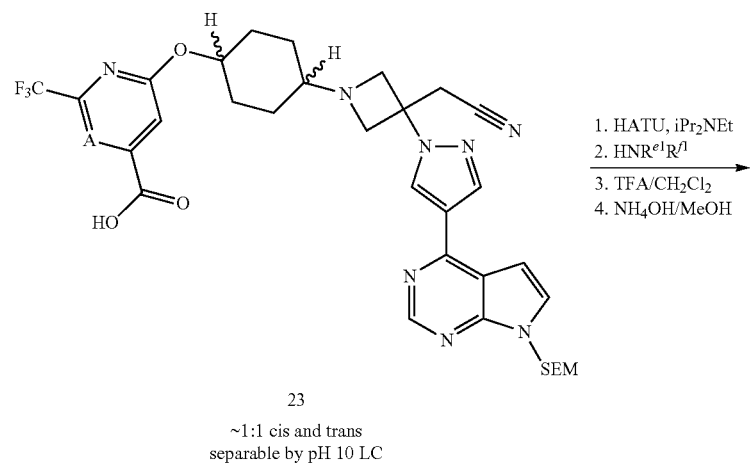

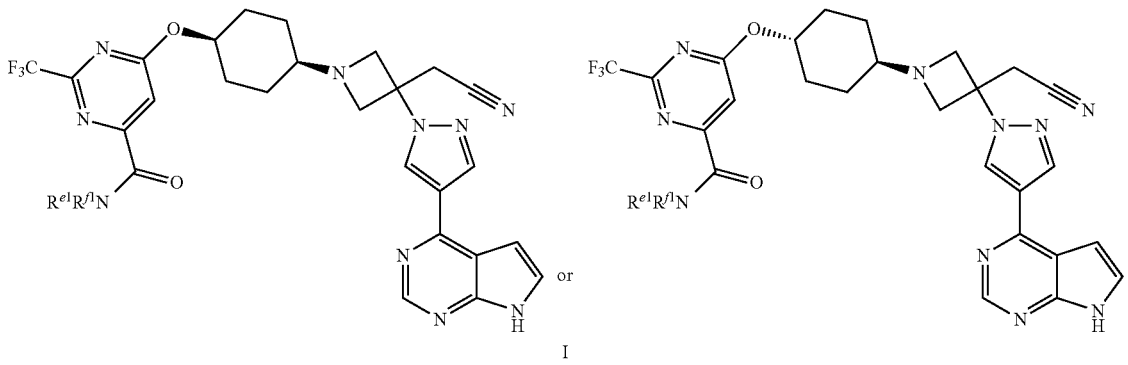

Specific compounds of Formula I, wherein X is N, V and W are CH, Y is C(CF$_3$), Z is CMe$_2$OH, and n is 0, can be formed as shown in Scheme VIII.

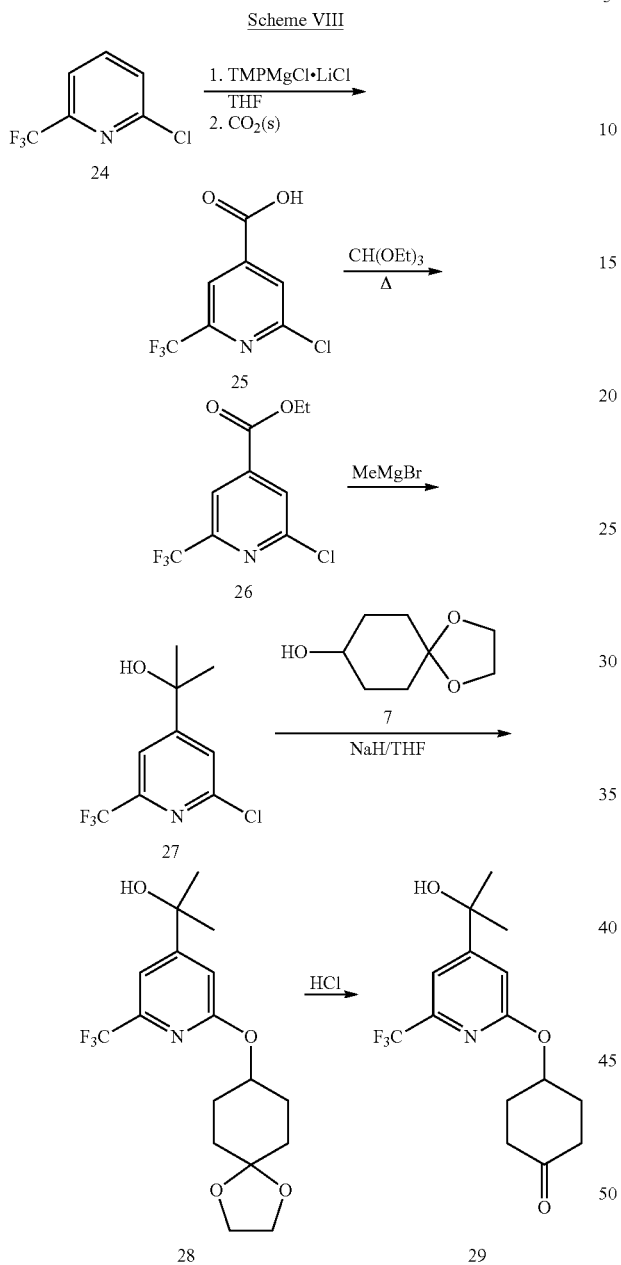

Deprotonation of 2-chloro-6-trifluoromethylpyridine 24 with 1.0 M lithium chloride-chloro(2,2,6,6-tetramethylpiperidin-1-yl)magnesium (1:1) in THF in an aprotic solvent such as THF, followed by addition of solid carbon dioxide afforded the 4-carboxylic acid 25 along with a regioisomeric carboxylic acid in a ratio of 2:1. The mixture can be converted to the corresponding ethyl esters by heating in ethyl orthoformate and the two esters can be separated by silica gel chromatography to give 26. Compound 26 can be treated with an excess solution of MeMgBr to give the corresponding alcohol 27, which can be reacted with the alcoxide of 1,4-dioxaspiro[4.5]decan-8-ol 7 to give the ether 28. The ketal group on 28 can be hydrolyzed under acidic conditions to give ketone 29.

The ketone 29 can then be converted to a compound of Formula I by the procedures set forth in Scheme I Specific compounds of Formula I, wherein X is N; V and W are CH; Y is C(CF$_3$); Z is CH$_2$OH, and n is 0, can be formed as shown in Scheme IX. For example, deprotonation of 2-chloro-6-trifluoromethylpyridine 24 with 1.0 M lithium chloride-chloro(2,2,6,6-tetramethylpiperidin-1-yl)magnesium (1:1) in THF in an aprotic solvent such as THF, followed by addition of addition of di-tert-butyldicarbonate afforded the tert-butylester 30 and a regioisomeric tert-butylester in a 3:1 ratio. Ester 30 can be purified by silica gel chromatography and can be treated with the sodium salt of cyclohexanol 7 in a manner similar to Scheme I to give the carboxylic acid 31 after addition of water upon completion of the reaction. The carboxylic acid 31 can be converted to the alcohol 32 by a reducing agent such as borane and the ketal group of alcohol 32 can be hydrolyzed with acid to give ketone 33. The ketone 33 can then be converted to a compound of Formula I by the procedures set forth in Scheme I

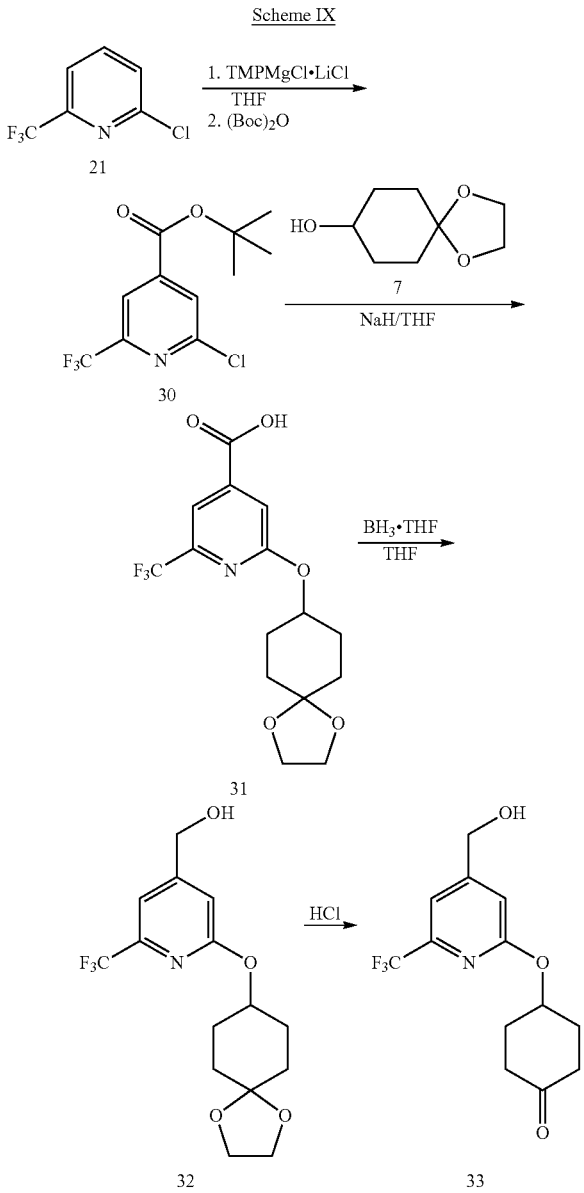

Alternatively, modifications to the CH$_2$OH group can be made by procedures analogous to those shown in Scheme IV to give compounds wherein Z is (CH$_2$NR$^{e1}$R$^{f1}$). Accordingly, the ketone 33 may be reacted with the azetidine 2, or hydrochloride salt thereof, in the presence of a reducing agent such as NaB(OAc)$_3$ to give a mixture of diastereomeric alcohols similar to 15 (except that the pyrimidine ring on the cyclohexane is replaced with a pyridine ring), which can then be separated by liquid chromatography. The separated alcohol can then be converted to the corresponding methanesulfonates and then treated with an appropriate amine (HNR$^{e1}$R$^{f1}$), followed by SEM deprotection (e.g., treatment with trifluoroacetic acid in dichloromethane, followed by solvent and TFA removal and treatment with concentrated ammonium hydroxide in methanol) to afford a corresponding amine of Formula I.

Methods

Compounds of the invention are JAK inhibitors, and the majority of the compounds of the invention, are JAK1 selective inhibitors. A JAK1 selective inhibitor is a compound that inhibits JAK1 activity preferentially over other Janus kinases. For example, the compounds of the invention preferentially inhibit JAK1 over one or more of JAK2, JAK3, and TYK2. In some embodiments, the compounds inhibit JAK1 preferentially over JAK2 (e.g., have a JAK1/JAK2 IC$_{50}$ ratio>1). In some embodiments, the compounds are about 10-fold more selective for JAK1 over JAK2. In some embodiments, the compounds are about 3-fold, about 5-fold, about 10-fold, about 15-fold, or about 20-fold more selective for JAK1 over JAK2 as calculated by measuring IC$_{50}$ at 1 mM ATP (e.g., see Example A).

JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, J. E. et al., Autoimmunity Reviews, 8:538-42, 2009). Because IL-6 signals, at least in part, through JAK1, antagonizing IL-6 directly or indirectly through JAK1 inhibition is expected to provide clinical benefit (Guschin, D., N., et al Embo J 14:1421, 1995; Smolen, J. S., et al. Lancet 371:987, 2008). Moreover, in some cancers JAK1 is mutated resulting in constitutive undesirable tumor cell growth and survival (Mullighan C G, Proc Natl Acad Sci USA. 106:9414-8, 2009; Flex E., et al. J Exp Med. 205:751-8, 2008). In other autoimmune diseases and cancers elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases.

Selective inhibitors of JAK1, relative to other JAK kinases, may have multiple therapeutic advantages over less selective inhibitors. With respect to selectivity against JAK2, a number of important cytokines and growth factors signal through JAK2 including, for example, erythropoietin (Epo) and thrombopoietin (Tpo) (Parganas E, et al. Cell. 93:385-95, 1998). Epo is a key growth factor for red blood cells production; hence a paucity of Epo-dependent signaling can result in reduced numbers of red blood cells and anemia (Kaushansky K, NEJM 354:2034-45, 2006). Tpo, another example of a JAK2-dependent growth factor, plays a central role in controlling the proliferation and maturation of megakaryocytes—the cells from which platelets are produced (Kaushansky K, NEJM 354:2034-45, 2006). As such, reduced Tpo signaling would decrease megakaryocyte numbers (megakaryocytopenia) and lower circulating platelet counts (thrombocytopenia). This can result in undesirable and/or uncontrollable bleeding. Reduced inhibition of other JAKs, such as JAK3 and Tyk2, may also be desirable as humans lacking functional version of these kinases have been shown to suffer from numerous maladies such as severe-combined immunodeficiency or hyperimmunoglobulin E syndrome (Minegishi, Y, et al. Immunity 25:745-55, 2006; Macchi P, et al. Nature. 377:65-8, 1995). Therefore a JAK1 inhibitor with reduced affinity for other JAKs would have significant advantages over a less-selective inhibitor with respect to reduced side effects involving immune suppression, anemia and thrombocytopenia.

Another aspect of the present invention pertains to methods of treating a JAK-associated disease or disorder in an individual (e.g., patient) by administering to the individual in need of such treatment a therapeutically effective amount or dose of a compound of the present invention or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, chronic obstructive pulmonary disease (COPD), and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, eszematous dermatitis, contact dermatitis, atopic dermatitis (atropic eczema), and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated disease include diseases associated with cartilage turnover, for example, gouty arthritis, septic or infectious arthritis, reactive arthritis, reflex sympathetic dystrophy, algodystrophy, Tietze syndrome, costal athropathy, osteoarthritis deformans endemica, Mseleni disease, Handigodu disease, degeneration resulting from fibromyalgia, systemic lupus erythematosus, scleroderma, or ankylosing spondylitis.

Further examples of JAK-associated disease include congenital cartilage malformations, including hereditary chrondrolysis, chrondrodysplasias, and pseudochrondrodysplasias (e.g., microtia, enotia, and metaphyseal chrondrodysplasia).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, uterine leiomyosarcoma, melanoma etc.), hematological cancers (e.g., lymphoma, leukemia such as acute lymphoblastic leukemia (ALL), acute myelogenous leukemia (AML) or multiple myeloma), and skin cancer such as cutaneous T-cell lymphoma (CTCL) and cutaneous B-cell lymphoma. Example CTCLs include Sezary syndrome and mycosis fungoides.

In some embodiments, the JAK inhibitors described herein, or in combination with other JAK inhibitors, such as those reported in U.S. Ser. No. 11/637,545, which is incorporated herein by reference in its entirety, can be used to treat inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer.

JAK-associated diseases can further include those characterized by expression of: JAK2 mutants such as those having at least one mutation in the pseudo-kinase domain (e.g., JAK2V617F); JAK2 mutants having at least one mutation outside of the pseudo-kinase domain; JAK1 mutants; JAK3 mutants; erythropoietin receptor (EPOR) mutants; or deregulated expression of CRLF2.

JAK-associated diseases can further include myeloproliferative disorders (MPDs) such as polycythemia vera (PV), essential thrombocythemia (ET), myelofibrosis with myeloid metaplasia (MMM), primary myelofibrosis (PMF), chronic myelogenous leukemia (CML), chronic myelomonocytic leukemia (CMML), hypereosinophilic syndrome (HES), systemic mast cell disease (SMCD), and the like. In some embodiments, the myeloproliferative disorder is myelofibrosis (e.g., primary myelofibrosis (PMF) or post polycythemia vera/essential thrombocythemia myelofibrosis (Post-PV/ET MF)). In some embodiments, the myeloproliferative disorder is post-essential thrombocythemia myelofibrosis (Post-ET MF). In some embodiments, the myeloproliferative disorder is post polycythemia vera myelofibrosis (Post-PV MF).

The present invention further provides methods of treating psoriasis or other skin disorders by administration of a topical formulation containing a compound of the invention.

In some embodiments, JAK inhibitors described herein can be used to treat pulmonary arterial hypertension.

The present invention further provides a method of treating dermatological side effects of other pharmaceuticals by administration of the compound of the invention. For example, numerous pharmaceutical agents result in unwanted allergic reactions which can manifest as acneiform rash or related dermatitis. Example pharmaceutical agents that have such undesirable side effects include anti-cancer drugs such as gefitinib, cetuximab, erlotinib, and the like. The compounds of the invention can be administered systemically or topically (e.g., localized to the vicinity of the dermatitis) in combination with (e.g., simultaneously or sequentially) the pharmaceutical agent having the undesirable dermatological side effect. In some embodiments, the compound of the invention can be administered topically together with one or more other pharmaceuticals, where the other pharmaceuticals when topically applied in the absence of a compound of the invention cause contact dermatitis, allergic contact sensitization, or similar skin disorder. Accordingly, compositions of the invention include topical formulations containing the compound of the invention and a further pharmaceutical agent which can cause dermatitis, skin disorders, or related side effects.

Further JAK-associated diseases include inflammation and inflammatory diseases. Example inflammatory diseases include sarcoidosis, inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases. In some embodiments, the inflammation disease of the eye is blepharitis.

The JAK inhibitors described herein can further be used to treat ischemia reperfusion injuries or a disease or condition related to an inflammatory ischemic event such as stroke or cardiac arrest. The JAK inhibitors described herein can further be used to treat endotoxin-driven disease state (e.g., complications after bypass surgery or chronic endotoxin states contributing to chronic cardiac failure). The JAK inhibitors described herein can further be used to treat anorexia, cachexia, or fatigue such as that resulting from or associated with cancer. The JAK inhibitors described herein can further be used to treat restenosis, sclerodermitis, or fibrosis. The JAK inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279(19):19936-47. Epub 2004 Mar. 2, both of which are incorporated herein by reference in their entirety. The JAK inhibitors described herein can be used to treat Alzheimer's disease.

The JAK inhibitors described herein can further be used to treat other inflammatory diseases such as systemic inflammatory response syndrome (SIRS) and septic shock.

The JAK inhibitors described herein can further be used to treat gout and increased prostate size due to, e.g., benign prostatic hypertrophy or benign prostatic hyperplasia.

Further JAK-associated diseases include bone resorption diseases such as osteoporosis, osteoarthritis. Bone resorption can also be associated with other conditions such as hormonal imbalance and/or hormonal therapy, autoimmune disease (e.g. osseous sarcoidosis), or cancer (e.g. myeloma). The reduction of the bone resorption due to the JAK inhibitors can be about 10%, about 20%, about 30%, about 40%, about 50%, about 60%, about 70%, about 80%, or about 90%.

In some embodiments, JAK inhibitors described herein can further be used to treat a dry eye disorder. As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye Workshop", *The Ocular Surface*, 5(2), 75-92 April 2007, which is incorporated herein by reference in its entirety. In some embodiments, the dry eye disorder is selected from aqueous tear-deficient dry eye (ADDE) or evaporative dry eye disorder, or appropriate combinations thereof. In some embodiments, the dry eye disorder is Sjogren syndrome dry eye (SSDE). In some embodiments, the dry eye disorder is non-Sjogren syndrome dry eye (NSSDE).

In a further aspect, the present invention provides a method of treating conjunctivitis, uveitis (including chronic uveitis), chorioditis, retinitis, cyclitis, sclieritis, episcleritis, or iritis; treating inflammation or pain related to corneal transplant, LASIK (laser assisted in situ keratomileusis), photorefractive keratectomy, or LASEK (laser assisted sub-epithelial keratomileusis); inhibiting loss of visual acuity related to corneal transplant, LASIK, photorefractive keratectomy, or LASEK; or inhibiting transplant rejection in a patient in need thereof, comprising administering to the patient a therapeutically effective amount of the compound of the invention, or a pharmaceutically acceptable salt thereof.

Additionally, the compounds of the invention, or in combination with other JAK inhibitors, such as those reported in U.S. Ser. No. 11/637,545, which is incorporated herein by reference in its entirety, can be used to treat respiratory dysfunction or failure associated with viral infection, such as influenza and SARS.

In some embodiments, the present invention provides a compound of Formula I, pharmaceutically acceptable salt thereof, as described in any of the embodiments herein, for use in a method of treating any of the diseases or disorders described herein. In some embodiments, the present invention provides the use of a compound of Formula I as described in any of the embodiments herein, for the preparation of a medicament for use in a method of treating any of the diseases or disorders described herein.

In some embodiments, the present invention provides a compound of Formula I as described herein, or a pharmaceutically acceptable salt thereof, for use in a method of modulating JAK1. In some embodiments, the present invention also provides use of a compound of Formula I as described herein, or a pharmaceutically acceptable salt thereof, for the preparation of a medicament for use in a method of modulating JAK1.

As used herein, the term "contacting" refers to the bringing together of indicated moieties in an in vitro system or an in vivo system. For example, "contacting" a JAK with a compound of the invention includes the administration of a compound of the present invention to an individual or patient, such as a human, having a JAK, as well as, for example, introducing a compound of the invention into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the therapeutically effective amount is about 5 mg to about 1000 mg, or about 10 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, which is incorporated herein by reference in its entirety, or other agents can be used in combination with the compounds described herein for treatment of JAK-associated diseases, disorders or conditions. The one or more additional pharmaceutical agents can be administered to a patient simultaneously or sequentially.

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491, all of which are incorporated herein by reference in their entirety.

Example suitable Flt-3 inhibitors include compounds, and their pharmaceutically acceptable salts, as disclosed in WO 03/037347, WO 03/099771, and WO 04/046120, all of which are incorporated herein by reference in their entirety.

Example suitable RAF inhibitors include compounds, and their pharmaceutically acceptable salts, as disclosed in WO 00/09495 and WO 05/028444, both of which are incorporated herein by reference in their entirety.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402, all of which are incorporated herein by reference in their entirety.

In some embodiments, one or more of the compounds of the invention can be used in combination with one or more other kinase inhibitors including imatinib, particularly for treating patients resistant to imatinib or other kinase inhibitors.

In some embodiments, one or more JAK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present invention with an additional agent. Furthermore, resistance of multiple myeloma cells to agents such as dexamethasone may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of one or more JAK inhibitors of the invention with other therapeutic agents can be administered to a patient prior to, during, and/or after a bone marrow transplant or stem cell transplant.

In some embodiments, the additional therapeutic agent is fluocinolone acetonide (Retisert®), or rimexolone (AL-2178, Vexol, Alcon).

In some embodiments, the additional therapeutic agent is cyclosporine (Restasis®).

In some embodiments, the additional therapeutic agent is a corticosteroid. In some embodiments, the corticosteroid is triamcinolone, dexamethasone, fluocinolone, cortisone, prednisolone, or flumetholone.

In some embodiments, the additional therapeutic agent is selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)—HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), $R^x$-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), actemra, gemcitabine, oxaliplatin, L-asparaginase, or thalidomide.

In some embodiments, the additional therapeutic agent is an anti-angiogenic agent, cholinergic agonist, TRP-1 receptor modulator, a calcium channel blocker, a mucin secretagogue, MUC1 stimulant, a calcineurin inhibitor, a corticosteroid, a P2Y2 receptor agonist, a muscarinic receptor agonist, an mTOR inhibitor, another JAK inhibitor, Bcr-Abl kinase inhibitor, Flt-3 kinase inhibitor, RAF kinase inhibitor, and FAK kinase inhibitor such as, for example, those described in WO 2006/056399, which is incorporated herein by reference in its entirety. In some embodiments, the additional therapeutic agent is a tetracycline derivative (e.g., minocycline or doxycline). In some embodiments, the additional therapeutic agent binds to FKBP12.

In some embodiments, the additional therapeutic agent is an alkylating agent or DNA cross-linking agent; an antimetabolite/demethylating agent (e.g., 5-fluorouracil, capecitabine or azacitidine); an anti-hormone therapy (e.g., hormone receptor antagonists, SERMs, or aromotase inhibitor); a mitotic inhibitor (e.g. vincristine or paclitaxel); an topoisomerase (I or II) inhibitor (e.g. mitoxantrone and irinotecan); an apoptotic inducers (e.g. ABT-737); a nucleic acid therapy (e.g. antisense or RNAi); nuclear receptor ligands (e.g., agonists and/or antagonists: all-trans retinoic acid or bexarotene); epigenetic targeting agents such as histone deacetylase inhibitors (e.g. vorinostat), hypomethylating agents (e.g. decitabine); regulators of protein stability such as Hsp90 inhibitors, ubiquitin and/or ubiquitin like conjugating or deconjugating molecules; or an EGFR inhibitor (erlotinib).

In some embodiments, the additional therapeutic agent(s) are demulcent eye drops (also known as "artificial tears"), which include, but are not limited to, compositions containing polyvinylalcohol, hydroxypropyl methylcellulose, glycerin, polyethylene glycol (e.g. PEG400), or carboxymethyl cellulose. Artificial tears can help in the treatment of dry eye by compensating for reduced moistening and lubricating capacity of the tear film. In some embodiments, the additional therapeutic agent is a mucolytic drug, such as N-acetyl-cysteine, which can interact with the mucoproteins and, therefore, to decrease the viscosity of the tear film.

In some embodiments, the additional therapeutic agent includes an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose, and polyethylene oxide. In some embodiments, the composition comprises at least one compound described herein, or a pharmaceutically acceptable salt thereof, and microcrystalline cellulose, lactose monohydrate, and hydroxypropyl methylcellulose. In some embodiments, the composition comprises at least one compound described herein, or a pharmaceutically acceptable salt thereof, and microcrystalline cellulose, lactose monohydrate, and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions of the invention contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions of the invention contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

In some embodiments, the compound, or pharmaceutically acceptable salt thereof, is administered as an ophthalmic composition. Accordingly, in some embodiments, the methods comprise administration of the compound, or pharmaceutically acceptable salt thereof, and an ophthalmically acceptable carrier. In some embodiments, the ophthalmic composition is a liquid composition, semi-solid composition, insert, film, microparticles or nanoparticles.

In some embodiments, the ophthalmic composition is a liquid composition. In some embodiments, the ophthalmic composition is a semi-solid composition. In some embodiments, the ophthalmic composition is a topical composition. The topical compositions include, but are not limited to liquid and semi-solid compositions. In some embodiments, the ophthalmic composition is a topical composition. In some embodiments, the topical composition comprises aqueous solution, an aqueous suspension, an ointment or a gel. In some embodiments, the ophthalmic composition is topically applied to the front of the eye, under the upper eyelid, on the lower eyelid and in the cul-de-sac. In some embodiments, the ophthalmic composition is sterilized. The sterilization can be accomplished by known techniques like sterilizing filtration of the solution or by heating of the solution in the ampoule ready for use. The ophthalmic compositions of the invention can further contain pharmaceutical excipients suitable for the preparation of ophthalmic formulations. Examples of such excipients are preserving agents, buffering agents, chelating agents, antioxidant agents and salts for regulating the osmotic pressure.

As used herein, the term "ophthalmically acceptable carrier" refers to any material that can contain and release the compound, or pharmaceutically acceptable salt thereof, and that is compatible with the eye. In some embodiments, the ophthalmically acceptable carrier is water or an aqueous solution or suspension, but also includes oils such as those used to make ointments and polymer matrices such as used in ocular inserts. In some embodiments, the composition may be an aqueous suspension comprising the compound, or pharmaceutically acceptable salt thereof. Liquid ophthalmic compositions, including both ointments and suspensions, may have a viscosity that is suited for the selected route of administration. In some embodiments, the ophthalmic composition has a viscosity in the range of from about 1,000 to about 30,000 centipoise.

In some embodiments, the ophthalmic compositions may further comprise one or more of surfactants, adjuvants, buffers, antioxidants, tonicity adjusters, preservatives (e.g., EDTA, BAK (benzalkonium chloride), sodium chlorite, sodium perborate, polyquaterium-1), thickeners or viscosity modifiers (e.g., carboxymethyl cellulose, hydroxymethyl cellulose, polyvinyl alcohol, polyethylene glycol, glycol 400, propylene glycol hydroxymethyl cellulose, hydroxpropylguar, hyaluronic acid, and hydroxypropyl cellulose) and the like. Additives in the formulation may include, but are not limited to, sodium chloride, sodium bicarbonate, sorbic acid, methyl paraben, propyl paraben, chlorhexidine, castor oil, and sodium perborate.

Aqueous ophthalmic compositions (solutions or suspensions) generally do not contain physiologically or ophthalmically harmful constituents. In some embodiments, purified or deionized water is used in the composition. The pH may be adjusted by adding any physiologically and ophthalmically acceptable pH adjusting acids, bases or buffers to within the range of about 5.0 to 8.5. Ophthalmically acceptable examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, trishydroxymethylamino-methane, and the like. Salts and buffers include citrate/dextrose, sodium bicarbonate, ammonium chloride and mixtures of the aforementioned acids and bases.

In some embodiments, the methods involve forming or supplying a depot of the therapeutic agent in contact with the external surface of the eye. A depot refers to a source of therapeutic agent that is not rapidly removed by tears or other eye clearance mechanisms. This allows for continued, sustained high concentrations of therapeutic agent to be present in the fluid on the external surface of the eye by a single application. Without wishing to be bound by any theory, it is believed that absorption and penetration may be dependent on both the dissolved drug concentration and the contact duration of the external tissue with the drug containing fluid. As the drug is removed by clearance of the ocular fluid and/or absorption into the eye tissue, more drug is provided, e.g. dissolved, into the replenished ocular fluid from the depot. Accordingly, the use of a depot may more easily facilitate loading of the ocular tissue for more insoluble therapeutic agents. In some embodiments, the depot can remain for up to eight hours or more. In some embodiments, the ophthalmic depot forms includes, but is not limited to, aqueous polymeric suspensions, ointments, and solid inserts.

In some embodiments, the ophthalmic composition is an ointment or gel. In some embodiment, the ophthalmic composition is an oil-based delivery vehicle. In some embodiments, the composition comprises a petroleum or lanolin base to which is added the active ingredient, usually as 0.1 to 2%, and excipients. Common bases may include, but are not limited to, mineral oil, petrolatum and combinations thereof. In some embodiments, the ointment is applied as a ribbon onto the lower eyelid.

In some embodiment, the ophthalmic composition is an ophthalmic insert. In some embodiments, the ophthalmic insert is biologically inert, soft, bio-erodible, viscoelastic, stable to sterilization after exposure to therapeutic agents, resistant to infections from air borne bacteria, bio-erodible, biocompatible, and/or viscoelastic. In some embodiments, the insert comprises an ophthalmically acceptable matrix, e.g., a polymer matrix. The matrix is typically a polymer and the therapeutic agent is generally dispersed therein or bonded to the polymer matrix. In some embodiments, the therapeutic agent may be slowly released from the matrix through dissolution or hydrolysis of the covalent bond. In some embodiments, the polymer is bioerodible (soluble) and the dissolution rate thereof can control the release rate of the therapeutic agent dispersed therein. In another form, the polymer matrix is a biodegradable polymer that breaks down such as by hydrolysis to thereby release the therapeutic agent bonded thereto or dispersed therein. In further embodiments, the matrix and therapeutic agent can be surrounded with an additional polymeric coating to further control release. In some embodiments, the insert comprises a biodegradable polymer such as polycaprolactone (PCL), an ethylene/vinyl acetate copolymer (EVA), polyalkyl cyanoacrylate, polyurethane, a nylon, or poly(dl-lactide-co-glycolide) (PLGA), or a copolymer of any of these. In some embodiments, the therapeutic agent is dispersed into the matrix material or dispersed amongst the monomer composition used to make the matrix material prior to polymerization. In some embodiments, the amount of therapeutic agent is from about 0.1 to about 50%, or from about 2 to about 20%. In further embodiments, the biodegradable or bioerodible polymer matrix is used so that the spent insert does not have to be removed. As the biodegradable or bioerodible polymer is degraded or dissolved, the therapeutic agent is released.

In further embodiments, the ophthalmic insert comprises a polymer, including, but are not limited to, those described in Wagh, et al., "Polymers used in ocular dosage form and drug delivery systems", *Asian J. Pharm., pages* 12-17 (January 2008), which is incorporated herein by reference in its entirety. In some embodiments, the insert comprises a polymer selected from polyvinylpyrrolidone (PVP), an acrylate or methacrylate polymer or copolymer (e.g., Eudragit® family of polymers from Rohm or Degussa), hydroxymethyl cellulose, polyacrylic acid, poly(amidoamine) dendrimers, poly (dimethyl siloxane), polyethylene oxide, poly(lactide-co-glycolide), poly(2-hydroxyethylmethacrylate), poly(vinyl alcohol), or polypropylene fumarate). In some embodiments, the insert comprises Gelfoam® R. In some embodiments, the insert is a polyacrylic acid of 450 kDa-cysteine conjugate.

In some embodiments, the ophthalmic composition is a ophthalmic film. Polymers suitable for such films include, but are not limited to, those described in Wagh, et al. (ibid), In some embodiments, the film is a soft-contact lens, such as ones made from copolymers of N,N-diethylacrylamide and methacrylic acid crosslinked with ethyleneglycol dimethacrylate.

In some embodiments, the ophthalmic composition comprises microspheres or nanoparticles. In some embodiment, the microspheres comprise gelatin. In some embodiments, the microspheres are injected to the posterior segment of the eye, in the chroroidal space, in the sclera, intravitreally or sub-retinally. In some embodiments, the microspheres or nanoparticles comprises a polymer including, but not limited to, those described in Wagh, et al. (ibid), which is incorporated herein by reference in its entirety. In some embodiments, the polymer is chitosan, a polycarboxylic acid such as polyacrylic acid, albumin particles, hyaluronic acid esters, polyitaconic acid, poly(butyl)cyanoacrylate, polycaprolactone, poly(isobutyl)caprolactone, poly(lactic acid-co-glycolic acid), or poly(lactic acid). In some embodiments, the microspheres or nanoparticles comprise solid lipid particles.

In some embodiments, the ophthalmic composition comprises an ion-exchange resin. In some embodiments, the ion-exchange resin is an inorganic zeolite or synthetic organic resin. In some embodiments, the ion-exchange resin includes, but is not limited to, those described in Wagh, et al. (ibid), which is incorporated herein by reference in its entirety. In some embodiments, the ion-exchange resin is a partially neutralized polyacrylic acid.

In some embodiments, the ophthalmic composition is an aqueous polymeric suspension. In some embodiments, the therapeutic agent or a polymeric suspending agent is suspended in an aqueous medium. In some embodiments, the aqueous polymeric suspensions may be formulated so that they retain the same or substantially the same viscosity in the eye that they had prior to administration to the eye. In some embodiments, they may be formulated so that there is increased gelation upon contact with tear fluid.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and a $^{131}$I. The radionuclide that is incorporated in the instant radio-labeled compounds will depend on the specific application of that radio-labeled compound. For example, for in vitro JAK labeling and competition assays, compounds that incorporate $^3$H, $^{14}$C, $^{82}$Br, $^{125}$I $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is to be understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a JAK by monitoring its concentration variation when contacting with the JAK, through tracking of the labeling. For example, a test compound (labeled) can be evaluated for its ability to reduce binding of another compound which is known to bind to a JAK (i.e., standard compound). Accordingly, the ability of a test compound to compete with the standard compound for binding to the JAK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be JAK inhibitors according to at least one assay described herein.

EXAMPLES

Experimental procedures for compounds of the invention are provided below. Open Access Prep LC-MS Purification of some of the compounds prepared was performed on Waters mass directed fractionation systems. The basic equipment setup, protocols, and control software for the operation of these systems have been described in detail in literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K.

Blom, B. Glass, R. Sparks, A. Combs, *J. Combi. Chem.*, 6, 874-883 (2004). The abbreviation "TFA" refers to trifluoroacetic acid.

Example 1

{1-(cis-4-{[6-[(Dimethylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tetrakis(trifluoroacetate)

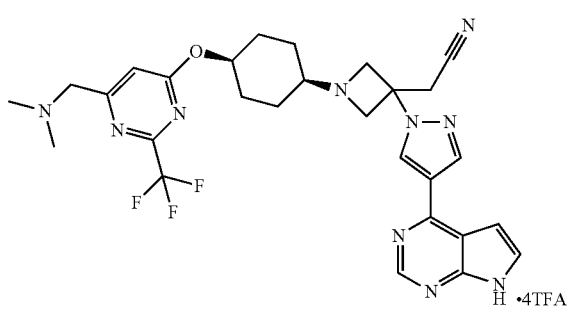 [SMILES: CN(C)Cc1cc(O[C@H]2CC[C@@H](N3CC(CC#N)(n4cc(-c5ncnc6[nH]ccc56)cn4)C3)CC2)nc(C(F)(F)F)n1]

Step 1: 4-chloro-6-(1,4-dioxaspiro[4.5]dec-8-yloxy)-2-(trifluoromethyl)pyrimidine

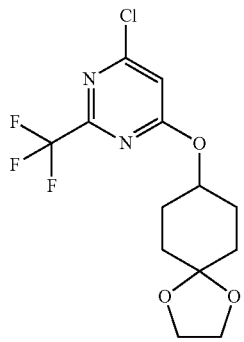 [SMILES: FC(F)(F)c1nc(Cl)cc(OC2CCC3(CC2)OCCO3)n1]

1,4-Dioxaspiro[4.5]decan-8-ol (3.64 g, 23.0 mmol, Acros Organics) and 4,6-dichloro-2-(trifluoromethyl)pyrimidine (5.00 g, 23.0 mmol SynChem, Inc.) were dissolved in tetrahydrofuran (41 mL) in a vial and cooled to 0° C. A 60% mixture of sodium hydride in oil (1.10 g, 27.5 mmol, Aldrich) was added. The reaction was stirred for 30 minutes at 0° C. and at 25° C. for 60 hours at which time TLC analysis showed that most of the starting material had been consumed. The reaction was quenched with water, and was extracted with ethyl acetate and the organic extracts were washed with water, saturated NaCl, dried (MgSO₄) and stripped in vacuo. The product was purified by silica gel chromatography using 10-20% ethyl acetate (EtOAc)/hexanes to give the product 4-113 chloro-6-(1,4-dioxaspiro[4.5]dec-8-yloxy)-2-(trifluoromethyl)pyrimidine as a white solid (5.35 g). ¹H NMR (400 MHz, CDCl₃) δ: 6.90 (s, 1H), 5.35 (m, 1H), 3.95 (s, 4H), 1.60-2.05 (m, 8H).

Step 2: 4-(1,4-Dioxaspiro[4.5]dec-8-yloxy)-6-[(E)-2-ethoxyvinyl]-2-(trifluoromethyl)pyrimidine

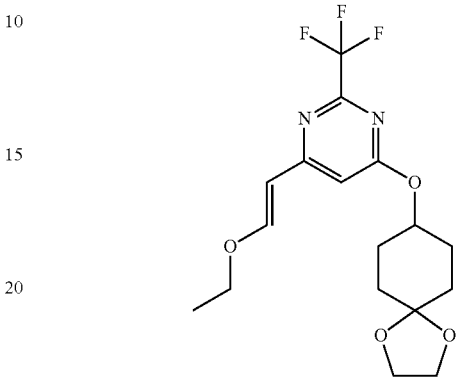

Into a 1-neck round-bottom flask, 4-chloro-6-(1,4-dioxaspiro[4.5]dec-8-yloxy)-2-(trifluoromethyl)pyrimidine (5.22 g, 15.4 mmol) was dissolved in toluene (18.4 mL) with (2-ethoxyethenyl)tri-n-butyltin (5.62 mL, 17.0 mmol, Synthonics Corporation) and tetrakis(triphenylphosphine)palladium(0) (0.9627 g, 0.8331 mmol, Aldrich) and then degassed. The reaction was heated at 110° C. for 48 hours until LCMS analysis showed no starting material present. The reaction was chromatographed using 10% and 20% EtOAc/hexanes to give the enol ether. (5.70 g). ¹H NMR (400 MHz, CDCl₃) δ: 7.35 (s, 1H), 6.64 (d, 1H), 5.46 (d, 1H), 5.28 (m, 1H), 4.13 (q, 2H), 3.97 (s, 4H), 1.20-2.05 (m, 8H), 1.40 (t, 3H); MS (ES): 375 (M+1).

Step 3: 6-(1,4-Dioxaspiro[4.5]dec-8-yloxy)-2-(trifluoromethyl)pyrimidine-4-carbaldehyde

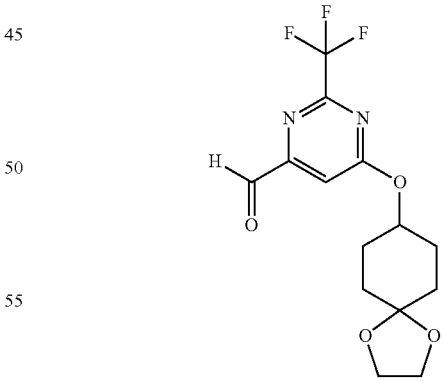

4-(1,4-Dioxaspiro[4.5]dec-8-yloxy)-6-[(E)-2-ethoxyvinyl]-2-(trifluoromethyl)pyrimidine (2.50 g, 6.68 mmol) was dissolved in 1,4-dioxane (190 mL,) and water (48 mL) and then sodium periodate (4.3 g, 20. mmol, Aldrich) was added, followed by a 4% solution of osmium tetraoxide in water (1.47 mL, 0.232 mmol). The solution began to form a whitish solid after a few minutes. The reaction was stirred at 25° C. for 48 hours until LCMS analysis of the reaction mixture showed no starting material present. The reaction was transferred to a separatory funnel and partitioned between water and EtOAc, the phases were separated, and then the aqueous phase was washed with EtOAc. The combined organic phase was washed with water, then saturated NaCl, dried over MgSO$_4$ and filtered and stripped to dryness to leave the crude product. The crude material was used in the next reaction without purification. $^1$H NMR (400 MHz, CDCl$_3$) δ: 10.01 (s, 1H), 7.33 (s, 1H), 5.38 (m, 1H), 3.97 (s, 4H), 1.20-2.05 (m, 8H).

Step 4: [6-(1,4-Dioxaspiro[4.5]dec-8-yloxy)-2-(trifluoromethyl)pyrimidin-4-yl]methanol

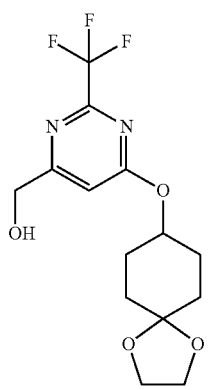

Into a 1-neck round-bottom flask, 6-(1,4-dioxaspiro[4.5]dec-8-yloxy)-2-(trifluoromethyl)pyrimidine-4-carbaldehyde (3.00 g, 9.03 mmol) was dissolved in isopropyl alcohol (40 mL) and cooled to 0° C. To this solution, NaBH$_4$ (0.27 g, 7.2 mmol) was added, and the reaction was stirred for 5 hours until LCMS analysis of the reaction mixture showed no starting material present. The reaction was transferred to a separatory funnel and partitioned between water and EtOAc, the phases were separated and the aqueous phase was washed with EtOAc. The combined organic phase was washed with water, then saturated NaCl, dried over MgSO$_4$ and filtered and stripped to dryness to leave the crude product. MS (ES): 335 (M+1).

Step 5: 4-{[6-(Hydroxymethyl)-2-(trifluoromethyl)pyrimidin-4-yl]oxy}cyclohexanone

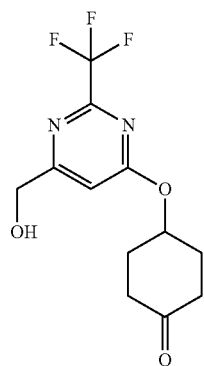 [SMILES: O=C1CCC(Oc2cc(CO)nc(C(F)(F)F)n2)CC1]

The product of the preceding reaction was dissolved in acetone (30.00 mL, 408.6 mmol) and 10.0 M hydrogen chloride in water (3.00 mL, 30.0 mmol) was added and stirred for 5 hours. LCMS analysis showed starting material still present. An additional 10.0 M hydrogen chloride in water (2.00 mL, 20.0 mmol) was added and stirred for 16 hours. The reaction was neutralized with NaHCO$_3$ and extracted with EtOAc (3×). The EtOAc was dried and removed in vacuo to give 4-{[6-(hydroxymethyl)-2-(trifluoromethyl)pyrimidin-4-yl]oxy}cyclohexanone which was used in the next reaction. MS (ES): 291 (M+1).

Step 6: {1-(cis-4-{[6-(Hydroxymethyl)-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile and {1-(trans-4-{[6-(hydroxymethyl)-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile

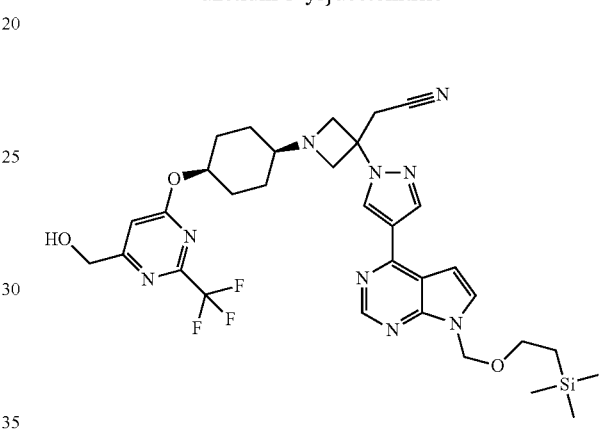

{3-[4-(7-{[2-(Trimethylsilyl)ethoxy]methyl}-7H-pyrrolo[2,3-d]pyrimidin-4-yl)-1H-pyrazol-1-yl]azetidin-3-yl}acetonitrile dihydrochloride (1.20 g, 2.49 mmol) (from WO 2009114512) and 4-{[6-(hydroxymethyl)-2-(trifluoromethyl)pyrimidin-4-yl]oxy}cyclohexanone (0.900 g, 3.10 mmol) in dry 1,2-dichloroethane (30.00 mL, 380.8 mmol) were stirred for 5 minutes, and sodium triacetoxyborohydride (1.87 g, 8.82 mmol) was added. The reaction mixture was stirred at room temperature for 16 hours, at which time LCMS analysis showed mainly the two diastereomeric products. The reaction was quenched with water, neutralized with NaHCO$_3$ and extracted with ethyl acetate. The mixture was purified by preparative-HPLC/MS (C18 column eluting with a gradient of ACN/H$_2$O containing 0.15% NH$_4$OH). Fractions containing the second peak were combined and stripped down to give {1-(cis-4-{[6-(hydroxymethyl)-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile. $^1$H NMR (500 MHz, CDCl$_3$) δ: 8.90 (s, 1H), 8.47 (s, 1H), 8.37 (s, 1H), 7.46 (d, 1H), 6.98 (s, 1H), 6.86 (d, 1H), 5.73 (s, 2H), 5.41 (m, 1H), 4.80 (s, 2H), 3.82 (d, 2H), 3.67 (d, 2H) 3.59 (m, 2H), 3.46 (s, 2H), 3.15 (m, 1H), 2.42 (m, 2H), 2.11 (m, 2H), 1.70-1.90 (m, 6H), 0.96 (m, 2H), −0.4 (s, 9H). MS (ES): 683 (M+1).

The first peak was also collected to give {1-(trans-4-{[6-(hydroxymethyl)-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile. $^1$H NMR (500 MHz, CDCl$_3$) δ: 8.90 (s, 1H), 8.47 (s, 1H), 8.37 (s, 1H), 7.46 (d, 1H), 6.86 (d, 5.73 (s, 2H), 5.24 (m, 1H), 4.80 (s, 2H), 3.82 (d, 2H), 3.67 (d, 2H) 3.59 (m, 2H), 3.45 (s, 2H), 3.15 (m, 1H), 2.36 (m, 2H), 2.22 (m, 2H), 2.19 (m, 2H), 1.59 (m, 2H), 1.40 (m, 2H), 0.97 (m, 2H), −0.4 (s, 9H). MS (ES): 683 (M+1).

Step 7: [6-[(cis-4-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}cyclohexyl)oxy]-2-(trifluoromethyl)pyrimidin-4-yl]methyl methanesulfonate

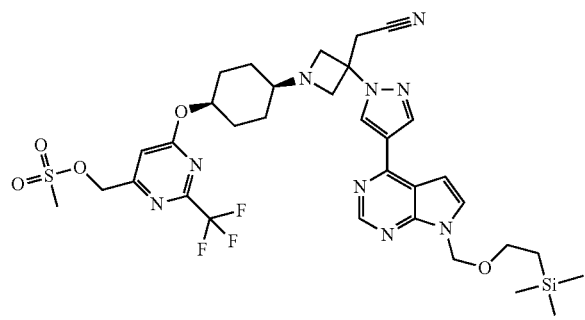 [SMILES: C[Si](C)(C)CCOCn1ccc2c(-c3cnn(C4(CC#N)CN([C@H]5CC[C@@H](Oc6cc(COS(C)(=O)=O)nc(C(F)(F)F)n6)CC5)C4)c3)ncnc21]

{1-(cis-4-{[6-(Hydroxymethyl)-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (110.0 mg, 0.1609 mmol) was dissolved in methylene chloride (2.22 mL) and was cooled to 0° C. To that was added N,N-diisopropylethylamine (45.8 µL, 0.263 mmol), followed by methanesulfonyl chloride (18 µL, 0.23 mmol). The reaction was stirred at 0° C. for 1 hour. The reaction was worked up using EtOAc and used in the next reaction. MS (ES): 762 (M+1).

Step 8: {1-(cis-4-{[6-[(Dimethylamino)methyl]-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile

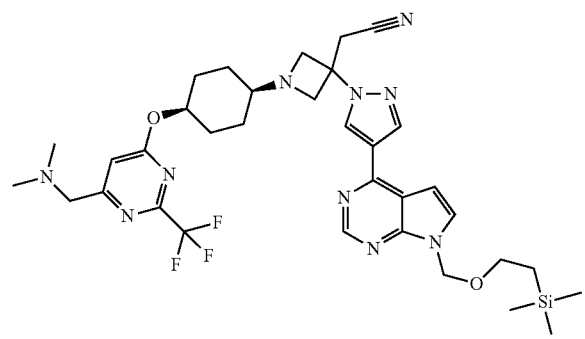

[6-[(cis-4-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}cyclohexyl)oxy]-2-(trifluoromethyl)pyrimidin-4-yl]methyl methanesulfonate (450.0 mg, 0.5906 mmol) was dissolved in tetrahydrofuran (10.00 mL) and 2.0 M dimethylamine in tetrahydrofuran (4.00 mL, 8.00 mmol) was added. The reaction were stirred at 25° C. for 16 hours at which time LCMS analysis showed that the reaction was completed. The solvent was then removed and the product was used in the next reaction without purification. MS (ES): 711(M+1).

Step 9: {1-(cis-4-{[6-[(Dimethylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tetrakis(trifluoroacetate)

{1-(cis-4-{[6-[(Dimethylamino)methyl]-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile from step 8 was dissolved in dichloromethane (5 mL), and ml TFA (2.5 mL) was added. The mixture was stirred for 2 hours, and then was concentrated. The residue was dissolved in methanol (MeOH) (10 mL), and concentrated NH$_4$OH was added (2 mL) The reaction was stirred for 2 hours and then the solvent was removed in vacuo. The residue was purified by preparative-HPLC/MS (C18 column eluting with a gradient of acetonitrile (ACN)/H$_2$O containing 0.1% TFA) was used to purify the product, which was obtained as the tristrifluoroacetate salt. $^1$H NMR (400 MHz, CD$_3$OD) δ: 9.07 (s, 1H), 8.87 (s, 1H), 8.58 (s, 1H), 7.78 (d, 1H), 7.25 (d, 1H), 7.14 (s, 1H), 5.52 (m, 1H), 5.07 (d, 2H), 4.84 (d, 2H), 4.54 (s, 2H), 3.74 (s, 2H), 3.51 (m, 1H), 2.97 (s, 6H), 2.28 (m, 2H), 2.02 (m, 2H), 1.70-1.90 (m, 4H). $^{19}$F NMR (376 MHz, CD$_3$OD) δ: −72.72 (s, 3F), −77.52 (s, 12F). MS (ES): 581 (M+1).

Example 2

{1-(cis-4-{[6-(Hydroxymethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile bis(trifluoroacetate)

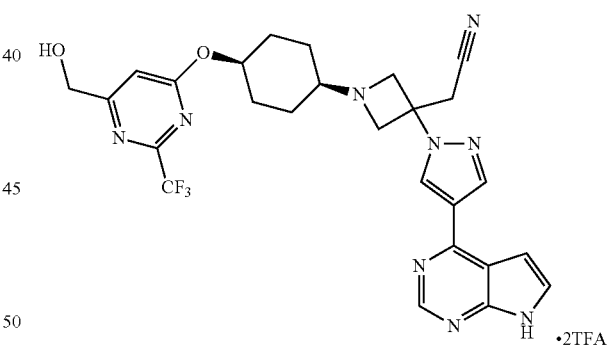

{1-(cis-4-{[6-(Hydroxymethyl)-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (40.0 mg, 0.0585 mmol) was dissolved in methylene chloride (1.0 mL) and then trifluoroacetic acid was added (0.50 mL, 6.5 mmol). The reaction was stirred at 25° C. for 2 hours and then the solvent was removed in vacuo. To the residue was added methanol (1.00 mL, 24.7 mmol) and 26.5 M ammonium hydroxide in water (0.20 mL, 5.3 mmol). The mixture was then stirred for 2 hours, and the solvent was removed in vacuo. The residue was purified by preparative-HPLC/MS (C18 column eluting with a gradient of ACN/H$_2$O containing 0.1% TFA), which was obtained as the bis(trifluoroacetate) salt. $^1$H NMR (400 MHz, CD$_3$OD) δ: 9.01 (s, 1H), 8.83 (s, 1H), 8.57 (s, 1H), 7.73

(d, 1H), 7.18 (d, 1H), 7.11 (s, 1H), 5.48 (m, 1H), 5.07 (d, 2H), 4.82 (d, 2H), 4.65 (s, 2H), 3.71 (s, 214), 3.50 (m, 1H), 2.28 (m, 2H), 2.02 (m, 2H), 1.70-1.90 (m, 4H). $^{19}$F NMR (400 MHz, CD$_3$OD) δ: −72.84 (s, 3F), −77.55 (s, 6F). MS (ES): 554 (M+1).

Example 3

{1-(cis-4-{[6-(Aminomethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tetrakis(trifluoroacetate)

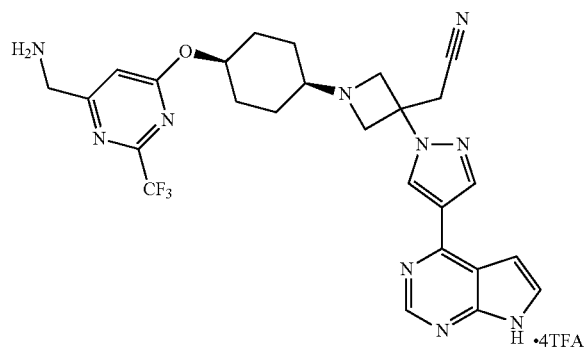 [SMILES: N#CCC1(n2cc(-c3ncnc4[nH]ccc34)cn2)CN([C@H]2CC[C@@H](Oc3cc(CN)nc(C(F)(F)F)n3)CC2)C1]

Step 1: 2-(1-((1s,4s)-4-(6-(Aminomethyl)-2-(trifluoromethyl)pyrimidin-4-yloxy)cyclohexyl)-3-(4-(7-((2-(trimethylsilyl)ethoxy)methyl)-7H-pyrrolo[2,3-d]pyrimidin-4-yl)-1H-pyrazol-1-yl)azetidin-3-yl)acetonitrile

[6-[(cis-4-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}cyclohexyl)oxy]-2-(trifluoromethyl)pyrimidin-4-yl]methyl methanesulfonate (60.0 mg, 0.08 mmol) was dissolved in tetrahydrofuran (1.0 mL) and 26.5 M ammonium hydroxide in water (0.40 mL, 10.6 mmol) was added, followed by dioxane (1.0 mL). The reaction were stirred at 25° C. for 16 hours, at which time LCMS analysis showed that the reaction was nearly complete. The solvent was removed in vacuo and the product was used in the next reaction without purification. MS (ES): 683(M+1).

Step 2: {1-(cis-4-{[6-(Aminomethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tetrakis(trifluoroacetate)

2-(1-((1s,4s)-4-(6-(Aminomethyl)-2-(trifluoromethyl)pyrimidin-4-yloxy)cyclohexyl)-3-(4-(7-((2-(trimethylsilyl)ethoxy)methyl)-7H-pyrrolo[2,3-d]pyrimidin-4-yl)-1H-pyrazol-1-yl)azetidin-3-yl)acetonitrile was deprotected as in Example 1 and purified by preparative-HPLC/MS (C18 column eluting with a gradient of ACN/H$_2$O containing 0.1% TFA) to give the product. $^1$H NMR (400 MHz, CD$_3$OD) δ: 8.96 (s, 1H), 8.83 (s, 1H), 8.56 (s, 1H), 7.72 (d, 1H), 7.18 (d, 1H), 7.11 (s, 1H), 5.50 (m, 1H), 5.02 (d, 2H), 4.75 (d, 2H), 4.32 (s, 2H), 3.72 (s, 2H), 3.47 (m, 1H), 2.28 (m, 2H), 2.02 (m, 2H), 1.70-1.90 (m, 4H). $^{19}$F NMR (400 MHz, CD$_3$OD) δ: −72.73 (s, 3F), −77.52 (s, 12F). MS (ES): 553 (M+1).

Example 4

{1-(cis-4-{[6-[(Methylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate)

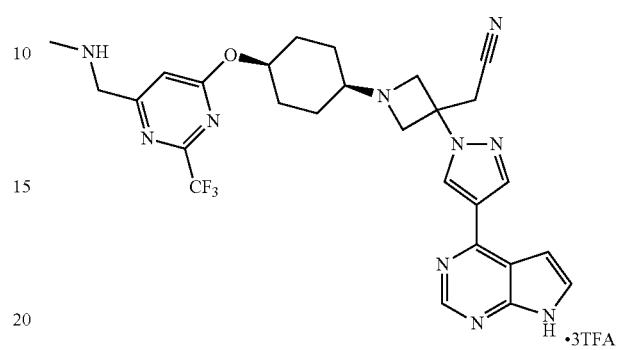

[6-[(cis-4-{3-(Cyanomethyl)-3-[4-(7-{[2-(trimethylsilyl)ethoxy]methyl}-7,4-pyrrolo[2,3-d]pyrimidin-4-yl)-1H-pyrazol-1-yl]azetidin-1-yl}cyclohexyl)oxy]-2-(trifluoromethyl)pyrimidin-4-yl]methyl methanesulfonate (60.00 mg, 0.07875 mmol) was dissolved in tetrahydrofuran (THF) (1.0 mL) and 10.0 M methylamine in ethanol (0.30 mL, 3.0 mmol) was added. The reaction was stirred at 25° C. for 16 hours, at which time LCMS analysis showed the reaction mixture consisted of mainly product. The solvent was removed in vacuo, and the residue was deprotected as in Example 1 to give the products, {1-(cis-4-{[6-[(methylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate). $^1$H NMR (400 MHz, CD$_3$OD) δ: 9.03 (s, 1H), 8.85 (s, 1H), 8.57 (s, 1H), 7.75 (d, 1H), 7.21 (d, 1H), 7.10 (s, 1H), 5.50 (m, 1H), 5.04 (d, 2H), 4.77 (d, 2H), 4.40 (s, 2H), 3.73 (s, 2H), 3.51 (m, 1H), 2.81 (s, 3H), 2.23 (m, 2H), 2.02 (m, 2H), 1.70-1.90 (m, 4H). $^{19}$F NMR (400 MHz, CD$_3$OD) δ: −72.72 (s, 3F), −77.52 (s, 9F). MS (ES): 567 (M+1).

Example 5

{1-(cis-4-{[6-[(Ethylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate)

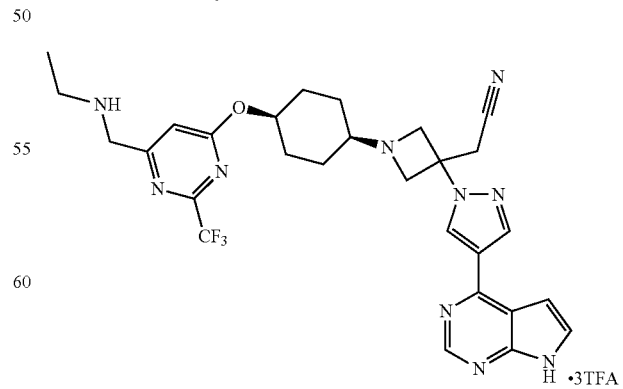

[6-[(cis-4-{3-(Cyanomethyl)-3-[4-(7-{[2-(trimethylsilyl)ethoxy]methyl}-7H-pyrrolo[2,3-d]pyrimidin-4-yl)-1H- pyrazol-1-yl]azetidin-1-yl}cyclohexyl)oxy]-2-(trifluoromethyl)pyrimidin-4-yl]methyl methanesulfonate (90.00 mg, 0.1181 mmol) was dissolved in tetrahydrofuran (2.50 mL, 30.8 mmol) and then 2.0 Methylamine in tetrahydrofuran (0.200 mL, 0.400 mmol) was added. The reaction was stirred at 25° C. for 16 hours, at which time LCMS analysis showed that the reaction mixture mainly contained {1-(cis-4-{[6-[(ethylamino)methyl]-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile. MS (ES): 711(M+1). The solvent was then removed in vacuo, and deprotected and purified by liquid chromatography as in Example 1. $^1$H NMR (400 MHz, CD$_3$OD) δ: 8.98 (brs, 1H), 8.82 (s, 1H), 8.55 (s, 1H), 7.70 (m, 1H), 7.17 (m, 1H), 7.12 (s, 1H), 5.50 (m, 1H), 5.01 (d, 2H), 4.75 (d, 2H), 4.42 (s, 2H), 3.72 (s, 2H), 3.45 (m, 1H), 3.20 (m, 2H), 2.26 (m, 2H), 2.02 (m, 2H), 1.70-1.90 (m, 4H), 1.37 (t, 3H). $^{19}$F NMR (400 MHz, CD$_3$OD) δ: −72.69 (s, 3F), −77.47 (s, 9F). MS (ES): 581 (M+1).

The compounds in Table 1 were prepared by methods analogous to those described for Example 1. Certain intermediates were obtained as described below.

TABLE 1

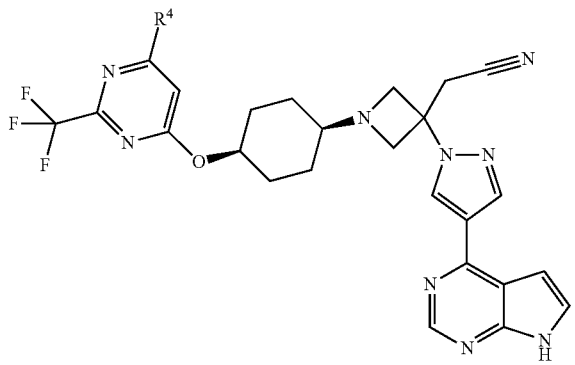

| Ex. No. | R$^4$ | MS (M + H)$^+$ | Name | Prep. |
|---|---|---|---|---|
| 6 | —CH$_2$NH(iPr) | 595 | {1-(cis-4-{[6-[(isopropylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 7 | —CH$_2$NH(cPr) | 593 | {1-(cis-4-{[6-[(cyclopropylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 8 | —CH$_2$N(Me)Et | 595 | {1-(cis-4-{[6-{[ethyl(methyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 9 | —CH$_2$NHCH$_2$(cPr) | 607 | {1-(cis-4-{[6-{[(cyclopropylmethyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 10 | —CH$_2$NH(cBu) | 607 | {1-(cis-4-{[6-[(cyclobutylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 11 | —CH$_2$NHCH$_2$CH$_2$OH | 597 | {1-(cis-4-{[6-{[(2-hydroxyethyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 1 |

TABLE 1-continued

| Ex. No. | R⁴ | MS (M + H)⁺ | Name | Prep. |
|---|---|---|---|---|
| 12 | —CH₂NMeCH₂CH₂OH | 611 | {1-(cis-4-{[6-{[(2-hydroxyethyl)(methyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 1 |
| 13 | —CH₂NEtCH₂CH₂OH | 625 | {1-(cis-4-{[6-{[ethyl(2-hydroxyethyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 1 |
| 14 | —CH₂NHCH₂CF₃ | 635 | [3-[4-(7H-pyrrolo[2,3-d]pyrimidin-4-yl)-1H-pyrazol-1-yl]-1-(cis-4-{[6-{[(2,2,2-trifluoroethyl)amino]methyl}-2-(trifluoromethyl)pyrimidin-4-yl]oxy}cyclohexyl)azetidin-3-yl]acetonitrile tris(trifluoroacetate) | Ex 1 |
| 15 | —CH₂NHCH₂CH₂F | 599 | {1-(cis-4-{[6-{[(2-fluoroethyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 16 | ~~CH₂~~N(H)—[(1S)-CH(CH₃)]—CH₂OH | 611 | {1-(cis-4-{[6-({[(1S)-2-hydroxy-1-methylethyl]amino}methyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile Ex 1 tris(trifluoroacetate) (salt) | Ex 1 |
| 17 | ~~CH₂~~N(H)—[(1R)-CH(CH₃)]—CH₂OH | 611 | {1-(cis-4-{[6-({[(1R)-2-hydroxy-1-methylethyl]amino}methyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 1 |
| 18 | ~~CH₂~~NH—CH₂—[(2S)-CH(OH)CH₃] | 611 | {1-(cis-4-{[6-({[(2S)-2-hydroxypropyl]amino}methyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 1 |
| 19 | ~~CH₂~~NH—CH₂—[(2R)-CH(OH)CH₃] | 611 | {1-(cis-4-{[6-({[(2R)-2-hydroxypropyl]amino}methyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 1 |

TABLE 1-continued

| Ex. No. | R⁴ | MS (M + H)⁺ | Name | Prep. |
|---|---|---|---|---|
| 20 | [CH₂-NH-CH₂-C(CH₃)₂-OH] | 625 | {1-(cis-4-{[6-{[(2-hydroxy-2-methylpropyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 1 |
| 21 | —CH₂NHCH₂CH₂CH₂OH | 611 | {1-(cis-4-{[6-{[(3-hydroxypropyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 1 |
| 22 | —CH₂NHCH₂CH₂OMe | 611 | {1-(cis-4-{[6-{[(2-methoxyethyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 23 | [CH₂-azetidin-1-yl] | 593 | {1-(cis-4-{[6-(azetidin-1-ylmethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 24 | [CH₂-(3-hydroxyazetidin-1-yl)] | 609 | {1-(cis-4-{[6-[(3-hydroxyazetidin-1-yl)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 1 |
| 25 | [CH₂-pyrrolidin-1-yl] | 607 | {1-(cis-4-{[6-(pyrrolidin-1-ylmethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 26 | [CH₂-(3S)-3-hydroxypyrrolidin-1-yl] | 623 | {1-(cis-4-{[6-{[(3S)-3-hydroxypyrrolidin-1-yl]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 1 |
| 27 | [CH₂-NH-CH₂-(tetrahydrofuran-2-yl)] | 637 | [3-[4-(7H-pyrrolo[2,3-d]pyrimidin-4-yl)-1H-pyrazol-1-yl]-1-(cis-4-{[6-({[(2S)-tetrahydrofuran-2-ylmethyl]amino}methyl)-2-(trifluoromethyl)pyrimidin-4-yl]oxy}cyclohexyl)azetidin-3-yl]acetonitrile tris(trifluoroacetate) | Ex 1 |

TABLE 1-continued

| Ex. No. | R⁴ | MS (M + H)⁺ | Name | Prep. |
|---|---|---|---|---|
| 28 | (S)-2-(hydroxymethyl)pyrrolidin-1-ylmethyl | 637 | {1-(cis-4-{[6-{[(2R)-2-(hydroxymethyl)pyrrolidin-1-yl]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 1 |
| 29 | (S)-2-(hydroxymethyl)pyrrolidin-1-ylmethyl | 637 | {1-(cis-4-{[6-{[(2S)-2-(hydroxymethyl)pyrrolidin-1-yl]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 1 |
| 30 | piperidin-1-ylmethyl | 621 | {1-(cis-4-{[6-(piperidin-1-ylmethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 31 | (3S)-3-fluoropyrrolidin-1-ylmethyl | 625 | {1-(cis-4-{[6-{[(3S)-3-fluoropyrrolidin-1-yl]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 32 | —CH₂NH(nPr) | 595 | {1-(cis-4-{[6-[(propylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 33 | —CH₂NHCH₂CH(OH)CH₂OH | 627 | {1-(cis-4-{[6-{[(2,3-dihydroxypropyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 1 |
| 34 | —CH₂NH(nBu) | 609 | {1-(cis-4-{[6-[(butylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 35 | —CH₂NHCH₂CH(CH₃)₂ | 609 | {1-(cis-4-{[6-[(isobutylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |

TABLE 1-continued

| Ex. No. | R⁴ | MS (M + H)⁺ | Name | Prep. |
|---|---|---|---|---|
| 36 | —CH₂NMe(nBu) | 623 | {1-(cis-4-{[6-{[butyl(methyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 37 | (azetidinylmethyl with 3-F) | 611 | {1-(cis-4-{[6-[(3-fluoroazetidin-1-yl)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 38 | —CH₂NHCH₂-[1-(hydroxymethyl)cyclopropyl] | 637 | {1-(cis-4-{[6-[({[1-(hydroxymethyl)cyclopropyl]methyl}amino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 1 |
| 39 | —CH₂NHCH₂CH₂-(1H-imidazol-4-yl) | 651 | 2-(1-(cis-4-((6-(((2-(1H-imidazol-4-yl)ethyl)amino)methyl)-2-(trifluoromethyl)pyrimidin-4-yl)oxy)cyclohexyl)-3-(4-(7H-pyrrolo[2,3-d]pyrimidin-4-yl)-1H-pyrazol-1-yl)azetidin-3-yl)acetonitrile tris(trifluoroacetate) (salt) | Ex 1 |
| 40 | —CH₂NHCH₂CH₂CH₂OMe | 625 | {1-(cis-4-{[6-{[(3-methoxypropyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 41 | —CH₂NHCH(Me)CH₂OMe | 625 | {1-(cis-4-{[6-{[(2-methoxy-1-methylethyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 42 | —CH₂NMeCH₂CH₂OMe | 625 | {1-(cis-4-{[6-{[(2-methoxyethyl)(methyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |

TABLE 1-continued

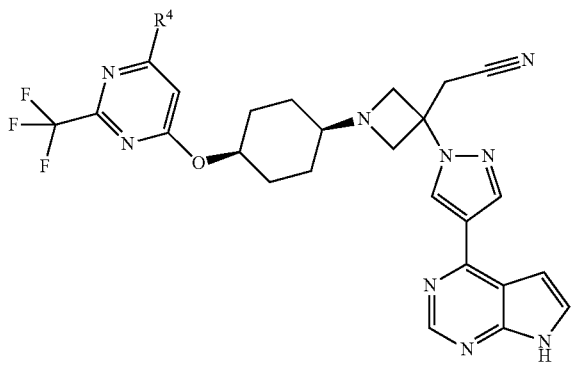

| Ex. No. | R⁴ | MS (M + H)⁺ | Name | Prep. |
|---|---|---|---|---|
| 49 | (isopropyl)C(O)NH-ethyl | 595 | 6-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-ethyl-2-(trifluoromethyl)pyrimidine-4-carboxamide bis(trifluoroacetate) | Ex 1 |
| 51 | (isopropyl)C(O)-pyrrolidin-1-yl | 621 | {1-(cis-4-{[6-(pyrrolidin-1-ylcarbonyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile bis(trifluoroacetate) | Ex 1 |
| 52 | —CH₂NHC(Me)₂CH₂OH | 625 | {1-(cis-4-{[6-{[(2-hydroxy-1,1-dimethylethyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tetrakis(trifluoroacetate) (salt) | Ex 1 |
| 53 | —CH₂NH(1-Me—cPr) | 607 | {1-(cis-4-{[6-{[(1-methylcyclopropyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 1 |
| 54 | —CN | 549 | 6-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-2-(trifluoromethyl)pyrimidine-4-carbonitrile bis(trifluoroacetate) | Ex 1 |
| 56 | —OCH₂CH₂OH | 584 | {1-(cis-4-{[6-(2-hydroxyethoxy)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile bis(trifluoroacetate) (salt) | Ex 45 |
| 57 | —C(Me)(OH)CH₂OH Peak 1 | 598 | {1-(cis-4-{[6-(1,2-dihydroxy-1-methylethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 45 |
| 57a | —C(Me)(OH)CH₂OH Peak 2 | 598 | {1-(cis-4-{[6-(1,2-dihydroxy-1-methylethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 45 |
| 58 | —CH(Me)(OH) Peak 1 | 568 | {1-(cis-4-{[6-(1-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 45 |

TABLE 1-continued

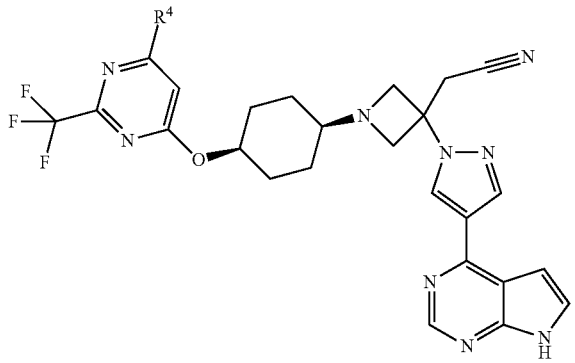

| Ex. No. | R⁴ | MS (M + H)⁺ | Name | Prep. |
|---|---|---|---|---|
| 58a | —CH(Me)(OH) Peak 2 | 568 | {1-(cis-4-{[6-(1-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 45 |
| 59 | —CH(Me)CH₂OH Peak 1 | 582 | {1-(cis-4-{[6-(2-hydroxy-1-methylethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile bis(trifluoroacetate) (salt) | Ex 45 |
| 59a | —CH(Me)CH₂OH Peak 2 | 582 | {1-(cis-4-{[6-(2-hydroxy-1-methylethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile bis(trifluoroacetate) (salt) | Ex 45 |
| 61 | —C(Me)₂F | 584 | {1-(cis-4-{[6-(1-fluoro-1-methylethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile bis(trifluoroacetate) | Ex 45 |
| 62 | —C(Me)₂CH₂OH | 596 | {1-(cis-4-{[6-(2-hydroxy-1,1-dimethylethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 45 |
| 63 | -1-(cPr)-1-CH₂OH | 594 | {1-(cis-4-{[6-[1-(hydroxymethyl)cyclopropyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile bis(trifluoroacetate) (salt) | Ex 45 |

The NMR data of some of the compounds are provided below in Table 2.

TABLE 2

| Ex. No. | NMR |
|---|---|
| 21 | ¹H NMR (300 MHz, DMSO-D6): δ 12.3 (s, 1H, NH); 10.9 (s, 1H, NH); 9.18 (br, 2H, NH₂); 9.08 (brs, 1H); 8.74 (s, 1H); 8.56 (s, 1H); 7.66 (m, 1H); 7.28 (s, 1H); 7.12 (m, 1H); 5.34 (br, 1H, OCH); 4.6-5.0 (m, 4H, azetidine); 4.4 (brs, 2H, ArCH₂); 3.74 (s, 2H, CH₂CN); 3.5 (t, 2H, CH₂); 3.5 (br, 1H, NCH); 3.06 (br, 2H, CH₂); 2.1 (m, 2H); 1.9 (m, 2H); 1.7 (m, 4H); 1.5 (m, 2H). |
| 37 | ¹H NMR (400 MHz, DMSO-D6): δ 12.3 (s, 1H, NH); 10.8 (s, 1H, NH); 9.08 (br, 1H); 8.74 (s, 1H); 8.56 (s, 1H); 7.58 (m, 1H); 7.20 (s, 1H); 7.10 (m, 1H); 5.40 (dm, 1H, FCH; $J_{FH}$ = 58 Hz); 5.30 (br, 1H, OCH); 4.7-5.0 (m, 4H, azetidine); 4.6 (brs, 2H, ArCH₂); 4.3-4.6 (m, 4H, azetidine); 3.7 (br, 2H, CH₂CN); 3.5 (br, 1H, NCH); 2.1 (m, 2H); 1.9 (m, 2H); 1.7 (m, 4H); 1.5 (m, 2H). |
| 52 | ¹H NMR (400 MHz, DMSO-D6): δ 12.4 (s, 1H, NH); 11.0 (s, 1H, NH); 9.08 (s, 1H); 8.92 (br, 2H, NH₂); 8.79 (s, 1H); 8.55 (s, 1H); 7.71 (m, 1H); 7.30 (s, 1H); 7.13 (m, 1H); 5.34 (s, 1H, OCH); 4.6-5.0 (m, 4H, azetidine); 4.33 (br, 2H, ArCH₂); 3.74 (s, 2H, CH₂CN); 3.5 (s, 1H, OCH₂); 3.5 (br, 1H, NCH); 2.1 (m, 2H); 1.9 (m, 2H); 1.7 (m, 2H); 1.5 (m, 2H); 1.30 (s, 6H). |
| 53 | ¹H NMR (400 MHz, DMSO-D6): δ 12.2 (s, 1H, NH); 10.8 (s, 1H, NH); 9.40 (br, 2H, NH₂); 9.08 (br, 1H); 8.75 (s, 1H); 8.55 (s, 1H); 7.68 (m, 1H); 7.30 (brs, 1H); 7.08 (m, 1H); 5.34 (s, 1H, OCH); 4.7-5.0 (m, 4H, azetidine); 4.44 (br, 2H, ArCH₂); 3.74 (s, 2H, |

TABLE 2-continued

| Ex. No. | NMR |
|---|---|
|  | CH$_2$CN); 3.53 (br, 1H, NCH); 2.1 (m, 2H); 1.9 (m, 2H); 1.7 (m, 2H); 1.5 (m, 2H); 1.4 (s, 3H); 1.0 (br, 2H); 0.7 (br, 2H). |
| 56 | $^1$H NMR (300 MHz, DMSO-D6): δ 12.4 (s, 1H, NH); 10.6 (brs, 1H, NH); 9.00 (br, 1H); 8.64 (s, 1H); 8.49 (s, 1H); 7.61 (m, 1H); 7.06 (m, 1H); 6.41 (s, 1H); 5.19 (m, 1H, OCH); 4.88 (br, 2H, NCH); 4.74 (br, 2H, NCH); 4.54 (br, 1H, OH); 4.25 (t, 2H, OCH$_2$); 3.72 (s, 2H, CH$_2$CN); 3.64 (t, 2H, OCH$_2$); 3.40 (m, 1H, NCH); 2.00 (m, 2H); 1.80 (m, 2H); 1.60 (m, 2H); 1.46 (m, 2H). |
| 57 | $^1$H NMR (300 MHz, CD$_3$OD): δ 9.09 (s, 1H); 8.91 (s, 1H); 8.59 (s, 1H); 7.80 (d, 1H); 7.24 (d, 1H); 7.24 (s, 1H); 5.46 (m, 1H, OCH); 5.10 (d, 2H, NCH); 4.81 (d, 2H, NCH); 3.84 & 3.44 (AB, 2H, OCH$_2$); 3.71 (s, 2H, CH$_2$CN); 3.51 (m, 1H, NCH); 2.26 (m, 2H); 2.01 (m, 2H); 1.77 (m, 4H); 1.42 (s, 3H, CH$_3$). |
| 58 | $^1$H NMR (300 MHz, DMSO-D6): δ 12.4 (s, 1H, NH); 10.9 (brs, 1H, NH); 9.08 (brs, 1H); 8.76 (s, 1H); 8.56 (s, 1H); 7.70 (m, 1H); 7.13 (m, 1H); 7.08 (s, 1H); 5.32 (br, 1H, OCH); 4.97 (d, 2H, NCH); 4.78 (br, 2H, NCH); 4.68 (q, 1H, OCH); 3.73 (brs, 2H, CH$_2$CN); 3.48 (brm, 1H, NCH); 2.08 (m, 2H); 1.88 (m, 2H); 1.67 (m, 2H); 1.53 (m, 2H); 1.34 (d, 3H, CH$_3$). |
| 59 | $^1$H NMR (400 MHz, DMSO-D6): δ 12.5 (s, 1H, NH); 10.7 (brs, 1H, NH); 9.00 (br, 1H); 8.71 (s, 1H); 8.55 (s, 1H); 7.64 (m, 1H); 7.08 (m, 1H); 6.96 (brs, 1H); 5.27 (br, 1H, OCH); 4.94 (br, 2H, NCH); 4.81 (br, 2H, NCH); 4.59 (br, 1H, OH); 3.4-3.8 (m, 5H, OCH$_2$, CH$_2$CN, NCH); 2.96 (brm, 1H, ArCH); 2.08 (m, 2H); 1.86 (m, 2H); 1.62 (m, 2H); 1.52 (m, 2H); 1.14 (d, 3H, CH$_3$). |
| 61 | $^1$H NMR (400 MHz, DMSO-D6): δ 12.22 (brs, 1H, NH); 10.7 (brs, 1H, NH); 9.00 (brs, 1H); 8.75 (s, 1H); 8.56 (s, 1H); 7.65 (m, 1H); 7.1 (m, 2H); 5.37 (brm, 1H, OCH); 4.6-5.0 (m, 4H azetidine); 3.8 (s, 2H, CH$_2$CN); 3.5 (m, 1H, NCH); 2.10 (m, 2H); 1.84 (m, 2H); 1.67 (m, 2H); 1.60 (d, 6H)); 1.5 (m, 2H). |
| 62 | $^1$H NMR (400 MHz, DMSO-D6): δ 12.4 (s, 1H, NH); 10.9 (brs, 1H, NH); 9.1 (br, 1H); 8.8 (s, 1H); 8.55 (s, 1H); 7.7 (m, 1H); 7.12 (m, 1H); 6.92 (s, 1H); 5.29 (br, 1H, OCH); 4.99 (d, 2H, NCH); 4.8 (br, 2H, NCH); 3.75 (br, 2H, CH$_2$CN); 3.48 (s, 2H, OCH$_2$); 3.44 (m, 1H, NCH); 2.08 (m, 2H); 1.86 (m, 2H); 1.64 (m, 2H); 1.54 (m, 2H); 1.20 (s, 6H, CH$_3$). |
| 63 | $^1$H NMR (400 MHz, DMSO-D6): δ 12.3 (s, 1H, NH); 10.6 (brs, 1H, NH); 9.02 (br, 1H); 8.78 (s, 1H); 8.57 (s, 1H); 7.70 (m, 1H); 7.12 (m, 2H); 5.28 (br, 1H, OCH); 4.99 (d, 2H, NCH); 4.75 (br, 2H, NCH); 3.8 (br, 2H, CH$_2$CN); 3.7 (s, 2H, OCH$_2$); 3.48 (m, 1H, NCH); 2.08 (m, 2H); 1.88 (m, 2H); 1.65 (m, 2H); 1.54 (m, 2H); 1.20 (s, 2H); 1.02 (s, 2H). |

Example 43

{1-(cis-4-{[6-(1-Hydroxy-1-methylethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile bis(trifluoroacetate)

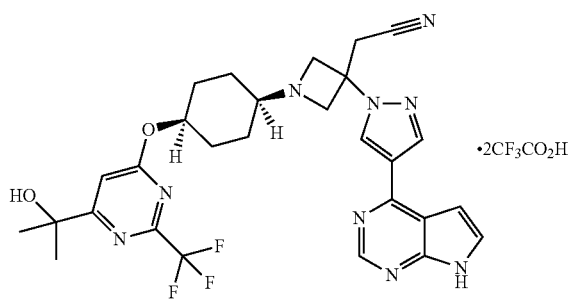 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)n1]

·2CF$_3$CO$_2$H

Step 1. 1-[6-(1,4-Dioxaspiro[4.5]dec-8-yloxy)-2-(trifluoromethyl)pyrimidin-4-yl]ethanol

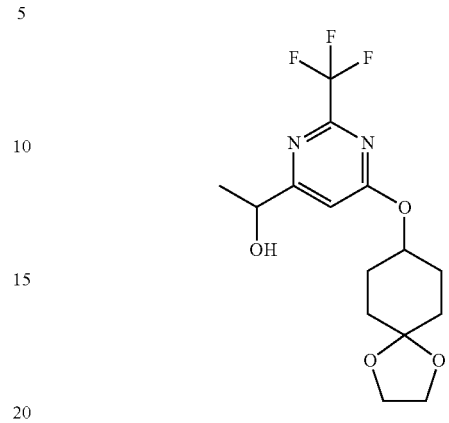

6-(1,4-Dioxaspiro[4.5]dec-8-yloxy)-2-(trifluoromethyl)pyrimidine-4-carbaldehyde (described in Example 1, Step 3) (0.20 g, 0.60 mmol) was dissolved in tetrahydrofuran (6.00 mL) and was cooled to −78° C., then 3.0 M methylmagnesium bromide in ether (0.30 mL, 0.90 mmol) was added. The reaction was stirred at −78° C. for 1 hour at which time LCMS analysis showed that it was mostly done. The reaction was quenched with sat. NH$_4$Cl and was and partitioned between water and EtOAc, the phases were separated and the aqueous phase was washed with additional EtOAc. The combined organic phase was washed with water, then sat. NaCl, dried over MgSO$_4$ and filtered and then the solvent removed in vacuo to leave the crude product. The crude material used in the next reaction without purification. MS: 371 (M+Na$^+$), 349 (M+1).

Step 2. 1-[6-(1,4-Dioxaspiro[4.5]dec-8-yloxy)-2-(trifluoromethyl)pyrimidin-4-yl]ethanone

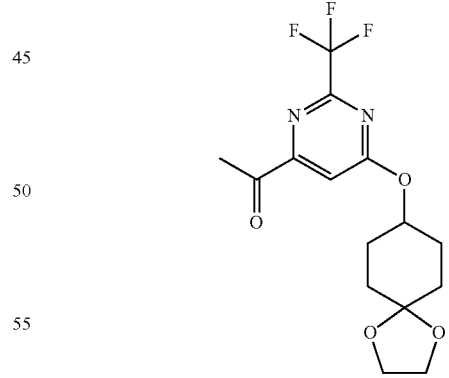

1-[6-(1,4-Dioxaspiro[4.5]dec-8-yloxy)-2-(trifluoromethyl)pyrimidin-4-yl]ethanol (0.20 g, 0.57 mmol) was dissolved in methylene chloride (5.00 mL) and cooled to 0° C. To this mixture, Dess-Martin periodinane (0.292 g, 0.689 mmol) was added. The mixture was stirred at 0° C. for 2 hours and then allowed to warm to 25° C. LCMS analysis indicated the reaction was complete. The mixture was extracted with EtOAc and the EtOAc extract was then washed with NaHCO$_3$, sat. NaCl, dried and then the solvent was removed in vacuo to give the product, which was used in the next reaction. MS: 369 (M+Na+). ¹H NMR (500 MHz, CDCl₃): δ 7.35 (s, 1H); 5.33 (m, 1H, OCH); 3.95 (s, 411, OCH₂); 2.63 (s, 3H, CH₃); 1.99 (m, 4H); 1.82 (m, 2H); 1.63 (m, 2H). ¹³C NMR (125 MHz, CDCl₃): δ 198 (s, O═C); 171 (s, OC); 161 (s, NC); 157 (q, N₂C); 119 (q, CF₃); 108 (s, CH and O₂C); 74 (s, OCH); 65 (s, OCH₂); 32 (s, CH₂); 28 (s, CH₂); 26 (s, CH₃).

Step 3. 2-[6-(1,4-Dioxaspiro[4.5]dec-8-yloxy)-2-(trifluoromethyl)pyrimidin-4-yl]propan-2-ol

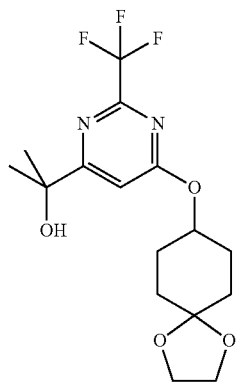 [SMILES: CC(C)(O)c1cc(OC2CCC3(CC2)OCCO3)nc(C(F)(F)F)n1]

1-[6-(1,4-Dioxaspiro[4.5]dec-8-yloxy)-2-(trifluoromethyl)pyrimidin-4-yl]ethanone (0.21 g, 0.60 mmol) was dissolved in tetrahydrofuran (6.00 mL, 74.0 mmol) and was cooled to −78° C., then 3.0 M methylmagnesium bromide in ether (0.30 mL, 0.90 mmol) was added. The reaction was stirred at −78° C. for 1 hour at which time LCMS analysis showed that it was mostly done. The reaction was quenched with sat. NH₄Cl and was transferred to a separatory funnel and partitioned between water and EtOAc, the phases were separated and the aqueous phase was washed with additional EtOAc. The combined organic phase was washed with water, then sat. NaCl, dried over MgSO₄ and filtered and the solvent removed in vacuo to leave the crude product. MS: 363 (M+H). ¹H NMR (500 MHz, CDCl₃): δ 6.90 (s, 1H); 5.30 (m, 1H, OCH); 3.96 (s, 4H, OCH₂); 1.98 (m, 4H); 1.82 (m, 2H); 1.63 (m, 2H); 1.50 (s, 311, CH₃). ¹³C NMR (125 MHz, CDCl₃): δ 176 (s, NC); 171 (s, OC); 156 (q, N₂C); 119 (q, CF₃); 108 (s, O₂C); 105 (s, CH); 74 (s, OCH); 73 (s, HOC); 65 (s, OCH₂); 32 (s, CH₂); 30 (s, CH₃); 28 (s, CH₂).

Step 4. 4-{[6-(1-Hydroxy-1-methylethyl)-2-(trifluoromethyl)pyrimidin-4-yl]oxy}cyclohexanone

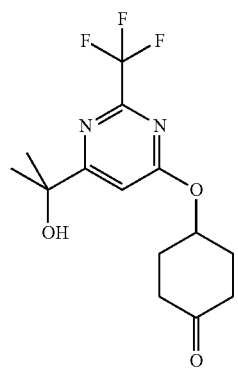 [SMILES: CC(C)(O)c1cc(OC2CCC(=O)CC2)nc(C(F)(F)F)n1]

The crude material was dissolved in acetone (7.00 mL) and 10.0 M hydrogen chloride in water (1.00 mL, 10.0 mmol) was added and stirred for 5 hours. LCMS analysis showed that the reaction was mostly complete. The reaction was neutralized with NaHCO₃ and extracted with EtOAc (3×). The EtOAc was dried and then removed in vacuo. The residue was used in the next reaction. MS: 319 (M+H).

Step 5: {1-(Cis-4-{[6-(1-hydroxy-1-methylethyl)-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile and {1-(trans-4-{[6-(1-hydroxy-1-methylethyl)-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile

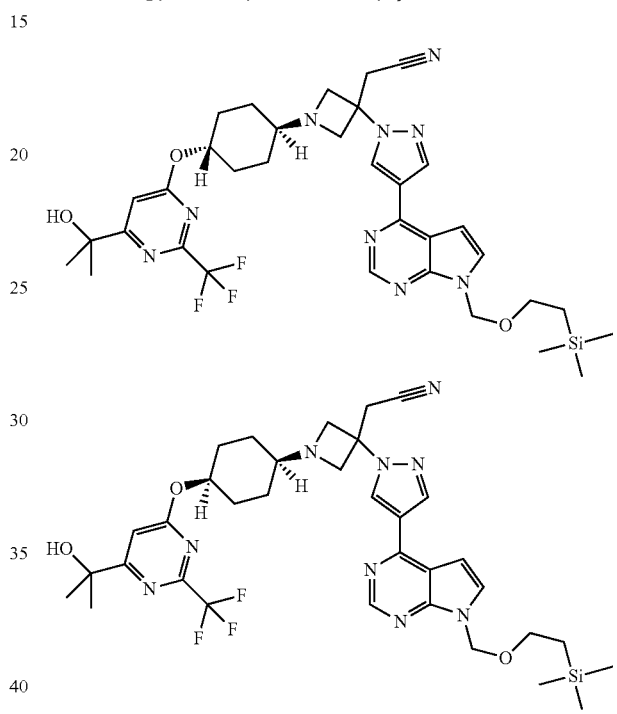

3-[4-(7-{[2-(Trimethylsilyl)ethoxy]methyl}-7H-pyrrolo[2,3-d]pyrimidin-4-yl)-1H-1-pyrazol-1-yl]azetidin-3-yl}acetonitrile dihydrochloride (0.119 g, 0.246 mmol) and 4-{[6-(1-hydroxy-1-methylethyl)-2-(trifluoromethyl)pyrimidin-4-yl]oxy}cyclohexanone (0.090 g, 0.28 mmol) in dry 1,2-dichloroethane (2.954 mL) were stirred for 5 minutes and sodium triacetoxyborohydride (0.185 g, 0.871 mmol) was added. The reaction mixture was stirred at 25° C. for 16 hours, at which time LCMS analysis showed mainly the two diastereomeric products. The reaction was quenched with water, neutralized with NaHCO₃ and extracted with ethyl acetate. The compounds were purified by LCMS (pH 10) and the fractions containing the second peak were combined and evaporated down. MS: 712 (M+H).

Step 6: {1-(cis-4-{[6-(1-Hydroxy-1-methylethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile bis(trifluoroacetate) (salt)

Methylene chloride (2.0 mL) and trifluoroacetic acid (0.40 mL, 5.2 mmol) were added to {1-(cis-4-{[6-(1-hydroxy-1-methylethyl)-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]

azetidin-3-yl}acetonitrile, stirred for 2 hours, and then concentrated to remove trifluoroacetic acids. LCMS showed clean conversion to the hydroxymethyl intermediate (M+2H 320). To the residue was added methanol (2.0 mL), then 15.0 M ammonium hydroxide in water (1.8 mL, 27 mmol). The solution was stirred 2.5 hours. LCMS showed the reaction was complete. The product was isolated by preparative LCMS using a Waters Fraction-Linx instrument and a 30 mm×100 mm Sunfire C18 column (5% $CH_3CN$—$H_2O$ (0.1% TFA), 4.0 minutes; 8.0 min gradient to 30%; 60 mL/min; 8 runs; retention time 11.0 minutes). The eluent was concentrated by 50%, then freeze-dried to give white solid. $^1H$ NMR (300 MHz, MeOH-D4): δ 8.99 (s, 1H); 8.82 (s, 1H); 8.57 (s, 1H); 7.71 (m, 1H); 7.20 (s, 1H); 7.16 (m, 1H); 5.48 (m, 1H, OCH); 5.06 (d, 2H azetidine) 4.8 (d, 2H, azetidine); 3.70 (s, 2H, $CH_2CN$); 3.50 (m, 1H, NCH); 2.30 (m, 2H); 2.01 (m, 2H); 1.80 (m, 2H); 1.75 (m, 2H); 1.50 (s, 6H). MS: 582 (M+H)

Example 44

{1-(cis-4-{[6-[(tert-Butylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tetrakis(trifluoroacetate)

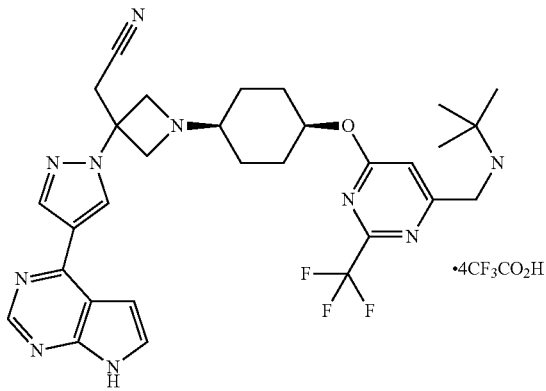 [SMILES: CC(C)(C)NCc1cc(O[C@H]2CC[C@@H](N3CC(CC#N)(n4cc(-c5ncnc6[nH]ccc56)cn4)C3)CC2)nc(C(F)(F)F)n1]

Step 1. [6-[(cis-4-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}cyclohexyl)oxy]-2-(trifluoromethyl)pyrimidin-4-yl]methyl methanesulfonate

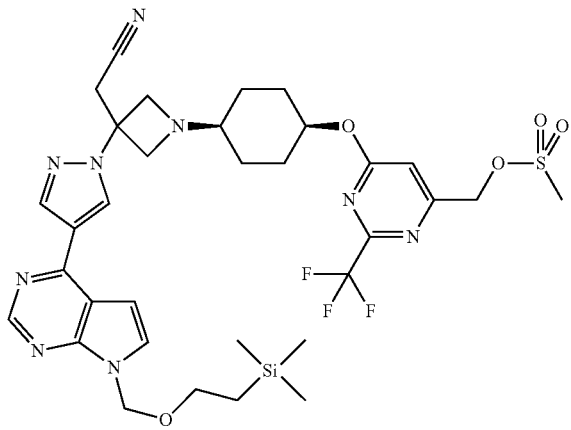 [SMILES: C[Si](C)(C)CCOCn1ccc2c(-c3cnn(C4(CC#N)CN([C@H]5CC[C@@H](Oc6cc(COS(C)(=O)=O)nc(C(F)(F)F)n6)CC5)C4)c3)ncnc21]

{1-(cis-4-{[6-(Hydroxymethyl)-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (0.22 g, 0.32 mmol) was dissolved in methylene chloride (4.4 mL) and was cooled to 0° C. To this mixture, N,N-diisopropylethylamine (84 µL, 0.48 mmol) was added, followed by methanesulfonic anhydride (78 mg, 0.45 mmol). The reaction was stirred at 0° C. for 1 hour. LCMS and HPLC showed 96% conversion to product. The solvent was removed by rotary evaporation, and the residue was used in the next reaction.

Step 2. {1-(cis-4-{[6-[(tert-Butylamino)methyl]-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile

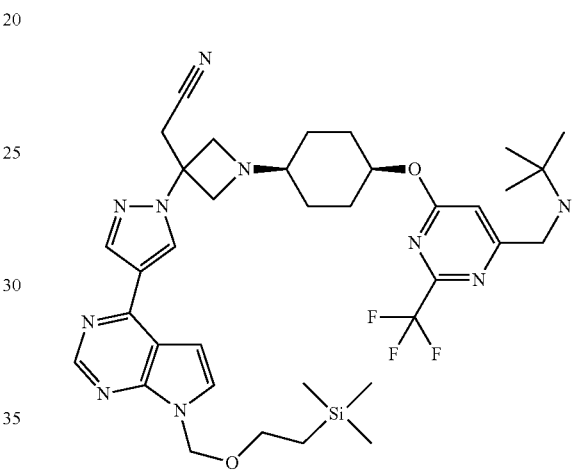

[6-[(cis-4-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}cyclohexyl)oxy]-2-(trifluoromethyl)pyrimidin-4-yl]methyl methanesulfonate (240 mg, 0.32 mmol) was dissolved in THF (2 mL), followed by addition of tert-butylamine (530 µL, 5.0 mmol). The flask was capped and heated in a 50° C. bath for 1 hour. LCMS and HPLC showed 92% conversion of the mesylate to product. HPLC showed the product to have $UV_{max}$ 224, 250 and 308 nm. After another hour, the solvent was removed by rotary evaporation.

Step 3. {1-(cis-4-{[6-[(tert-Butylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tetrakis(trifluoroacetate)

Methylene chloride (4.0 mL) and trifluoroacetic acid (4.0 mL, 52 mmol) were added to the {1-(cis-4-{[6-[(tert-butylamino)methyl]-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile, stirred for 1 hour, and then concentrated to remove TFA. LCMS showed clean conversion to the hydroxymethyl intermediate (M+2H 320) and no loss of tert-butyl group. To the residue was added methanol (7.0 mL), followed by 1,2-propanediamine (30 µL, 0.35 mmol), followed by 15.0 M ammonium hydroxide in water (1.8 mL, 27 mmol). The solution was stirred 2.5 hours. LCMS showed complete reaction with no loss of tert-butyl group and no primary amine detected. The product was isolated by preparative LCMS using a Waters Fraction-Linx instrument and a 30 mm×100 mm Sunfire C18 column; 5% CH3CN—H2O (0.1% TFA), 4.0 minutes; 8.0 minute gradient to 30%; 60 mL/min; 8 runs; retention time 11.0 min. The eluent was concentrated by 50%, then freeze-dried to give white solid. Yield 238 mg. NMR showed it to be the tetra-TFA salt. $^1$H NMR (300 MHz, DMSO-D6): δ 12.5 (s, 1H, NH); 11.0 (s, 1H, NH); 9.13 (t, 2H, NH$_2$); 9.08 (s, 1H); 8.77 (s, 1H); 8.56 (s, 1H); 7.71 (m, 1H); 7.29 (s, 1H); 7.13 (m, 1H); 5.34 (s, 1H, OCH); 4.98 & 4.7 (m, 4H, azetidine); 4.33 (t, 2H, CH$_2$); 3.75 (s, 2H, CH$_2$CN); 3.48 (s, 1H, NCH); 2.08 (m, 2H); 1.90 (m, 2.1-1); 1.71 (m, 2H); 1.50 (m, 2H); 1.33 (s, 9H). LCMS calculated for $C_{30}H_{36}F_3N_{10}O$ (M+H)$^+$: m/z=609.67.

Example 45

{1-(cis-4-{[6-(2-hydroxyethyl)-2-(trifluoromethyl) pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate)

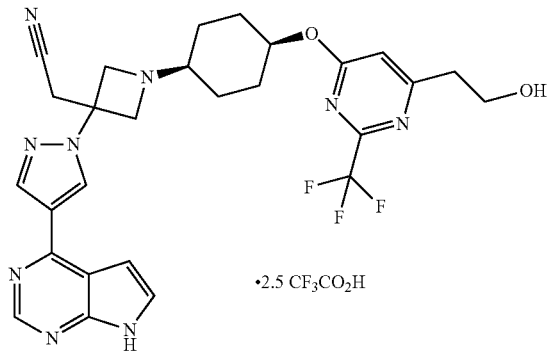 [SMILES: N#CCC1(n2cc(-c3ncnc4[nH]ccc34)cn2)CN([C@H]2CC[C@@H](Oc3cc(CCO)nc(C(F)(F)F)n3)CC2)C1]

·2.5 CF$_3$CO$_2$H

Step 1: Diethyl [6-(1,4-dioxaspiro[4.5]dec-8-yloxy)-2-(trifluoromethyl)pyrimidin-4yl]malonate

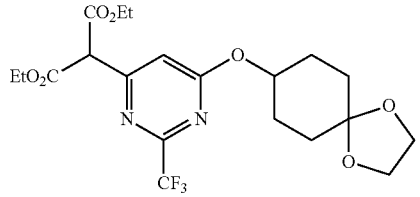 [SMILES: CCOC(=O)C(C(=O)OCC)c1cc(OC2CCC3(CC2)OCCO3)nc(C(F)(F)F)n1]

To a mixture of tetrahydrofuran (40 mL) and NaH in mineral oil (1.1 g, 28 mmol) at 0° C. was added ethyl malonate (4.2 mL, 28 mmol), dropwise. 4-chloro-6-(1,4-dioxaspiro[4.5]dec-8-yloxy)-2-(trifluoromethyl)pyrimidine (described in Example 1, Step 1) (3.75 g, 11.1 mmol), was then added. The reaction mixture was stirred at 64° C. After 3 hours, HPLC & LCMS analysis showed 70% reaction completion. Heated for another 6 hours, and then cooled to 20° C. Only a trace of decarboxylation product formed. The reaction was diluted with aqueous bicarbonate, and extracted with EtOAc. The EtOAc extract was washed with brine, dried over Na$_2$SO$_4$, and evaporated in vacuo to give 8.5 g oil (includes excess ethyl malonate and mineral oil). The crude product was purified by chromatography on a 120 g silica gel column, using solvent A=hexane; solvent B=EtOAc; flow 60 mL/min; A, 3 min; Gradient to 40% B in 40 min; detector set at 254 nm; collected 47 mL fractions; retention time, 28 min. The combined fractions were evaporated to give 4.6 g, colorless oil, 90% yield. $^1$H NMR (300 MHz, CDCl$_3$): δ7.05 (s, 1H); 5.30 (m, 1H, OCH); 4.85 (s, 1H, CH); 4.25 (m, 2H, OCH$_2$); 3.95 (s, 4H, OCH$_2$); 1.6-2.1 (m, 8H); 1.28 (t, 3H, CH$_3$).

Step 2: Ethyl [6-(1,4-dioxaspiro[4.5]dec-8-yloxy)-2-(trifluoromethyl)pyrimidin-4-yl]acetate

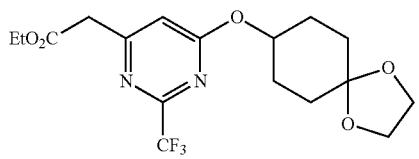

Diethyl [6-(1,4-dioxaspiro[4.5]dec-8-yloxy)-2-(trifluoromethyl)pyrimidin-4-yl]malonate (4.60 g, 9.95 mmol), was dissolved in ethanol (46 mL). Water (18 µL, 1.0 mmol) and 21% Sodium ethoxide in ethanol (0.37 mL, 1.0 mmol) were added. The reaction mixture was stirred at 75° C. for 1 hour. HPLC & LCMS analysis showed 60% decarboxylation. The heating was continued for another 2 hours (reaction complete). The reaction was diluted with aqueous bicarbonate, and extracted with EtOAc. The EtOAc extract was washed with brine, then dried (Na$_2$SO$_4$), and evaporated in vacuo to 3.4 g oil (88% yield). LCMS, HPLC, & NMR showed it to be clean enough to proceed. $^1$H NMR (400 MHz, DMSO-D$_6$): δ7.20 (s, 1H); 5.20 (m, 1H, OCH); 4.10 (q, 2H, OCH$_2$); 3.89 (s, 2H, CH$_2$); 3.85 (s, 4H, OCH$_2$); 1.5-2.0 (m, 8H); 1.15 (t, 3H, CH$_3$). HPLC showed it to have UV$_{max}$ 222 & 252 nm.

Step 3: 2-[6-(1,4-dioxaspiro[4.5]dec-8-yloxy)-2-(trifluoromethyl)pyrimidin-4-yl]ethanol

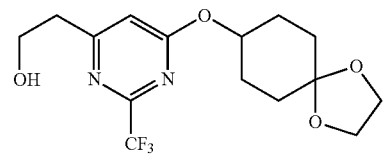 [SMILES: OCCc1cc(OC2CCC3(CC2)OCCO3)nc(C(F)(F)F)n1]

Ethyl [6-(1,4-dioxaspiro[4.5]dec-8-yloxy)-2-(trifluoromethyl)pyrimidin-4-yl]acetate (3.0 g) was dissolved in tetrahydrofuran (40 mL), and cooled in an ice bath. Sodium tetrahydroborate (884 mg, 23.4 mmol) was added followed by methanol (4.8 mL, 120 mmol), in portions. The reaction mixture was stirred for 20 min, removed the ice bath, and stirred at 21° C. for 0.5 hour. HPLC & LCMS showed no remaining ester, and showed conversion to the desired M+H 349; and also showed several over reduction products (at least one of which has no UV absorbance). The reaction mixture was quenched with water and evaporated. The reaction mixture was diluted with aqueous bicarbonate and EtOAc, and stirred for 0.5 hour. The EtOAc layer was washed with brine, dried (Na$_2$SO$_4$), and evaporated to give 3.0 g oil. The product was purified by chromatography on a 120 g silica gel column, using solvent A=hexane; solvent B=3% iPA/EtOAc; flow 60 mL/min; A, 3 min; Gradient to 50% B in 30 min, then 50% B for 15 min; detector set at 254 nm; collected 47 mL fractions; retention time, 34 min. evaporated to yield 1.5 g, a light yellow viscous oil, 56% yield. ¹H NMR (300 MHz, DMSO-D₆): δ7.10 (s, 1H); 5.20 (m, 1H, OCH); 4.71 (t, 1H, OH); 3.85 (s, 4H, OCH₂); 3.72 (q, 2H, OCH₂); 2.85 (t, 2H, CH₂); 1.5-2.0 (m, 8H).

Step 4: 4-{[6-(2-hydroxyethyl)-2-(trifluoromethyl)pyrimidin-4-yl]oxy}cyclohexanone

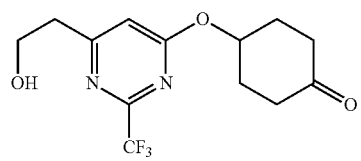 [SMILES: O=C1CCC(Oc2cc(CCO)nc(C(F)(F)F)n2)CC1]

2-[6-(1,4-Dioxaspiro[4.5]dec-8-yloxy)-2-(trifluoromethyl)pyrimidin-4-yl]ethanol was dissolved in acetone (60 mL, 900 mmol), and 5.0 M hydrogen chloride in water (20 mL, 98 mmol) was added and stirred for 17 hours. LCMS and HPLC analysis showed nearly complete conversion to M+H 305. Aqueous bicarbonate was added and the reaction mixture was stirred, then concentrated. This mixture was extracted with EtOAc. The EtOAc was dried (Na₂SO₄), and evaporated in vacuo to give 1.3 g light yellow viscous oil (used in the next reaction without purification). ¹H NMR (300 MHz, CDCl₃): δ6.80 (s, 1H); 5.60 (m, 1H, OCH); 4.06 (t, 2H, OCH₂); 3.04 (t, 2H, CH₂); 2.61 (m, 2H); 2.45 (m, 2H); 2.25 (m, 2H).

Step 5: {1-(4-{[6-(2-hydroxyethyl)-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile

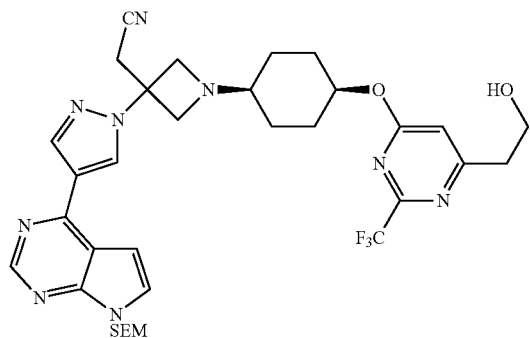 [SMILES: C[Si](C)(C)CCOCn1ccc2c(-c3cnn(C4(CC#N)CN([C@H]5CC[C@@H](Oc6cc(CCO)nc(C(F)(F)F)n6)CC5)C4)c3)ncnc21]

{3-[4-(7-{[2-(Trimethylsilyl)ethoxy]methyl}-7H-pyrrolo[2,3-d]pyrimidin-4-yl)-1H-pyrazol-1-yl]azetidin-3-yl}acetonitrile dihydrochloride (1.9 g, 3.9 mmol), and 4-{[6-(2-hydroxyethyl)-2-(trifluoromethyl)pyrimidin-4-yl]oxy}cyclohexanone (1.3 g, 4.3 mmol), in dry tetrahydrofuran (36 mL) were stirred for 15 min under nitrogen. Sodium triacetoxyborohydride (1.7 g, 8.2 mmol) was then added. The mixture was stirred at 20° C. for 16 hours. HPLC and LCMS analysis showed clean conversion to the trans and cis products (M+H 698; 1:1 ratio). The reaction was quenched with water, concentrated, stirred with 20% KHCO₃ and extracted with ethyl acetate, dried (Na₂SO₄), filtered, and evaporated to give 2.8 g. The isomeric products were separated by prep LCMS using a Waters instrument and a 30 mm×100 mm Xbridge C18 column; 60 mL/min; 55% CH₃CN—H₂O (0.1% NH₄OH); 0.5 min; 4.5 gradient to 72%; 24 runs; retention time trans isomer, 4.6 min; cis isomer, 5.4 min. The isolated cis isomer contained <1% residual trans isomer. Yield 1.00 g cis isomer, 37% yield. ¹H NMR (500 MHz, CDCl₃; also COSY, HSQC, and HMBC): δ8.83 (s, 1H); 8.40 (s, 1H); 8.28 (s, 1H); 7.40 (m, 1H); 6.80 (m, 1H); 6.67 (s, 1H); 5.64 (s, 2H, SEM); 5.17 (m, 1H, OCH); 4.01 (t, 2H, OCH₂); 3.74 (s, 2H, NCH); 3.59 (m, 2H, NCH); 3.55 (t, 2H, SEM); 3.38 (s, 2H, CH₂CN); 2.95 (t, 2H, CH₂); 2.30 (m, 1H, NCH); 2.15 (m, 2H); 1.84 (m, 2H); 1.50 (m, 2H); 1.30 (m, 2H); 0.90 (t, 2H, SEM); −0.92 (s, 9H, SEM).

Step 6: {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate)

{1-(4-{[6-(2-Hydroxyethyl)-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile isomer was dissolved in methylene chloride (18 mL) and trifluoroacetic acid (TFA, 18 mL, 230 mmol) and was stirred for 1.0 hour. The solution was concentrated to remove TFA. LCMS showed conversion to the hydroxymethyl intermediate, M+H 598, some of its TFA ester, M+H 694, and <5% residual SEM. The residue was dissolved in methanol (36 mL) and 15.0 M ammonium hydroxide in water (9.0 mL, 130 mmol) was added. The solution was stirred at 21° C. for 18 hours. HPLC & LCMS showed no remaining M+H 598 peak or TFA ester. The solution was evaporated. Ammonium trifluoroacetate was removed by adding aqueous bicarbonate and extracting the product with EtOAc. The combined EtOAc extract was evaporated to give 0.96 g. This was dissolved in 70 mL of 10% H₂O/ACN containing 1.5 equiv TFA (180 μL). The product was isolated by prep LCMS using a Waters Fraction-Linx instrument and a 30 mm×100 mm Sunfire C18 column; 60 mL/min; 15% ACN-H₂O (0.1% TFA), 0.5 min; 4.5 min gradient to 33%; detector set at m/z 568; 14 runs; retention time 5.0 min. HPLC showed $UV_{max}$ 224, 252, 294, and 318 nm. The combined fractions were freeze-dried. Yield 1.0 g white solid (80% yield). NMR showed it to be the 2.5 TFA salt. ¹H NMR (500 MHz, CD₃CN; also COSY, HSQC, and HMBC): δ10.84 (s, 1H, NH); 9.00 (s, 1H); 8.90 (s, 1H); 8.56 (s, 1H); 7.66 (m, 1H); 7.10 (m, 1H); 6.86 (s, 1H); 5.39 (m, 1H, OCH); 4.86 (brs, 2H, NCH); 4.66 (m, 2H, NCH); 3.90 (t, 2H, OCH₂); 3.78 (s, 2H, CH₂CN); 3.39 (m, 1H, NCH); 2.92 (t, 2H, CH₂); 2.20 (m, 2H); 1.92 (m, ²H); 1.76 (m, 4H). ¹⁹F NMR (400 MHz, DMSO-D₆): δ−69.8 (s); −74.8 (s, TFA); LCMS calculated for C₂₇H₂₉F₃N₉O₂ (M+H)⁺: m/z=568.24

Example 46

6-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N,N-dimethyl-2-(trifluoromethyl)pyrimidine-4-carboxamide bis(trifluoroacetate)

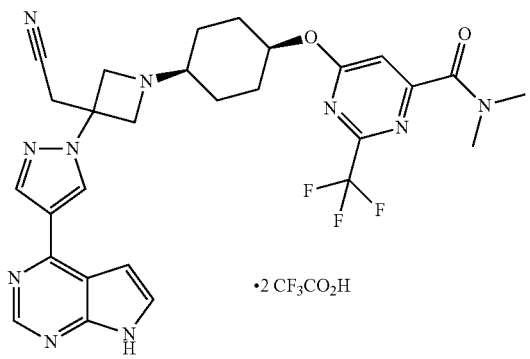 [SMILES: CN(C)C(=O)c1cc(O[C@H]2CC[C@@H](N3CC(CC#N)(n4cc(-c5ncnc6[nH]ccc56)cn4)C3)CC2)nc(C(F)(F)F)n1]

Step 1: 6-(1,4-dioxaspiro[4.5]dec-8-yloxy)-2-(trifluoromethyl)pyrimidine-4-carboxylic

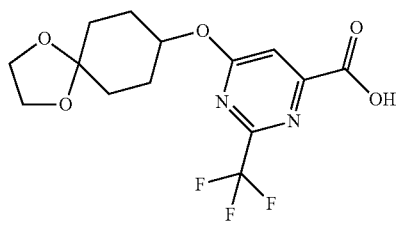 [SMILES: O=C(O)c1cc(OC2CCC3(CC2)OCCO3)nc(C(F)(F)F)n1]

4-(1,4-Dioxaspiro[4.5]dec-8-yloxy)-6-[(E)-2-ethoxyvinyl]-2-(trifluoromethyl)pyrimidine (described in Example 1, step 2) (1.00 g, 2.67 mmol) was dissolved in acetone (10.0 mL) and cooled to 0° C. and potassium permanganate (1.48 g, 9.35 mmol) was added and the reaction was stirred for 30 minutes at 0° C. and at 25° C. for 60 minutes. LCMS analysis showed, as the main component, formation of product (M+H, 349), and little remaining starting material. The reaction was quenched with aqueous bicarbonate, and filtered through Celite. It was acidified with citric acid, extracted with EtOAc, dried (MgSO$_4$), and evaporated in vacuo to 900 mg white crystalline solid. This solid was used in the next reaction without purification. MS (ES): 349(M+1).

Step 2: 6-[(4-oxocyclohexyl)oxy]-2-(trifluoromethyl)pyrimidine-4-carboxylic acid

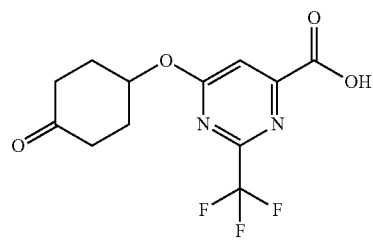 [SMILES: O=C1CCC(Oc2cc(C(=O)O)nc(C(F)(F)F)n2)CC1]

6-(1,4-Dioxaspiro[4.5]dec-8-yloxy)-2-(trifluoromethyl)pyrimidine-4-carboxylic acid (0.50 g, 1.4 mmol) was dissolved in acetone (12.8 mL) To this solution was added a solution of 12.0 M hydrogen chloride in water (1.5 mL, 18 mmol) and stirred at RT for 16 hours at which time LCMS showed the reaction was compete. The reaction mixture was extracted with EtOAc and was evaporated to give the product. The crude product was used in the next step. MS (ES): 305 (M+1).

Step 3: 6-[(cis-4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}cyclohexyl)oxy]-2-(trifluoromethyl)pyrimidine-4-carboxylic acid

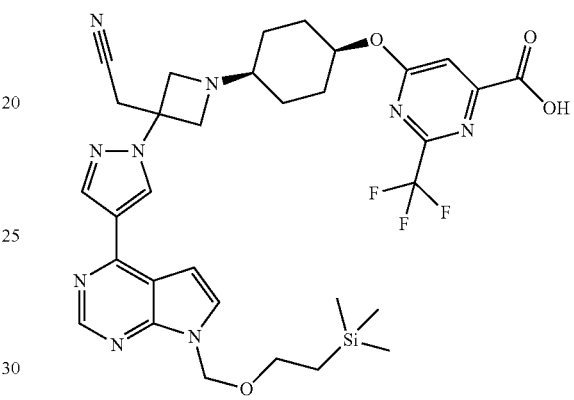

{3-[4-(7-{[2-(Trimethylsilyl)ethoxy]methyl}-7H-pyrrolo[2,3-d]pyrimidin-4-yl)-1H-pyrazol-1-yl]azetidin-3-yl}acetonitrile dihydrochloride (500.0 mg, 1.036 mmol) and 6-[(4-oxocyclohexyl)oxy]-2-(trifluoromethyl)pyrimidine-4-carboxylic acid in dry 1,2-dichloroethane (14.36 mL, 182.3 mmol) were stirred for 5 minutes and sodium triacetoxyborohydride (898 mg, 4.24 mmol) was added. The reaction mixture was stirred at 25° C. for 16 hours, at which time LCMS analysis showed mainly the two diastereomeric products. The reaction was quenched with water, neutralized with NaHCO$_3$ and extracted with ethyl acetate and the solvent was evaporated. The residue was purified by LCMS (pH 10) and the fractions containing the second peak were combined and evaporated. $^1$H NMR (400 MHz, CD$_3$OD) δ 8.90 (m, 1H), 8.83 (s, 1H), 8.55 (m, 1H), 7.75 (d, 1H), 7.51 (d, 1H), 7.15 (d, 1H), 5.78 (s, 4H), 5.23 (m, 1H), 3.50-3.70 (m, 3H), 1.40-2.40 (m, 8H). $^{19}$F NMR (376 MHz, CD$_3$OD) δ −70.52 (s), −77.53 (s). MS (ES): 698(M+1).

Step 4: 6-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N,N-dimethyl-2-(trifluoromethyl)pyrimidine-4-carboxamide bis(trifluoroacetate)

N,N-Diisopropylethylamine (10.31 μL, 0.05920 mmol) and 6-[(cis-4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}cyclohexyl)oxy]-2-(trifluoromethyl)pyrimidine-4-carboxylic acid (20.00 mg, 0.02866 mmol) were dissolved in N,N-dimethylformamide (0.53 mL) and N,N,N',N'-tetramethyl-O-(7-azabenzotriazol-1-yl)uronium hexafluorophosphate (19.60 mg, 0.05154 mmol) in N,N-dimethylformamide (1.00 mL) was added. The reaction mixture was stirred for 10 minutes and dimethylamine hydrochloride (6.09 mg, 0.0747 mmol) was added. The reactions were stirred at 25° C. overnight at which time LCMS analysis showed that the reaction was mostly complete and was purified by LC and evaporated and deprotected as in Example 1 (CH$_2$Cl$_2$/TFA; MeOH/NH$_4$OH) and purified to give the product. $^1$H NMR (300 MHz, CD$_3$OD) δ 9.11 (s, 1H), 8.90 (s, 1H), 8.60 (s, 1H), 7.82 (d, 1H), 7.28 (d, 1H), 7.18 (s, 1H), 5.52 (m, 1H), 5.10 (d, 2H), 4.90 (d, 2H), 3.74 (s, 2H), 3.53 (m, 1H), 3.12 and 3.04 (2 s, 3H), 2.30 (m, 2H), 2.03 (m, 2H), 1.75 (m, 4H). MS (ES): 595(M+1).

Example 48

6-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-ethyl-N-methyl-2-(trifluoromethyl)pyrimidine-4-carboxamide bis(trifluoroacetate)

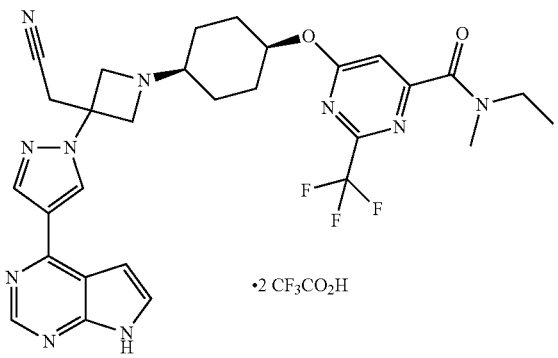 [SMILES: CCN(C)C(=O)c1cc(O[C@H]2CC[C@@H](N3CC(CC#N)(n4cc(-c5ncnc6[nH]ccc56)cn4)C3)CC2)nc(C(F)(F)F)n1]

·2 CF$_3$CO$_2$H

This compound was prepared by a procedure similar to that of Example 46 using 6-[(cis-4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}cyclohexyl)oxy]-2-(trifluoromethyl)pyrimidine-4-carboxylic acid (20.00 mg, 0.02866 mmol) (Example 46, Step 4) and N-methylethylamine, (4.41 mg, 0.0747 mmol). $^1$H NMR (300 MHz, CD$_3$OD) δ 9.15 (s, 1H), 8.92 (d, 1H), 8.61 (s, 1H), 7.85 (d, 1H), 7.31 (d, 1H), 7.17 (s, 1H), 5.52 (m, 1H), 5.11 (d, 2H), 4.83 (d, 2H), 3.75 (s, 2H), 3.64-3.47 (m, 3H), 3.08 and 3.00 (2 s, 3H), 2.30 (m, 2H), 2.03 (m, 2H), 1.91-1.58 (m, 4H), 1.24 (t, 3H). MS (ES): 609(M+1).

Example 50

6-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-(2-methoxyethyl)-2-(trifluoromethyl)pyrimidine-4-carboxamide bis(trifluoroacetate)

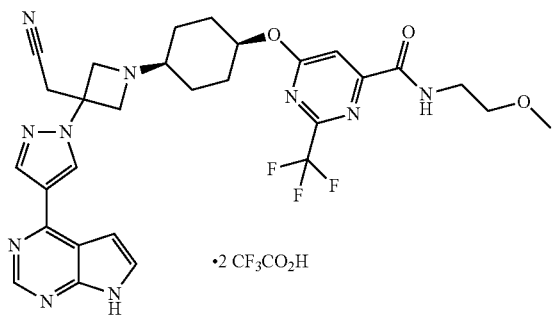 [SMILES: COCCNC(=O)c1cc(O[C@H]2CC[C@@H](N3CC(CC#N)(n4cc(-c5ncnc6[nH]ccc56)cn4)C3)CC2)nc(C(F)(F)F)n1]

·2 CF$_3$CO$_2$H

This compound was prepared by a procedure similar to that of Example 46 using 6-[(cis-4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}cyclohexyl)oxy]-2-(trifluoromethyl)pyrimidine-4-carboxylic acid (20.00 mg, 0.02866 mmol) (Example 46, Step 4) and 2-methoxyethylamine (4.98 μL, 0.0573 mmol). $^1$H NMR (300 MHz, CD$_3$OD) δ 9.09 (s, 1H), 8.88 (s, 1H), 8.79 (brs, 1H), 8.59 (s, 1H), 7.79 (d, 1H), 7.58 (s, 1H), 7.25 (d, 1H), 5.53 (m, 1H), 5.10 (d, 2H), 4.82 (d, 2H), 3.73 (s, 2H), 3.65-3.45 (m, 5H), 3.37 (d, 3H), 2.31 (m 2H), 2.04 (m, 2H), 1.90-1.55 (m, 4H). MS (ES): 625(M+1).

Example 60

{1-(cis-4-{[6-(2-fluoro ethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate)

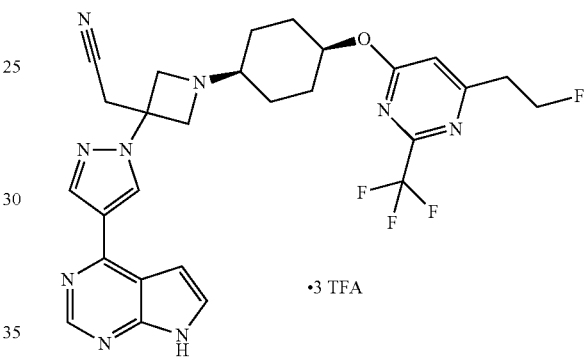

·3 TFA

{1-(cis-4-{[6-(2-Hydroxyethyl)-2-(trifluoromethyl)pyrimidin-4-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (Example 45, Step 5) (24 mg, 0.035 mmol) was dissolved in methylene chloride (1 mL), and 2-methoxy-N-(2-methoxyethyl)-N-(trifluoro-λ(4)-sulfanyl)ethanamine (10 μL, 0.056 mmol) was added. The mixture was stirred at 21° C. for 2 h. LCMS showed conversion to product. The reaction was quenched with aqueous bicarbonate. The organic layer was concentrated. The product was isolated by prep LCMS using a Waters Fraction-Linx instrument and a 30 mm×100 mm Xbridge C18 column; 60 mL/min; 50% CH$_3$CN—H2O (0.1% NH$_4$OH), 2 min; 10 min gradient to 75%; detector set at m/z 700; retention time, 12.2 min. The solvent was removed by rotary evaporation. To deprotect to give the final product, the intermediate product was dissolved in methylene chloride (0.5 mL) and trifluoroacetic acid was added (0.5 mL, 6 mmol). The mixture was stirred for 1 h, and then the solution was concentrated to remove TFA. The residue was dissolved in acetonitrile (1.0 mL). Ammonium hydroxide (15.0 M) in water (0.41 mL, 6.2 mmol) was added, and then the solution was stirred at 21° C. for 18 h. The reaction mixture was then concentrated. The product was isolated by preparative LCMS using a Waters Fraction-Linx instrument and a 19 mm×100 mm Sunfire C18 column; 30 mL/min; 12% CH$_3$CN—H$_2$O (0.1% TFA), 4 min; 8 min gradient to 36%; detector set at m/z 570; retention time 11.8 min. The product was freeze-dried to give the white solid. $^1$H NMR was consistent with the structure and 2.5 TFA salt. $^1$H NMR (400 MHz, DMSO-D6): δ 12.2 (brs, 1H, NH);

10.3 (brs, 1H, NH); 9.00 (brs, 1H); 8.70 (s, 1H); 8.55 (brs, 1H); 7.65 (m, 1H); 7.10 (m, 2H); 5.30 (brm, 1H, OCH); 4.5-5.0 (m, 4H, NCH and 2H, FCH$_2$); 3.8 (s, 2H, CH$_2$CN); 3.4 (m, 1H, NCH); 3.19 (dt, 2H, CH$_2$); 2.16 (m, 2H); 1.82 (m, 2H); 1.68 (m, 2H)); 1.49 (m, 2H). $^{19}$F NMR (376 MHz, DMSO-D6): δ −69.9 (ArCF3); −74.4 (TFA); −218.5 (tt, CH$_2$-F).

Intermediates Used in the Synthesis of the Examples in Table 1

Synthetic intermediate for the preparation of Example 54: 6-(1,4-dioxaspiro[4.5]dec-8-yloxy)-2-(trifluoromethyl)pyrimidine-4-carbonitrile

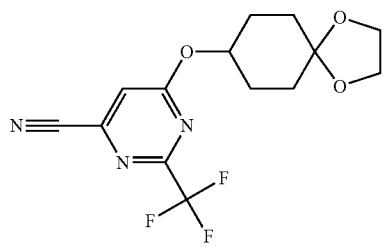 [SMILES: N#Cc1cc(OC2CCC3(CC2)OCCO3)nc(C(F)(F)F)n1]

4-Chloro-6-(1,4-dioxaspiro[4.5]dec-8-yloxy)-2-(trifluoromethyl)pyrimidine (described in Example 1, Step 1) (27.1 mg, 0.0800 mmol) was stirred in N,N-dimethylformamide (1.3 mL). Zinc cyanide (23 mg, 0.20 mmol) was adde, followed by tetrakis(triphenylphosphine)palladium(0) (11 mg, 0.0096 mmol). The solution was flushed with nitrogen (subsurface). The vial was sealed, and the solution was heated at 140° C. for 10 minutes in a microwave reactor. LCMS showed no remaining starting material and showed a new peak that did not ionize. The product was isolated by preparative LC using a Waters Fraction-Linx instrument and a 30 mm×100 mm Sunfire C18 column; 62% CH3CN—H2O (0.1% TFA), 0.5 min, 4.5 min gradient to 82%; 60 mL/min; detector set at 254 nm; retention time=3.8 min. The solvent was removed by rotary evaporation to give 21 mg. $^1$H NMR (400 MHz, acetone-d6): δ 7.78 (s, 1H); 5.41 (m, 1H, OCH); 3.94 (s, 4H, OCH$_2$); 1.9-2.1 (m, 4H); 1.83 (m, 2H); 1.67 (m, 2H). $^{13}$C NMR (100 MHz, acetone-d6): δ 171.6 (s, OC); 142.1 (s, C—N); 117.8 (s, CH); 115.8 (s, CN); 108.2 (s, O$_2$C); 76.1 (s, OCH); 65.0 (s, OCH$_2$); 31.7 (s, CH$_2$); 28.6 (s, CH$_2$); two quartets were not resolved due to insufficient number of scans. The compound of Example 54 was then obtained by following the steps described for Example 45.

Synthetic intermediate for the preparation of Example 56: 2-{[6-(1,4-dioxaspiro[4.5]dec-8-yloxy)-2-(trifluoromethyl)pyrimidin-4-yl]oxy}ethanol

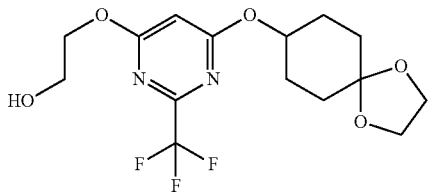 [SMILES: OCCOc1cc(OC2CCC3(CC2)OCCO3)nc(C(F)(F)F)n1]

1,2-Ethanediol (60 μL, 1.1 mmol) and 4-chloro-6-(1,4-dioxaspiro[4.5]dec-8-yloxy)-2-(trifluoromethyl)pyrimidine (described in Example 1, Step 1) (91 mg, 0.27 mmol) were dissolved in tetrahydrofuran (1.4 mL) and cooled to 0° C. Sodium hydride (60%/mineral oil, 22 mg, 0.56 mmol) was added and stirred for 30 minutes at 0° C., then at 22° C. for 20 hours. LCMS analysis showed no remaining starting material, and as the main component, formation of the product, M+H 365. The reaction was quenched with aqueous bicarbonate. The aqueous solution was extracted with ethyl acetate and the organic extracts were washed with water, saturated NaCl, dried (Na$_2$SO$_4$) and the solvent removed in vacuo. The product was purified by preparative LCMS using a Waters Fraction-Linx instrument and a 30 mm×100 mm Sunfire C18 column; 38% CH$_3$CN—H$_2$O (0.1% TFA), 0.5 min, 4.5 min gradient to 56%; 60 mL/min; detector set at M+H 365; retention time, 5.7 min. HPLC found the UVmax as 240 nm. The solvent was removed by rotary evaporation to give 56 mg of product (57% yield). The compound of Example 56 was then obtained by following the steps described for Example 45.

Synthetic intermediates for the preparation of Examples 57 and 57a. (2S)-2-[6-(1,4-dioxaspiro[4.5]dec-8-yloxy)-2-(trifluoromethyl)pyrimidin-4-yl]propane-1,2-diol; (2R)-2-[6-(1,4-dioxaspiro[4.5]dec-8-yloxy)-2-(trifluoromethyl)pyrimidin-4-yl]propane-1,2-diol

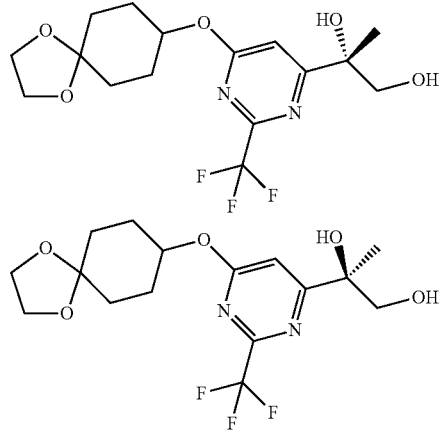

Step 1: 4-(1,4-dioxaspiro[4.5]dec-8-yloxy)-6-isopropenyl-2-(trifluoromethyl)pyrimidine

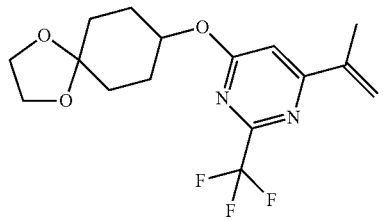 [SMILES: C=C(C)c1cc(OC2CCC3(CC2)OCCO3)nc(C(F)(F)F)n1]

4-Chloro-6-(1,4-dioxaspiro[4.5]dec-8-yloxy)-2-(trifluoromethyl)pyrimidine (described in Example 1, Step 1) (1.69 g, 4.99 mmol), was dissolved in toluene (5.8 mL) with tributyl (isopropenyl)stannane (1.76 mL, 5.49 mmol) and tetrakis (triphenylphosphine)-palladium(0) (0.31 g, 0.27 mmol) and was degassed. The reaction was heated at 110° C. until LCMS analysis showed complete consumption of the starting material, and showed the product (M+H 345). Saturated bicarbonate was added and the product was extracted into an organic layer. The organic extract was dried (Na$_2$SO$_4$), and evaporated to give 3.8 g of yellow oil. The oil was subjected to silica gel chromatography on a 100 g silica gel column, using solvent A=hexane; solvent B=EtOAc; flow 60 mL/min; A, 3 min; Gradient to 25% B in 25 min, then 25% B for 1 min; detector set at 254 nm; collected 45 mL fractions. The product eluted at 18-24 min; HPLC showed it to have UV$_{max}$ 220, 242, & 268 nm. Ph$_3$P eluted at 13 min. The combined fractions were evaporated to give the product, 1.5 g as a clear colorless oil. $^1$H NMR (400 MHz, CD$_3$OD): δ7.05 (s, 1H); 6.30 (s, 1H, vinyl); 5.50 (s, 1H, vinyl); 5.30 (m, 1H, OCH); 3.95 (s, 4H, OCH$_2$); 2.20 (s, 3H, CH$_3$) 2.00 (m, 4H); 1.84 (m, 2H); 1.66 (m, 2H). $^{13}$C NMR (100 MHz, CDCl$_3$): δ172 (s, OC); 168 (s, NC); 157 (q, N$_2$C); 142 (s, =C); 121 (s, =CH$_2$); 121 (q, CF$_3$); 109 (s, O$_2$C); 107 (s, CH); 75 (s, OCH); 66 (s, OCH$_2$); 32 (s, CH$_2$); 29 (s, CH$_2$); 20 (s, CH$_3$).

Step 2. 2-[6-(1,4-dioxaspiro[4,5]dec-8-yloxy)-2-(trifluoromethyl)pyrimidin-4-yl]propane-1,2-diol 4-(1,4-Dioxaspiro[4.5]dec-8-yloxy)-6-isopropenyl-2-(trifluoromethyl)pyrimidine (0.838 g, 2.43 mmol), was dissolved in 1,4-dioxane (70 mL) and water (18 mL), then sodium periodate (0.8 g, 3.65 mmol) was added followed by mixture of osmium tetraoxide (0.536 mL, 0.0844 mmol). The reaction was stirred at 21° C. for 1 hour. The diol was isolated by prep LCMS using a Waters Fraction-Linx instrument and a 30 mm×100 mm Xbridge C18 column; 60 mL/min; 32% CH3CN—H2O (0.1% NH4OH), 0.5 min; 4.5 min gradient to 50%; retention time, 5.3 min.

Step 3. (2S)-2-[6-(1,4-dioxaspiro[4.5]dec-8-yloxy)-2-(trifluoromethyl)pyrimidin-4-yl]propane-1,2-diol and (2R)-2-[6-(1,4-dioxaspiro[4.5]dec-8-yloxy)-2-(trifluoromethyl)pyrimidin-4-yl]propane-1,2-diol 2-[6-(1,4-Dioxaspiro[4.5]dec-8-yloxy)-2-(trifluoromethyl)pyrimidin-4-yl]propane-1,2-diol (55 mg, 0.14 mmol), was resolved into its enantiomers by preparative HPLC using a ChiralPak IA column (20×250 mm) and 30% EtOH-hexane; flow 12 mL/min; retention time peak 1, 6.4 min; peak 2, 9.0 min.

The compounds of Examples 57 and 57a were then obtained by following the steps described for Example 45.

Synthetic intermediates for the preparation of Examples 58 and 58a. (1S)-1-[6-(1,4-dioxaspiro[4.5]dec-8-yloxy)-2-(trifluoromethyl)pyrimidin-4-yl]ethanol and (1R)-1-[6-(1,4-dioxaspiro[4.5]dec-8-yloxy)-2-(trifluoromethyl)pyrimidin-4-yl]ethanol

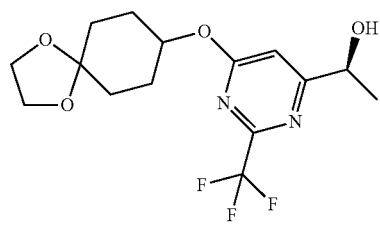

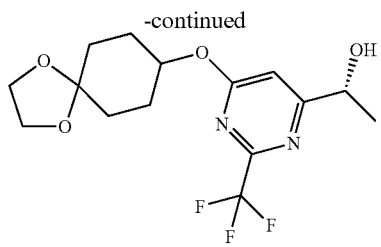

1-[6-(1,4-Dioxaspiro[4.5]dec-8-yloxy)-2-(trifluoromethyl)pyrimidin-4-yl]ethanol (described in Example 43, Step 1) (90 mg, 0.2 mmol), was resolved into its enantiomers by preparative HPLC using a Phenomenex Lux Cellulose-1 column (21×250 mm) and 5% EtOH-hexane; flow rate 18 mL/min; retention time: peak 1, 10.7 min; peak 2, 12.7 min. The combined fractions were evaporated to give 40 mg of peak 1 and 40 mg of peak 2. These synthetic intermediates were carried to the final products Examples 58 and 58a using the synthetic sequence described in Example 45.

Synthetic Intermediates for the Preparation of Examples 59 and 59a

Step 1: Diethyl [6-(1,4-dioxaspiro[4.5]dec-8-yloxy)-2-(trifluoromethyl)pyrimidin-4-yl](methyl)malonate and ethyl 2-[6-(1,4-dioxaspiro[4.5]dec-8-yloxy)-2-(trifluoromethyl)pyrimidin-4-yl]propanoate To a mixture of tetrahydrofuran (4 mL) and NaH in mineral oil (120 mg, 2.9 mmol) at 0° C. was added methylpropanedioic acid, diethyl ester (0.50 mL, 2.9 mmol) dropwise. 4-chloro-6-(1,4-dioxaspiro[4.5]dec-8-yloxy)-2-(trifluoromethyl)pyrimidine (0.39 g, 1.2 mmol) (described in Example 1, Step 1), was then added and was stirred at 20° C. for 16 hours. HPLC & LCMS analysis, showed 4% remaining sm, 70% malonate, and 20% of the monoester. Added Water (25 μL, 1.4 mmol). Stirred at 20° C. for 2 h. HPLC showed 1:1 mono and diesters. The reaction was stirred another h. and was quenched with aq bicarbonate. The reaction was stopped before decarboxylation was complete since both products were needed. The reaction was extracted with EtOAc and The EtOAc was shaken with brine, then dried (Na$_2$SO$_4$), and stripped in vacuo to give 0.7 g oil (includes excess B and mineral oil). This was dissolved in a small amount of 30% EtOAc/hexane. Both products were isolated by automatic silica gel chromatography on a 40 g silica gel column, using solvent A=hexane; solvent B=EtOAc; flow 40 mL/min; A, 2 min; Gradient to 30% B in 32 min; detector set at 254 nm; collected 47 mL fractions; retention time C, 22 min; D, 21 min. This method did not give complete separation. HPLC showed D to have UVmax 220 & 250 nm rotovapped to give D 0.28 g, and C, 0.06 g, colorless oils. Mass spec: 477 (M+1) and 405(M+1) for each product.

Step 2. (2S)-2-[6-(1,4-dioxaspiro[4.5]dec-8-yloxy)-2-(trifluoromethyl)pyrimidin-4-yl]propan-1-ol and (2R)-2-[6-(1,4-dioxaspiro[4.5]dec-8-yloxy)-2-(trifluoromethyl)pyrimidin-4-yl]propan-1-ol Ethyl 2-[6-(1,4-dioxaspiro[4.5]dec-8-yloxy)-2-(trifluoromethyl)pyrimidin-4-yl]propanoate (0.268 g, 0.686 mmol), was dissolved in tetrahydrofuran (4 mL). Sodium tetrahydroborate was add (57 mg, 1.5 mmol), followed by methanol (440 μL, 11 mmol) in portions over 1 h. The reaction mixture was then stirred 1 h. HPLC showed 80% conversion of ester to the alcohol (UV$_{max}$ 222 & 248 nm) and showed a small amount of over-reduction. The reaction was quenched with water, then rotovapped. Aqueous bicarbonate was added, and then EtOAc was added. The mixture was then stirred 0.5 h. The EtOAc layer was shaken with brine, dried (Na$_2$SO$_4$), and then the solvent was removed by rotary evaporation. The alcohol was purified by automatic silica gel chromatography on a 20 g silica gel column, using solvent A=hexane; solvent B=3% iPA/EtOAc; flow 25 mL/min; A, 2 min; Gradient to 45% B in 35 min; detector set at 254 nm; retention time, 24-29 min. The solvent was then removed by rotary evaporation to yield 150 mg of a colorless viscous oil. The oil was resolved into its enantiomers by preparative HPLC using a Phenomenex Lux cellulose-1 column (21×250 mm; 5 u) and 20% EtOH-hexane; flow 18 mL/min; 7 runs; retention time peak 1, 5.2 min; peak 2, 6.3 min. The solvent was removed to give 70 mg for each fraction.

Step 3: 4-{[6-[(1S)-2-hydroxy-1-methylethyl]-2-(trifluoromethyl)pyrimidin-4-yl]oxy}cyclohexanone and 4-{[6-[(1R)-2-hydroxy-1-methylethyl]-2-(trifluoromethyl)pyrimidin-4-yl]oxy}cyclohexanone

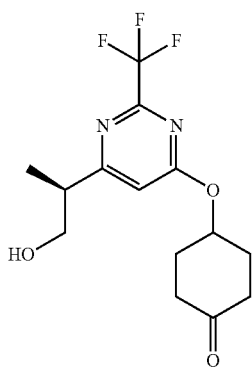 [SMILES: C[C@H](CO)c1cc(OC2CCC(=O)CC2)nc(C(F)(F)F)n1]

(2S)-2-[6-(1,4-Dioxaspiro[4.5]dec-8-yloxy)-2-(trifluoromethyl)pyrimidin-4-yl]propan-1-ol (70. mg, 0.19 mmol) and (2R)-2-[6-(1,4-dioxaspiro[4.5]dec-8-yloxy)-2-(trifluoromethyl)pyrimidin-4-yl]propan-1-ol (70. mg, 0.19 mmol) (referred to as peak 1 and peak 2) were dissolved separately in acetone (5 mL), and 5.0 M hydrogen chloride in water (1.6 mL, 8.0 mmol) was added to each and was stirred for 1.5 h. LCMS & HPLC analysis showed 96% & 97% conversion to M+H 319 for peak 1 and 2. HPLC showed UV$_{max}$ at 220 & 248 nm. Aqueous bicarbonate was added, the reaction mixture stirred, then the acetone was removed by rotary evaporation. The aqueous layer was with EtOAc. The organic layer was dried (Na$_2$SO$_4$) and stripped in vacuo to give 60 mg each. Each enantiomer was carried to the final product, Examples 59 and 59a as described in example 45.

Synthetic Intermediates for the Preparation of Example 62

Step 1. Diethyl [6-(1,4-dioxaspiro[4.5]dec-8-yloxy)-2-(trifluoromethyl)pyrimidin-4-yl](methyl)malonate and 2-[6-(1,4-dioxaspiro[4.5]dec-8-yloxy)-2-(trifluoromethyl)pyrimidin-4-yl]propanoic acid To a mixture of tetrahydrofuran (5 mL) and NaH in mineral oil (140 mg, 3.6 mmol) at 0° C. was added methylpropanedioic acid, diethyl ester (0.62 mL, 3.6 mmol) dropwise. 4-Chloro-6-(1,4-dioxaspiro[4.5]dec-8-yloxy)-2-(trifluoromethyl)pyrimidine (0.49 g, 1.4 mmol) (described in Example 1, Step 1), was then added, and then the reaction mixture was stirred at 20° C. for 18 hours. HPLC showed conversion to M+H 477. Water (94 µL, 5.2 mmol) and lithium hydroxide (97 mg, 4.0 mmol) were added, and the reaction mixture was stirred at 20° C. until decarboxylation and hydrolysis of the ester were complete to give M+H 377. Citric acid (20%) was added, and then the aqueous phase was extracted with EtOAc. The ethyl acetate layer was extracted with brine, dried (Na$_2$SO$_4$), and the solvent removed in vacuo. The product was isolated by preparative LCMS using a Waters Fraction-Linx instrument and a 30 mm×100 mm Sunfire C18 column; 60 mL/min; 42% CH$_3$CN—H2O (0.1% TFA), 0.5 min; 4.5 min gradient to 60%; detector set at m/z 377; 4 runs; retention time 5.2 min. The eluate was freeze dried to give 0.35 g of product.

Step 2: methyl 2-[6-(1,4-dioxaspiro[4.5]dec-8-yloxy)-2-(trifluoromethyl)pyrimidin-4-yl]-2-methylpropanoate Cesium carbonate (1.2 g, 3.7 mmol) was stirred in tetrahydrofuran (3.5 mL). Into the reaction was added 2-[6-(1,4-dioxaspiro[4.5]dec-8-yloxy)-2-(trifluoromethyl)pyrimidin-4-yl]propanoic acid (350 mg, 0.93 mmol) and methyl iodide (220 µL, 3.5 mmol). The reaction mixture was stirred at 20° C. for 64 hours. LCMS analysis showed the reaction to be complete to give the desired product, M+H 405. Water was added, and then extracted with EtOAc. EtOAc extract was washed with brine, dried (Na$_2$SO$_4$), and the solvent removed in vacuo to give 360 mg of product, which was purified by automatic silica gel chromatography on a 40 g silica gel column, using solvent A=hexane; solvent B=EtOAc; flow 40 mL/min; A, 2 min; gradient to 25% B in 30 min; detector set at 254 nm; collected 47 mL fractions; retention time, 22 min. The solvent was then removed to give 0.30 g of product.

Step 3: 2-[6-(1,4-dioxaspiro[4.5]dec-8-yloxy)-2-(trifluoromethyl)pyrimidin-4-yl]-2-methylpropan-1-ol Methyl 2-[6-(1,4-dioxaspiro[4.5]dec-8-yloxy)-2-(trifluoromethyl)pyrimidin-4-yl]-2-methylpropanoate (0.299 g, 0.739 mmol) was dissolved in tetrahydrofuran (6 mL, 80 mmol). Sodium tetrahydroborate was then added (70. mg, 1.8 mmol), followed by methanol (450 µL, 11 mmol) in portions. The reaction mixture was stirred 30 min, at which point LCMS showed 50% conversion. After 2 h, LCMS showed no remaining ester, and showed the product (M+H 377), and several over-reduction by-products. The reaction was quenched with water, the solvent removed by rotary evaporation. Aqueous bicarbonate was added, and then EtOAc was added. The mixture was then stirred 0.5 h. The EtOAc layer was shaken with brine, dried (Na$_2$SO$_4$), and the solvent removed by rotary evaporation. The product was purified by automatic silica gel chromatography on a 40 g silica gel column, using solvent A=hexane; solvent B=2% iPA/EtOAc; flow 40 mL/min; A, 2 min; gradient to 30% B in 35 min; detector set at 254 nm; retention time, 26 min. The solvent was removed by rotary evaporation to yield 230 mg of a colorless viscous oil.

Step 4: 4-{[6-(2-hydroxy-1,1-dimethylethyl)-2-(trifluoromethyl)pyrimidin-4-yl]oxy}cyclohexanone

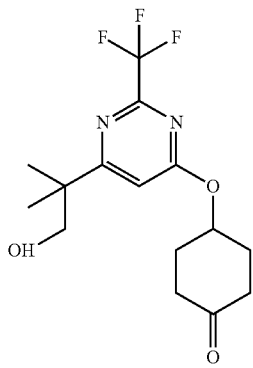 [SMILES: CC(C)(CO)c1cc(OC2CCC(=O)CC2)nc(C(F)(F)F)n1]

The product from step 2 was dissolved in acetone (20 mL, 200 mmol), and 5.0 M hydrogen chloride in water (5 mL, 20 mmol) was added. The reaction mixture was stirred for 17 hours. Aqueous bicarbonate was added, and then the reaction mixture stirred and concentrated, and then extracted with EtOAc. The EtOAc was dried (Na$_2$SO$_4$), and stripped in vacuo to give 0.19 g white crystalline solid (95% conversion to the ketone, M+H 333). NMR (300 MHz, CDCl$_3$) δ 6.86 (s, 1H); 5.61 (m, 1H); 3.75 (d, 2H); 3.33 (t, 1H, OH); 2.63 (m, 2H); 2.13-2.49 (m, 6H); 1.33 (s, 6H). This was used in the next reaction without purification. The product was then carried on to make the final product of Example 62 following the sequence described for Example 45.

Synthetic Intermediates for the Preparation of Example 63

Step 1: methyl [6-hydroxy-2-(trifluoromethyl)pyrimidin-4-yl]acetate 2,2,2-Trifluoroethanimidamide (6.7 g, 50. mmol, Oakwood) was dissolved in 0.5 M sodium methoxide in methanol (120 mL, 60. mmol) and 3-oxopentanedioic acid dimethyl ester (8.4 mL, 55 mmol, Aldrich Co.) was added. The reaction solution was stirred 50° C. for 18 h. LCMS showed it to be mostly done to give the product, M+H 237. The solvent was rotovapped. 1 N HCl was added (50 mL) (pH5), followed 4M HCl (10 mL). The mixture was then extracted with ethyl acetate. The organic solution was washed with brine, dried over sodium sulfate, filtered and concentrated to 12 g of a yellow semisolid. The product was isolated by automatic silica gel chromatography on a 120 g silica gel column, using solvent A=hexane; solvent B=3% iPrOH/EtOAc; flow 60 mL/min; A, 3 min; gradient to 30% B in 40 min, then 30% B for 20 min; detector set at 256 nm; collected 47 mL fractions. The product eluted at 10-25 min. HPLC showed UV$_{max}$ at 222 and 254 nm (dropping off to 320 nm). The solvent was removed to give 9 g of product. The product was purified by automatic silica gel chromatography on a 120 g silica gel column, using solvent A=hexane; solvent B=iPrOH; flow 60 mL/min; A, 3 min; gradient to 20% B in 25 min, then 20% B for 10 min; detector set at 264 nm; collected 47 mL fractions. The product eluted at 22-27 min. The solvent was removed by rotary evaporation to give the desired product as light yellow viscous oil, 5.2 g, which slowly began to crystallize. NMR (400 MHz, DMSO-D6) δ 6.95 (s, 1H); 3.87 (s, 2H, ArCH$_2$); 3.63 (s, 3H).

Step 2: methyl [6-(1,4-dioxaspiro[4.5]dec-8-yloxy)-2-(trifluoromethyl)pyrimidin-4-yl]acetate Under N$_2$, a flask containing 1,4-dioxaspiro[4.5]decan-8-ol (3.92 g, 24.8 mmol), triphenylphosphine (6.70 g, 25.6 mmol), and tetrahydrofuran (47 mL) was cooled in an ice bath. Diisopropyl azodicarboxylate (5.03 mL, 25.6 mmol) was added, and the reaction mixture stirred 10 min A voluminous white solid precipitate formed. Methyl [6-hydroxy-2-(trifluoromethyl)pyrimidin-4-yl]acetate was added (4.68 g, 19.8 mmol) and then the mixture was stirred for 10 min, then the ice bath was removed. The reaction was stirred at 21° C. for 1 h to give a clear light yellow solution. LCMS showed the product, m/z 377, and no remaining pyridone. The reaction was quenched with water. The solvent was removed by rotary evaporation, then saturated sodium bicarbonate (70 mL) and EtOAc was added. The EtOAc layer was shaken with brine, then dried (Na$_2$SO$_4$), and the solvent was removed by rotary evaporation to give 20 g of product. The product was isolated by automatic silica gel chromatography on a 120 g silica gel column, using solvent A=hexane; solvent B=EtOAc; flow 60 mL/min; A, 3 min; gradient to 30% B in 40 min, then 30% B for 15 min; detector set at 254 nm; collected 47 mL fractions. The product eluted at 32 min; HPLC showed it to have UV$_{max}$ 222 & 252 nm). The solvent was removed by rotary evaporation to give 2.0 g of a colorless oil. $^1$H NMR (300 MHz, DMSO-D6) δ 7.19 (s, 1H); 5.19 (m, 1H; OCH); 3.90 (s, 2H, ArCH$_2$); 3.86 (s, 4H); 3.63 (s, 3H); 1.5-2.0 (m, 8H).

Step 3: methyl 1-[6-(1,4-dioxaspiro[4.5]dec-8-yloxy)-2-(trifluoromethyl)pyrimidin-4-yl]cyclopropanecarboxylate Methyl [6-(1,4-dioxaspiro[4.5]dec-8-yloxy)-2-(trifluoromethyl)pyrimidin-4-yl]acetate (0.46 g, 1.2 mmol) was dissolved in tetrahydrofuran (23 mL), then 1,2-dibromoethane (300 μL, 3.4 mmol) was added and the reaction mixture cooled to 0° C. NaH in mineral oil (136 mg, 3.4 mmol) was then added and the reaction mixture was heated to 67° C. for 18 h. LCMS showed 50% reaction. The reaction was quenched with saturated NH$_4$Cl and was partitioned between EtOAc and water. The EtOAc extract was washed with brine, dried (Na$_2$SO$_4$), and stripped in vacuo. The ester was purified by automatic silica gel chromatography on a 40 g silica gel column, using solvent A=hexane; solvent B=EtOAc; flow 40 mL/min; A, 2 min; Gradient to 30% B in 30 min; detector set at 254 nm; collected 47 mL fractions; retention time starting ester, 26 min; product, 19 min. The solvent was removed by rotary evaporation to give 0.17 g of product. $^1$H NMR (300 MHz, CDCl$_3$) δ 7.35 (s, 1H); 5.30 (m, 1H); 3.97 (s, 4H); 3.74 (s, 3H); 1.8-2.0 (m, 6H); 1.6-1.8 (m, 6H).

Step 4: {1-[6-(1,4-dioxaspiro[4.5]dec-8-yloxy)-2-(trifluoromethyl)pyrimidin-4-yl]cyclopropyl}methanol

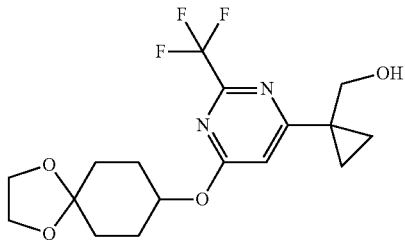 [SMILES: OCC1(c2cc(OC3CCC4(CC3)OCCO4)nc(C(F)(F)F)n2)CC1]

Methyl 1-[6-(1,4-dioxaspiro[4.5]dec-8-yloxy)-2-(trifluoromethyl)pyrimidin-4-yl]cyclopropanecarboxylate (0.17 g, 0.42 mmol), was dissolved in tetrahydrofuran (5 mL) Sodium tetrahydroborate (38 mg, 1.0 mmol) was added, followed by methanol (260 μL, 6.3 mmol) in portions. The reaction mixture was stirred 1 h, at which point LCMS showed 60% conversion. After another hour, LCMS showed no remaining ester, and showed the alcohol (M+H 375), and several over-reduction by-products. The reaction was quenched with water, and then the solvent was removed by rotary evaporation. Aqueous bicarbonate and EtOAc were added, and the mixture stirred 0.5 h. The EtOAc layer was shaken with brine, dried (Na$_2$SO$_4$), and the solvent was removed by rotary evaporation. The alcohol was purified by automatic silica gel chromatography on a 40 g silica gel column, using solvent A=hexane; solvent B=2% iPA/EtOAc; flow 40 mL/min; A, 2 min; Gradient to 35% B in 35 min, then 35% for 10 min; detector set at 254 nm The solvent was removed by rotary evaporation to yield 120 mg of a colorless viscous oil. The intermediate was carried on to the final product of Example 63 following the sequence described for Example 45.

Example 64

{1-(cis-4-{[4-(hydroxymethyl)-6-(trifluoromethyl) pyridin-2-yl]oxy}cyclohexyl)-3-[4-(7H-pyrrolo[2,3-d]pyrimidin-4-yl)-1H-pyrazol-1-yl]azetidin-3-yl}acetonitrile bis(trifluoroacetate)

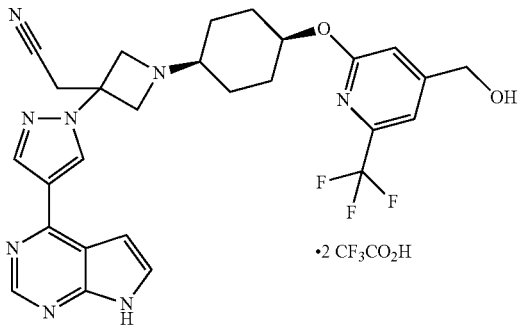 [SMILES: N#CCC1(n2cc(-c3ncnc4[nH]ccc34)cn2)CN([C@H]2CC[C@@H](Oc3cc(CO)cc(C(F)(F)F)n3)CC2)C1]

•2 CF$_3$CO$_2$H

Step 1: tert-butyl 2-chloro-6-(trifluoromethyl)isonicotinate

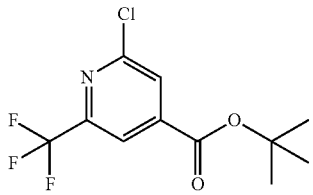 [SMILES: CC(C)(C)OC(=O)c1cc(Cl)nc(C(F)(F)F)c1]

2-Chloro-6-(trifluoromethyl)pyridine (2.00 g, 11.0 mmol Oakwood Products) was dissolved in tetrahydrofuran (40 mL) and 1.0 M lithium chloride-chloro(2,2,6,6-tetramethylpiperidin-1-yl)magnesium (1:1) in THF (13.22 mL, 13.22 mmol, Aldrich Co.) was added at 25° C. The reaction was stirred at 25° C. for 1 hour and was cooled to −78° C., and di-tert-butyldicarbonate (4 g, 18.3 mmol) in tetrahydrofuran (13.5 mL) was added. The reaction was stirred at −78° C. for 1 hour at which time TLC analysis showed no change. Then the reaction was allowed to warm to room temperature at which time a new product with higher R$_f$ value on TLC was identified. The reaction was stirred at 25° C. and most of the starting material was gone. The reaction was quenched with saturated NH$_4$Cl and extracted with EtOAc. The EtOAc extract was washed with 1N HCl, NaHCO$_3$, dried and evaporated in vacuo. NMR analysis of the crude showed residual BOC anhydride, t-BuOH and a mixture of the two esters in a ~3:1 ratio and some starting material remaining. The crude was chromatographed on silica gel using 5% EtOAc/hexanes to give the product contaminated with a small amount of impurity. This was allowed to crystallize and washed with 5% EtOAc/hexanes to give clean product. $^1$H NMR (400 MHz, CDCl$_3$) δ 7.07 (s, 1H), 8.01 (s, 1H), 1.47 (s, 9H).

Step 2: 2-(1,4-dioxaspiro[4.5]dec-8-yloxy)-6-(trifluoromethyl)isonicotinic acid

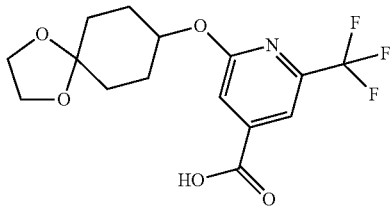 [SMILES: O=C(O)c1cc(OC2CCC3(CC2)OCCO3)nc(C(F)(F)F)c1]

In a vial, 1,4-dioxaspiro[4.5]decan-8-ol (0.400 g, 2.53 mmol) was dissolved in tetrahydrofuran (8.44 mL) with tert-butyl 2-chloro-6-(trifluoromethyl)isonicotinate (0.510 g, 1.81 mmol) and cooled to 0° C. and a 60% mixture of sodium hydride in mineral oil (123 mg, 3.08 mmol) was added and the mixture was stirred for 30 minutes at 0° C. and at 25° C. for 30 minutes at which time TLC analysis showed most of the ester was consumed and a new spot with lower R$_f$ was formed. The reaction was continued for 16 hours. LCMS analysis showed that it consisted mainly of the acid. TLC analysis showed the original product was not present. The reaction was quenched with water and extracted with EtOAc. The crude product was used in the next reaction without further purification. MS (ES): 348 (M+1).

Step 4: [2-(1,4-dioxaspiro[4.5]dec-8-yloxy)-6-(trifluoromethyl)pyridin-4-yl]methanol

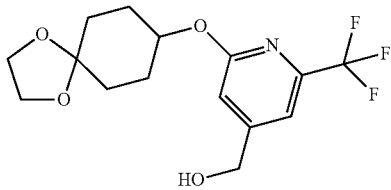 [SMILES: OCc1cc(OC2CCC3(CC2)OCCO3)nc(C(F)(F)F)c1]

2-(1,4-Dioxaspiro[4.5]dec-8-yloxy)-6-(trifluoromethyl) isonicotinic acid (490.0 mg, 1.411 mmol) was dissolved in tetrahydrofuran (17.5 mL) and cooled to 0° C. 1.0 M Borane in THF (4.23 mL, 4.23 mmol) was then added and stirred at 0° C. for 10 min and at 25° C. for 16 hours when LCMS analysis showed the absence of starting material. The reaction was quenched with 1N NaOH and water, and extracted with EtOAc. The EtOAc extract was evaporated in vacuo and the residue was used in the next reaction without further purification. MS (ES): 334 (M+1).

Step 5: 4-{[4-(hydroxymethyl)-6-(trifluoromethyl) pyridin-2-yl]oxy}cyclohexanone

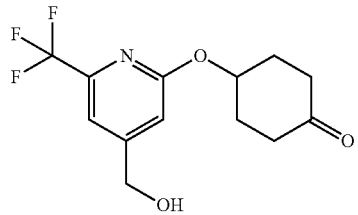 [SMILES: O=C1CCC(Oc2cc(CO)cc(C(F)(F)F)n2)CC1]

[2-(1,4-Dioxaspiro[4.5]dec-8-yloxy)-6-(trifluoromethyl) pyridin-4-yl]methanol was dissolved in acetone (8 mL) and 10.0 M hydrogen chloride in water (1.5 mL, 15 mmol) was added. The reaction was stirred for 16 hours and LCMS analysis showed it was mostly complete. The reaction was neutralized with NaHCO₃ and partitioned between EtOAc and water. The EtOAc extracts were washed with brine, dried and evaporated in vacuo. The crude product was used in the next reaction. MS (ES): 290 (M+1)

Step 6: {1-(cis-4-{[4-(hydroxymethyl)-6-(trifluoromethyl)pyridin-2-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile

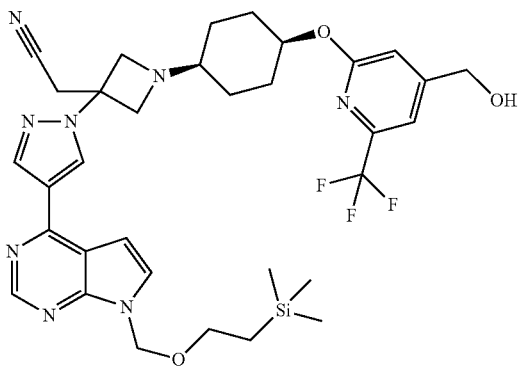 [SMILES: C[Si](C)(C)CCOCn1ccc2c(-c3cnn(C4(CC#N)CN([C@H]5CC[C@@H](Oc6cc(CO)cc(C(F)(F)F)n6)CC5)C4)c3)ncnc21]

{3-[4-(7-{[2-(Trimethylsilyl)ethoxy]methyl}-7H-pyrrolo[2,3-d]pyrimidin-4-yl)-1H-pyrazol-1-yl]azetidin-3-yl}acetonitrile dihydrochloride (400.0 mg, 0.829 mmol) and 4-{[4-(hydroxymethyl)-6-(trifluoromethyl)pyridin-2-yl]oxy}cyclohexanone (300.0 mg, 1.037 mmol) were mixed in dry 1,2-dichloroethane (11.33 mL) and were stirred for 5 minutes. Sodium triacetoxyborohydride (708 mg, 3.34 mmol) was added to this mixture. The reaction mixture was stirred at 25 C for 16 hours, at which time LCMS analysis showed mainly the two diastereomeric products. The reaction was quenched with water, neutralized with NaHCO₃ and extracted with ethyl acetate and the solvent was evaporated. The residue was purified by LCMS (pH 10) and the fractions containing the second peak were combined and evaporated to give 1-(cis-4-{[4-(hydroxymethyl)-6-(trifluoromethyl)pyridin-2-yl]oxy}cyclohexyl)-3-[4-(7-{[2-(trimethyl silyl)ethoxy]methyl}-7H-pyrrolo[2,3-d]pyrimidin-4-yl)-1H-pyrazol-1-yl]azetidin-3-yl}acetonitrile. MS (ES): 683 (M+1). The first peak contained {1-(trans-4-{[4-(hydroxymethyl)-6-(trifluoromethyl)pyridin-2-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile. MS (ES): 683 (M+1).

Step 7: {1-(cis-4-([4-(hydroxymethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile bis(trifluoroacetate)

1-(cis-4-{[4-(Hydroxymethyl)-6-(trifluoromethyl)pyridin-2-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile was deprotected under the same conditions described in Example 1 to give the title compound. ¹H NMR (300 MHz, CD₃OD) δ 9.00 (s, 1H), 8.83 (s, 1H), 8.57 (s, 1H), 7.71 (m, 1H), 7.32 (s, 1H), 7.17 (m, 1H), 6.99 (s, 1H), 5.36 (m, 1H), 5.06 (d, 2H), 4.80 (d, 2H), 4.66 (s, 2H), 3.70 (s, 2H), 3.52 (m, 1H), 2.28 (m, 2H), 2.01 (m, 2H), 1.74 (m, 4H). MS (ES): 553(M+1).

Example 65

{1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate)

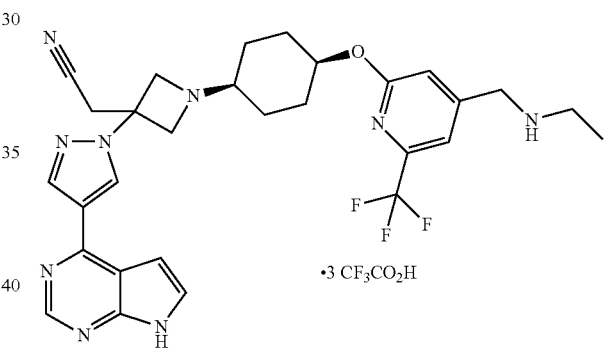

Step 1: [2-[(cis-4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}cyclohexyl)oxy]-6-(trifluoromethyl)pyridin-4-yl]methyl methanesulfonate

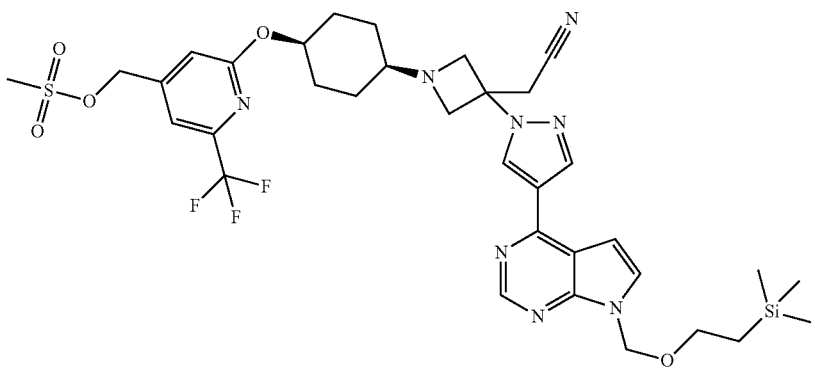

{1-(cis-4-{[4-(Hydroxymethyl)-6-(trifluoromethyl)pyridin-2-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (from Example 64, 145.0 mg, 0.2124 mmol) was dissolved in methylene chloride (2.93 mL) and was cooled to 0° C. To that N,N-diisopropylethylamine (60.5 μL, 0.347 mmol) was added followed by methanesulfonyl chloride (23 μL, 0.30 mmol). The reaction was stirred at 0° C. for 1 hour. Then the reaction mixture was worked up with EtOAc and used in the next reaction. MS (ES): 761(M+1).

Step 2: {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate)

[2-[(cis-4-{3-(Cyanomethyl)-3-[4-(7-{[2-(trimethyl silyl)ethoxy]methyl}-7H-pyrrolo[2,3-d]pyrimidin-4-yl)-1H-pyrazol-1-yl]azetidin-1-yl}cyclohexyl)oxy]-6-(trifluoromethyl)pyridin-4-yl]methyl methanesulfonate (50 mg, 0.06571 mmol) was dissolved in 1,4-dioxane (2.5 mL) and, 2.0 Methylamine in THF (300 μL, 0.6 mmol) was added. The reaction was stirred at 25° C. for 16 hours at which time LCMS analysis showed mainly product. The product were purified by LC, evaporated, and deprotected as in Example 1 and purified by LC to give the product. $^1$H NMR (400 MHz, CD$_3$OD) δ 9.08 (s, 1H), 8.87 (s, 1H), 8.58 (s, 1H), 7.78 (d, 1H), 7.50 (s, 1H), 7.25 (d, 1H), 7.13 (s, 1H), 5.38 (m, 1H), 5.08 (d, 2H), 4.80 (d, 2H), 4.27 (s, 2H), 3.74 (s, 2H), 3.50 (m, 1H), 3.16 (q, 2H), 2.24 (m, 2H), 2.01 (m, 2H), 1.76 (m, 4H), 1.34 (t, 3H). $^{19}$F NMR (376 MHz, CD$_3$OD) δ−70.52 (s), −77.49 (s). MS (ES): 580(M+1).

Example 66

{1-(cis-4-{[4-(aminomethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate)

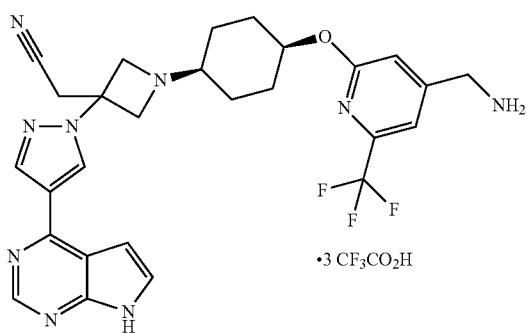 [SMILES: N#CCC1(n2cc(-c3ncnc4[nH]ccc34)cn2)CN([C@H]2CC[C@@H](Oc3cc(CN)cc(C(F)(F)F)n3)CC2)C1]

This compound was prepared by a procedure similar to that of Example 65 starting from 1: [2-[(cis-4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}cyclohexyl)oxy]-6-(trifluoromethyl)pyridin-4-yl]methyl methanesulfonate and a solution of 20 M ammonia in water. $^1$H NMR (400 MHz, CD$_3$OD) δ 9.00 (s, 1H), 8.83 (s, 1H), 8.56 (s, 1H), 7.71 (d, 1H), 7.47 (s, 1H), 7.17 (d, 1H), 7.08 (s, 1H), 5.38 (s, 1H), 5.04 (m, 2H), 4.77 (m, 2H), 4.21 (s, 2H), 3.72 (s, 2H), 3.48 (m, 1H), 2.25 (m, 2H), 2.01 (m, 2H), 1.74 (m, 4H). $^{19}$F NMR (376 MHz, CD$_3$OD) δ, −70.52 (s), −77.53 (s). MS (ES): 552(M+1).

Example 67

{1-(cis-4-{[4-[(methylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate)

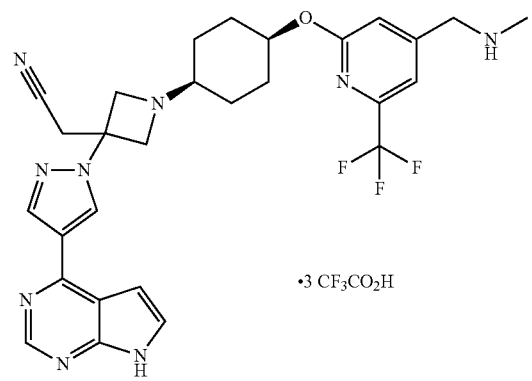 [SMILES: CNCc1cc(O[C@H]2CC[C@@H](N3CC(CC#N)(n4cc(-c5ncnc6[nH]ccc56)cn4)C3)CC2)nc(C(F)(F)F)c1]

This compound was prepared by a procedure similar to that of Example 65 starting from [2-[(cis-4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}cyclohexyl)oxy]-6-(trifluoromethyl)pyridin-4-yl]methyl methanesulfonate and methylammonium chloride. $^1$H NMR (300 MHz, CD$_3$OD) δ 9.00 (s, 1H), 8.83 (s, 1H), 8.56 (s, 1H), 7.71 (d, 1H), 7.47 (s, 1H), 7.17 (d, 1H), 7.08 (s, 1H), 5.38 (s, 1H), 5.04 (m, 2H), 4.77 (m, 2H), 4.21 (s, 2H), 3.72 (s, 2H), 3.48 (m, 1H), 2.77 (s, 3H), 2.25 (m, 2H), 2.01 (m, 2H), 1.74 (m, 4H). $^{19}$F NMR (376 MHz, CD$_3$OD) δ −70.52 (s), −77.54 (s). MS (ES): 566(M+1).

Example 68

{1-(cis-4-{[4-[(dimethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate)

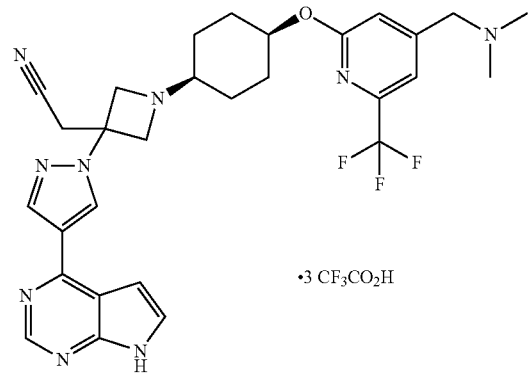 [SMILES: CN(C)Cc1cc(O[C@H]2CC[C@@H](N3CC(CC#N)(n4cc(-c5ncnc6[nH]ccc56)cn4)C3)CC2)nc(C(F)(F)F)c1]

This compound was prepared by a procedure similar to that of Example 65 starting from [2-[(cis-4-{3-(cyanomethyl)-3-

[4-(7-{[2-(trimethylsilyl)ethoxy]methyl}-7H-pyrrolo[2,3-d]pyrimidin-4-yl)-1H-pyrazol-1-yl]azetidin-1-yl}cyclohexyl)oxy]-6-(trifluoromethyl)pyridin-4-yl]methyl methanesulfonate and a 2M solution of dimethylamine in THF. $^1$H NMR (300 MHz, CD$_3$OD) δ 8.97 (s, 1H), 8.81 (s, 1H), 8.54 (s, 1H), 7.68 (s, 1H), 7.53 (s, 114), 7.17 (m, 2H), 5.39 (m, 1H), 5.01 (m, 2H), 4.76 (m, 2H), 4.39 (s, 2H), 3.71 (s, 2H), 3.45 (m, 1H), 2.90 (s, 6H), 2.25 (m, 2H), 2.01 (m, 2H), 1.78 (m, 4H). $^{19}$F NMR (376 MHz, CD$_3$OD) δ, −70.51 (s), −77.45 (s). MS (ES): 580(M+1).

Example 69

{1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile bis(trifluoroacetate)

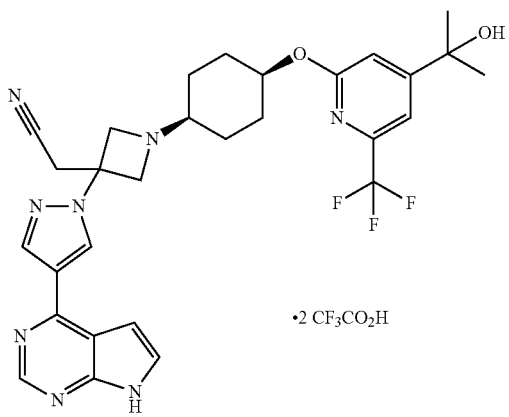 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1]

•2 CF$_3$CO$_2$H

Step 1: 2-chloro-6-(trifluoromethyl)isonicotinic acid

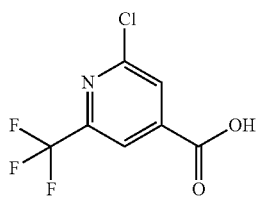 [SMILES: O=C(O)c1cc(Cl)nc(C(F)(F)F)c1]

2-Chloro-6-(trifluoromethyl)pyridine (1.0 g, 5.51 mmol, Oakwood Products) was dissolved in tetrahydrofuran (20 mL) and 1.0 M lithium chloride-chloro(2,2,6,6-tetramethylpiperidin-1-yl)magnesium (1:1) in THF (6.610 mL, 6.610 mmol, Aldrich Co.) was added at 25° C. The reaction was stirred at 25° C. for 1 hour and was cooled to −78° C. The reaction was stirred at −78° C. for 1 hour and allowed to warm to room temperature, quenched with water, and was partitioned between 1N NaOH and ether. The phases were separated and the aqueous phase was washed with additional ether and acidified with concentrated HCl to pH~1 and extracted with ether. The combined organic phase was washed with water, saturated NaCl, dried over MgSO$_4$, filtered, and evaporated to dryness to provide the crude product. NMR analysis showed that it consisted of a ~2:1 mixture of the para and meta carboxylic acids. The mixture was carried over to the next reaction. 440 MHz NMR (CDCl$_3$) δ 8.17 (s, 1H), 8.11 (s, 1H).

Step 2: ethyl 2-chloro-6-(trifluoromethyl)isonicotinate and ethyl 2-chloro-6-(trifluoromethyl)nicotinate

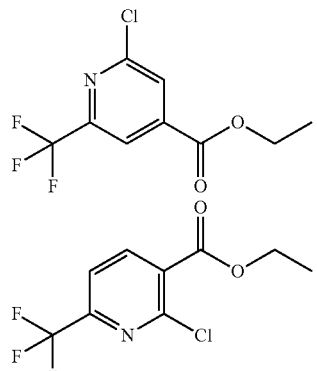

In a vial, 2-chloro-6-(trifluoromethyl)nicotinic acid (0.98 g, 4.4 mmol) and 2-chloro-6-(trifluoromethyl)isonicotinic acid (1.85 g, 8.2 mmol) were dissolved in ethyl orthoformate (5.0 mL, 30.1 mmol) and heated at 120° C. for 5 hours at which time TLC analysis showed that most of the starting material had been consumed and the products were formed. The reaction mixture was evaporated in vacuo and the residue was purified by silica gel chromatography using 10% EtOAc/hexanes to give the two ethyl ester products. $^1$H NMR (400 MHz, CDCl$_3$): δ 8.14 (s, 1H), 8.08 (s, 1H), 4.47 (q, 2H), 1.44 (t, 3H).

Step 3: 2-[2-chloro-6-(trifluoromethyl)pyridin-4-yl]propan-2-ol

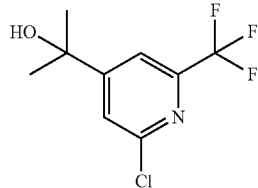

Ethyl 2-chloro-6-(trifluoromethyl)isonicotinate (0.35 g, 1.4 mmol) was dissolved in tetrahydrofuran (13.8 mL) and was cooled to −78° C., then 3.0 M methylmagnesium bromide in ether (1.4 mL, 4.1 mmol) was added. The reaction was stirred at −78° C. for 3 hours at which time LCMS analysis showed absence of starting material. The reaction was quenched with saturated NH$_4$Cl and was partitioned between water/1 N HCl and EtOAc, the phases were separated and the aqueous phase was washed with additional EtOAc. The combined organic phase was washed with water, saturated NaCl, dried over MgSO$_4$, filtered and evaporated to dryness to provide the crude product. NMR analysis showed that it consisted of a ~1:1 mixture of the alcohol and the methyl ketone intermediate. The crude material used in the next reaction without purification. NMR 400 MHz NMR (CDCl₃): δ 7.70 (s, 1H), 7.63 (s, 1H), 1.60 (s, 6H)

Step 4: 2-[2-(1,4-dioxaspiro[4.5]dec-8-yloxy)-6-(trifluoromethyl)pyridin-4-yl]propan-2-ol

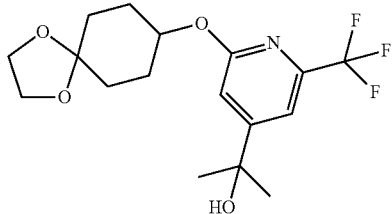 [SMILES: CC(C)(O)c1cc(OC2CCC3(CC2)OCCO3)nc(C(F)(F)F)c1]

1,4-Dioxaspiro[4.5]decan-8-ol (0.25 g, 1.58 mmol) and 2-[2-chloro-6-(trifluoromethyl)pyridin-4-yl]propan-2-ol (0.2 g, 0.835 mmol) were dissolved in tetrahydrofuran (2 mL) and cooled to 0° C. and a 60% mixture of sodium hydride (70.0 mg, 1.75 mmol) in mineral oil was added and the reaction was stirred for 30 minutes at 0° C. and at 25° C. for 60 hours at which time TLC analysis indicated the presence of some product. The reaction was quenched with water, and was extracted with ethyl acetate and the organic extracts were washed with water, saturated NaCl, dried (MgSO₄), and evaporated in vacuo. The residue was purified by LC (pH 2) to give the product. MS (ES): 362 (M+1).

Step 5: 4-{[4-(1-hydroxy-1-methylethyl)-6-(trifluoromethyl)pyridin-2-yl]oxy}cyclohexanone

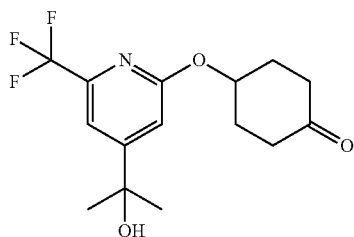 [SMILES: CC(C)(O)c1cc(OC2CCC(=O)CC2)nc(C(F)(F)F)c1]

2-[2-(1,4-Dioxaspiro[4.5]dec-8-yloxy)-6-(trifluoromethyl)pyridin-4-yl]propan-2-ol (0.049 g, 0.14 mmol) was dissolved in acetone (3.7 mL) A solution of 12.0 M hydrogen chloride in water (0.43 mL, 5.2 mmol) was added and was stirred at 25° C. for 16 hours at which time LCMS showed about 70% reaction was complete. An additional 12.0 M hydrogen chloride in water (0.43 mL, 5.2 mmol) was added and was stirred for 3 hours; LCMS showed ~90% reaction was complete and was quenched into excess NaHCO₃, extracted with EtOAc and the organic extract was evaporated to give the product. This was used in the next reaction without purification. MS (ES): 318 (M+1).

Step 5: {1-(cis-4-{[4-(1-hydroxy-1-methylethyl)-6-(trifluoromethyl)pyridin-2-yl]oxy}cyclohexyl)-3-[4-(7-{[2-(trimethylsilyl)ethoxy]methyl}-7H-pyrrolo[2,3-c]pyrimidin-4-yl)-1H-pyrazol-1-yl]azetidin-3-yl}acetonitrile

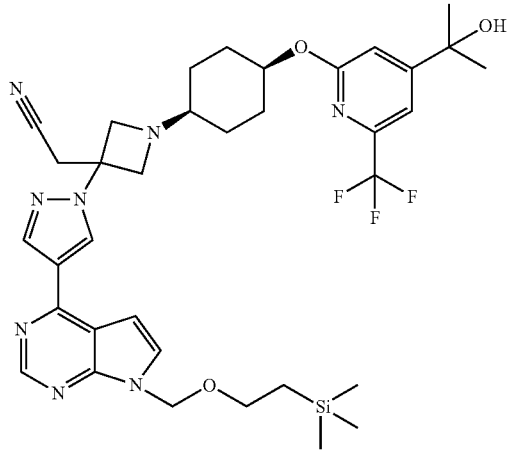 [SMILES: CC(C)(O)c1cc(O[C@H]2CC[C@@H](N3CC(CC#N)(n4cc(-c5ncnc6c5ccn6COCC[Si](C)(C)C)cn4)C3)CC2)nc(C(F)(F)F)c1]

{3-[4-(7-{[2-(Trimethylsilyl)ethoxy]methyl}-7H-pyrrolo[2,3-d]pyrimidin-4-yl)-1H-pyrazol-1-yl]azetidin-3-yl}acetonitrile dihydrochloride (55.3 mg, 0.115 mmol) and 4-{[4-(1-hydroxy-1-methylethyl)-6-(trifluoromethyl)pyridin-2-yl]oxy}cyclohexanone were dissolved in dry 1,2-dichloroethane (1.38 mL) and were stirred for 5 min and sodium triacetoxyborohydride (86.1 mg, 0.406 mmol) was added. The reaction mixture was stirred at 25° C. for 16 h, at which time LCMS analysis showed mainly the two diastereomeric products. The reaction was quenched with water, neutralized with NaHCO₃ and extracted with ethyl acetate and the solvent was evaporated. The residue was purified by LCMS (pH 10) and the fractions containing the second peak were combined and evaporated to give {1-(cis-4-{[4-(1-hydroxy-1-methylethyl)-6-(trifluoromethyl)pyridin-2-yl]oxy}cyclohexyl)-3-[4-(7-{[2-(trimethylsilyl)ethoxy]methyl}-7H-pyrrolo [2,3-d]pyrimidin-4-yl)-1H-pyrazol-1-yl]azetidin-3-yl}acetonitrile. The first peak was also isolated to give {1-(trans-4-{[4-(1-hydroxy-1-methyl ethyl)-6-(trifluoromethyl)pyridin-2-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile. MS (ES): 712(M+1).

Step 6: {1-(cis-4-([4-(1-hydroxy-1-methylethyl)-6-(trifluoromethyl)pyridin-2-yl]oxy}cyclohexyl)-3-{[2-(7H-pyrrolo[2,3-d]pyrimidin-4-yl)-1H-pyrazol-1-yl]azetidin-3-yl}acetonitrile bis(trifluoroacetate)

{1-(cis-4-{[4-(1-Hydroxy-1-methylethyl)-6-(trifluoromethyl)pyridin-2-yl]oxy}cyclohexyl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile was deprotected as described in Example 1 and was purified by liquid chromatography (pH 2) to give 1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]

azetidin-3-yl}acetonitrile bis(trifluoroacetate). In a similar manner {1-(trans-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile bis(trifluoroacetate) was prepared and characterized. $^1$H NMR (400 MHz, CD$_3$OD) δ 9.07 (s, 1H), 8.87 (s, 1H), 8.59 (s, 1H), 7.78 (d, J=3.7 Hz, 1H), 7.44 (s, 1H), 7.24 (d, J=3.7 Hz, 1H), 7.05 (s, 1H), 5.35 (s, 1H), 5.09 (d, J=12.2 Hz, 2H), 4.82 (d, J=12.2 Hz, 2H), 3.72 (s, 2H), 3.5 (m, 1H), 2.27 (m, 2H), 2.0 (m, 2H), 1.74 (m, 4H), 1.50 (s, 6H). MS (ES): 581(M+1).

Additional compounds shown in Table 3 were prepared analogously to the procedure of Example 65.

TABLE 3

| Ex. No. | R$^4$ | MS (M + H)$^+$ | Name | Prep. |
|---|---|---|---|---|
| 70 | -CH$_2$NH(CH$_2$)$_3$OH | 610 | {1-(cis-4-{[4-{[(3-hydroxypropyl)amino]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 65 |
| 71 | -CH$_2$NHC(CH$_3$)$_2$CH$_2$OH | 624 | {1-(cis-4-{[4-{[(2-hydroxy-1,1-dimethylethyl)amino]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) (salt) | Ex 65 |
| 72 | -CH$_2$NH-cyclopropyl | 592 | {1-(cis-4-{[4-[(cyclopropylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 65 |
| 73 | -CH$_2$NH-(S)-CH(CH$_3$)CH$_2$OH | 610 | {1-(cis-4-{[4-({[(1S)-2-hydroxy-1-methylethyl]amino}methyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 65 |
| 74 | -CH$_2$NHCH$_2$CH$_2$OH | 596 | {1-(cis-4-{[4-{[(2-hydroxyethyl)amino]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 65 |
| 75 | -CH$_2$NH-(R)-CH(CH$_3$)CH$_2$OH | 610 | {1-(cis-4-{[4-({[(1R)-2-hydroxy-1-methylethyl]amino}methyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 65 |

TABLE 3-continued

| Ex. No. | R⁴ | MS (M + H)⁺ | Name | Prep. |
|---|---|---|---|---|
| 76 | -CH₂-NH-CH₂-cyclopropyl | 606 | {1-(cis-4-{[4-{[(cyclopropylmethyl)amino]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 65 |
| 77 | -CH₂-NH-cyclobutyl | 606 | {1-(cis-4-{[4-[(cyclobutylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 65 |
| 78 | -CH₂-azetidin-1-yl | 592 | {1-(cis-4-{[4-(azetidin-1-ylmethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 65 |
| 79 | -CH₂-(3-hydroxyazetidin-1-yl) | 608 | {1-(cis-4-{[4-[(3-hydroxyazetidin-1-yl)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 65 |
| 80 | -C(O)NHCH₃ | 580 | 2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-methyl-6-(trifluoromethyl)isonicotinamide bis(trifluoroacetate) | Ex 46 |
| 81 | -C(O)N(CH₃)₂ | 594 | 2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N,N-dimethyl-6-(trifluoromethyl)isonicotinamide bis(trifluoroacetate) | Ex 46 |
| 82 | -C(O)N(CH₃)CH₂CH₂OH | 624 | 2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-(2-hydroxyethyl)-N-methyl-6-(trifluoromethyl)isonicotinamide bis(trifluoroacetate) | Ex 46 |
| 83 | -C(O)NH-iPr | 608 | 2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-isopropyl-6-(trifluoromethyl)isonicotinamide bis(trifluoroacetate) | Ex 46 |

TABLE 3-continued

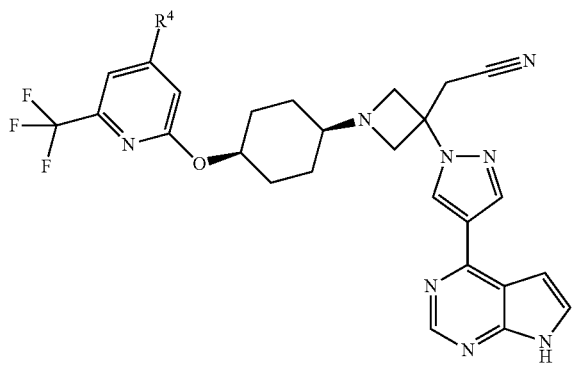

| Ex. No. | R⁴ | MS (M + H)⁺ | Name | Prep. |
|---|---|---|---|---|
| 84 | (S)-CH(CH₃)CH₂OH amide | 624 | 2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-[(1S)-2-hydroxy-1-methylethyl]-6-(trifluoromethyl)isonicotinamide bis(trifluoroacetate) | Ex 46 |
| 85 | (R)-CH(CH₃)CH₂OH amide | 624 | 2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-[(1R)-2-hydroxy-1-methylethyl]-6-(trifluoromethyl)isonicotinamide bis(trifluoroacetate) | Ex 46 |
| 86 | N-cyclopropyl amide | 606 | 2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-cyclopropyl-6-(trifluoromethyl)isonicotinamide bis(trifluoroacetate) | Ex 46 |
| 87 | N-cyclopropyl-N-methyl amide | 620 | 2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-cyclopropyl-N-methyl-6-(trifluoromethyl)isonicotinamide bis(trifluoroacetate) | Ex 46 |
| 88 | N-(sec-butyl) amide | 622 | N-(sec-butyl)-2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-6-(trifluoromethyl)isonicotinamide bis(trifluoroacetate) | Ex 46 |
| 89 | 3-hydroxyazetidin-1-yl carbonyl | 622 | {1-(cis-4-{[4-[(3-hydroxyazetidin-1-yl)carbonyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile bis(trifluoroacetate) | Ex 46 |
| 90 | N-cyclobutyl amide | 620 | 2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-N-cyclobutyl-6-(trifluoromethyl)isonicotinamide bis(trifluoroacetate) | Ex 46 |
| 91 | 3-cyanoazetidin-1-yl carbonyl | 631 | 1-[2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-6-(trifluoromethyl)isonicotinoyl]azetidine-3-carbonitrile bis(trifluoroacetate) | Ex 46 |

TABLE 3-continued

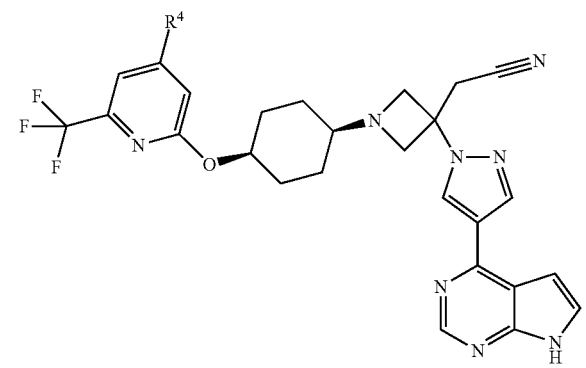

| Ex. No. | R⁴ | MS (M + H)⁺ | Name | Prep. |
|---|---|---|---|---|
| 92 | (morpholin-4-ylmethyl) | 622 | {1-(cis-4-{[4-(morpholin-4-ylmethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 65 |
| 93 | [(2R)-2-(hydroxymethyl)pyrrolidin-1-yl]methyl | 636 | {1-(cis-4-{[4-{[(2R)-2-(hydroxymethyl)pyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 65 |
| 94 | [(2S)-2-(hydroxymethyl)pyrrolidin-1-yl]methyl | 636 | {1-(cis-4-{[4-{[(2S)-2-(hydroxymethyl)pyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 65 |
| 95 | [(3R)-3-hydroxypyrrolidin-1-yl]methyl | 622 | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile pentakis(trifluoroacetate) | Ex 65 |
| 96 | [(3S)-3-hydroxypyrrolidin-1-yl]methyl | 622 | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 65 |
| 97 | (4-hydroxypiperidin-1-yl)methyl | 636 | {1-(cis-4-{[4-[(4-hydroxypiperidin-1-yl)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 65 |
| 98 | [(3-methyloxetan-3-yl)amino]methyl | | {1-(cis-4-{[4-{[(3-methyloxetan-3-yl)amino]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tetrakis(trifluoroacetate) | Ex 65 |

TABLE 3-continued

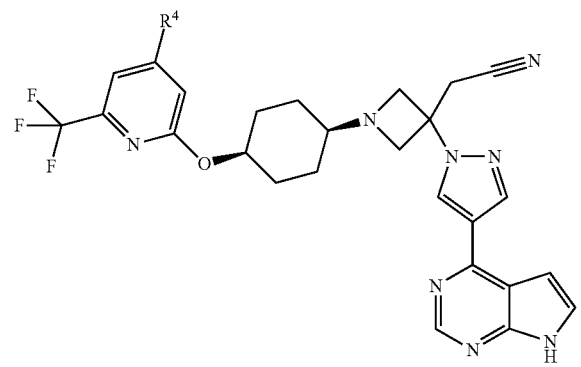

| Ex. No. | R⁴ | MS (M + H)⁺ | Name | Prep. |
|---|---|---|---|---|
| 99 | ![imidazolylmethyl] | | {1-(cis-4-{[4-(1H-imidazol-1-ylmethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tetrakis(trifluoroacetate) | Ex 65 |
| 100 | ![pyrazolylmethyl] | | {1-(cis-4-{[4-(1H-pyrazol-1-ylmethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile tris(trifluoroacetate) | Ex 65 |

The ¹H NMR data of some of the compounds are provided below in Table 3a.

TABLE 3a

| Ex. No. | NMR |
|---|---|
| 80 | ¹H NMR (300 MHz, CD₃OD) δ 9.03 (s, 1H), 8.84 (s, 1H), 8.83 (brs, 1H), 8.57 (s, 1H), 7.74 (d, J = 3.7 Hz, 1H), 7.70 (s, 1H), 7.37 (s, 1H), 7.19 (d, J = 3.6 Hz, 1H), 5.39 (m, 1H), 5.08 (d, J = 11.4 Hz, 2H), 4.80 (d, J = 11.4 Hz, 2H), 3.71 (s, 2H), 3.50 (m, 1H), 2.92 (d, J = 3.3 Hz, 3H), 2.29 (m, 2H), 2.03 (m, 2H), 1.77 (m, 4H). ¹⁹F NMR (282 MHz, CD₃OD) δ −70.41 (s), −77.55 (s). |
| 86 | ¹H NMR (300 MHz, CD₃OD) δ 9.03 (s, 1H), 8.84 (s, 1H), 8.57 (s, 1H), 7.74 (d, J = 3.7 Hz, 1H), 7.70 (s, 1H), 7.36 (s, 1H), 7.19 (d, J = 3.7 Hz, 1H), 5.38 (m, 1H), 5.08 (d, J = 11.9 Hz, 2H), 4.80 (d, J = 11.9 Hz, 2H), 3.71 (s, 2H), 3.50 (m, 1H), 2.87 (dt, J = 7.2, 3.4 Hz, 1H), 2.28 (m, 2H), 2.00 (m, 2H), 1.86-1.63 (m, 4H), 0.89-0.74 (m, 2H), 0.71-0.56 (m, 2H). ¹⁹F NMR (282 MHz, CD₃OD) δ −70.39 (s), −77.50 (s). |
| 92 | ¹H NMR (400 MHz, CD₃OD) δ 9.03 (s, 1H), 8.82 (s, 1H), 8.55 (s, 2H), 7.71 (d, 1H), 7.56 (s, 1H), 7.20 (d, 1H), 5.38 (m, 1H), 5.08 (d, 2H), 4.74 (m, 3H), 4.32 (d, 1H), 3.85 (m, 1H), 3.72 (s, 2H), 3.40 (m, 4H), 1.60-2.50 (m, 12H). |
| 95 | ¹H NMR (300 MHz, CD₃OD) δ 9.18 (s, 1H), 8.94 (s, 1H), 8.61 (s, 1H), 7.88 (d, J = 3.7 Hz, 1H), 7.55 (s, 1H), 7.34 (d, J = 3.7 Hz, 1H), 7.18 (s, 1H), 5.38 (s, 1H), 5.12 (d, J = 11.9 Hz, 2H), 4.83 (d, J = 11.9 Hz, 2H), 4.53 (m, 4H), 3.76 (s, 2H), 3.53 (m, 3H), 2.25 (m, 3H), 2.01 (m, 30H), 1.77 (m, 4H). ¹⁹F NMR (282 MHz, CD₃OD) δ −70.50 (s), −77.67 (s). |
| 98 | ¹H NMR (300 MHz, CD₃OD): δ 9.07 (s, 1H); 8.86 (s, 1H); 8.58 (s, 1H); 7.79 (d, 1H); 7.22 (d, 1H); 7.17 (s, 1H); 5.51 (br, 1H, OCH); 5.07 (d, 2H); 4.82 (m, 4H, ArCH₂); 4.59 (d, 2H); 3.74 (s, 2H, CH₂CN); 3.5 (m, 1H, NCH); 2.24 (m, 2H); 2.02 (m, 2H); 1.6-1.9 (m, 4H); 1.75 (s, 3H). |
| 99 | ¹H NMR (400 MHz, DMSO-D6): δ 12.3 (s, 1H, NH); 10.9 (s, 1H, NH); 9.20 (s, 1H); 9.07 (br, 1H); 8.74 (s, 1H); 8.57 (s, 1H); 7.80 (s, 1H); 7.72 (s, 1H); 7.69 (m, 1H); 7.54 (s, 1H); 7.10 (m, 1H); 6.88 (s, 1H); 5.52 (s, 2H, ArCH₂); 5.20 (br, 1H, OCH); 4.55-5.0 (m, 4H, azetidine); 3.74 (br, 2H, CH₂CN); 3.44 (br, 1H, NCH); 2.07 (m, 2H); 1.85 (m, 2H); 1.62 (m, 4H); 1.48 (m, 2H). |

Example A

In Vitro JAK Kinase Assay

Compounds herein were tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds were measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions was 1 mM. Reactions were carried out at room temperature for 1 hour and then stopped with 20 µL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.). See Tables 4 and 5 for data for compounds of the examples as tested by the assay of Example A.

TABLE 4

| Ex. No. | JAK1 $IC_{50}$ (nM)* | JAK2/JAK1 $IC_{50}$ ratio |
|---|---|---|
| 1 | + | ≥10 |
| 2 | + | ≥10 |
| 3 | + | ≥10 |

TABLE 4-continued

| Ex. No. | JAK1 IC$_{50}$ (nM)* | JAK2/JAK1 IC$_{50}$ ratio |
|---|---|---|
| 4 | + | ≥10 |
| 5 | + | ≥10 |
| 6 | + | ≥10 |
| 7 | + | ≥10 |
| 8 | + | ≥10 |
| 9 | + | ≥10 |
| 10 | + | ≥10 |
| 11 | + | ≥10 |
| 12 | + | ≥10 |
| 13 | + | ≥10 |
| 14 | + | ≥10 |
| 15 | + | ≥10 |
| 16 | + | ≥10 |
| 17 | + | ≥10 |
| 18 | + | ≥10 |
| 19 | + | ≥10 |
| 20 | + | ≥10 |
| 21 | + | ≥10 |
| 22 | + | ≥10 |
| 23 | + | ≥10 |
| 24 | + | ≥10 |
| 25 | + | ≥10 |
| 26 | + | ≥10 |
| 27 | + | ≥10 |
| 28 | + | ≥10 |
| 29 | + | ≥10 |
| 30 | + | ≥10 |
| 31 | + | ≥10 |
| 32 | + | ≥10 |
| 33 | + | ≥10 |
| 34 | + | ≥10 |
| 35 | + | ≥10 |
| 36 | + | ≥10 |
| 37 | + | ≥10 |
| 38 | + | ≥10 |
| 39 | + | ≥10 |
| 40 | + | ≥10 |
| 41 | + | ≥10 |
| 42 | + | ≥10 |
| 43 | + | ≥10 |
| 44 | + | ≥10 |
| 45 | + | ≥10 |
| 46 | + | ≥10 |
| 47 | + | ≥10 |
| 48 | + | ≥10 |
| 49 | + | ≥10 |
| 50 | + | ≥10 |
| 51 | + | ≥10 |
| 52 | + | ≥10 |
| 53 | + | ≥10 |
| 54 | + | ≥10 |
| 56 | + | ≥10 |
| 57 | + | ≥10 |
| 57a | + | ≥10 |
| 58 | + | ≥10 |
| 58a | + | ≥10 |
| 59 | + | ≥10 |
| 59a | + | ≥10 |
| 60 | + | ≥10 |
| 61 | + | ≥10 |
| 62 | + | ≥10 |
| 63 | + | ≥10 |

*<10 nM (+)

TABLE 5

| Ex. No. | JAK1 IC$_{50}$ (nM)** | JAK2/JAK1 IC$_{50}$ ratio |
|---|---|---|
| 64 | + | ≥10 |
| 65 | + | ≥10 |
| 66 | + | ≥10 |
| 67 | + | ≥10 |
| 68 | + | ≥10 |
| 69 | + | ≥10 |
| 70 | + | ≥10 |
| 71 | + | ≥10 |
| 72 | ++ | ≥10 |
| 73 | + | ≥10 |
| 74 | + | ≥10 |
| 75 | + | ≥10 |
| 76 | + | ≥10 |
| 77 | + | ≥10 |
| 78 | + | ≥10 |
| 79 | + | ≥10 |
| 80 | + | ≥10 |
| 81 | + | ≥10 |
| 82 | + | ≥10 |
| 83 | + | ≥10 |
| 84 | + | ≥10 |
| 85 | + | ≥10 |
| 86 | + | ≥10 |
| 87 | + | ≥10 |
| 88 | + | ≥10 |
| 89 | + | ≥10 |
| 90 | + | ≥10 |
| 91 | + | ≥10 |
| 92 | + | ≥10 |
| 93 | + | ≥10 |
| 94 | + | ≥10 |
| 95 | + | ≥10 |
| 96 | + | ≥10 |
| 97 | + | ≥10 |
| 98 | + | ≥10 |
| 99 | + | ≥10 |
| 100 | + | ≥10 |

**<10 nM (+); <20 nM (++)

Example B

Cellular Assays

Cancer cell lines dependent on cytokines and hence JAK/STAT signal transduction, for growth, can be plated at 6000 cells per well (96 well plate format) in RPMI 1640, 10% FBS, and 1 nG/mL of appropriate cytokine. Compounds can be added to the cells in DMSO/media (final concentration 0.2% DMSO) and incubated for 72 hours at 37° C., 5% CO$_2$. The effect of compound on cell viability is assessed using the CellTiter-Glo Luminescent Cell Viability Assay (Promega) followed by TopCount (Perkin Elmer, Boston, Mass.) quantitation. Potential off-target effects of compounds are measured in parallel using a non-JAK driven cell line with the same assay readout. All experiments are typically performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. Nature 434:1144-1148; Staerk, J., et al. JBC 280:41893-41899). Endpoints include the effects of compounds on cell survival, proliferation, and phosphorylated JAK, STAT, Akt, or Erk proteins.

Certain compounds herein can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 μg/ml streptomycin) at a density of $2 \times 10^6$ cells/ml at 37° C. for up to 2 days. For IL-2 stimulated cell proliferation analysis, T-cells are first treated with Phytohemagglutinin (PHA) at a final concentration of 10 μg/mL for 72 hours. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, Wis.).

Example C

In Vivo Anti-Tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. Hematol J. 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. Bcr-Abl) such as the K562 tumor model.

Example D

Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (Immunol Today. 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 μL (10 μL on the internal pinna and 10 μL on the external pinna) at a concentration of 0.2%. Twenty-four to seventy-two hours after the challenge, ears are measured again. Treatment with the test compounds is given throughout the sensitization and challenge phases (day −1 to day 7) or prior to and throughout the challenge phase (usually afternoon of day 4 to day 7). Treatment of the test compounds (in different concentration) is administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E

In Vivo Anti-Inflammatory Activity

Compounds herein can be evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al, Wiley Press.; *Methods in Molecular Biology*: Vol. 225, Inflammation Protocols., Winyard, P. G. and Willoughby, D. A., Humana Press, 2003.).

Example F

Animal Models for the Treatment of Dry Eye, Uveitis, and Conjunctivitis

Agents may be evaluated in one or more preclinical models of dry eye known to those schooled in the art including, but not limited to, the rabbit concanavalin A (ConA) lacrimal gland model, the scopolamine mouse model (subcutaneous or transdermal), the Botulinumn mouse lacrimal gland model, or any of a number of spontaneous rodent autoimmune models that result in ocular gland dysfunction (e.g. NOD-SCID, MRL/lpr, or NZB/NZW) (Barabino et al., Experimental Eye Research 2004, 79, 613-621 and Schrader et al., Developmental Opthalmology, Karger 2008, 41, 298-312, each of which is incorporated herein by reference in its entirety). Endpoints in these models may include histopathology of the ocular glands and eye (cornea, etc.) and possibly the classic Schirmer test or modified versions thereof (Barabino et al.) which measure tear production. Activity may be assessed by dosing via multiple routes of administration (e.g. systemic or topical) which may begin prior to or after measurable disease exists.

Agents may be evaluated in one or more preclinical models of uveitis known to those schooled in the art. These include, but are not limited to, models of experimental autoimmune uveitis (EAU) and endotoxin induced uveitis (EIU). EAU experiments may be performed in the rabbit, rat, or mouse and may involve passive or activate immunization. For instance, any of a number or retinal antigens may be used to sensitize animals to a relevant immunogen after which animals may be challenged ocuarly with the same antigen. The EIU model is more acute and involves local or systemic administration of lipopolysaccharide at sublethal doses. Endpoints for both the EIU and EAU models may include fundoscopic exam, histopathology amongst others. These models are reviewed by Smith et al. (Immunology and Cell Biology 1998, 76, 497-512, which is incorporated herein by reference in its entirety). Activity is assessed by dosing via multiple routes of administration (e.g. systemic or topical) which may begin prior to or after measurable disease exists. Some models listed above may also develop scleritis/episcleritis, chorioditis, cyclitis, or iritis and are therefore useful in investigating the potential activity of compounds for the therapeutic treatment of these diseases.

Agents may also be evaluated in one or more preclinical models of conjunctivitis known those schooled in the art. These include, but are not limited to, rodent models utilizing guinea-pig, rat, or mouse. The guinea-pig models include those utilizing active or passive immunization and/or immune challenge protocols with antigens such as ovalbumin or ragweed (reviewed in Groneberg, D. A., et al., Allergy 2003, 58, 1101-1113, which is incorporated herein by reference in its entirety). Rat and mouse models are similar in general design to those in the guinea-pig (also reviewed by Groneberg).

Activity may be assessed by dosing via multiple routes of administration (e.g. systemic or topical) which may begin prior to or after measurable disease exists. Endpoints for such studies may include, for example, histological, immunological, biochemical, or molecular analysis of ocular tissues such as the conjunctiva.

Example G

In Vivo Protection of Bone

Compounds may be evaluated in various preclinical models of osteopenia, osteoporosis, or bone resorption known to those schooled in the art. For example, ovariectomized rodents may be used to evaluate the ability of compounds to affect signs and markers of bone remodeling and/or density (W. S. S. Jee and W. Yao, J Musculoskel. Neuron. Interact., 2001, 1(3), 193-207, which is incorporated herein by reference in its entirety). Alternatively, bone density and architecture may be evaluated in control or compound treated rodents in models of therapy (e.g. glucocorticoid) induced osteopenia (Yao, et al. Arthritis and Rheumatism, 2008, 58(6), 3485-3497; and id. 58(11), 1674-1686, both of which are incorporated herein by reference in its entirety). In addition, the effects of compounds on bone resorption and density may be evaluable in the rodent models of arthritis discussed above (Example E). Endpoints for all these models may vary but often include histological and radiological assessments as well as immunohisotology and appropriate biochemical markers of bone remodeling.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

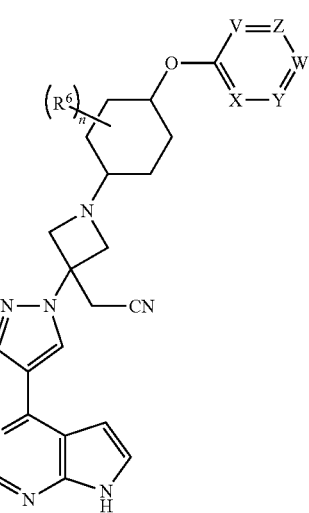

or a pharmaceutically acceptable salt thereof, wherein:
X is $CR^1$ or N;
Y is $CR^2$ or N;
W is $CR^3$ or N;
Z is $CR^4$ or N;
V is $CR^5$ or N;

wherein the 6-membered aromatic ring formed by carbon atom, X, Y, W, Z, and V has 0, 1, or 2 nitrogen ring members;

$R^1$, $R^2$, $R^3$, $R^4$, and $R^5$ are each independently selected from H, halo, CN, $NO_2$, $C_{1-6}$ alkyl, $C_{2-6}$ alkenyl, $C_{2-6}$ alkynyl, $C_{1-6}$ haloalkyl, Cy, —$C_{1-3}$ alkylene-Cy, $OR^a$, $NR^eR^f$, $SR^b$, $S(=O)_2R^b$, $S(=O)_2NR^eR^f$, $C(=O)R^b$, $C(=O)OR^a$, $C(=O)NR^eR^f$, $OC(=O)R^b$, $OC(=O)NR^eR^f$, $NR_cC(=O)R^d$, $NR^cC(=O)OR^d$, $NR^cS(=O)_2R^d$, $NR^cS(=O)_2NR^eR^f$, and $CR^oR^pOR^{a1}$, and $CR^oR^pNR^{e1}R^{f1}$; wherein said $C_{1-6}$ alkyl is optionally substituted by 1, 2, or 3 independently selected $R^x$ groups;

$R^6$ is F, methyl, —OH, or —$OCH_3$;

each Cy is independently selected from 3-6-membered monocyclic cycloalkyl, 4-6 membered monocyclic heterocycloalkyl, phenyl, and 5-6 membered monocyclic heteroaryl, which are each optionally substituted by 1, 2, or 3 independently selected Regroups;

each $R^a$, $R^c$, $R^d$, $R^e$, and $R^f$ is independently selected from H, $C_{1-6}$ alkyl, $C_{1-6}$ haloalkyl, $Cy^1$, and —$C_{1-3}$ alkylene-$Cy^1$; wherein said $C_{1-6}$ alkyl is optionally substituted with 1, 2, or 3 independently selected $R^h$ groups; or each $R^e$ and $R^f$, together with the nitrogen atom to which they are attached, form a 4-6 membered monocyclic heterocycloalkyl ring; which is optionally substituted with 1, 2, or 3 independently selected $R^g$ groups;

each $R^b$ is independently selected from $C_{1-6}$ alkyl, $C_{1-6}$ haloalkyl, $Cy^1$, and —$C_{1-3}$ alkylene-$Cy^1$; wherein said $C_{1-6}$ alkyl is optionally substituted with 1, 2, or 3 independently selected $R^h$ groups;

$R^o$ and $R^p$, taken together with the carbon atom to which they are attached, form a 3-4 membered monocyclic cycloalkyl ring;

each $Cy^1$ is independently selected from 3-6-membered monocyclic cycloalkyl, 4-6 membered monocyclic heterocycloalkyl, phenyl, and 5-6 membered monocyclic heteroaryl, which are each optionally substituted by 1, 2, or 3 independently selected $R^g$ groups;

each $R^g$ is independently selected from halo, CN, hydroxy, $C_{1-4}$ alkyl, $C_{1-4}$ haloalkyl, $C_{1-4}$ alkoxy, $C_{1-4}$ haloalkoxy, hydroxyl-$C_{1-4}$ alkyl, $C_{1-4}$ alkoxy-$C_{1-4}$ alkyl, cyano-$C_{1-4}$ alkyl, amino, $C_{1-4}$ alkylamino, di-$C_{1-4}$-alkylamino, carbamyl, $C_{1-4}$ alkylcarbamyl, di($C_{1-4}$ alkyl)carbamyl, $C_{1-4}$ alkylcarbonyl, $C_{1-4}$ alkoxycarbonyl, $C_{1-4}$ alkylcarbonyloxy, $C_{1-4}$ alkylsulfonyl, $C_{1-4}$ alkylcarbonylamino, $C_{1-4}$ alkylsulfonylamino, aminosulfonyl, $C_{1-4}$ alkylaminosulfonyl, di-$C_{1-4}$ alkylaminosulfonyl, aminosulfonylamino, $C_{1-4}$ alkylaminosulfonylamino, and di-$C_{1-4}$ alkylaminosulfonylamino;

each $R^h$ is independently selected from halo, CN, hydroxy, $C_{1-4}$ alkoxy, $C_{1-4}$ haloalkoxy, hydroxyl-$C_{1-4}$ alkyl, $C_{1-4}$ alkoxy-$C_{1-4}$ alkyl, cyano-$C_{1-4}$ alkyl, amino, $C_{1-4}$ alkylamino, carbamyl, $C_{1-4}$ alkylcarbamyl, di($C_{1-4}$ alkyl) carbamyl, $C_{1-4}$ alkylcarbonyl, $C_{1-4}$ alkoxycarbonyl, $C_{1-4}$ alkylcarbonyloxy, $C_{1-4}$ alkylcarbonylamino, $C_{1-4}$ alkylsulfonylamino, aminosulfonyl, $C_{1-4}$ alkylaminosulfonyl, alkylaminosulfonyl, aminosulfonylamino, $C_{1-4}$ alkylaminosulfonylamino, and di-$C_{1-4}$ alkylaminosulfonylamino;

each RX group is independently selected from halo, CN, $NO_2$, $OR^{a1}$, $NR^{e1}R^{f1}$, $SR^{b1}$, $S(=O)_2R^{b1}$, $S(=O)_2NR^{e1}R^{f1}$, $C(=O)R^{b1}$, $C(=O)OR^{a1}$, $C(=O)NR^{e1}R^{f1}$, $OC(=O)R^{b1}$, $OC(=O)NR^{e1}R^{f1}$, $NR^{c1}C(=O)R^{d1}$, $NR^{c1}C(=O)OR^{d1}$, $NR^{c1}S(=O)_2R^{d1}$, and $NR^{c1}S(=O)_2NR^{e1}R^{f1}$;

each $R^{a1}$, $R^{c1}$, $R^{d1}$, $R^{e1}$ and $R^{f1}$ is independently selected from H, $C_{1-6}$ alkyl, $C_{1-6}$ haloalkyl, $Cy^2$, and —$C_{1-3}$ alkylene-$Cy^2$; wherein said $C_{1-6}$ alkyl is optionally substituted by 1, 2, or 3 independently selected $R^k$ groups; or each $R^{e1}$ and $R^{f1}$, together with the nitrogen atom to which they are attached, forms a 4-6 membered monocyclic heterocycloalkyl ring; which is optionally substituted with 1, 2, or 3 independently selected $R^m$ groups;

each $R^{b1}$ is independently selected from $C_{1-6}$ alkyl, $C_{1-6}$ haloalkyl, $Cy^2$, and —$C_{1-3}$ alkylene-$Cy^2$; wherein said $C_{1-6}$ alkyl is optionally substituted by 1, 2, or 3 independently selected $R^k$ groups;

each $Cy^2$ is independently selected from 3-6-membered monocyclic cycloalkyl, 4-6 membered monocyclic heterocycloalkyl, phenyl, and 5-6 membered monocyclic heteroaryl, which are each optionally substituted by 1, 2, or 3 independently selected $R^m$ groups;

each $R^k$ is independently selected from halo, CN, hydroxy, $C_{1-4}$ alkoxy, $C_{1-4}$ haloalkoxy, hydroxyl-$C_{1-4}$ alkyl, $C_{1-4}$ alkoxy-$C_{1-4}$ alkyl, cyano-$C_{1-4}$ alkyl, amino, $C_{1-4}$ alkylamino, carbamyl, $C_{1-4}$ alkylcarbamyl, di($C_{1-4}$ alkyl) carbamyl, $C_{1-4}$ alkylcarbonyl, $C_{1-4}$ alkoxycarbonyl, $C_{1-4}$ alkylcarbonyloxy, $C_{1-4}$ alkylcarbonylamino, $C_{1-4}$ alkylsulfonyl, $C_{1-4}$ alkylsulfonylamino, aminosulfonyl, $C_{1-4}$ alkylaminosulfonyl, alkylaminosulfonyl, aminosulfonylamino, $C_{1-4}$ alkylaminosulfonylamino, and di-$C_{1-4}$ alkylaminosulfonylamino;

each $R^m$ is independently selected from halo, CN, hydroxy, $C_{1-4}$ alkyl, $C_{1-4}$ haloalkyl, $C_{1-4}$ alkoxy, $C_{1-4}$ haloalkoxy, hydroxyl-$C_{1-4}$ alkyl, $C_{1-4}$ alkoxy-$C_{1-4}$ alkyl, cyano-$C_{1-4}$ alkyl, amino, $C_{1-4}$ alkylamino, carbamyl, $C_{1-4}$ alkylcarbamyl, di($C_{1-4}$ alkyl)carbamyl, $C_{1-4}$ alkylcarbonyl, $C_{1-4}$ alkoxycarbonyl, $C_{1-4}$ alkylcarbonyloxy, $C_{1-4}$ alkylsulfonyl, $C_{1-4}$ alkylcarbonylamino, $C_{1-4}$ alkylsulfonylamino, aminosulfonyl, $C_{1-4}$ alkylaminosulfonyl, alkylaminosulfonyl, aminosulfonylamino, $C_{1-4}$ alkylaminosulfonylamino, and di-$C_{1-4}$ alkylaminosulfonylamino; and n is 0, 1, or 2.

2. The compound of claim 1, or a pharmaceutically acceptable salt thereof, wherein $R^1$, $R^2$, $R^3$, $R^4$, and $R^5$ are each independently selected from H, —$CF_3$, —$CH_2R^x$, and —$C(CH_3)_2R^x$.

3. The compound of claim 2, or a pharmaceutically acceptable salt thereof, wherein each $R^x$ group is independently selected from $OR^{a1}$ and $NR^{e1}R^{f1}$.

4. The compound of claim 1, or a pharmaceutically acceptable salt thereof, wherein each $R^{a1}$, $R^{c1}$, $R^{d1}$, $R^{e1}$, and $R^{f1}$ is independently selected from H, methyl, ethyl, n-propyl, isopropyl, n-butyl, isobutyl, tert-butyl, $Cy^2$, and —$C_{1-3}$ alkylene-$Cy^2$; wherein said $C_{1-6}$ alkyl is optionally substituted by 1, 2, or 3 independently selected $R^k$ groups; or each $R^{e1}$ and $R^{f1}$, together with the nitrogen atom to which they are attached, forms a 4-6 membered monocyclic heterocycloalkyl ring; which is optionally substituted with 1, 2, or 3 independently selected $R^m$ groups.

5. The compound of claim 4, or a pharmaceutically acceptable salt thereof, wherein each $Cy^2$ is independently selected from cyclopropyl, cyclobutyl, cyclopentyl, cyclohexyl, tetrahydrofuran-2-yl, and 1H-imidazol-4-yl, which are each optionally substituted by 1, 2, or 3 independently selected $R^m$ groups.

6. The compound of claim 4, or a pharmaceutically acceptable salt thereof, wherein each $R^m$ is independently selected from halo, hydroxy, $C_{1-4}$ alkoxy, hydroxyl-$C_{1-4}$ alkyl, and $C_{1-4}$ alkoxy-$C_{1-4}$ alkyl.

7. The compound of claim 4, or a pharmaceutically acceptable salt thereof, wherein each $R^k$ is independently selected from hydroxy, $C_{1-4}$ alkoxy, hydroxyl-$C_{1-4}$ alkyl, and $C_{1-4}$ alkoxy-$C_{1-4}$ alkyl.

8. The compound of claim 1, or a pharmaceutically acceptable salt thereof, wherein the 6-membered aromatic ring formed by carbon atom, X, Y, W, Z, and V is selected from:

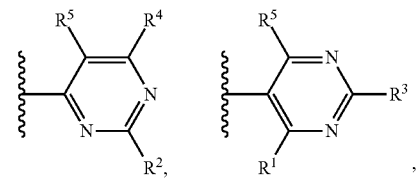

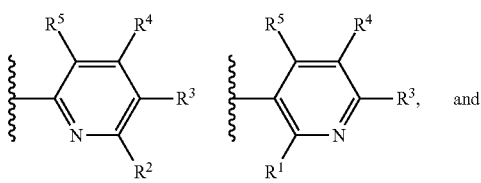, and

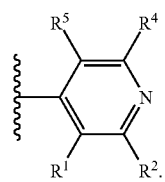

9. The compound of claim 1, or a pharmaceutically acceptable salt thereof, wherein:
X is N;
Y is $CR^2$;
W is $CR^3$ or N;
Z is $CR^4$;
V is $CR^5$;
$R^2$, $R^3$, $R^4$, and $R^5$ are each independently selected from H, halo, CN, $C_{1-6}$ alkyl, $C_{1-6}$ haloalkyl, Cy, $OR^a$, C(=O)$OR^a$, and C(=O)$NR^eR^f$; wherein said $C_{1-6}$ alkyl is optionally substituted by 1, 2, or 3 independently selected $R^x$ groups;
each Cy is independently selected from 3-6-membered monocyclic cycloalkyl optionally substituted by 1, 2, or 3 independently selected $R^g$ groups;
each $R^a$, $R^e$, and $R^f$ is, independently, H or $C_{1-6}$ alkyl; wherein said $C_{1-6}$ alkyl is optionally substituted with 1, 2, or 3 independently selected $R^h$ groups; or
each $R^e$ and $R^f$, together with the nitrogen atom to which they are attached, form a 4-6 membered monocyclic heterocycloalkyl ring;
each $R^g$ is independently selected from hydroxy and hydroxyl-$C_{1-4}$ alkyl;
each $R^h$ is independently selected from halo, hydroxy, and $C_{1-4}$ alkoxy;
each $R^x$ group is independently selected from $OR^{a1}$ and $NR^{e1}R^{f1}$;
each $R^{a1}$, $R^{e1}$ and $R^{f1}$ is independently selected from H, $C_{1-6}$ alkyl, $C_{1-6}$ haloalkyl, $Cy^2$, and —$C_{1-3}$ alkylene-$Cy^2$; wherein said $C_{1-6}$ alkyl is optionally substituted by 1, 2, or 3 independently selected $R^k$ groups; or each $R^{e1}$ and $R^{f1}$, together with the nitrogen atom to which they are attached, forms a 4-6 membered monocyclic heterocycloalkyl ring; which is optionally substituted with 1, 2, or 3 independently selected $R^m$ groups;
each $Cy^2$ is independently selected from 3-6-membered monocyclic cycloalkyl, 4-6 membered monocyclic heterocycloalkyl, and 5-6 membered monocyclic heteroaryl, which are each optionally substituted by 1, 2, or 3 independently selected $R^m$ groups;
each $R^k$ is independently selected from hydroxy, $C_{1-4}$ alkoxy, hydroxyl-$C_{1-4}$ alkyl, and $C_{1-4}$ alkoxy-$C_{1-4}$ alkyl; and
each $R^m$ is independently selected from halo, hydroxy, $C_{1-4}$ alkoxy, hydroxyl-$C_{1-4}$ alkyl, and $C_{1-4}$ alkoxy-$C_{1-4}$ alkyl.

10. The compound of claim 1, having Formula II:

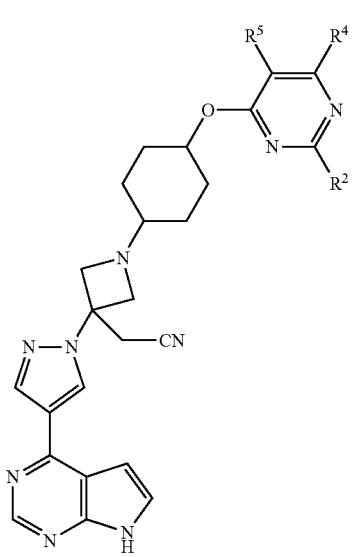

II or a pharmaceutically acceptable salt thereof.

11. The compound of claim 10, or a pharmaceutically acceptable salt thereof, wherein:
$R^2$ is $C_{1-3}$ haloalkyl;
$R^4$ is selected from —$CH_2OH$, —$C(CH_3)_2OH$, and —$CH_2NR^{e1}R^{f1}$;
$R^{e1}$ is H or $C_{1-4}$ alkyl;
$R^{f1}$ is H, $C_{1-6}$ alkyl, $C_{1-6}$ haloalkyl, $Cy^2$, or —$C_{1-2}$ alkylene-$Cy^2$; wherein said $C_{1-6}$ alkyl is optionally substituted with 1 or 2 groups selected from —OH and —$OCH_3$;
or $R^{e1}$ and $R^{f1}$ together with the nitrogen atom to which they are attached form a 4-6-membered monocyclic heterocycloalkyl ring, which is optionally substituted by one —F, —OH, or —$CH_2OH$ group; and
$Cy^2$ is cyclopropyl, cyclobutyl, 5-membered monocyclic heterocycloalkyl, or 5-membered monocyclic heteroaryl; each of which is optionally substituted by a —$CH_2OH$ group.

12. The compound of claim 10, or a pharmaceutically acceptable salt thereof, wherein:
$R^2$ is $C_{1-3}$ haloalkyl;
$R^4$ is selected from —$CH_2OH$, —$C(CH_3)_2OH$, and —$CH_2NR^{e1}R^{f1}$ wherein
$R^{e1}$ is H, methyl or ethyl; and
$R^{f1}$ is H, methyl, ethyl, isopropyl, n-propyl, n-butyl, isobutyl, tert-butyl, 2-fluoroethyl, 2,2,2-trifluoroethyl, cyclopropyl, cyclobutyl, 2-hydroxyethyl, 3-hydroxypropyl, 2-methoxyethyl, 3-methoxypropyl, 2-hydroxy-1-methylethyl, 2-methoxy-1-methylethyl, 2-hydroxy-2-methylethyl, 2-hydroxy-2,2-dimethylethyl, 2,3-dihydroxypropyl, cyclopropylmethyl, (1-(hydroxymethyl)cyclopropyl)methyl, 2-(hydroxymethyl)tetrahydrofuran-2-yl, or 1H-imidazol-4-ylethyl; or $R^{e1}$ and $R^{f1}$, together with the nitrogen atom to which they are attached, form a group selected from azetidinyl, 3-hydroxy-azetidinyl, 3-fluoro-azetidinyl, pyrrolidinyl, 3-hydroxypyrrolidinyl, 3-fluoropyrrolidinyl, 2-(hydroxymethyl)pyrrolidinyl, and piperidinyl.

13. The compound of claim 1, having Formula III:

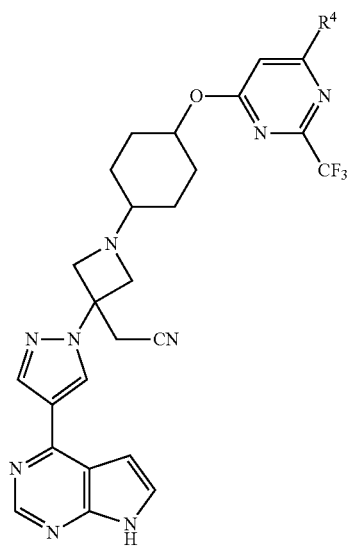

or a pharmaceutically acceptable salt thereof.

14. The compound of claim 1, having Formula IV:

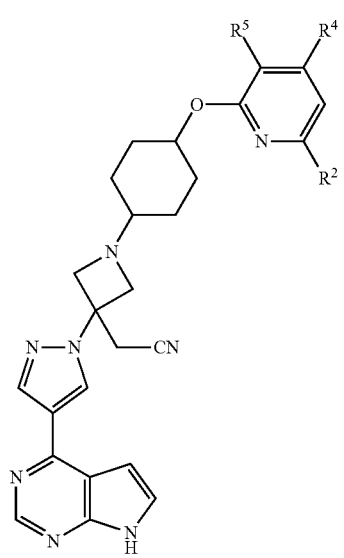

or a pharmaceutically acceptable salt thereof.

15. The compound of claim 1, having Formula V:

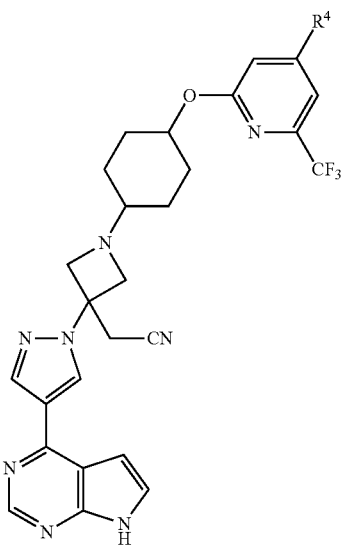

or a pharmaceutically acceptable salt thereof.

16. The compound of claim 15, or a pharmaceutically acceptable salt thereof, wherein:

$R^4$ is selected from —$CH_2OH$, —$C(CH_3)_2OH$, —$CH_2NR^{e1}R^{f1}$ and $C(=O)NR^eR^f$;

or $R^4$ is —$CH_2$-pyrazolyl or —$CH_2$-imidazolyl;

$R^{e1}$ is H, methyl or ethyl;

$R^{f1}$ is H, methyl, ethyl, isopropyl, n-propyl, n-butyl, isobutyl, tert-butyl, cyclopropyl, cyclobutyl, 2-hydroxyethyl, 3-hydroxypropyl, 2-hydroxy-1-methylethyl, or cyclopropylmethyl; or $R^{e1}$ and $R^{f1}$, together with the nitrogen atom to which they are attached, form a group selected from azetidinyl, 3-hydroxy-azetidinyl, 3-fluoro-azetidinyl, 3-cyano-azetidinyl, pyrrolidinyl, 3-hydroxypyrrolidinyl, 3-fluoropyrrolidinyl, 2-(hydroxymethyl)pyrrolidinyl, piperidinyl, 4-hydroxypiperidinyl, and 3-methyloxetan-3-yl;

$R^e$ is H or methyl; and $R^f$ is H, methyl, ethyl, isopropyl, n-propyl, n-butyl, isobutyl, tert-butyl, cyclopropyl, or cyclobutyl; or $R^e$ and $R^f$, together with the nitrogen atom to which they are attached, form a group selected from azetidinyl, 3-hydroxy-azetidinyl, 3-fluoro-azetidinyl, 3-cyano-azetidinyl, pyrrolidinyl, 3-hydroxypyrrolidinyl, 3-fluoropyrrolidinyl, 2-(hydroxymethyl)pyrrolidinyl, and piperidinyl.

17. The compound of claim 1, having Formula III-A:

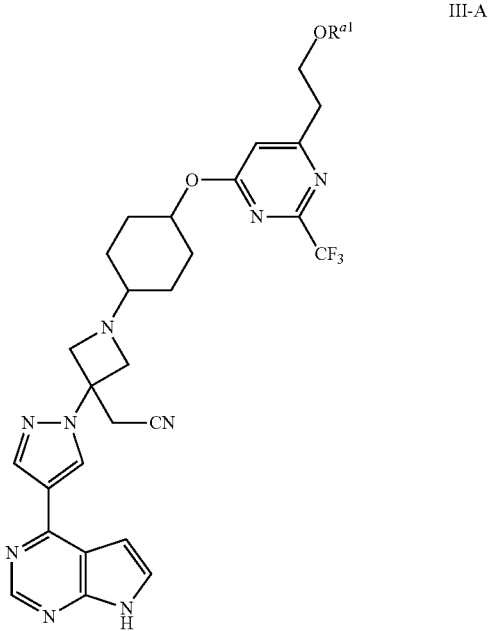

or a pharmaceutically acceptable salt thereof.

18. The compound of claim 17, wherein $R^{a1}$ is H, methyl or ethyl.

19. A compound of claim 1, selected from:
{1-(cis-4-{[6-[(dimethylamino)methyl]-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-(hydroxymethyl)-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-(aminomethyl)-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-[(methylamino)methyl]-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-[(ethylamino)methyl]-2-(trifluoromethyl) pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-[(isopropylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;
{1-(cis-4-{[6-[(cyclopropylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;
{1-(cis-4-{[6-{[ethyl(methyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;
{1-(cis-4-{[6-{[(cyclopropylmethyl)amino]methyl}-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-[(cyclobutylamino)methyl]-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-{[(2-hydroxyethyl)amino]methyl}-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-{[(2-hydroxyethyl)(methyl)amino]methyl}-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-{[ethyl(2-hydroxyethyl)amino]methyl}-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
[3-[4-(7H-pyrrolo [2,3-d]pyrimidin-4-yl)-1H-pyrazol-1-yl]-1-(cis-4-{[6-{[(2,2,2-trifluoroethyl)amino]methyl}-2-(trifluoromethyl)pyrimidin-4-yl]oxy}cyclohexyl)azetidin-3-yl]acetonitrile;
{1-(cis-4-{[6-{[(2-fluoroethyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;
{1-(cis-4-{[6-({[(1 S)-2-hydroxy-1-methylethyl]amino}methyl)-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-({[(1R)-2-hydroxy-1-methylethyl]amino}methyl)-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-({[(2S)-2-hydroxypropyl]amino}methyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;
{1-(cis-4-{[6-({[(2R)-2-hydroxypropyl]amino}methyl)-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-{[(2-hydroxy-2-methylpropyl)amino]methyl}-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-{[(3-hydroxypropyl)amino]methyl}-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-{[(2-methoxyethyl)amino]methyl}-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-(azetidin-1-ylmethyl)-2-(trifluoromethyl) pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-[(3-hydroxyazetidin-1-yl)methyl]-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;
{1-(cis-4-{[6-(pyrrolidin-1-ylmethyl)-2-(trifluoromethyl) pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;
{1-(cis-4-{[6-{[(3S)-3-hydroxypyrrolidin-1-yl]methyl}-2-(trifluoromethyl)pyrimidin-4-yl]oxy}cyclohexyl)-3-

[4-(7H-pyrrolo[2,3-d]pyrimidin-4-yl)-1H-pyrazol-1-yl]azetidin-3-yl}acetonitrile;

[3-[4-(7H-pyrrolo [2,3-d]pyrimidin-4-yl)-1H-pyrazol-1-yl]-1-(cis-4-{[6-({[(2S)-tetrahydrofuran-2-ylmethyl]amino}methyl)-2-(trifluoromethyl)pyrimidin-4-yl]oxy}cyclohexyl)azetidin-3-yl]acetonitrile;

{1-(cis-4-{[6-{[(2R)-2-(hydroxymethyl)pyrrolidin-1-yl]methyl}-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[6-{[(2S)-2-(hydroxymethyl)pyrrolidin-1-yl]methyl}-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[6-(piperidin-1-ylmethyl)-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[6-{[(3 S)-3-fluoropyrrolidin-1-yl]methyl}-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[6-[(propylamino)methyl]-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[6-{[(2,3-dihydroxypropyl)amino]methyl}-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[6-[(butylamino)methyl]-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[6-[(isobutylamino)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[butyl(methyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-[(3-fluoroazetidin-1-yl)methyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-[({[1-(hydroxymethyl)cyclopropyl]methyl}amino)methyl]-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

2-(1-(cis-4-((6-(((2-(1H-imidazol-4-yl)ethyl)amino)methyl)-2-(trifluoromethyl)pyrimidin-4-yl)oxy)cyclohexyl)-3-(4-(7H-pyrrolo [2,3-d]pyrimidin-4-yl)-1H-pyrazol-1-yl)azetidin-3-yl)acetonitrile;

{1-(cis-4-{[6-{[(3-methoxypropyl)amino]methyl}-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[6-{[(2-methoxy-1-methylethyl)amino]methyl}-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[(2-methoxyethyl)(methyl)amino]methyl}-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[6-(1-hydroxy-1-methylethyl)-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile; and {1-(cis-4-{[6-[(tert-butylamino)methyl]-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

or a pharmaceutically acceptable salt thereof.

20. The compound of claim 1, selected from:

6-[(cis-4-{3-(cyanomethyl)-3-[4-(7H-pyrrolo [2,3-d]pyrimidin-4-yl)-1H-pyrazol-1-yl]azetidin-1-yl}cyclohexyl)oxy]-N-ethyl-2-(trifluoromethyl)pyrimidine-4-carboxamide;

{1-(cis-4-{[6-(pyrrolidin-1-ylcarbonyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-{[(2-hydroxy-1,1-dimethylethyl)amino]methyl}-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[6-{[(1-methylcyclopropyl)amino]methyl}-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

6-[(cis-4-{3-(cyanomethyl)-3-[4-(7H-pyrrolo [2,3-d]pyrimidin-4-yl)-1H-pyrazol-1-yl]azetidin-1-yl}cyclohexyl)oxy]-2-(trifluoromethyl)pyrimidine-4-carbonitrile;

{1-(cis-4-{[6-(2-hydroxyethoxy)-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[6-(1,2-dihydroxy-1-methylethyl)-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[6-(1-hydroxyethyl)-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[6-(2-hydroxy-1-methylethyl)-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[6-(1-fluoro-1-methylethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-(2-hydroxy-1,1-dimethylethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-[1-(hydroxymethyl)cyclopropyl]-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[6-(2-hydroxyethyl)-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

6-[(cis-4-{3-(cyanomethyl)-3-[4-(7H-pyrrolo [2,3-d]pyrimidin-4-yl)-1H-pyrazol-1-yl]azetidin-1-yl}cyclohexyl)oxy]-N,N-dimethyl-2-(trifluoromethyl)pyrimidine-4-carboxamide;

6-[(cis-4-{3-(cyanomethyl)-3-[4-(7H-pyrrolo [2,3-d]pyrimidin-4-yl)-1H-pyrazol-1-yl]azetidin-1-yl}cyclohexyl)oxy]-N-ethyl-N-methyl-2-(trifluoromethyl)pyrimidine-4-carboxamide;

6-[(cis-4-{3-(cyanomethyl)-3-[4-(7H-pyrrolo [2,3-d]pyrimidin-4-yl)-1H-pyrazol-1-yl]azetidin-1-yl}cyclohexyl)oxy]-N-(2-methoxyethyl)-2-(trifluoromethyl)pyrimidine-4-carboxamide;

{1-(cis-4-{[6-(2-fluoroethyl)-2-(trifluoromethyl)pyrimidin-4-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-(hydroxymethyl)-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-[(ethylamino)methyl]-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-(aminomethyl)-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-[(methylamino)methyl]-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-[(dimethylamino)methyl]-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-(1-hydroxy-1-methylethyl)-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-{[(3-hydroxypropyl)amino]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-{[(2-hydroxy-1, 1-dimethylethyl)amino]methyl}-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-[(cyclopropylamino)methyl]-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-({[(1 S)-2-hydroxy-1-methylethyl]amino}methyl)-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-{[(2-hydroxyethyl)amino]methyl}-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-({[(1R)-2-hydroxy-1-methylethyl]amino}methyl)-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-{[(cyclopropylmethyl)amino]methyl}-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-[(cyclobutylamino)methyl]-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-(azetidin-1-ylmethyl)-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-[(3-hydroxyazetidin-1-yl)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

2-[(cis-4-{3-(cyanomethyl)-3-[4-(7H-pyrrolo [2,3-d]pyrimidin-4-yl)-1H-pyrazol-1-yl]azetidin-1-yl}cyclohexyl)oxy]-N-methyl-6-(trifluoromethyl)isonicotinamide;

2-[(cis-4-{3-(cyanomethyl)-3-[4-(7H-pyrrolo [2,3-d]pyrimidin-4-yl)-1H-pyrazol-1-yl]azetidin-1-yl}cyclohexyl)oxy]-N,N-dimethyl-6-(trifluoromethyl)isonicotinamide;

2-[(cis-4-{3-(cyanomethyl)-3-[4-(7H-pyrrolo [2,3-d]pyrimidin-4-yl)-1H-pyrazol-1-yl]azetidin-1-yl}cyclohexyl)oxy]-N-(2-hydroxyethyl)-N-methyl-6-(trifluoromethyl)isonicotinamide;

2-[(cis-4-{3-(cyanomethyl)-3-[4-(7H-pyrrolo [2,3-d]pyrimidin-4-yl)-1H-pyrazol-1-yl]azetidin-1-yl}cyclohexyl)oxy]-N-isopropyl-6-(trifluoromethyl)isonicotinamide;

2-[(cis-4-{3-(cyanomethyl)-3-[4-(7H-pyrrolo [2,3-d]pyrimidin-4-yl)-1H-pyrazol-1-yl]azetidin-1-yl}cyclohexyl)oxy]-N-[(1S)-2-hydroxy-1-methylethyl]-6-(trifluoromethyl)isonicotinamide;

2-[(cis-4-{3-(cyanomethyl)-3-[4-(7H-pyrrolo [2,3-d]pyrimidin-4-yl)-1H-pyrazol-1-yl]azetidin-1-yl}cyclohexyl)oxy]-N-[(1R)-2-hydroxy-1-methylethyl]-6-(trifluoromethyl)isonicotinamide;

2-[(cis-4-{3-(cyanomethyl)-3-[4-(7H-pyrrolo [2,3-d]pyrimidin-4-yl)-1H-pyrazol-1-yl]azetidin-1-yl}cyclohexyl)oxy]-N-cyclopropyl-6-(trifluoromethyl)isonicotinamide;

2-[(cis-4-{3-(cyanomethyl)-3-[4-(7H-pyrrolo [2,3-d]pyrimidin-4-yl)-1H-pyrazol-1-yl]azetidin-1-yl}cyclohexyl)oxy]-N-cyclopropyl-N-methyl-6-(trifluoromethyl)isonicotinamide;

N-(sec-butyl)-2-[(cis-4-{3-(cyanomethyl)-3-[4-(7H-pyrrolo[2,3-d]pyrimidin-4-yl)-1H-pyrazol-1-yl]azetidin-1-yl}cyclohexyl)oxy]-6-(trifluoromethyl)isonicotinamide;

{1-(cis-4-{[4-[(3-hydroxyazetidin-1-yl)carbonyl]-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

2-[(cis-4-{3-(cyanomethyl)-3-[4-(7H-pyrrolo [2, 3-d]pyrimidin-4-yl)-1H-pyrazol-1-yl]azetidin-1-yl}cyclohexyl)oxy]-N-cyclobutyl-6-(trifluoromethyl)isonicotinamide;

1-[2-[(cis-4-{3-(cyanomethyl)-3-[4-(7H-pyrrolo [2,3-d]pyrimidin-4-yl)-1H-pyrazol-1-yl]azetidin-1-yl}cyclohexyl)oxy]-6-(trifluoromethyl)isonicotinoyl]azetidine-3-carbonitrile;

{1-(cis-4-{[4-(morpholin-4-ylmethyl)-6-(trifluoromethyl)pyridin-2-yl]oxy}cyclohexyl)-3-[4-(7H-pyrrolo [2, 3-d]pyrimidin-4-yl)-1H-pyrazol-1-yl]azetidin-3-yl}acetonitrile;

{1-(cis-4-{[4-{[(2R)-2-(hydroxymethyl)pyrrolidin-1-yl]methyl}-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-{[(2S)-2-(hydroxymethyl)pyrrolidin-1-yl]methyl}-6-(trifluoromethyl)pyridin-2-yl]

oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-{[(3 S)-3-hydroxypyrrolidin-1-yl]methyl}-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-[(4-hydroxypiperidin-1-yl)methyl]-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-{[(3-methyloxetan-3-yl)amino]methyl}-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-(1H-imidazol-1-ylmethyl)-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

{1-(cis-4-{[4-(1H-pyrazol-1-ylmethyl)-6-(trifluoromethyl)pyridin-2-yl]oxy}cyclohexyl)-3-[4-(7H-pyrrolo [2,3-d]pyrimidin-4-yl)-1H-pyrazol-1-yl]azetidin-3-yl}acetonitrile;

or a pharmaceutically acceptable salt thereof.

21. A composition comprising a compound according to claim 1, or a pharmaceutically acceptable salt thereof, and a pharmaceutically acceptable carrier.

22. A method of inhibiting an activity of JAK1 comprising contacting JAK1 with a compound according to claim 1, or a pharmaceutically acceptable salt thereof.

23. A method according to claim 22, wherein said compound, or pharmaceutically acceptable salt thereof, is selective for JAK1 over JAK2.

24. A method of treating a myeloproliferative disorder in a patient in need thereof, comprising administering to said patient a therapeutically effective amount of a compound of claim 1, or a pharmaceutically acceptable salt thereof, wherein said myeloproliferative disorder is myelofibrosis, primary myelofibrosis (PMF), post polycythemia vera myelofibrosis (Post-PV MF), post-essential thrombocythemia myelofibrosis (Post-ET MF), polycythemia vera (PV), essential thrombocythemia (ET), primary myelofibrosis (PMF), chronic myelogenous leukemia (CIVIL), chronic myelomonocytic leukemia (CMML), hypereosinophilic syndrome (HES), idiopathic myelofibrosis (IMF), or systemic mast cell disease (SMCD).

25. A compound of claim 1, which is {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile, or a pharmaceutically acceptable salt thereof.

26. A compound of claim 1, which is {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile, or a pharmaceutically acceptable salt thereof.

27. A compound of claim 1, which is {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile, or a pharmaceutically acceptable salt thereof.

28. A compound of claim 1, which is {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile, or a pharmaceutically acceptable salt thereof.

29. A compound, which is {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile, or a pharmaceutically acceptable salt thereof.

30. A composition, comprising a compound of claim 29, or a pharmaceutically acceptable salt thereof, and a pharmaceutically acceptable carrier.

* * * * *